(12) United States Patent
Bar-Yoseph et al.

(10) Patent No.: US 8,923,970 B2
(45) Date of Patent: Dec. 30, 2014

(54) STIMULATION OF THE URINARY SYSTEM

(75) Inventors: Gill Bar-Yoseph, Haifa (IL); Alon Polsky, Misgav (IE)

(73) Assignee: Nephera Ltd., Caesarea (IL)

( * ) Notice: Subject to any disclaimer, the term of this patent is extended or adjusted under 35 U.S.C. 154(b) by 12 days.

(21) Appl. No.: 13/156,753

(22) Filed: Jun. 9, 2011

(65) Prior Publication Data
US 2011/0301662 A1    Dec. 8, 2011

Related U.S. Application Data

(63) Continuation-in-part of application No. PCT/IL2009/001163, filed on Dec. 9, 2009.

(60) Provisional application No. 61/120,901, filed on Dec. 9, 2008, provisional application No. 61/173,228, filed on Apr. 28, 2009, provisional application No. 61/180,957, filed on May 26, 2009, provisional application No. 61/218,139, filed on Jun. 18, 2009, provisional application No. 61/225,226, filed on Jul. 14, 2009, provisional application No. 61/233,500, filed on Aug. 13, 2009, provisional application No. 61/355,522, filed on Jun. 16, 2010.

(51) Int. Cl.
*A61N 1/00* (2006.01)
*A61F 2/00* (2006.01)
*A61N 1/36* (2006.01)
*A61N 1/05* (2006.01)

(52) U.S. Cl.
CPC ........... *A61N 1/36007* (2013.01); *A61N 1/0556* (2013.01); *A61N 1/0514* (2013.01); *A61N 1/0558* (2013.01)
USPC .................................. 607/40; 607/2; 600/29

(58) Field of Classification Search
USPC ................ 607/2–3, 41, 44, 62, 117–118, 40; 600/29, 31
See application file for complete search history.

(56) References Cited

U.S. PATENT DOCUMENTS

| 4,850,963 A | 7/1989 | Sparks et al. |
| 5,374,261 A | 12/1994 | Yoon |

(Continued)

FOREIGN PATENT DOCUMENTS

| CN | 2598571 Y | 1/2004 |
| RU | 2271840 | 2/2004 |

(Continued)

OTHER PUBLICATIONS

Bakunts SA, Muradian KM (1977) Effect of electric stimulation on ureteral function. Zh Eksp Klin Med 17:8-15, including English Abstract.

(Continued)

*Primary Examiner* — Catherine Voorhees
(74) *Attorney, Agent, or Firm* — Edwards Wildman Palmer LLP; Barry Kramer; Joshua L. Jones

(57) ABSTRACT

Apparatus and methods are provided, including a bladder stimulator that includes an elongate element adapted to pass through a urethra or adapted to pass through another opening in the bladder, an expandable body coupled to said elongate element, and an array of one or more stimulator contacts coupled to the expandable body, the array including at least one contact adapted to contact a portion of a bladder of a subject when the expandable body is inserted in the bladder and expanded. A controller stimulates the portion of the bladder by driving a pulse into the bladder via the contact, the pulse having a frequency of 5 Hz-1 kHz. Other applications are also described.

15 Claims, 70 Drawing Sheets

(56) References Cited

U.S. PATENT DOCUMENTS

| | | | |
|---|---|---|---|
| 5,425,703 A | 6/1995 | Feiring | |
| 5,443,470 A | 8/1995 | Stern et al. | |
| 5,449,971 A | 9/1995 | Scott et al. | |
| 5,505,730 A | 4/1996 | Edwards | |
| 5,531,676 A | 7/1996 | Edwards et al. | |
| 5,536,240 A | 7/1996 | Edwards et al. | |
| 5,588,960 A | 12/1996 | Edwards et al. | |
| 5,704,908 A | 1/1998 | Hofmann et al. | |
| 5,733,319 A | 3/1998 | Neilson et al. | |
| 5,749,845 A | 5/1998 | Hildebrand et al. | |
| 5,769,880 A | 6/1998 | Truckai et al. | |
| 5,840,076 A | 11/1998 | Swanson et al. | |
| 5,861,431 A | 1/1999 | Hildebrand et al. | |
| 6,009,877 A | 1/2000 | Edwards | |
| 6,056,744 A | 5/2000 | Edwards | |
| 6,061,596 A * | 5/2000 | Richmond et al. | 607/41 |
| 6,254,599 B1 | 7/2001 | Lesh et al. | |
| 6,425,877 B1 | 7/2002 | Edwards | |
| 6,500,158 B1 | 12/2002 | Ikeguchi | |
| 6,662,052 B1 | 12/2003 | Sarwal et al. | |
| 6,685,744 B2 | 2/2004 | Gellman et al. | |
| 6,692,490 B1 | 2/2004 | Edwards | |
| 6,699,216 B2 | 3/2004 | Ikeguchi | |
| 6,743,197 B1 | 6/2004 | Edwards | |
| 6,743,226 B2 | 6/2004 | Cosman et al. | |
| 6,978,174 B2 | 12/2005 | Gelfand et al. | |
| 6,990,376 B2 | 1/2006 | Tanagho et al. | |
| 6,994,706 B2 | 2/2006 | Chornenky et al. | |
| 7,162,303 B2 | 1/2007 | Levin et al. | |
| 7,326,235 B2 | 2/2008 | Edwards | |
| 7,433,734 B2 * | 10/2008 | King | 607/2 |
| 7,617,005 B2 | 11/2009 | Demarais et al. | |
| 7,620,451 B2 | 11/2009 | Demarais et al. | |
| 2001/0003798 A1 | 6/2001 | McGovern et al. | |
| 2001/0031941 A1 | 10/2001 | Edwards et al. | |
| 2005/0143783 A1 | 6/2005 | Boveja et al. | |
| 2005/0228459 A1 * | 10/2005 | Levin et al. | 607/40 |
| 2005/0228460 A1 | 10/2005 | Levin et al. | |
| 2005/0234523 A1 | 10/2005 | Levin et al. | |
| 2005/0288730 A1 | 12/2005 | Deem et al. | |
| 2006/0025821 A1 | 2/2006 | Gelfand et al. | |
| 2006/0041277 A1 | 2/2006 | Deem et al. | |
| 2006/0116720 A1 | 6/2006 | Knoblich | |
| 2006/0142801 A1 | 6/2006 | Demarais et al. | |
| 2006/0206002 A1 | 9/2006 | Frassica et al. | |
| 2006/0206150 A1 | 9/2006 | Demarais et al. | |
| 2006/0212076 A1 | 9/2006 | Demarais et al. | |
| 2006/0212078 A1 | 9/2006 | Demarais et al. | |
| 2006/0235474 A1 | 10/2006 | Demarais | |
| 2006/0265014 A1 | 11/2006 | Demarais et al. | |
| 2006/0265015 A1 | 11/2006 | Demarais et al. | |
| 2006/0271111 A1 | 11/2006 | Demarais et al. | |
| 2006/0276852 A1 | 12/2006 | Demarais et al. | |
| 2007/0066957 A1 | 3/2007 | Demarais et al. | |
| 2007/0083239 A1 | 4/2007 | Demarais et al. | |
| 2007/0112327 A1 | 5/2007 | Yun et al. | |
| 2007/0129760 A1 | 6/2007 | Demarais et al. | |
| 2007/0129761 A1 | 6/2007 | Demarais et al. | |
| 2007/0135875 A1 | 6/2007 | Demarais et al. | |
| 2007/0173899 A1 | 7/2007 | Levin et al. | |
| 2007/0203549 A1 | 8/2007 | Demarais et al. | |
| 2007/0207959 A1 * | 9/2007 | Pisegna et al. | 514/12 |
| 2007/0208382 A1 | 9/2007 | Yun | |
| 2007/0265687 A1 | 11/2007 | Deem et al. | |
| 2007/0282184 A1 | 12/2007 | Roberts | |
| 2008/0065167 A1 | 3/2008 | Boggs et al. | |
| 2008/0119907 A1 | 5/2008 | Stahmann | |
| 2008/0213331 A1 | 9/2008 | Gelfand et al. | |
| 2008/0255642 A1 | 10/2008 | Zarins et al. | |
| 2009/0024195 A1 | 1/2009 | Rezai et al. | |
| 2009/0036948 A1 * | 2/2009 | Levin et al. | 607/44 |
| 2009/0054950 A1 * | 2/2009 | Stephens | 607/41 |
| 2009/0062873 A1 | 3/2009 | Wu et al. | |
| 2009/0076409 A1 | 3/2009 | Wu et al. | |
| 2009/0221939 A1 | 9/2009 | Demarais et al. | |
| 2009/0247817 A1 * | 10/2009 | Forsell | 600/31 |
| 2009/0264967 A1 * | 10/2009 | Giftakis et al. | 607/62 |
| 2010/0121220 A1 | 5/2010 | Nishtala | |
| 2010/0274310 A1 | 10/2010 | Boggs, Ii et al. | |
| 2011/0144468 A1 | 6/2011 | Boggs et al. | |
| 2012/0226098 A1 * | 9/2012 | Bar-Yoseph et al. | 600/29 |

FOREIGN PATENT DOCUMENTS

| | | |
|---|---|---|
| WO | WO-97/44088 A1 | 11/1997 |
| WO | WO-03/020124 A2 | 3/2003 |
| WO | WO-2004/075948 A2 | 9/2004 |
| WO | WO-2010/067360 A2 | 6/2010 |
| WO | WO-2012/027734 A1 | 3/2012 |

OTHER PUBLICATIONS

Bencsath P, Szenasi G, Asztalos B, Takacs L (1985) Time course of denervation diuresis and natriuresis in the anaesthetized rat. Acta Physiol Hung 66:47-50, Abstract Only.

Blair JE, Khan S, Konstam MA, Swedberg K, Zannad F, Burnett JC, Jr., Grinfeld L, Maggioni AP, Udelson JE, Zimmer CA, Ouyang J, Chen CF, Gheorghiade M (2009) Weight changes after hospitalization for worsening heart failure and subsequent re-hospitalization and mortality in the EVEREST trial. Eur Heart J 30:1666-1673.

Caterina MJ, Schumacher MA, Tominaga M, Rosen TA, Levine JD, Julius D (1997) The capsaicin receptor: a heat-activated ion channel in the pain pathway. Nature 389:816-824.

Chen SS, Chen WC, Hayakawa S, Li PC, Chien CT (2009) Acute urinary bladder distension triggers ICAM-1-mediated renal oxidative injury via the norepinephrine-renin-angiotensin II system in rats. J Formos Med Assoc 108:627-635.

Chien CT, Yu HJ, Cheng YJ, Wu MS, Chen CF, Hsu SM (2000) Reduction in renal haemodynamics by exaggerated vesicovascular reflex in rats with acute urinary retention. J Physiol 526 Pt 2:397-408.

Chuang YC, Fraser MO, Yu Y, Beckel JM, Seki S, Nakanishi Y, Yokoyama H, Chancellor MB, Yoshimura N, de Groat WC (2001) Analysis of the afferent limb of the vesicovascular reflex using neurotoxins, resiniferatoxin and capsaicin. Am J Physiol Regul Integr Comp Physiol 281:R1302-1310.

De Bock F, De Wachter S, Wyndaele JJ (2009) Can the use of different parameters and waveforms improve the results of intravesical electrical stimulation: a pilot study in the rat. Neurourol Urodyn 28:246-250.

Deng PY, Li YJ (2005) Calcitonin gene-related peptide and hypertension. Peptides 26:1676-1685.

Derzhavin VM, Vishnevskii EL, Dzheribal'di OA, Bruk SD, Vasil'ev AI (1989) Electric stimulation of the ureterovesical anastomosis in the treatment of hyperreflexia of the urinary bladder. Pediatriia: 53-57 with English Abstract.

DiBona GF (2004) The sympathetic nervous system and hypertension: recent developments. Hypertension 43:147-150.

DiBona GF, Kopp UC (1997) Neural control of renal function. Physiol Rev 77:75-197.

DiBona GF, Sawin LL (1999) Renal hemodynamic effects of activation of specific renal sympathetic nerve fiber groups. Am J Physiol 276:R539-549.

Dwyer TM, Schmidt-Nielsen B (2003) The renal pelvis: machinery that concentrates urine in the papilla. News Physiol Sci 18:1-6.

Fagius J, Karhuvaara S (1989) Sympathetic activity and blood pressure increases with bladder distension in humans. Hypertension 14:511-517.

Gardiner SM, Compton AM, Kemp PA, Bennett T, Foulkes R, Hughes B (1991) Regional haemodynamic effects of prolonged infusions of human alpha-calcitonin gene-related peptide in conscious, Long Evans rats. Br J Pharmacol 103:1509-1514.

Gotloib L, Fudin R, Yakubovich M, Vienken J (2005) Peritoneal dialysis in refractory end-stage congestive heart failure: a challenge facing a no-win situation. Nephrol Dial Transplant 20 Suppl 7:vii32-36.

International Preliminary Report on Patentability dated Jun. 14, 2011, which issued during the prosecution of Applicant's PCT/IL2009/001163.

(56) References Cited

OTHER PUBLICATIONS

Jiang CH, Lindstrom S (1999) Prolonged enhancement of the micturition reflex in the cat by repetitive stimulation of bladder afferents. J Physiol 517 ( Pt 2):599-605.
Kazarian K.V., V. Vanstain et al. Activation of latent pacemakers in the guinea pig ureter. Ross Fiziol Zhlm M. Sechenova 87(7): 953-9, 2001. Abstract Only.
Kenton K, Simmons J, FitzGerald MP, Lowenstein L, Brubaker L (2007) Urethral and bladder current perception thresholds: normative data in women. J Urol 178:189-192; discussion 192.
Kolesnikow GP, Karpenko WX (1987) Development and assessment of an artificial pacemaker of the ureter with feedback. Z Urol Nephrol 80:25-29 with English Abstract.
Kopp UC, Smith LA (1987) Renorenal reflex responses to renal sensory receptor stimulation in normotension and hypertension. Clin Exp Hypertens A 9 Suppl 1:113-125.
Kopp UC, Olson LA, DiBona GF (1984) Renorenal reflex responses to mechano- and chemoreceptor stimulation in the dog and rat. Am J Physiol 246:F67-77.
Kopp UC, Jones SY, DiBona GF (2008) Afferent renal denervation impairs baroreflex control of efferent renal sympathetic nerve activity. Am J Physiol Regul Integr Comp Physiol 295:R1882-1890.
Lang RJ, Davidson ME, Exintaris B (2002) Pyeloureteral motility and ureteral peristalsis: essential role of sensory nerves and endogenous prostaglandins. Exp Physiol 87:129-146.
Lazzeri M, Barbanti G, Beneforti P, Maggi CA, Taddei I, Andrea U, Cantini C, Castellani S, Turini D (1995) Vesical-renal reflex: diuresis and natriuresis activated by intravesical capsaicin. Scand J Urol Nephrol 29:39-43.
Li J, Wang DH (2008) Increased GFR and renal excretory function by activation of TRPV1 in the isolated perfused kidney. Pharmacol Res 57:239-246.
Ma MC, Huang HS, Chen CF (2002) Impaired renal sensory responses after unilateral ureteral obstruction in the rat. J Am Soc Nephrol 13:1008-1016.
Ma MC, Huang HS, Chen YS, Lee SH (2008) Mechanosensitive N-methyl-D-aspartate receptors contribute to sensory activation in the rat renal pelvis. Hypertension 52:938-944.
Melick WF, Brodeur AE, Herbig F, Naryka JJ (1966) Use of a ureteral pacemaker in the treatment of ureteral reflux. J Urol 95:184-196.
Ming Z, Smyth DD, Lautt WW (2002) Decreases in portal flow trigger a hepatorenal reflex to inhibit renal sodium and water excretion in rats: role of adenosine. Hepatology 35:167-175.
Office Action dated Jul. 30, 2012 in connection with Australian Patent Application No. 2009325847.
Palla R, Parrini M, Panichi V, Andreini B, De Pietro S, Migliori M, Bianchi AM, Giovannini L, Bertelli A, Bertelli AA, et al. (1995) Acute effects of calcitonin gene related peptide on renal haemodynamics and renin and angiotensin II secretion in patients with renal disease. Int J Tissue React 17:43-49.
Petersson M, Friberg P, Eisenhofer G, Lambert G, Rundqvist B (2005) Long-term outcome in relation to renal sympathetic activity in patients with chronic heart failure. Eur Heart J 26:906-913.
Polsky A, Mel B, Schiller J (2009) Encoding and decoding bursts by NMDA spikes in basal dendrites of layer 5 pyramidal neurons. J Neurosci 29:11891-11903.
Ronco C, Chionh CY, Haapio M, Anavekar NS, House A, Bellomo R (2009) The cardiorenal syndrome. Blood Purif 27:114-126.
Schlaich MP, Sobotka PA, Krum H, Whitbourn R, Walton A, Esler MD (2009) Renal Denervation as a Therapeutic Approach for Hypertension: Novel Implications for an Old Concept. Hypertension 54:1195-1201.
Schramm LP, Carlson DE (1975) Inhibition of renal vasoconstriction by elevated ureteral pressure. Am J Physiol 228:1126-1133.
Shekhar YC, Anand IS, Sarma R, Ferrari R, Wahi PL, Poole-Wilson PA (1991) Effects of prolonged infusion of human alpha calcitonin gene-related peptide on hemodynamics, renal blood flow.
Tsuchida S, Kumagai I (1978) Effect of urinary bladder distension on renal blood flow, blood pressure and plasma renin activity. Tohoku J Exp Med 126:335-341.
van Balken MR, Vergunst H, Bemelmans BL (2004) the use of electrical devices for the treatment of bladder dysfunction: a review of methods. J Urol 172:846-851.
Walter JS et al. Evaluation of direct bladder stimulation with stainless steel woven eye electrodes. J. Urol. Dec. 1993; 150(6): 1990-69. Abstract Only.
Xie C, Sachs JR, Wang DH (2008) Interdependent regulation of afferent renal nerve activity and renal function: role of transient receptor potential vanilloid type 1, neurokinin 1, and calcitonin gene-related peptide receptors. J Pharmacol Exp Ther 325:751-757.
Zhu Y, Wang Y, Wang DH (2005) Diuresis and natriuresis caused by activation of VR1-positive sensory nerves in renal pelvis of rats. Hypertension 46:992-997.
Zhu Y, Xie C, Wang DH (2007) TRPV1-mediated diuresis and natriuresis induced by hypertonic saline perfusion of the renal pelvis. Am J Nephrol 27:530-537.
Chinese Office Action for Chinese Patent Application No. 200980156494.X dated Jul. 1, 2013; including English Translation of the Office Action.
Patent Examination Report dated Mar. 18, 2013, issued on corresponding Australian Patent application No. 2009325847.
An Office Action dated Sep. 13, 2013, which issued during the prosecution of U.S. Appl. No. 13/415,594.

* cited by examiner

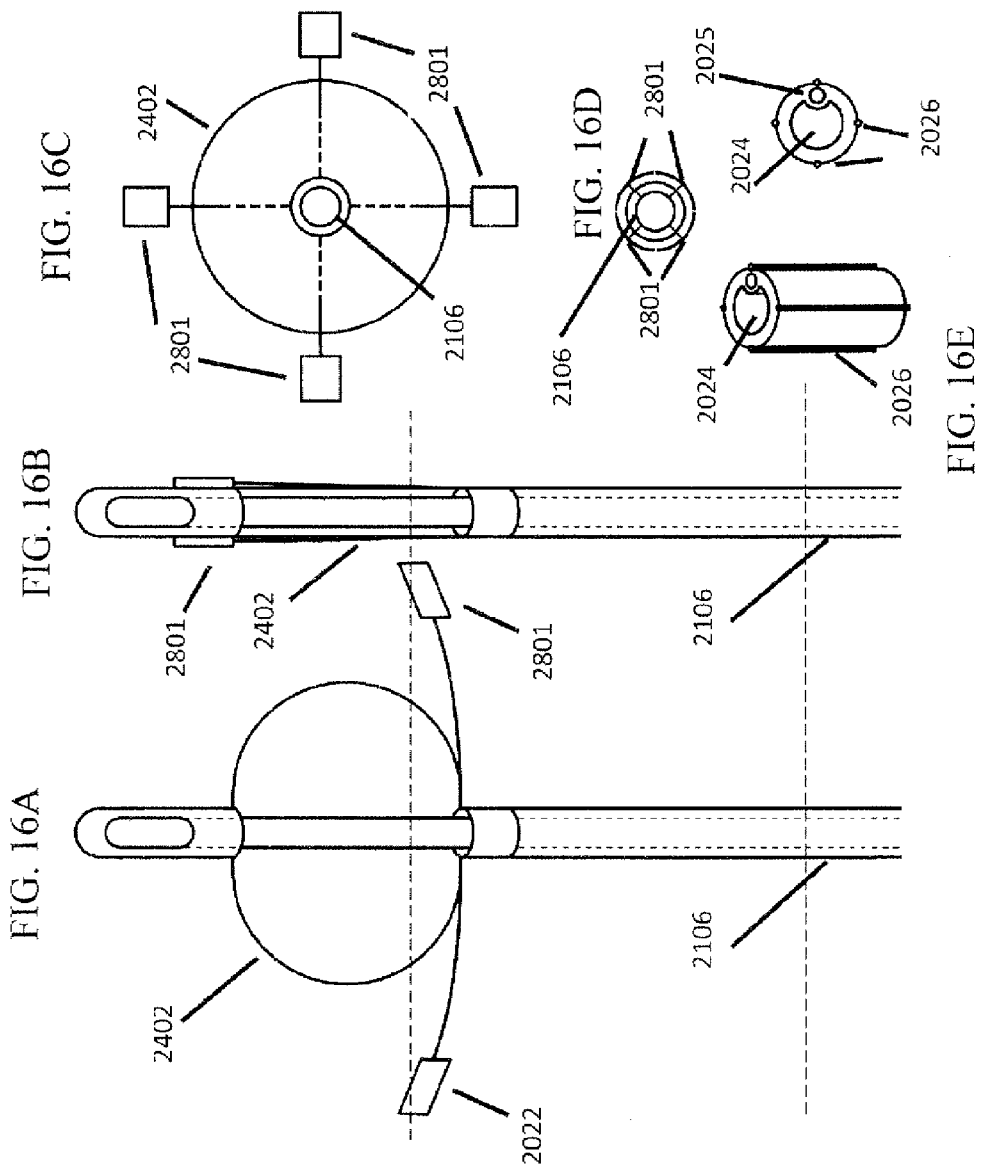

FIG. 17A    FIG. 17B        FIG. 17C
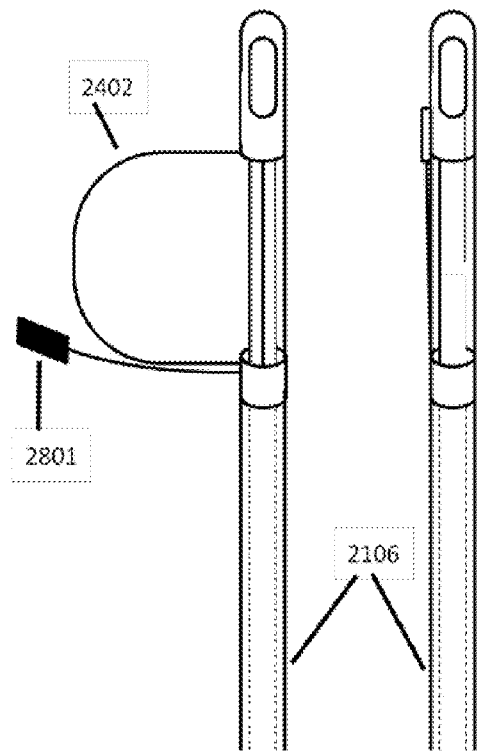
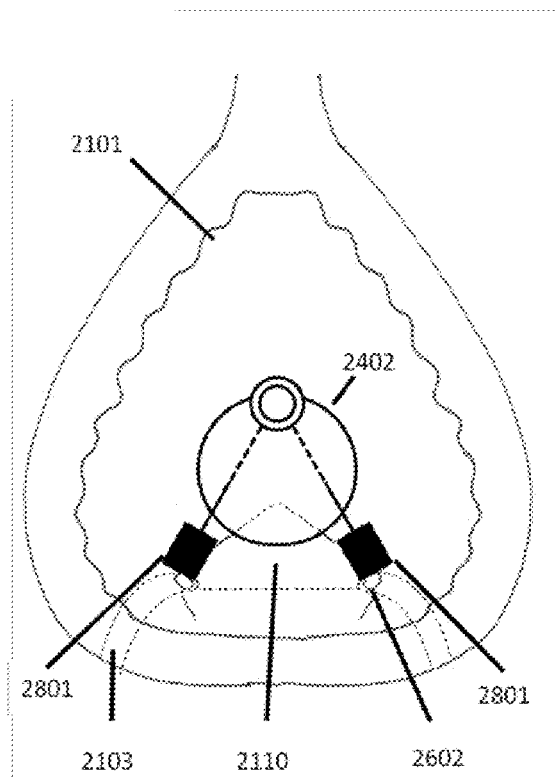

FIG. 18A FIG. 18B    FIG. 18C
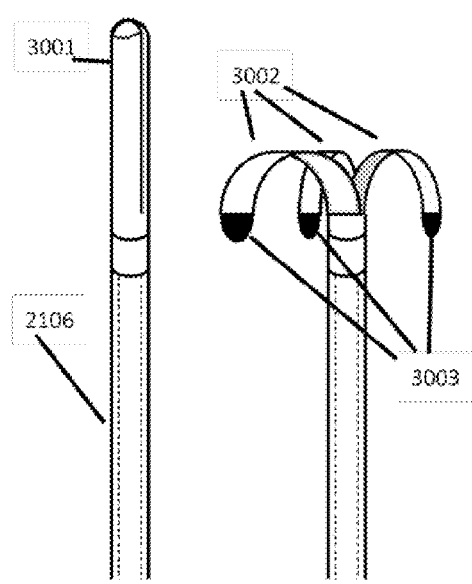
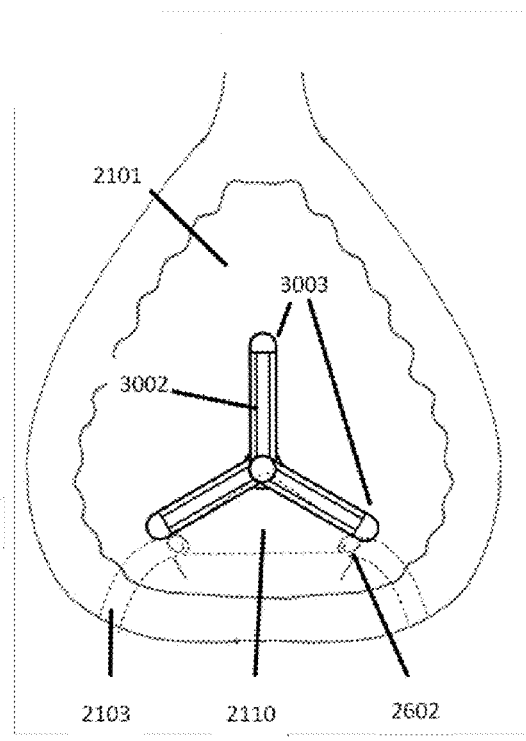

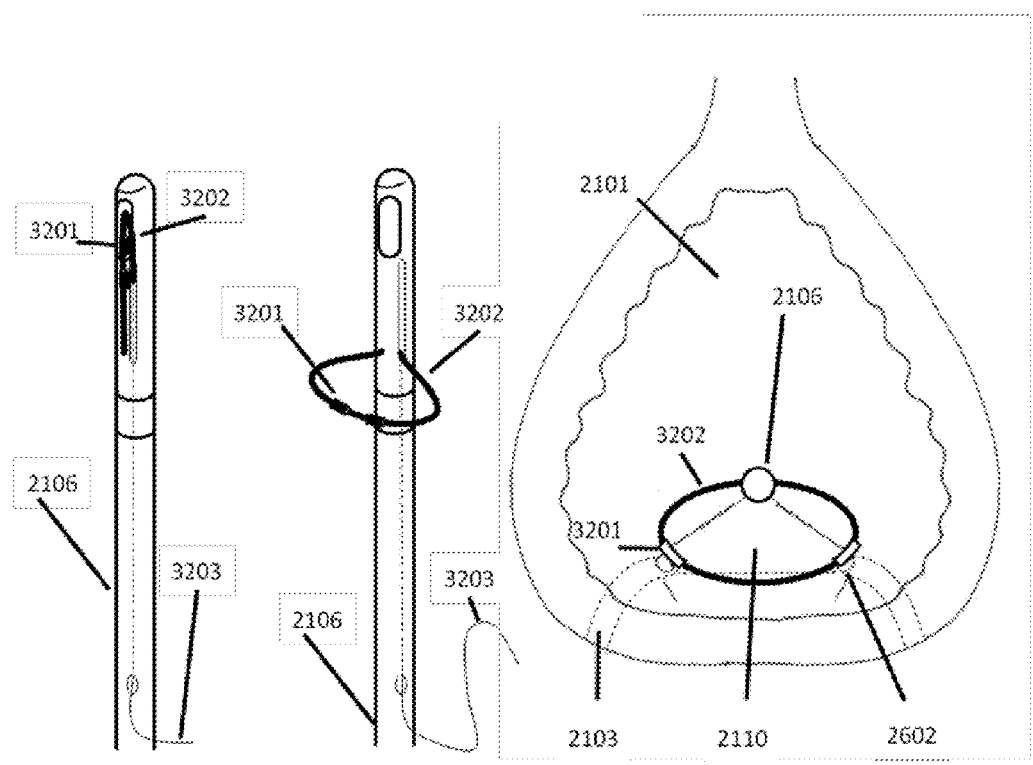

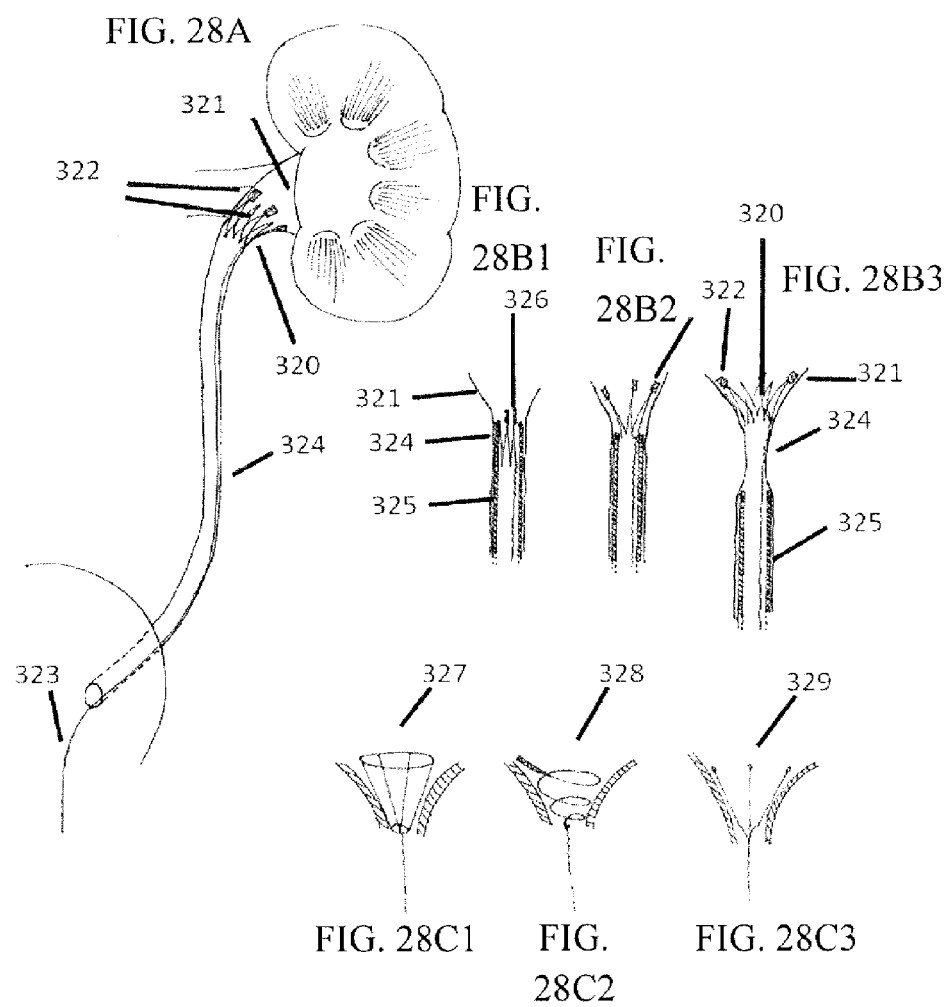

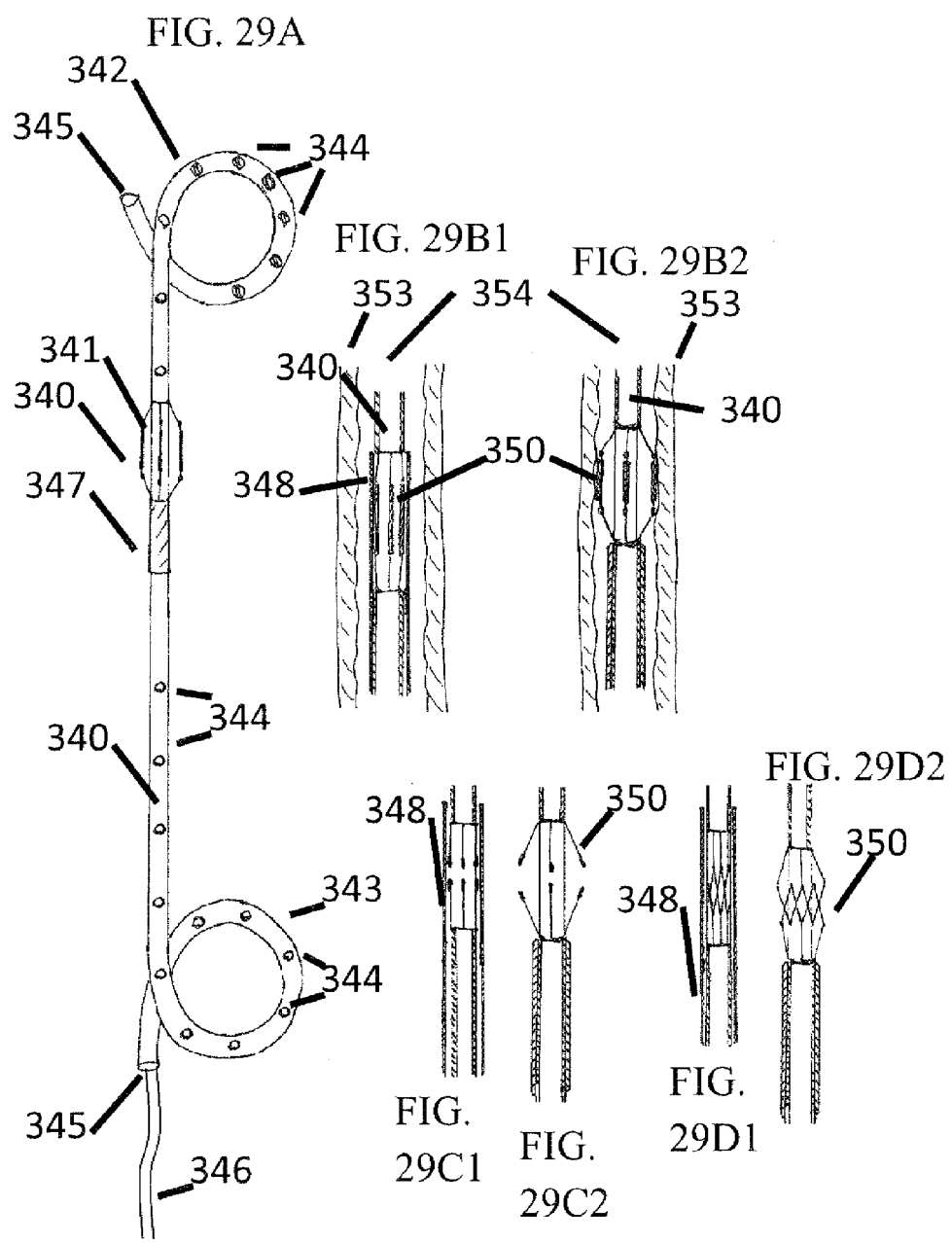

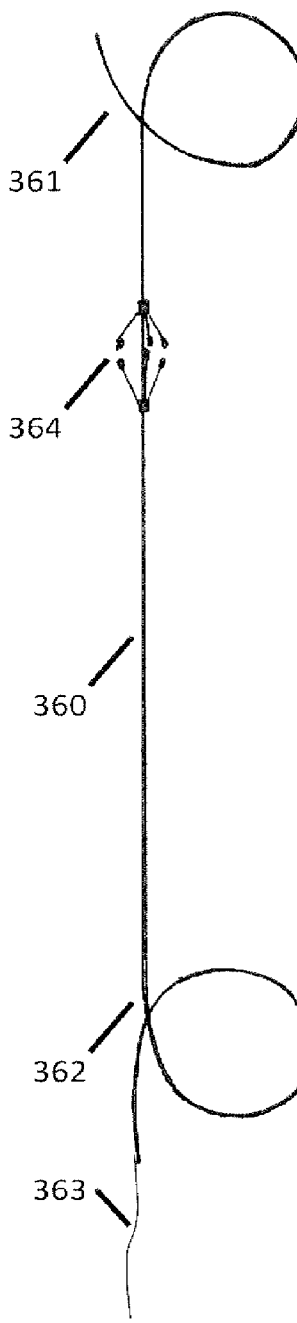
FIG. 30A
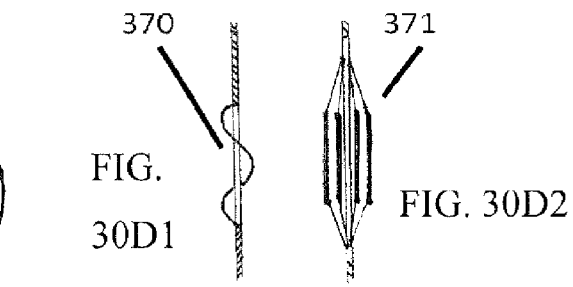
FIG. 30B1
FIG. 30C1
FIG. 30B2
FIG. 30C2
FIG. 30D1
FIG. 30D2

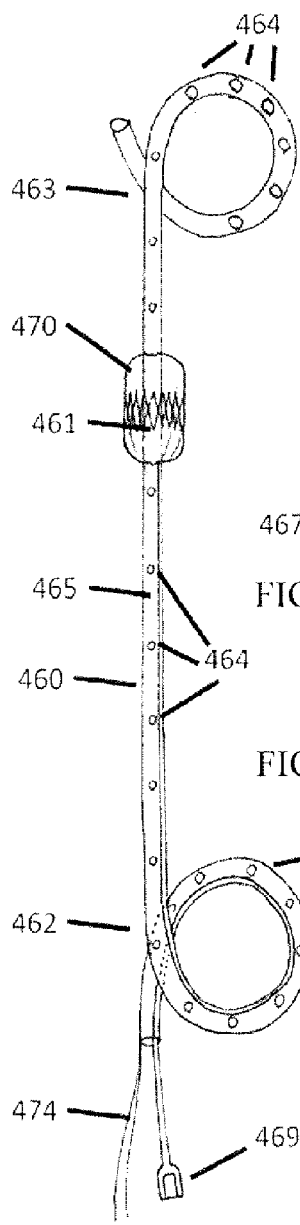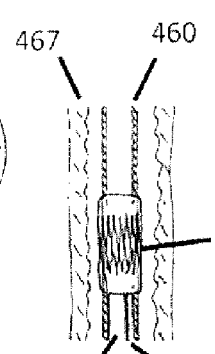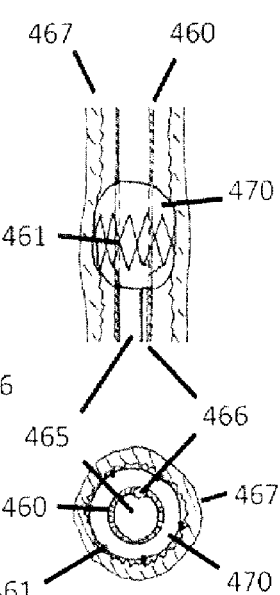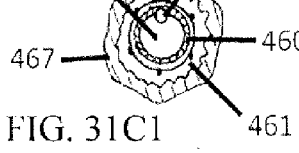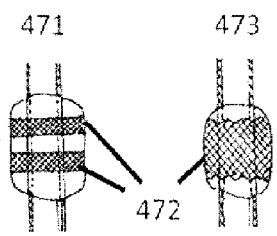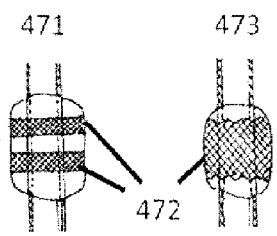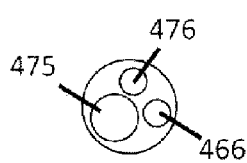
FIG. 31A    FIG. 31B1    FIG. 31B2
FIG. 31C1    FIG. 31C2
FIG. 31D1    FIG. 31D2
FIG. 31E

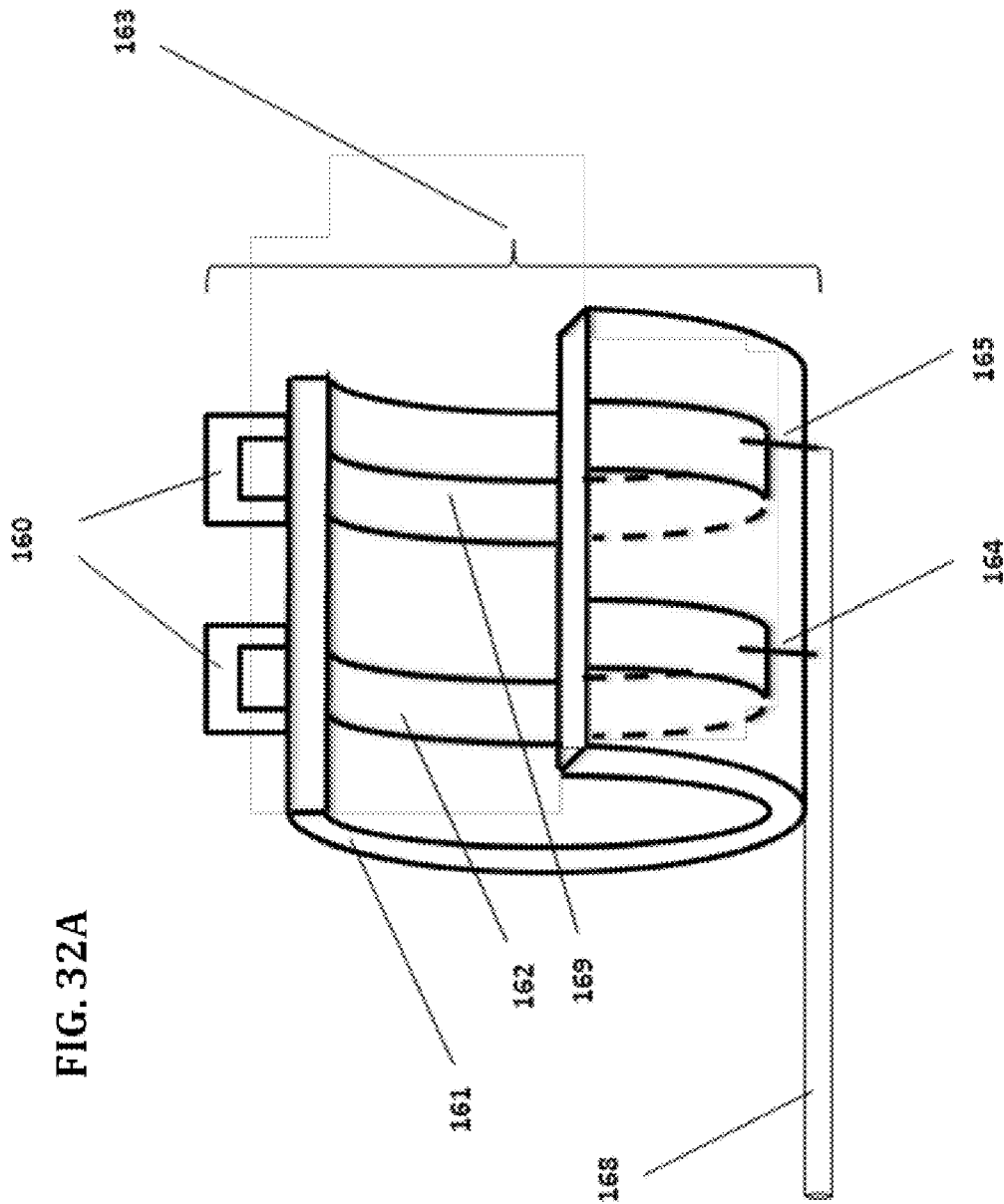

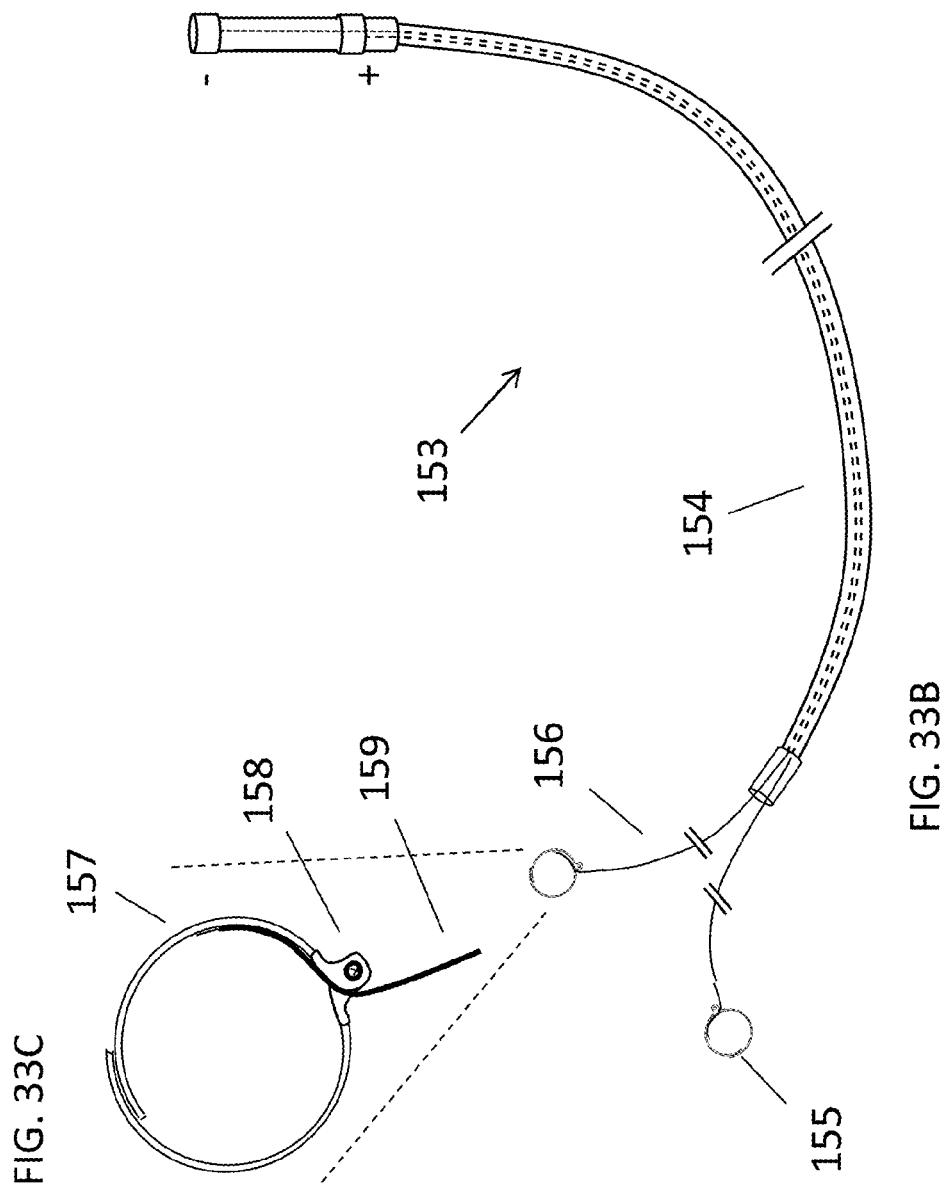

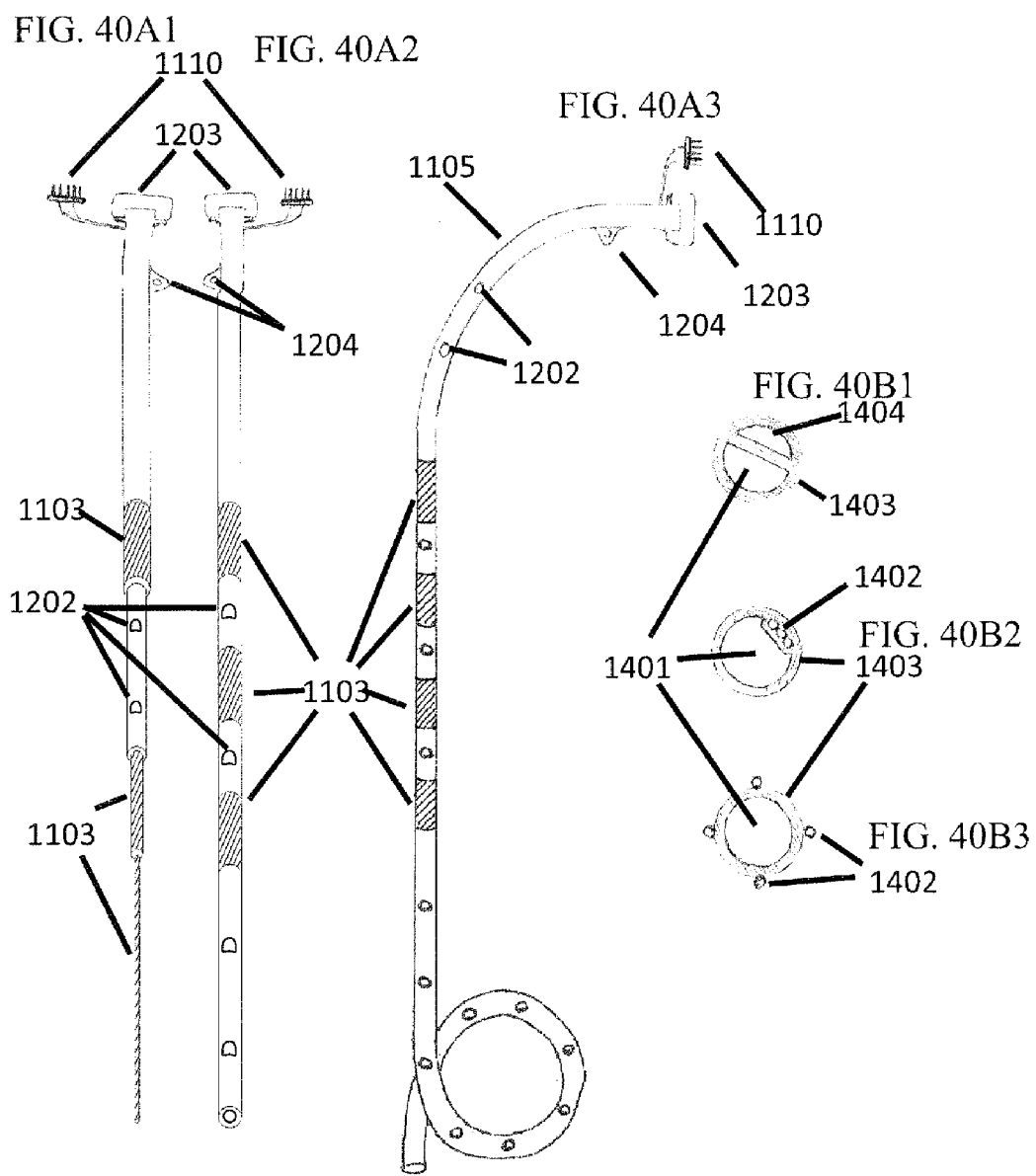

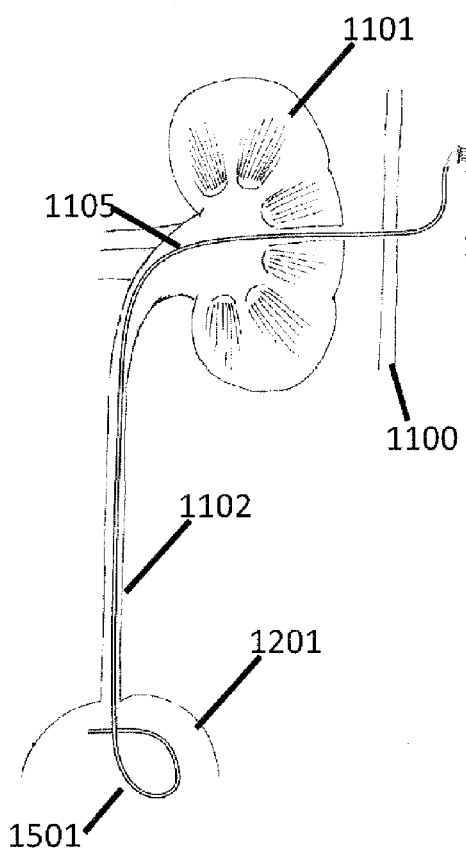
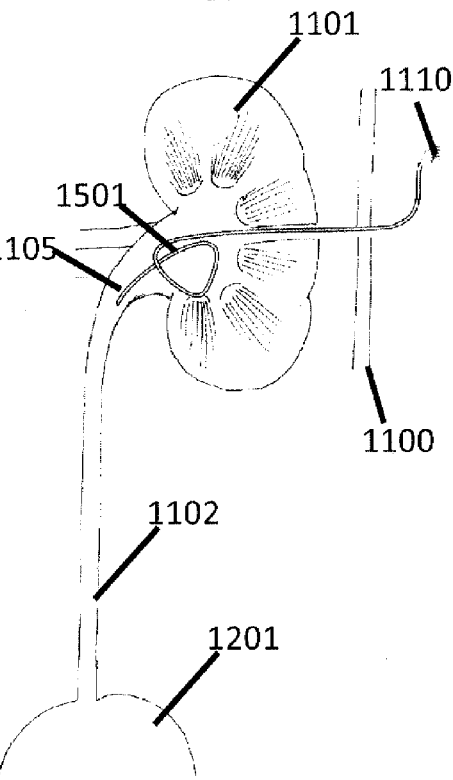
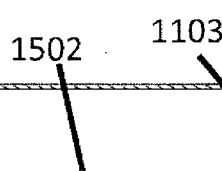
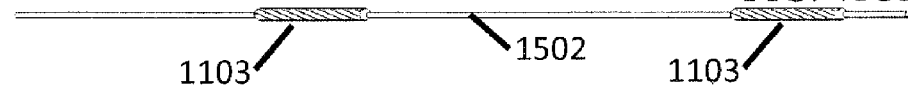

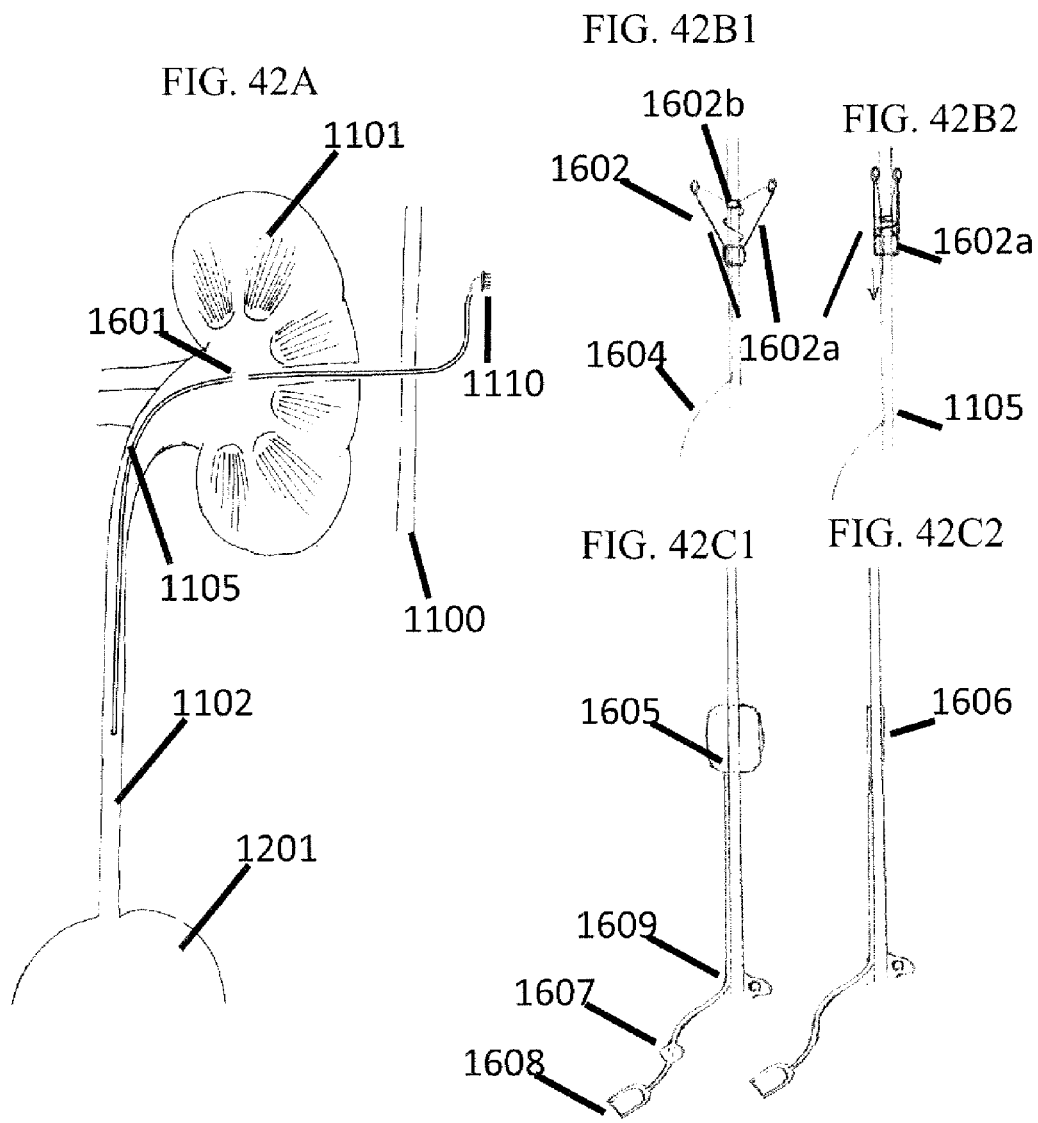

FIG. 49A  FIG. 49B
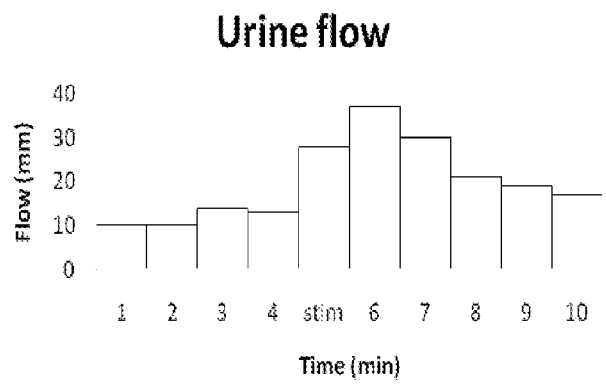
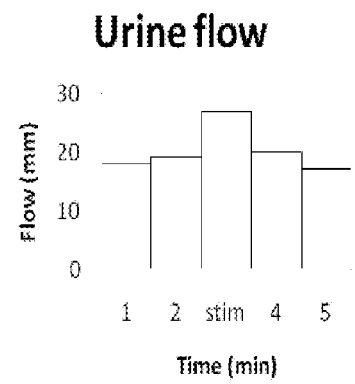
FIG. 50
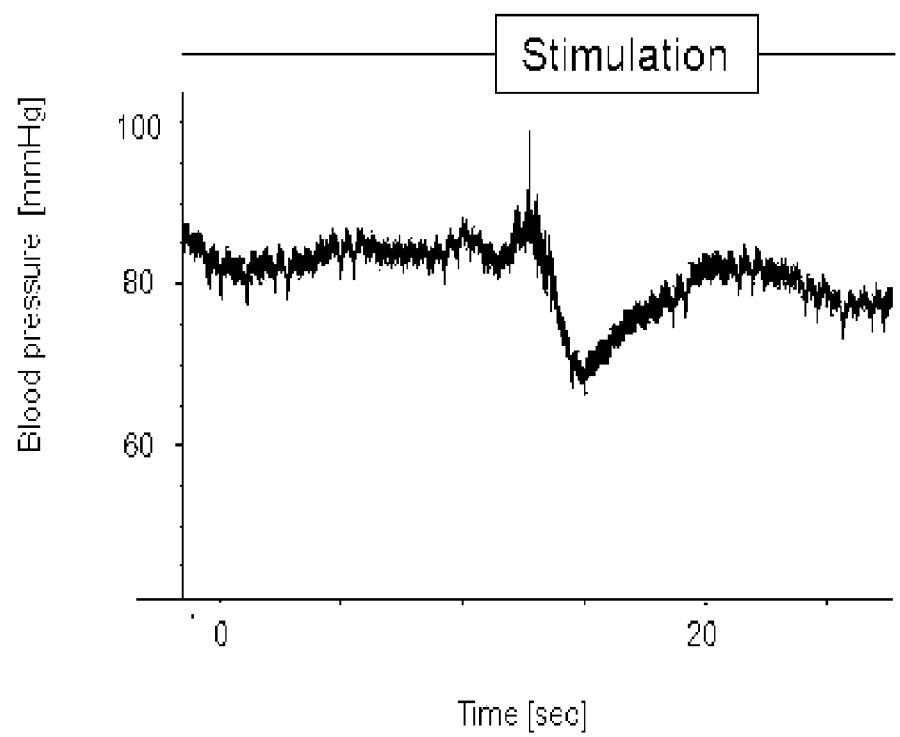

FIG. 53A1     FIG. 53A2     FIG. 53A3
Trigone stimulation
Urine flow     GFR     Sodium excretion
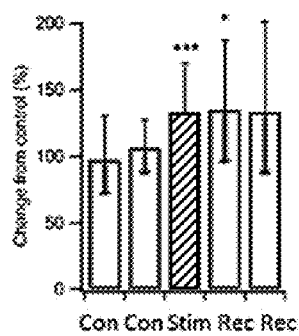 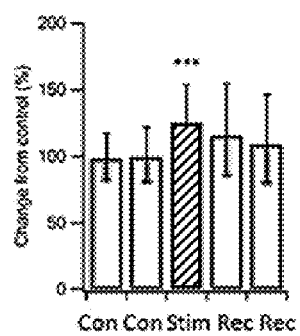 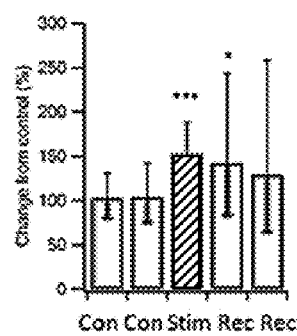
Ventral intravesical stimulation
Urine flow     GFR     Sodium excretion
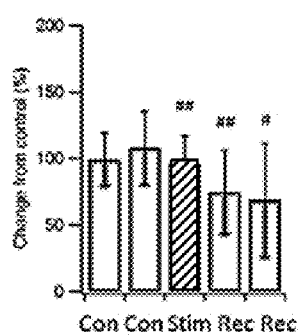 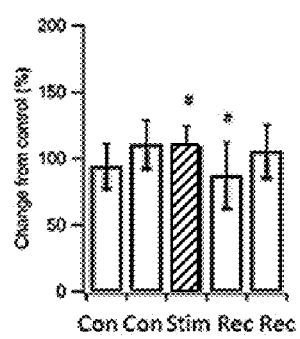 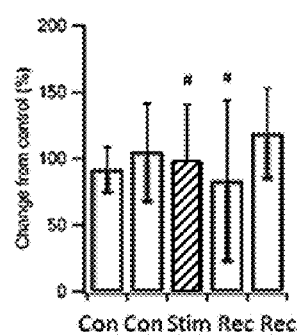
FIG. 53B1     FIG. 53B2     FIG. 53B3

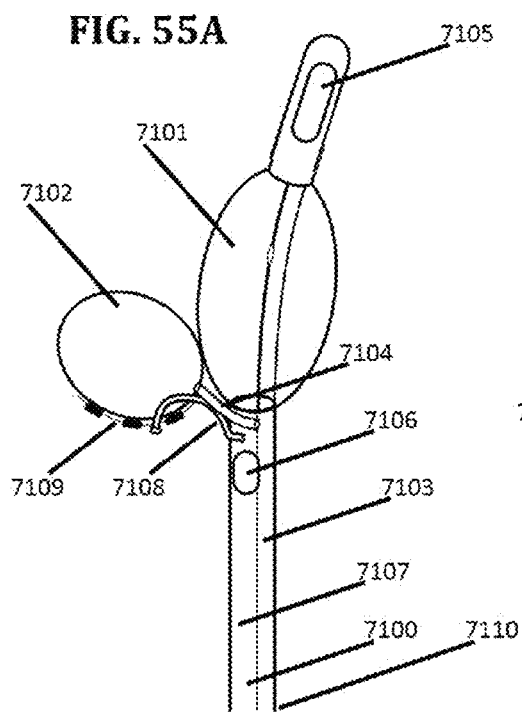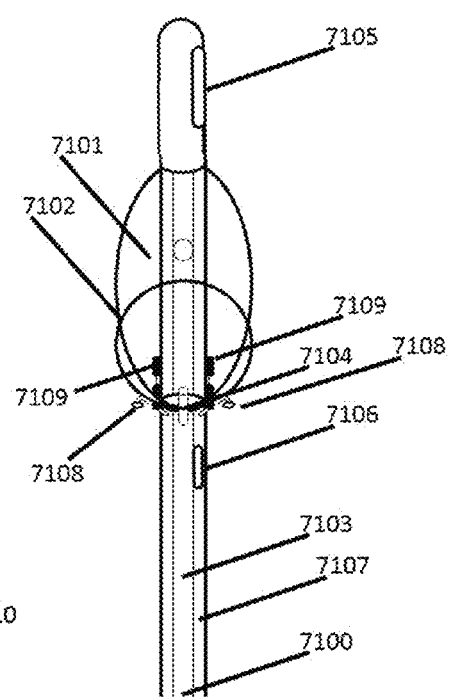

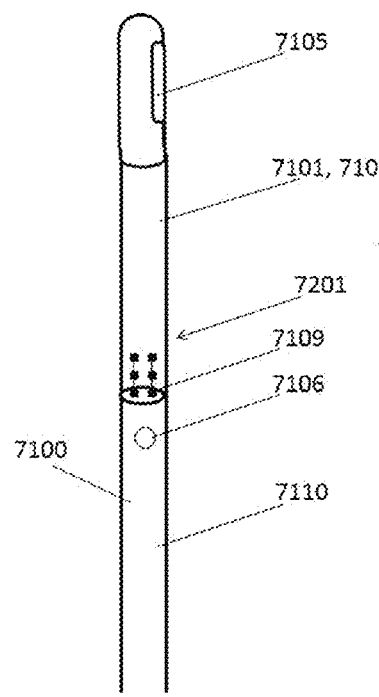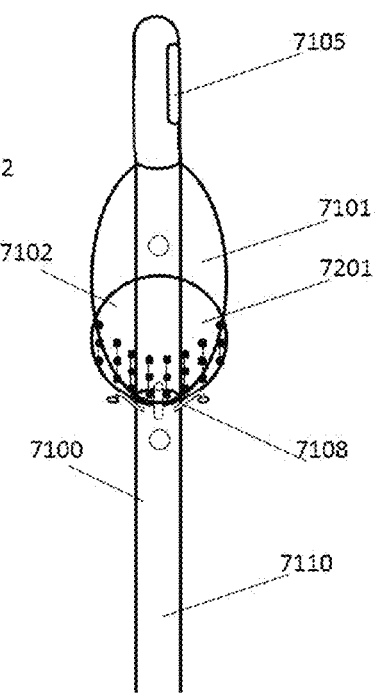

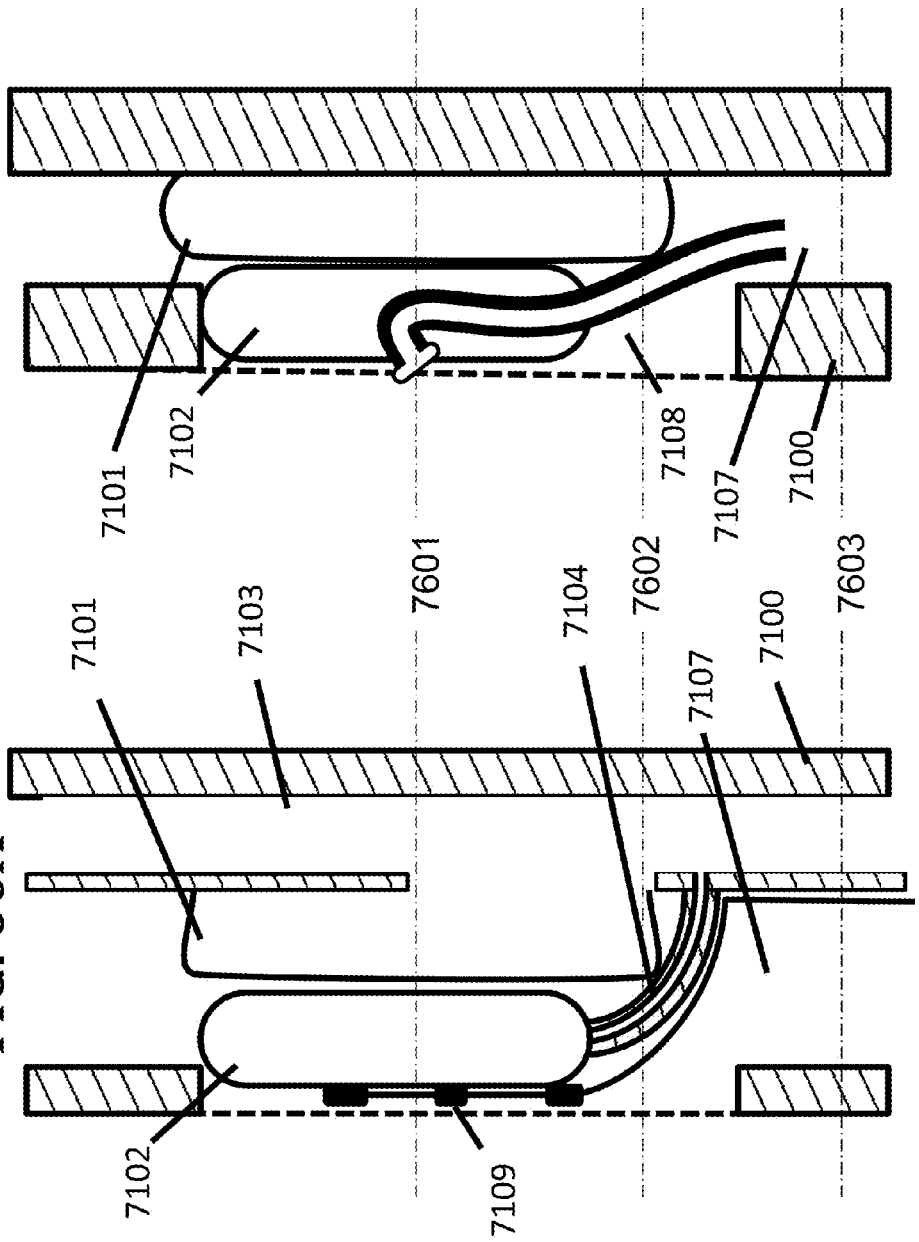

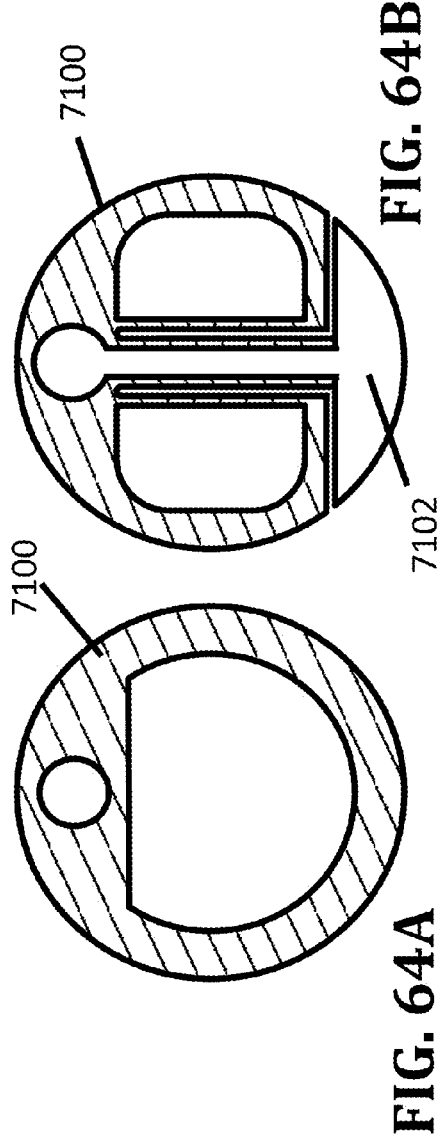
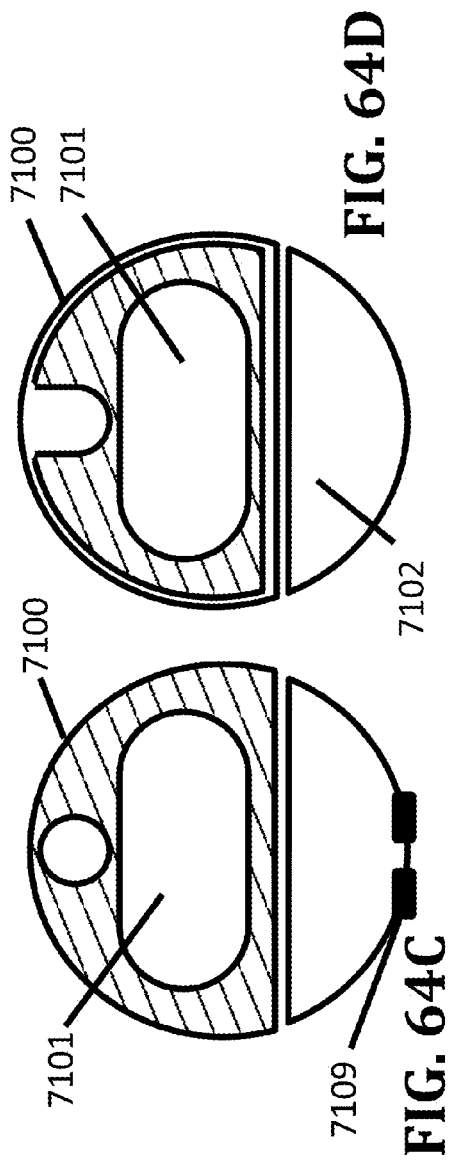

STIMULATION OF THE URINARY SYSTEM

CROSS-REFERENCES TO RELATED APPLICATIONS

The present application is a continuation-in-part of International Application PCT/IL2009/001163 to Bar-Yoseph, (published as WO 10/067360), filed on 9 Dec. 2009, which claims the benefit of:

U.S. provisional application Ser. No. 61/120,901, filed on 9 Dec. 2008,

U.S. provisional application Ser. No. 61/173,228, filed on 28 Apr. 2009,

U.S. provisional application Ser. No. 61/180,957, filed on 26 May 2009,

U.S. provisional application Ser. No. 61/218,139, filed on 18 Jun. 2009,

U.S. provisional application Ser. No. 61/225,226, filed on 14 Jul. 2009, and

U.S. provisional application Ser. No. 61/233,500, filed on 13 Aug. 2009; and the present application claims the benefit of U.S. provisional application Ser. No. 61/355,522 to Bar-Yoseph, filed on Jun. 16, 2010.

The contents of all of the above-mentioned references are incorporated by reference as if fully set forth herein.

FIELD OF THE INVENTION

Some embodiments of the present invention relate to control of human physiology and, more particularly, but not exclusively, to devices and methods of controlling human physiology, such as kidney or cardiovascular function, by stimulation of the urinary system.

BACKGROUND

Typical Anatomy of the Upper Urinary System

The kidneys are organs that have numerous biological roles. Their primary role is to maintain the homeostatic balance of bodily fluids by filtering and secreting metabolites and minerals from the blood and excreting them, along with water, as urine. The ureters are muscular ducts that propel urine from the kidneys to the urinary bladder. In the adult, the ureters are usually 25-30 cm (10-12 inches) long.

The upper urinary system receives autonomic (mostly sympathetic) innervation, by the efferent nervous system. The sensory information is conveyed to the central nervous system (CNS) via the afferent nervous systems. The two systems have different regional distribution; the efferent sympathetic innervation reaches all the segments of the renal vasculature and to a much lesser extent the tubular nephron. The afferent sensory fibers are localized and predominate in the renal pelvis and ureter. The corticomedullary connective tissue contains both types of innervation with a more prominent afferent innervation.

Congestive Heart Failure

Congestive heart failure (CHF) is a very common disorder, affecting 6 million Americans and more than 22 million worldwide. CHF is a disease of the old; it is the leading hospital discharge diagnosis in individuals aged 65 years or older. CHF is the number one reason for hospitalization in people 65 years or older in the United States, accounting for approximately 1 million hospitalizations annually. The cost of hospitalizations for CHF is twice that for all forms of cancer and myocardial infarction combined. Treatment of heart failure costs an estimated $40 billion per year in the United States and nearly $80 billion worldwide.

The Cardio-Renal Syndrome

Renal impairment is an independent and significant predictor of morbidity and mortality in CHF patients. Mortality increases incrementally across the range of renal function, with 7% increased risk for every 10-mL/min decrease in glomerular filtration rate (GFR). CHF triggers kidney dysfunction by a pathological process dubbed the cardio-renal syndrome. The cardio-renal syndrome can be acute, characterized by a rapid decrease in cardiac output together with worsening renal function or chronic, in which gradual worsening of heart and/or kidney function develops over months.

The cardio-renal syndrome is a common condition; in the US, more than 500,000 patients are admitted to hospital every year with acute heart failure, and up 80% of these patients suffer from deteriorating renal functions. High renal sympathetic activity constitutes an important link between CHF and renal dysfunction. Signals of shock and hypoperfusion, present in CHF patients, activate a number of compensation systems to increase the blood pressure and prevent fluid losses. Of these, the renal sympathetic system is one of the most important ones; it effectively reduces renal blood flow and kidney functions, including sodium and water excretion to urine. In addition it activates the renin-angiotensin-aldosterone axis and therefore leads to hypertension, fluid retention and kidney dysfunction. It is now known that increased renal sympathetic drive is an independent factor in terms of progressive deterioration of renal function and adverse outcome in CHF patients as was shown by (Petersson et al., 2005).

The Current Treatment of CHF and the Cardio-Renal Syndrome

As of now, CHF is a progressive, incurable disease. Surgical treatment options are few and are reserved for end-stage patients.

In patients with CHF and volume overload, initial therapy focuses on salt and water restriction and diuretics. Diuretics improve symptoms and quality of life but do not necessarily prolong life. When patients experience persistent pulmonary congestion despite adequate diuretic treatment, they are defined as diuretic resistant. It is unadvised to increase the dose of the diuretic as the potential negative side effects outweigh the possible benefit of fluid removal. One of the most serious side effects of diuretic administration is activation of the renin-angiotensin-aldosterone axis and the sympathetic nervous system that leads to vasoconstriction and hypoperfusion.

Angiotensin-converting enzyme inhibitors (ACEI) and beta blockers are prescribed to most patients for control of hypertension and to reduce cardiac remodeling. Although ACEI and adrenergic blockers are extensively used in these patients, these agents work on a systemic level. As such they cannot be used in an adequate dosage to selectively inhibit the pathological sympathetic renal drive.

Hypertension

Hypertension is one of the most common worldwide diseases afflicting humans. In the US, forty-three million people are estimated to have hypertension, the age-adjusted prevalence of hypertension varying from 18-32%. Because of the associated morbidity and mortality and the cost to society, hypertension is an important public health challenge; hypertension is the most important modifiable risk factor for coronary heart disease (which is the leading cause of death in North America), stroke (the third leading cause), congestive heart failure, end-stage renal disease, and peripheral vascular disease.

Abnormal renal excretory function is one of the most important mechanisms of the initiation and progression of hypertension. Variations of arterial pressure signals the kidney to alter urinary sodium and water excretion. On the long term, maintenance of sodium and water balance by the kidneys is believed to be primary in the long-term control of arterial pressure. Thus, factors that decrease renal excretory function lead to an increase in arterial pressure, which is required to reestablish and maintain sodium and water balance.

The dramatic positive effect of renal denervation on the development of hypertension is evident in a wide variety of animal models in multiple species, suggesting that increased renal nerve activity may be a final common pathway for the defect in renal sodium excretory ability required for the development and maintenance of hypertension.

Chronic Kidney Disease

Chronic kidney disease (CKD) is a major cause of morbidity and mortality, particularly at the later stages. More than 400,000 patients (US) are on dialysis per year at an annual cost up to $67,000 for each patient. The 5-year survival rate for a patient undergoing chronic dialysis in the United States is approximately 35%. The most common cause of death in the dialysis population is cardiovascular disease.

A large body of evidence indicates the presence of functional abnormalities of the sympathetic nervous system in uremic animals and humans. In patients with bilateral nephrectomy, the rate of sympathetic discharge was lower than in patients with their native kidneys, and this increased rate was accompanied by lower mean arterial pressure and regional vascular resistance.

Sympathetic activation contributes to progressive kidney damage by elevation of blood pressure and by promoting atherosclerosis. Increased sympathetic activity, progressive atherosclerosis and elevated blood pressure contribute to the development of cardiac remodeling and functional alterations. These conditions are highly prevalent in patients with CKD.

Current treatment aims for CKD are to halt the progression of the renal damage by controlling the underlying condition that triggers the damage, i.e. hypertension and diabetes. Prescription of ACEI in such patients should take into account the potential influence of renal impairment on ACEI metabolism, and adverse effects on the renal function itself (especially hypotension and acute reductions in glomerular filtration rate which if untreated can escalate to acute renal failure).

Drugs that act on the sympathetic overactivity, such as alpha and beta adrenergic blockers are second or third line of treatment. These agents have significant side effects; alpha blockers were recently shown to increase the risk for stroke in patients with essential hypertension. Beta blockers are associated with intradyalitic hypotension.

As GFR decreases, diuretics are increasingly required for excretion of the daily water load. However, for a number of reasons diuretics become relatively ineffective in patients with a moderate to severe degree of chronic kidney disease (creatinine clearance below approximately 35 ml·min-1). Diuretics can lead to further rise in the serum creatinine and blood urea nitrogen concentrations and a high incidence of hypokalemia and electrolyte disorders. Furthermore, net losses of sodium and fluid during regular diuretic administration are limited by postdiuretic renal sodium and fluid retention. Because of these complications, diuretic use in the final stages of chronic kidney disease, although desirable theoretically to maintain body water balance is impractical because of the severe side effects Acute Renal Failure Causes of acute renal failure (ARF) can be broadly divided into three clinical categories: a) Prerenal, which is an adaptive response to severe volume depletion b) renal (or intrinsic), in response to kidney insult, including contrast material and c) postrenal.

Prerenal ARF is the most common cause of ARF. It often leads to intrinsic ARF if it is not promptly corrected. Acute reduction of renal blood flow (RBF), either because of blood loss or hypotension can result in this syndrome. The hallmark of intrinsic ARF and the most common form is acute tubular injury (ATN). Prerenal ARF and ATN occur on a continuum of the same pathophysiological process and together account for 75% of the cases of ARF.

It cannot be overstated that the current treatment of ARF is mainly supportive in nature and no therapeutic modalities to date have shown efficacy in treating the condition. Indications of immediate dialysis treatment include hyperkalemia not responsive to conventional treatment, pulmonary edema, and uremia.

Mortality rate estimates in ARF patients vary from 25-90%. The in-hospital mortality rate is 40-50%; in intensive care settings, the rate is 70-80%. The mortality in patients requiring dialysis is about 50%. Mortality rates have changed little over the last two decades, reflecting the fact that there is no adequate treatment for this condition.

The following patents and publication may relate to stimulation of the urinary system. Their disclosures are incorporated herein by reference. Some embodiments of the invention use apparatus described therein and/or processes and/or physiological effects described therein, with the appropriate changes, and/or in combination with methods and/or apparatus described herein, to provide functionality in accordance with some embodiments of the invention.

U.S. Patent Application Publications:

2005/0228459, 2005/0228460, 2005/0234523, 2005/0288730, 2006/0025821, 2006/0041277, 2006/0116720, 2006/0142801, 2006/0206150, 2006/0212076, 2006/0212078, 2006/0235474, 2006/0265014, 2006/0265015, 2006/0271111, 2006/0276852, 2007/0066957, 2007/0083239, 2007/0112327, 2007/0129760, 2007/0129761, 2007/0135875, 2007/0173899, 2007/0203549, 2007/0208382, 2007/0265687, 2007/0282184, 2008/0119907, 2008/0213331, 2008/0255642, 2009/0024195, 2009/0036948, 2009/0062873, 2009/0076409 and 2009/0221939.

U.S. Patents:

U.S. Pat. Nos. 5,749,845, 6,425,877, 6,500,158, 6,692,490, 6,699,216, 6,743,197, 6,978,174, 7,162,303, 7,326,235, 7,617,005 and 7,620,451.

Non-U.S. Patents and Publications:

RU 2004103992/14, RU 2271840 C2, WO 97/44088 and WO 2004/075948.

Other Publications:

Bakunts SA, Muradian KM (1977) Effect of electric stimulation on ureteral function. Zh Eksp Klin Med 17:8-15.

Bencsath P, Szenasi G, Asztalos B, Takacs L (1985) Time course of denervation diuresis and natriuresis in the anaesthetized rat. Acta Physiol Hung 66:47-50.

Blair JE, Khan S, Konstam MA, Swedberg K, Zannad F, Burnett JC, Jr., Grinfeld L, Maggioni AP, Udelson JE, Zimmer CA, Ouyang J, Chen CF, Gheorghiade M (2009) Weight changes after hospitalization for worsening heart failure and subsequent re-hospitalization and mortality in the EVEREST trial. Eur Heart J 30:1666-1673.

Caterina MJ, Schumacher MA, Tominaga M, Rosen TA, Levine JD, Julius D (1997) The capsaicin receptor: a heat-activated ion channel in the pain pathway. Nature 389:816-824.

Chen SS, Chen WC, Hayakawa S, Li P C, Chien CT (2009) Acute urinary bladder distension triggers ICAM-1-mediated renal oxidative injury via the norepinephrine-renin-angiotensin II system in rats. J Formos Med Assoc 108:627-635.

Chien CT, Yu HJ, Cheng YJ, Wu MS, Chen CF, Hsu SM (2000) Reduction in renal haemodynamics by exaggerated vesicovascular reflex in rats with acute urinary retention. J Physiol 526 Pt 2:397-408.

Chuang YC, Fraser MO, Yu Y, Beckel JM, Seki S, Nakanishi Y, Yokoyama H, Chancellor MB, Yoshimura N, de Groat WC (2001) Analysis of the afferent limb of the vesicovascular reflex using neurotoxins, resiniferatoxin and capsaicin. Am J Physiol Regul Integr Comp Physiol 281:R1302-1310.

De Bock F, De Wachter S, Wyndaele JJ (2009) Can the use of different parameters and waveforms improve the results of intravesical electrical stimulation: a pilot study in the rat. Neurourol Urodyn 28:246-250.

Deng PY, Li YJ (2005) Calcitonin gene-related peptide and hypertension. Peptides 26:1676-1685.

Derzhavin VM, Vishnevskii EL, Dzheribal'di OA, Bruk SD, Vasil'ev AI (1989) Electric stimulation of the ureterovesical anastomosis in the treatment of hyperreflexia of the urinary bladder. Pediatriia: 53-57.

DiBona GF (2004) The sympathetic nervous system and hypertension: recent developments. Hypertension 43:147-150.

DiBona GF, Kopp UC (1997) Neural control of renal function. Physiol Rev 77:75-197.

DiBona GF, Sawin LL (1999) Renal hemodynamic effects of activation of specific renal sympathetic nerve fiber groups. Am J Physiol 276:R539-549.

Dwyer TM, Schmidt-Nielsen B (2003) The renal pelvis: machinery that concentrates urine in the papilla. News Physiol Sci 18:1-6.

Fagius J, Karhuvaara S (1989) Sympathetic activity and blood pressure increases with bladder distension in humans. Hypertension 14:511-517.

Gardiner SM, Compton AM, Kemp PA, Bennett T, Foulkes R, Hughes B (1991) Regional haemodynamic effects of prolonged infusions of human alpha-calcitonin gene-related peptide in conscious, Long Evans rats. Br J Pharmacol 103:1509-1514.

Gotloib L, Fudin R, Yakubovich M, Vienken J (2005) Peritoneal dialysis in refractory end-stage congestive heart failure: a challenge facing a no-win situation. Nephrol Dial Transplant 20 Suppl 7:vii32-36.

Jiang CH, Lindstrom S (1999) Prolonged enhancement of the micturition reflex in the cat by repetitive stimulation of bladder afferents. J Physiol 517 (Pt 2):599-605.

Kenton K, Simmons J, FitzGerald M P, Lowenstein L, Brubaker L (2007) Urethral and bladder current perception thresholds: normative data in women. J Urol 178:189-192; discussion 192.

Kolesnikow GP, Karpenko WS (1987) Development and assessment of an artificial pacemaker of the ureter with feedback. Z Urol Nephrol 80:25-29.

Kopp UC, Smith LA (1987) Renorenal reflex responses to renal sensory receptor stimulation in normotension and hypertension. Clin Exp Hypertens A 9 Suppl 1:113-125.

Kopp UC, Olson LA, DiBona GF (1984) Renorenal reflex responses to mechano- and chemoreceptor stimulation in the dog and rat. Am J Physiol 246:F67-77.

Kopp UC, Jones SY, DiBona GF (2008) Afferent renal denervation impairs baroreflex control of efferent renal sympathetic nerve activity. Am J Physiol Regul Integr Comp Physiol 295:R1882-1890.

Lang RJ, Davidson ME, Exintaris B (2002) Pyeloureteral motility and ureteral peristalsis: essential role of sensory nerves and endogenous prostaglandins. Exp Physiol 87:129-146.

Lazzeri M, Barbanti G, Beneforti P, Maggi CA, Taddei I, Andrea U, Cantini C, Castellani S, Turini D (1995) Vesicalrenal reflex: diuresis and natriuresis activated by intravesical capsaicin. Scand J Urol Nephrol 29:39-43.

Li J, Wang DH (2008) Increased GFR and renal excretory function by activation of TRPV1 in the isolated perfused kidney. Pharmacol Res 57:239-246.

Ma MC, Huang H S, Chen CF (2002) Impaired renal sensory responses after unilateral ureteral obstruction in the rat. J Am Soc Nephrol 13:1008-1016.

Ma MC, Huang H S, Chen YS, Lee SH (2008) Mechanosensitive N-methyl-D-aspartate receptors contribute to sensory activation in the rat renal pelvis. Hypertension 52:938-944.

Melick WF, Brodeur AE, Herbig F, Naryka JJ (1966) Use of a ureteral pacemaker in the treatment of ureteral reflux. J Urol 95:184-196.

Ming Z, Smyth DD, Lautt WW (2002) Decreases in portal flow trigger a hepatorenal reflex to inhibit renal sodium and water excretion in rats: role of adenosine. Hepatology 35:167-175.

Palla R, Parrini M, Panichi V, Andreini B, De Pietro S, Migliori M, Bianchi AM, Giovannini L, Bertelli A, Bertelli AA, et al. (1995) Acute effects of calcitonin gene related peptide on renal haemodynamics and renin and angiotensin II secretion in patients with renal disease. Int J Tissue React 17:43-49.

Petersson M, Friberg P, Eisenhofer G, Lambert G, Rundqvist B (2005) Long-term outcome in relation to renal sympathetic activity in patients with chronic heart failure. Eur Heart J 26:906-913.

Petkov P (1975) Electrostimulation of the ureter as a treatment method in ureteral calculi. Khirurgiia (Sofia) 28:292-294.

Polsky A, Mel B, Schiller J (2009) Encoding and decoding bursts by NMDA spikes in basal dendrites of layer 5 pyramidal neurons. J Neurosci 29:11891-11903.

Ronco C, Chionh CY, Haapio M, Anavekar NS, House A, Bellomo R (2009) The cardiorenal syndrome. Blood Purif 27:114-126.

Schlaich MP, Sobotka PA, Krum H, Whitbourn R, Walton A, Esler MD (2009) Renal Denervation as a Therapeutic Approach for Hypertension: Novel Implications for an Old Concept. Hypertension 54:1195-1201.

Schramm LP, Carlson DE (1975) Inhibition of renal vasoconstriction by elevated ureteral pressure. Am J Physiol 228:1126-1133.

Shekhar YC, Anand IS, Sarma R, Ferrari R, Wahi PL, Poole-Wilson PA (1991) Effects of prolonged infusion of human alpha calcitonin gene-related peptide on hemodynamics, renal blood flow Tsuchida S, Kumagai I (1978) Effect of urinary bladder distension on renal blood flow, blood pressure and plasma renin activity. Tohoku J Exp Med 126:335-341.

van Balken MR, Vergunst H, Bemelmans BL (2004) The use of electrical devices for the treatment of bladder dysfunction: a review of methods. J Urol 172:846-851.

Xie C, Sachs JR, Wang DH (2008) Interdependent regulation of afferent renal nerve activity and renal function: role of transient receptor potential vanilloid type 1, neurokinin 1, and calcitonin gene-related peptide receptors. J Pharmacol Exp Ther 325:751-757.

Zhu Y, Wang Y, Wang DH (2005) Diuresis and natriuresis caused by activation of VR1-positive sensory nerves in renal pelvis of rats. Hypertension 46:992-997.

Zhu Y, Xie C, Wang DH (2007) TRPV1-mediated diuresis and natriuresis induced by hypertonic saline perfusion of the renal pelvis. Am J Nephrol 27:530-537.

SUMMARY OF THE INVENTION

The present invention, in some embodiments of the invention relates to controlling kidney and/or body function by stimulation of the urinary system, particularly, but not only, using stimulation of urine transport systems and/or afferent nerves. In some embodiments of the invention, the stimulation is specific enough to modulate and/or control natural reflexes.

There is provided in accordance with an exemplary embodiment of the invention, a bladder stimulator, comprising:

an elongate element adapted to pass through a urethra or adapted to pass through another opening in the bladder;

an expandable body coupled to said elongate element at a coupling location; and an array of one or more stimulator contacts mechanically coupled to said expandable body, wherein said array includes at least one contact adapted to contact and selectively stimulate a trigone or a distal part of a ureter when said expandable body is inserted in a bladder and expanded.

In an exemplary embodiment of the invention, said expandable body comprises at least one arm carrying a contact and adapted to extend away from said element. Optionally or alternatively, said array is configured with so that when it is anchored in place, said contact is in good contact with said trigone or distal ureter part. Optionally or alternatively, said expandable body comprises a balloon and wherein said coupling location is configured to lie at an exit from the bladder to the urethra.

In an exemplary embodiment of the invention, said elongate element comprises a tube adapted to allow urine flow therethrough and is configured to substantially evacuate a bladder via an opening to a lumen of said tube, which opening is located at an expected location of a urethral entrance to the bladder.

In an exemplary embodiment of the invention, said expandable body is asymmetric in a manner that prevents rotation around said elongate body when inserted in a bladder.

In an exemplary embodiment of the invention, said elongate body is selectively bendable when inserted.

In an exemplary embodiment of the invention, said array covers less than one hemisphere of said expandable body.

In an exemplary embodiment of the invention, said array includes fewer than 10 stimulator contacts.

In an exemplary embodiment of the invention, said array is sized so as to be able to stimulate two UVJs (ureter-vesico junctions) of a bladder, distanced between 2 and 5 cm from each other. Optionally, said array includes at least one contact for each ureter.

In an exemplary embodiment of the invention, said contacts are electrical contacts. Optionally or alternatively, said contacts are expandable with said expandable body.

In an exemplary embodiment of the invention, the stimulator comprises at least one lead extending along said element and adapted to extend out of a body in which said catheter is inserted.

In an exemplary embodiment of the invention, the stimulator comprises an integrated pulse generator for applying a pulse sequence to at least one of said contacts.

In an exemplary embodiment of the invention, at least one of said contacts is a thermal stimulator contact.

In an exemplary embodiment of the invention, the stimulator comprises at least one RF generator.

In an exemplary embodiment of the invention, at least one of said contacts is a chemical stimulator contact.

In an exemplary embodiment of the invention, said expandable body defines at least one channel for urine flow one or more of therethrough, underneath and thereby.

In an exemplary embodiment of the invention, said stimulator is concave at a point matching a location of an enlarged prostate.

In an exemplary embodiment of the invention, said elongate element is soft enough and flexible enough to not interfere with a mobility of a patient when inserted in a urethra thereof.

In an exemplary embodiment of the invention, the stimulator comprises at least one additional contact positioned and shaped to stimulate a non-trigone portion of the bladder.

In an exemplary embodiment of the invention, the stimulator comprises a controller which stimulates said stimulator contact with a sequence suitable for controlling one or more of a reno-renal reflex, a vesico-vascular reflex, a cardiovascular function and a kidney function. Optionally, said controller includes a single manual control for adjusting an intensity of effect of said stimulation. Optionally or alternatively, said controller includes a feedback circuit to control said stimulation, said feedback including one or both of feedback of a physiological effect of said stimulation and feedback on a quality of contact between said stimulator contact and said trigone.

There is provided in accordance with an exemplary embodiment of the invention, apparatus for stimulating the urinary system, comprising:

(a) a housing suitable for long term implantation of over 2 weeks;

(b) at least one stimulator coupled to said housing and adapted to stimulate a part of the urinary system which contains urine or an afferent nerve; and (c) a controller within said housing configured to stimulate said at least one stimulator with a stimulation sequence suitable to modify a physiological functioning of a tissue that is not directly stimulated. Optionally, said stimulator is configured to be in contact with urine. Optionally or alternatively, said stimulator is configured to stimulate an afferent nerve.

In an exemplary embodiment of the invention, said stimulator is configured to stimulate a part of the urinary system which contains urine.

In an exemplary embodiment of the invention, said stimulator is configured with a stimulation sequence which affects a kidney function even when not applied directly to a nephron. Optionally or alternatively, said stimulator is configured with a stimulation sequence which affects a cardio-vascular function when applied to a urinary system. Optionally or alternatively, said stimulator is configured with a stimulation sequence which affects or modulates a renal reflex. Optionally, said reflex is one or both of a reno-renal reflex and a vesico-vascular reflex.

In an exemplary embodiment of the invention, said stimulator is configured with a stimulation sequence suitable to affect the release of a hormone.

In an exemplary embodiment of the invention, said stimulator is configured with a stimulation sequence suitable to modify the sensitivity of a sensory receptor or a nerve pathway thereof.

In an exemplary embodiment of the invention, said stimulator is configured with a stimulation sequence suitable to have a therapeutic effect of ongoing change in physiological activity which lasts at least 30 minutes after the sequence is stopped.

In an exemplary embodiment of the invention, said stimulator comprises a chemical stimulator. Optionally, the apparatus comprises a chemical reservoir for elution by said stimulator.

In an exemplary embodiment of the invention, said stimulator comprises an electrical stimulator. Optionally, said stimulator includes a contact adapted to lie on an outside of a ureter. Optionally or alternatively, said stimulator includes a contact adapted to selectively electrically stimulate a trigone of a bladder. Optionally or alternatively, the apparatus comprises at least one insulation portion positioned to reduce electrical leaks away of said stimulated part. Optionally or alternatively, the apparatus comprises at least one circuit configured to ensure a quality of contact between said stimulator and tissue. Optionally or alternatively, said stimulator includes an elongate body adapted to lie within a ureter. Optionally or alternatively, said stimulator is configured not to interfere mechanically with peristalsis or mobility of a ureter to which it applies stimulation.

In an exemplary embodiment of the invention, the apparatus comprises at least one input for an input signal and wherein said control modifies said electrical stimulation in response to said input signal. Optionally, said controller has stored therein at least one target value for said input signal and wherein said modifying comprises modifying in a manner which approaches said target value. Optionally or alternatively, input signal is an input of an indication of a physiological parameter. Optionally or alternatively, the apparatus comprises a separate sensor which provides said input signal. Optionally or alternatively, the apparatus comprises a physiological sensor which provides said input signal.

In an exemplary embodiment of the invention, said stimulation sequence is set at an amplitude below a pain level.

In an exemplary embodiment of the invention, said stimulation sequence includes pauses of at least 1 hour and less than 10 hours.

In an exemplary embodiment of the invention, said functioning is selected from a group comprising: renal blood flow, GFR, diuresis, natriuresis, renal hormone secretion, blood pressure, vascular resistance, cardiac output, dyspnea level, body fluid balance and urine and plasma composition.

In an exemplary embodiment of the invention, said apparatus is functionally coupled to a stimulator which a portion of the body other than a urinary system.

In an exemplary embodiment of the invention, said stimulator is adapted to screw into bladder tissue.

In an exemplary embodiment of the invention, said stimulator is adapted to mount on the outside of a ureter.

There is provided in accordance with an exemplary embodiment of the invention, apparatus for stimulating the urinary system, comprising:

(a) at least one stimulator adapted to stimulate a part of the urinary system;
(b) at least one input circuit configured to receive an input indication indicating one or more of a kidney function and a cardio-vascular function; and
(c) a controller configured to stimulate said at least one stimulator with a stimulation sequence suitable to modify a function of one or both of a kidney and a cardio-vascular system and also configured to receive an indication of said input indication from said at least one input circuit and modify said stimulation in response thereto. Optionally, said input comprises an outside input of a physiological parameter of a patient. Optionally, said input used by said controller comprises one or more of an on/off command, a weight, a laboratory result and a feeling.

In an exemplary embodiment of the invention, said input comprises a physiological sensor.

In an exemplary embodiment of the invention, said stimulator comprises an electrical stimulator.

In an exemplary embodiment of the invention, said indication is an indication of one or more of a urinary tract function, a vascular function, a cardio-vascular function and a chemical property of the body.

In an exemplary embodiment of the invention, said input circuitry comprises a sensor comprising is one or more of an electrical sensor, an impedance sensor, a flow sensor, a pH sensor, an ion sensor, a pressure sensor, a heart rate sensor, a blood pressure sensor, a sensor of peristalsis, a sensor of nerve activity, a urinary system pressure sensor and/or a thermal sensor.

In an exemplary embodiment of the invention, said controller activates said sequence over a period of treatment of at least 1 hour between input indications.

In an exemplary embodiment of the invention, said controller activates said sequence over a period of treatment of less than 5 minutes between input indications.

In an exemplary embodiment of the invention, said controller activates said sequence intermittently. Alternatively, said controller activates said sequence continuously.

In an exemplary embodiment of the invention, said sequence is applied with rest periods of at least 20 minutes between applications of stimulation sequences.

In an exemplary embodiment of the invention, said sequence is applied with rest periods of at least 60 minutes and less than 12 hours between applications.

In an exemplary embodiment of the invention, said controller spends at least 80% of the time waiting for said input indication in order to determine a next stimulation. In an exemplary embodiment of the invention, said sequence is less than 20 minutes long.

In an exemplary embodiment of the invention, said sequence is configured at a stimulation amplitude, shape and frequencies which avoid pain and/or which avoid discomfort.

In an exemplary embodiment of the invention, said controller includes a memory having stored therein a table or a software linking desired effects and stimulation sequences which achieved such effects.

In an exemplary embodiment of the invention, said stimulation is neurostimulation suitable to modulate a reflex that modifies renal function.

In an exemplary embodiment of the invention, said stimulation is suitable to modulate a reflex that modifies a cardio-vascular function. Optionally or alternatively, said reflex is a reno-renal reflex or a vesico-vascular reflex.

In an exemplary embodiment of the invention, said controller is programmed to apply therapy for one or more of congestive heart failure (CHF), chronic kidney disease (CKD), acute renal failure (ARF), hypertension, contrast nephropathy, hepatorenal syndrome and cardio-renal syndrome.

In an exemplary embodiment of the invention, the apparatus comprises at least an additional stimulator configured for control by said controller for additional and different stimulation of the body and wherein said controller is programmed with at least one stimulation protocol directed at providing an effect utilizing said stimulation and said additional stimulation. Optionally, said additional stimulation interacts with an effect of said stimulation. Optionally or alternatively, said apparatus controls both a kidney function and a peristaltic pattern in the urinary system.

In an exemplary embodiment of the invention, said apparatus controls both a kidney function and a cardiovascular system parameter.

In an exemplary embodiment of the invention, said at least one stimulator is adapted to mount on one or more of an outside of the urinary system, a ureter, a nerve of the urinary system and a bladder and is selected from a group comprising a stimulator adapted to mount inside the urinary system; a stimulator which forms a part of a ureteral catheter, a stimulator which forms a part of a urethral catheter; a stimulator which forms a part of kidney piercing element; a stimulator which is sized, shaped and adapted to dwell inside a bladder; a stimulator including a controller which is encased in an implantable housing; a stimulator including a controller which is configured for remaining outside a body.

In an exemplary embodiment of the invention, the apparatus comprises a tissue ablation setting.

There is provided in accordance with an exemplary embodiment of the invention, apparatus for stimulating the urinary system, comprising:
(a) at least one elongate element configured to lie within the ureter, allowing free urine flow within the ureter and configured to not interfere with operation of ureter valves; and
(b) at least one stimulator element mechanically coupled to said elongate element; and
(c) a controller configured to stimulate said at least one stimulator element with a stimulation sequence suitable to modify a function of at least one kidney or a cardiovascular system. Optionally, said stimulator element comprises an electrical contact. Optionally, said stimulator element comprises an expandable element. Optionally, said stimulator element is configured to expand past a resting diameter of a ureter.

In an exemplary embodiment of the invention, said stimulator element comprises one or more of a mechanical stimulator; a chemical stimulator and a thermal stimulator. Optionally or alternatively, said element is thin enough and soft enough to not interfere with operation of ureter valves.

In an exemplary embodiment of the invention, said stimulator contact is in the form of a tubular element of at least 3 mm in length mounted on an elongate element of at least 20 cm in length, which apparatus lodges in a ureter or renal pelvis.

In an exemplary embodiment of the invention, said stimulator contact is in the form of a conical element that lodges in a renal pelvis.

In an exemplary embodiment of the invention, said elongate element is adapted for an insertion via a nephrostomic route.

There is provided in accordance with an exemplary embodiment of the invention, apparatus for stimulating the urinary system, comprising:
(a) at least one non-electrical stimulator adapted to stimulate a part of the urinary system; and
(b) a controller configured to activate said at least one non-electrode stimulator in a manner suitable to affect an activity of said urinary system. Optionally, said controller modifies said activation in response to feedback.

There is provided in accordance with an exemplary embodiment of the invention, a stimulator adapted for urinary tract stimulation, comprising:
(a) an elongate body adapted to fit along the inside of a ureter from a bladder to a kidney;
(b) a widening section at a distal end of said body, said widening section including at least one electrical contact.

There is provided in accordance with an exemplary embodiment of the invention, a stimulator adapted for urinary tract stimulation, comprising:
(a) a coupling adapted to mount on the outside of a cylindrical body;
(b) a stimulator contact mounted on said coupling and adapted to stimulate a portion of the urinary system. Optionally, said coupling is configured to maintain a contact of said stimulator contact with said cylindrical body over radial expansion of said body. Optionally or alternatively, said coupling is configured to allow axial deformation of said cylindrical body.

There is provided in accordance with an exemplary embodiment of the invention, a stimulator adapted for urinary tract stimulation, comprising:
(a) an elongate body adapted to fit along the inside of a ureter from a bladder to at least 10 cm;
(b) a widening section formed on said body, said widening section including at least one electrical contact and said widening section configured to widen to at least a diameter of a ureter while allowing urine flow therepast. Optionally, said widening section includes an inflatable section.

There is provided in accordance with an exemplary embodiment of the invention, a stimulator adapted for urinary tract stimulation, comprising:
(a) an elongate body adapted to pass through body tissue from a skin to a kidney;
(b) at least one electrical contact formed at a distal part of said body, wherein said distal part is configured to anchor in a kidney pelvis.

There is provided in accordance with an exemplary embodiment of the invention, apparatus for stimulating the urinary system, comprising:
(a) at least one stimulator adapted to stimulate a part of the urinary system;
(b) at least one accelerometer; and
(c) a controller configured to stimulate said at least one stimulator responsive to an input signal from said accelerometer.

There is provided in accordance with an exemplary embodiment of the invention, a method of controlling a physiological state, comprising:
(a) determining that it is desired to affect a functioning of a kidney or other body system in a certain manner; and
(b) stimulating a urine carrying portion of the urinary system or an afferent nerve thereof in a manner which causes said effect on said functioning of said kidney or other body system.

In an exemplary embodiment of the invention, determining comprises determining a desired effect on a cardio-vascular system via an effect on a kidney function. Optionally or alternatively, determining comprises determining a desired direct effect on a cardio-vascular system, not via an effect on a kidney function. Optionally or alternatively, stimulating modulates the gain of the sympathetic drive to the kidney. Optionally or alternatively, said stimulating comprises exciting an afferent nerve innervating the urinary system. Optionally or alternatively, said stimulating comprises inhibiting an afferent nerve innervating the urinary system. Optionally or alternatively, said stimulating comprises affecting said kidney or other body system via the modulation or triggering of at least one a nervous reflex. Optionally, said reflex comprises one or both of a reno-renal reflex and a vesico-vascular reflex.

In an exemplary embodiment of the invention, said stimulating comprises affecting said kidney or other body system by providing at least two competing effects on said kidney or body system.

In an exemplary embodiment of the invention, said stimulating comprises affecting said kidney or said other body system via a hormonal effect. Optionally or alternatively, said stimulating comprises stimulating to have an effect on said functioning for at least twice the length of stimulation after said stimulating is completed. Optionally or alternatively, the method comprises also providing a systemic medication which interacts with said stimulating.

In an exemplary embodiment of the invention, said stimulating comprises stimulating in a manner which affects said kidney or said other body system for at least 30 minutes after stimulation is stopped. Optionally or alternatively, said stimulating comprises stimulating in a manner which affects a cardio-vascular system for at least 30 minutes after stimulation is stopped. Optionally or alternatively, said stimulating causes an increase in one or more of glomerular filtration rate, renal blood flow, diuresis and natriuresis by at least a factor of 1.1. Optionally, said factor is at least a factor of 2.

In an exemplary embodiment of the invention, said stimulating comprises stimulating one or more of a ureter, a kidney pelvis, a trigone and a bladder. Optionally or alternatively, said stimulating modulates ureteral or pyeloureteral peristalsis. Optionally or alternatively, said stimulating modulates pressure within the urinary system. Optionally or alternatively, said stimulating comprises inserting a stimulator through the skin to a stimulation target. Optionally or alternatively, said stimulating comprises implanting a stimulator. Optionally or alternatively, said stimulating comprises inserting a stimulator via a urethra. Optionally or alternatively, said stimulating comprises stimulating via a stimulator that remains in said body for at least two weeks. Optionally or alternatively, said stimulating comprises stimulating via a stimulator that remains in said body for less than 2 months. Optionally or alternatively, said stimulating comprises stimulating as part of a treatment for one or more of acute heart failure, congestive heart failure, hypertension, acute renal failure, chronic renal failure, hepato-renal syndrome, nephrotic syndrome, cardio-renal syndrome and myocardial infarct. Optionally or alternatively, said stimulating comprises stimulating for at least 2 hours a day. Optionally or alternatively, said stimulating comprises stimulating for less than 8 hours a day. Optionally or alternatively, said stimulating comprises stimulating using a same catheter as used for measuring urine flow.

In an exemplary embodiment of the invention, said stimulating comprises ablating a portion of said urinary system in response to a measured effect of said stimulating.

In an exemplary embodiment of the invention, said stimulating comprises minimally-invasively implanting a stimulator in contact with the urinary system.

There is provided in accordance with an exemplary embodiment of the invention, a method of urinary system control, comprising:
(a) applying a first stimulation having an effect on a kidney function or a cardiovascular system; and
(b) applying a second stimulation to the urinary system which interacts with said first stimulation. Optionally, said first stimulation is a systemic stimulation. Optionally or alternatively, said first stimulation is a provision of a medication.

There is provided in accordance with an exemplary embodiment of the invention, a method of urinary system control, comprising stimulating a ureter or a renal pelvis to modulate peristalsis therein for a period of at least 1 hour to above normal peristalsis.

Optionally, said stimulation comprises electrical stimulation to overpace peristaltic waves in said ureter. Optionally or alternatively, the method comprises collecting and measuring urine flow during said stimulation and modifying said stimulation in view of a result of said measurement.

There is provided in accordance with an exemplary embodiment of the invention, a method of diagnosing a patient, comprising:
(a) stimulating a urinary tract of the patient;
(b) measuring a response of kidney function of cardiovascular function to said stimulation; and
(c) diagnosing a pathology or physiological parameter in said patient based on a result of said measurement. In an exemplary embodiment of the invention, said pathology or physiological parameter is selected from one or more of: receptor sensitivity, reflex damage, a kidney function, a cardio-vascular function, a urinary system function, blood analysis and kidney function availability. Optionally or alternatively, said pathology or physiological parameter comprises determining a need for stimulation and further comprising providing a therapy over a period of at least two weeks in response to said diagnosis.

There is provided in accordance with an exemplary embodiment of the invention, an integrated urinary system stimulator adapted for stimulation of the bladder comprising a body having at least one stimulation contact formed thereon, a lead long enough to exit the body and an integrated control circuitry with a power source. Optionally, the system is less than 50 cm long and said lead is adapted to path through a urethra and allow urine flow. Optionally or alternatively, the system is configured to be disposable after a single use. Optionally or alternatively, the system includes only a single control, for setting a stimulation power. Optionally or alternatively, the system is configured to apply a stimulation to a trigone area of the bladder, with a signal suitable for activating a reno-renal reflex.

There is provided in accordance with an exemplary embodiment of the invention, a urinary system stimulation system including a control circuitry, at least one lead extending from the control circuitry and adapted to attach to a bladder or a urethra, wherein the circuitry is set to activate one or both of a reno-renal reflex and a vesico-vascular reflex. Optionally, the control circuitry is adapted to close a feedback loop using an input and maintain a value related to one or both of kidney function and cardiovascular function within a desired range. Optionally or alternatively, the leads are configured to not interfere with motion of the ureter. Optionally or alternatively, the system is configured for operation of at least one year.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

There is therefore provided, in accordance with some applications of the present invention, apparatus including:
a bladder stimulator that includes:
an elongate element adapted to pass through a urethra or adapted to pass through another opening in the bladder;
an expandable body coupled to said elongate element;
an array of one or more stimulator contacts coupled to said expandable body, said array including at least one contact adapted to contact a portion of a bladder of a subject when said expandable body is inserted in the bladder and expanded; and
a controller configured to stimulate the portion of the bladder by driving a pulse into the bladder via the contact, the pulse having a frequency of 5 Hz-1 kHz.

For some applications, the controller is configured to drive the pulse, the pulse having an energy of between 0.00001 Joule and 0.1 Joule.

For some applications, the at least one contact is configured to contact a portion of the bladder selected from the group consisting of: a trigone, a ureter, a uretero-vesical junction, and a distal portion of a ureter, and the controller is configured to stimulate the selected portion of the bladder.

For some applications, the stimulator is configured to remain in a subject's body for three days to two weeks.

For some applications, the stimulator is configured to be implanted in a subject's body for at least two weeks.

For some applications, the controller is configured to stimulate the portion of the bladder for at least two hours a day.

For some applications, the controller is configured to stimulate an afferent nerve by driving the pulse.

For some applications, the controller is configured to modify the sensitivity of a sensory receptor or a nerve pathway thereof by driving the pulse.

For some applications, by driving the pulse, the controller is configured to modify a physiological functioning of a tissue that is not directly stimulated by the controller, said functioning being selected from the group consisting of: renal blood flow, GFR, diuresis, and blood pressure.

For some applications, the controller is configured to drive the pulse using parameters that are such as to avoid causing pain to the subject.

For some applications, said elongate element includes a tube that defines a lumen and an opening to the lumen, and that is adapted to allow urine flow therethrough and is configured to substantially evacuate a bladder via the opening to the lumen of the tube.

For some applications, said array covers one hemisphere or less of said expandable body, and said array includes fewer than 10 stimulator contacts.

For some applications, said contact is expandable with said expandable body.

For some applications, said contact includes conducting silicone.

For some applications, the stimulator is configured to measure urine flow through the elongate element.

For some applications, the controller is configured to drive the pulse with a sequence suitable for controlling a function selected from the group consisting of: a reflex, a cardiovascular function and a kidney function.

For some applications, the stimulator includes a single manual control for adjusting an intensity of effect of said stimulation.

For some applications, said elongate element is flexible.

For some applications, said elongate element is soft enough and flexible enough to not interfere with a mobility of a patient when inserted in a urethra thereof.

For some applications, said stimulator is configured to facilitate placement of the contact in contact with the portion of the subject's bladder by being shaped to match a distortion of the bladder.

For some applications, said stimulator is concave at a point matching a location of an enlarged prostate.

For some applications, said stimulator includes a protecting element configured to prevent damage to a urethra by the contact during insertion of the contact through the urethra.

For some applications, said protecting element includes a covering sheath.

For some applications, the stimulator includes a feedback circuit to control said stimulation, said feedback including one or both of feedback of a physiological effect of said stimulation and feedback on a quality of contact between said stimulator contact and tissue of the subject.

For some applications, the feedback circuit includes one or more of an electrical sensor, a flow sensor and a pressure sensor.

There is further provided, in accordance with some applications of the present invention, apparatus including:
a bladder stimulator that includes:
a flexible elongate element adapted to pass through a urethra or adapted to pass through another opening in the bladder;
an expandable body coupled to said elongate element;
an array of one or more stimulator contacts coupled to said expandable body, said array including at least one contact adapted to contact a portion of a bladder of a subject when said expandable body is inserted in the bladder and expanded; and
a controller configured to stimulate the portion of the bladder by driving a pulse into the bladder via the contact,
the flexible elongate element defining a lumen and an opening to the lumen, and being adapted to allow urine flow therethrough and to substantially evacuate the subject's bladder via the opening to the lumen.

There is additionally provided, in accordance with some applications of the present invention, a method of controlling a physiological state of a subject, including:
(a) determining that it is desired to affect functioning of a system of the subject selected from the group consisting of: a renal system and a cardiovascular system; and (b) in response thereto, affecting the functioning of the selected system in the desired manner, by stimulating a urine carrying portion of a urinary system of the subject.

For some applications, said stimulating includes modulating a gain of a sympathetic drive to the kidney.

For some applications, said stimulating includes modulating activity of an afferent nerve innervating the urinary system.

For some applications, said stimulating includes affecting the functioning of the selected system by performing an action selected from the group consisting of: activating and modulating, with respect to at least one nervous reflex.

For some applications, the method further includes administering systemic medication to the subject, the stimulating being configured to interact with the administration of the medication to the subject.

For some applications, said stimulating includes causing an increase by at least a factor of 1.1 in one or more parameters selected from the group consisting of: glomerular filtration rate, renal blood flow, diuresis, and natriuresis.

For some applications, said stimulating includes stimulating one or more portions of the subject's body selected from the group consisting of: a ureter, a trigone, a uretero-vesical junction, and a bladder.

For some applications, said stimulating includes stimulating via a stimulator that remains in the subject's body for three days to two weeks.

For some applications, said stimulating includes stimulating via a stimulator that is implanted in the subject's body for at least two weeks.

For some applications, said stimulating includes treating at least partially one or more conditions selected from the group consisting of: acute heart failure, congestive heart failure, hypertension, acute renal failure, contrast nephropathy, chronic renal failure, shock, septic shock, nephrotic syndrome, cardio-renal syndrome and myocardial infarct.

For some applications, said stimulating includes stimulating for at least 2 hours a day.

For some applications, said stimulating includes stimulating in such a manner that the functioning of the selected system is affected for at least 30 minutes after stimulation is stopped.

For some applications, the method further includes receiving an input during the stimulation, and modifying a parameter of the stimulation in response thereto.

For some applications, the method further includes determining a physiological parameter of the subject during the stimulation, and receiving the input includes receiving an input that is indicative of the physiological parameter of the subject.

For some applications, determining the physiological parameter includes determining urine flow of the subject during the stimulation, and modifying the parameter of the stimulation includes modifying the parameter of the stimulation in response to the determined urine flow.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings:

FIGS. 16A-F illustrate an intra-bladder stimulator with extending electrodes, in accordance with an exemplary embodiment of the invention;

FIGS. 17A-C illustrate an asymmetric intra-bladder stimulator with extending electrodes, in accordance with an exemplary embodiment of the invention;

FIGS. 18A-C illustrate an split-tip intra-bladder stimulator, in accordance with an exemplary embodiment of the invention;

FIGS. 20A-C illustrate an intra-bladder stimulator with side-extending electrodes, in accordance with an exemplary embodiment of the invention;

FIGS. 28A-28C3 illustrate designs for a stimulator including contacts and/or anchoring in the kidney pelvis in accordance with exemplary embodiments of the invention.

FIG. 29A illustrates an intra-luminal stimulator with medial electrical contacts, according to an exemplary embodiment of the invention;

FIGS. 29B1-29D2 illustrate medial contact designs in accordance with an exemplary embodiment of the invention;

FIGS. 30A-30D2 show exemplary intra-luminal stimulators having a thin body, in accordance with an exemplary embodiment of the invention;

FIG. 31A-E show intra-luminal stimulators having balloon-expandable electrical contacts, in accordance with exemplary embodiments of the invention.

FIGS. 32A-C illustrate a stimulator adapted for extraluminal mounting on a tubular physiological structure, optionally such as a ureter, in accordance with an exemplary embodiment of the invention;

FIG. 33B-C illustrate an extraluminal stimulator with cuff contacts, in accordance with an exemplary embodiment of the invention;

FIGS. 40A1-40B3 illustrate an exemplary nephrostomic stimulation device and cross-sections thereof, in accordance with an exemplary embodiment of the invention;

FIGS. 41A-B illustrate exemplary implantation locations for a nephrostomic stimulation device, according to an exemplary embodiment of the invention;

FIGS. 41C1-41C3 illustrate stimulator designs, according to an exemplary embodiment of the invention;

FIG. 42A illustrates an exemplary implantation location for a nephrostomic stimulation device, according to an exemplary embodiment of the invention;

FIGS. 42B-42C2 illustrate exemplary anchoring mechanisms for a nephrostomic stimulation device, according to an exemplary embodiment of the invention;

FIGS. 49A-B illustrate two examples of single kidney urine flow, as measured in a ureter catheter. In the left example, stimulation of the ureter for one minute sharply increased urine flow, the effect lasting after discontinuation of the stimulation. In the right example ureteral stimulation transiently increased urine flow, without the long term effect;

FIG. 50 illustrates the mean arterial pressure (MAP) measurement during electrical stimulation of the ureter. After an initial drop the MAP stabilizes to near the control values;

FIGS. 53A1-53B3 are a set of charts showing the effect of intra-bladder stimulation on urine flow, GFR and sodium excretion;

FIGS. 55A-B illustrate a double balloon bladder catheter with electrical contacts, in accordance with some applications of the present invention;

FIGS. 56A-B illustrate an inflated and deflated front view of a double balloon bladder catheter with an array of electrical contacts, in accordance with some applications of the present invention;

FIGS. 60A-B illustrate side views of the inflatable portion of the double balloon bladder catheter shown in FIG. 55, in accordance with some applications of the present invention;

FIGS. 64A-D illustrate cross-sectional views of the inflatable portion of the double balloon bladder catheter of FIG. 63, in accordance with some applications of the present invention;

DESCRIPTION OF EXEMPLARY EMBODIMENTS

Overview

Figure 1:
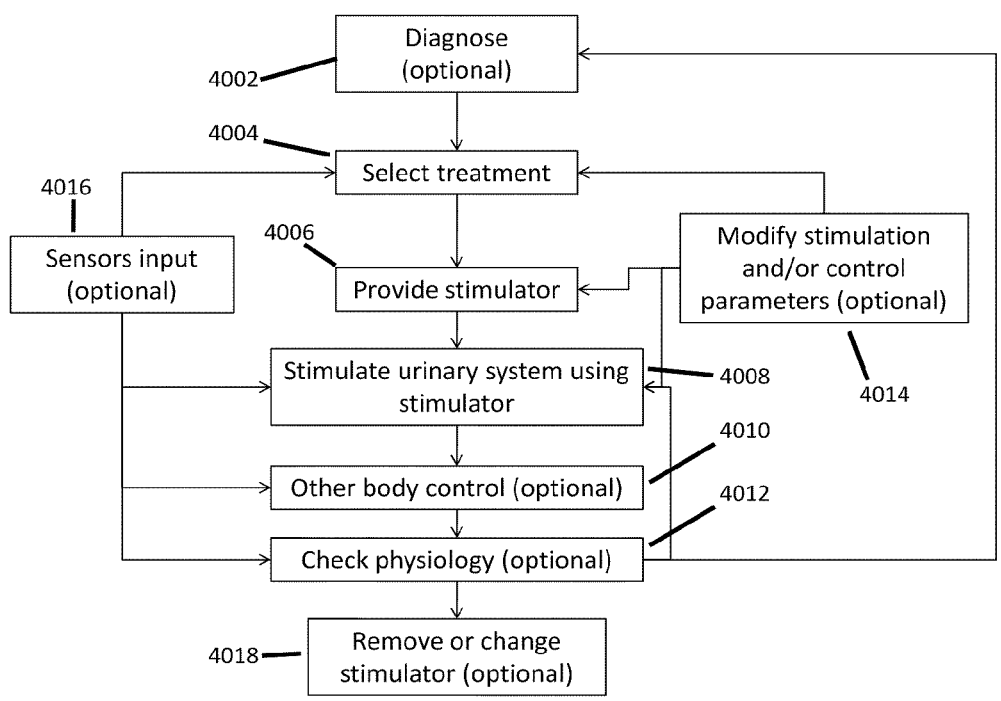
FIG. 1 is a flowchart of a method of controlling body physiology using stimulation of the urinary system, in accordance with an exemplary embodiment of the invention.

The present invention, in some embodiments thereof, relates to a method of controlling body functions using stimulation of the urinary system.

A broad aspect of some embodiments of the invention relates to controlling body functions by stimulating the urinary system. In an exemplary embodiment of the invention, the body functions are kidney functions such as glomerular filtration rate (GFR), urine flow rate, urine composition, urine density and renal hormone secretion. Optionally or alternatively, the body functions are cardiovascular functions, such as blood pressure, portal pressure, pulmonary pressure, organ (including renal) blood flow, cardiac output, heart rate, intravascular and extravascular fluid volume, pulmonary and body edema levels. Optionally or alternatively, the functions are bodywide systems such as blood chemistry or sympathetic nerve activity. In some embodiments, body functions are affected by modifying kidney function. In an exemplary embodiment of the invention, kidney function is modified by controlling a renal reflex, for example, the reno-renal reflex, or the vesico-vascular reflex. Optionally, kidney function is modified by changing a peristalsis (e.g., by overpacing, with sensing of self-pacing or at an enforced frequency) of one or both ureters, possibly such stimulation modulating a reno-renal reflex mediated by the ureter and/or by affecting urine pressure in the kidney. In an exemplary embodiment of the invention, the parts of the urinary system stimulated are parts which are adapted to carry urine, such as the kidney pelvis, the ureter and/or the bladder. Optionally, the stimulated part comprises afferent nerves which are affected by the stimulation. Optionally, stimulation in accordance with an exemplary embodiment of the invention is used, optionally with other treatment, such as medication or stimulation of other parts of the body, affect, for example, to control, to compensate, force, manage, modulate and/or stand-in for natural body feedback cycles; damaged and/or healthy such cycles. Optionally, the stimulation and/or control of body physiology are used as a long term treatment, optionally with a goal of treating, preventing degradation and/or maintaining a patient.

Various embodiments of the invention are based on the inventors' surprising discovery that stimulation of the urinary system can affect kidney function and/or other bodywide functions, rather than merely affecting local function such as peristalsis or bladder voiding. In particular, the inventors have discovered that stimulating the bladder, bladder trigone, the ureters, as well as other parts of the urinary system affect kidney and/or other body functions, including functions not directly related to urinary such as cardiovascular functions, for example blood pressure. It is believed, but this need not limit the scope of the invention, that such stimulation latches onto existing feedback cycles in the body, possibly by affect the source of feedback signals (e.g., the afferent nerves), or by causing activity of the stimulated portions which then modulates existing reflex feedback cycles.

In an exemplary embodiment of the invention, the stimulation is electrical. However, in other embodiments of the invention, other simulation methods may be used instead or in addition, for example, chemical stimulation, thermal stimulation and/or mechanical stimulation. In particular, ureter receptors may be stimulated by providing sodium ions therein.

In an exemplary embodiment of the invention, an implanted device is used for stimulating the urinary system. Alternatively or additionally, the device includes a transurethraly or transcutanesouly inserted stimulator, which may, optionally, extend out of the urethra to an external stimulator controller and/or power source. Optionally, the device includes a stimulator inside the bladder, inside the kidney and/or inside the ureter. Optionally, the device operates by expanding the ureter.

In an exemplary embodiment of the invention, an intra-ureteral stimulator is made thin and/or soft enough so it allows urine flow past it and/or does not interfere with valves of the urinary tract. Optionally, such a stimulator is equipped with an anchoring mechanism, such as for example, such a stimulator ends in a curved element, for example a pig tail at one or both sides or alternatively in a widening form, for example, radially extending arms or a conical coil, which lodges in the urinary system, for example, in the kidney pelvis and/or bladder and/or is optionally used to stimulate said system at said widening.

In an exemplary embodiment of the invention, an intra-ureteral stimulator comprises a tubular element (e.g., a stent-like hollow tube, optionally formed of a mesh) which engages the walls of the ureter. In another example, the stimulator includes one or more rings which lodge in the ureter, optionally connected by a wire or cable.

In an exemplary embodiment of the invention, an intra-ureteral device operates by mechanical or thermal stimulation of the ureter, for example, by an expanding element. Optionally, this expansion simulates the effect on the sensory nerves in a manner similar to a ureteral blockage and/or chemical irritation and/or directly stimulates sensory nerve endings.

In an alternative embodiment of the invention a stimulator is mounted on a double pigtail ureteral catheter.

In an alternative embodiment of the invention, the stimulator is mounted on an outside of a ureter. Optionally, such a stimulator is designed to not interfere with ureteral peristalsis and/or ureteral repositioning, for example, the mounting on the ureter being flexible, optionally axially. Such flexibilities are optionally provided for intra-ureteral catheters as well. Optionally, the stimulator provides stimulation specifically to the desired location without stimulating other targets, for example by isolation of the stimulator from other organs.

In an alternative embodiment of the invention, a stimulator is inserted transcutaneously directly into the kidney. Optionally, the stimulator is inserted transcutaneously. In an alternative embodiment of the invention a stimulator is mounted on a nephrostomy catheter.

Optionally, the stimulator includes a distal expanding portion, for example, a single wire which folds into a spatial shape, to help anchor in the kidney, bladder, and/or kidney pelvis. Such a design may also be used for a stimulator which lies in the ureter.

In an exemplary embodiment of the invention, a stimulating device can apply multiple therapies, for example, applying, in addition to modification of kidney or body function or alternatively thereto, one or more of bladder stimulation to assist, prevent modify and/or otherwise modulate voiding, nerve stimulation and/or sphincter function and/or is used for treating one or more of stress incontinence, neurogenic bladder, atonic bladder, cystocele and/or urinary tract infection (e.g., by better drainage of urine). Additionally, for example as described below, stimulation can include multiple stimulations in the urinary system, such as ureters and in addition nerve(s) and/or blood vessel(s) and/or stimulation of other body systems, such as the heart or baro-receptors in the carotid arteries or vagus nerves or nervous plexuses. Optionally, renal stimulation is used to counteract a negative systemic effect which would affect the kidneys and caused by vagal (or other nerve) stimulation. For example, reduced blood pressure may reduce renal blood flow to a damaging level. Stimulation in accordance with some embodiments of the invention can increase renal flow while not be strong enough to negate the systemic treatment. Optionally, renal stimulation is used to modulate such a systemic (e.g., vagal nerve stimulation, medication) treatment.

An aspect of some embodiments of the invention relates to treating modifying or maintaining body functions using a urinary system stimulator device (or system). While in some embodiments of the invention a device may apply an open loop treatment, whereby a therapy is set for a desired effect, in an exemplary embodiment of the invention, the device includes an input, optionally from internal or external sensor (or more than one sensor) which generates an indication of body function, or input from other devices, such as a pacemaker or urine analysis system and/or input form a user, such as a subjective feeling. Optionally or alternatively, the stimulation device is used to command and/or control such systems and/or interoperate, for example, preventing interference of function and/or of sensing, allowing a feedback loop to be closed. In an exemplary embodiment of the invention, the sensor includes a sensor of kidney function and urinary parameters, such as one or more of urine chemistry, urine volume and urine flow. Optionally or alternatively, the sensor includes a physiological sensor for kidney function, for example, GFR, urine flow, urine composition, secretion of hormones from the kidney (in blood and/or urine), creatinine levels, inulin levels. Optionally or alternatively, the sensor includes a sensor of urinary systems function, for example, urinary parameters, peristalsis and/or pressure. Optionally or alternatively, the sensor includes a physiological sensor for non-urinary systems, for example, blood chemistry, blood pressure, heart rate, breathing rate, lung fluid volume and/or ECG. Optionally or alternatively, the sensor includes an input for user entry of a command or of a physiological parameter. Optionally or alternatively to a physiological sensor, an environmental sensor is used, for example, an acceleration sensor may indicate movement (and thus suggest blood pressure changes) or body posture (e.g., supine, possibly indicating a rest period when cardiac demand is lower) and a temperature sensor may indicate environmental temperature (and thus suggest sweating rate).

In an exemplary embodiment of the invention, the stimulation applied by the device is set so as not to cause pain or even not to cause a perceptual feeling. Typically subjective feeling of electrical stimulation depends on the waveform, the frequency and the amplitude of stimulation, as well as on the stimulated area (above and beyond a sensed functional effect), for example, due to nearby tissue muscle contractions and/or pain receptors in that tissue. In the bladder, sine waves are generally less tolerated than square waves, possibly due to the larger current flowing in the sine waveform. In general, higher frequencies are less irritating; bladder stimulation is not felt up to 2 mA stimulation with a 2000 Hz sine wave, 1 mA with 250 Hz and 0.5 mA with 5 Hz, suggesting that bladder sensation is mediated by C-fibers that are sensitive to low frequency stimulation. The urethra is about 4-10 times more sensitive to electrical stimulation. The trigone appears to not generate sensations up to 16v with 2500 Hz square wave stimulation. In an exemplary embodiment of the invention, stimulation is maintained below these values. In some cases, even pain or sensation causing stimulations may be used, depending on the importance of stimulation. Optionally, larger electrodes are used to reduce the current density and possibly pain which relates to current density.

In an exemplary embodiment of the invention, the stimulation has a continuing effect even after it is stopped, for example, an effect lasting at least 3 minutes, 20 minutes, 1 hour, 2 hours or intermediate times. In an exemplary embodiment of the invention, longer periods are used for having a useful lasting physiological effect. Shorter periods are optionally used for feedback and/or to determine stimulation parameters. Optionally, the stimulation is not repeated for such time periods while the effect lasts.

In some experiments it was observed that the duration of an after effect appeared dependent on the duration of stimulation. In an exemplary embodiment of the invention, the stimulation sequence used assumes a factor of, for example 1.5, 2, 3, 5, 10 or intermediate or greater factors, between stimulation time and expected useful effect duration. Optionally, the link for a particular patient is determined, for example, during calibration, and used as part of a plan for and/or selection of for stimulation sequences therefore.

In an exemplary embodiment of the invention, the stimulation includes positively affecting or controlling two kidneys, optionally, controlling one kidney in opposite to an effect expected by control of the other kidney.

In an exemplary embodiment of the invention, the device is used for treating one or more of acute or chronic high blood pressure, acute or chronic heart failure, myocardial infarct, acute or chronic renal failure, nephrotic syndrome, hepatorenal syndrome, cardiorenal syndrome and other disease states. Optionally, the sensing is used to indicate when a particular therapy is working and can be stopped or slowed down and/or when a specific therapy is not working and should be changed.

In an exemplary embodiment of the invention, the following treatment protocols are used for particular disease states. For shock patients (e.g., including septic shock), it is noted that these patients suffer from reduced blood pressure and can be treated by vasoconstrictors in order to increase systemic vascular resistance and increase blood pressure; but it often results in renal failure, due to reduced renal perfusion. Optionally, increase of the reno-renal reflex is used to protect the kidneys during the treatment. For detoxication, for example of substances that are excreted by the kidneys, increased kidney perfusion can be used to eliminate the toxins more quickly. For acute renal failure there are anecdotal reports showing that increasing renal function during acute tubular necrosis phase of renal failure can improve the clinical condition. Optionally, a treatment starts as early as possible, lasting up to a few days following the initial damage. Optionally, renal blood flow is increased using a reno-renal reflex or other stimulation, while renal function is reduced, for example, by adrenaline. For chronic renal failure, in general, these patients benefit from diuretics, if not for their harming effects on the GFR. A chronic stimulation of the reno-renal reflex (to increase it) with diuretic administration may be used for such patients.

In an exemplary embodiment of the invention, the device coordinates with another device that applies a non-urinary system stimulation, for example, cardiac pacing or a medication pump or a transdermal medication application patch.

In an exemplary embodiment of the invention, the device is programmed with a plurality of possible stimulation protocols. Optionally, a table or algorithm is provided which matches stimulation profiles with desired effects, physiological conditions and/or possible side effects. Optionally or alternatively, a correction is provided for various situations, such as age or diabetes, in which cases the stimulation intensity required for desired effect may be doubled and/or optionally programmed by a user.

An aspect of some embodiments of the invention relates to devices for stimulating tissues near the bladder, for example, the urinary bladder trigone and/or distal ureter area. In an exemplary embodiment of the invention, such a device includes a stimulator which resides, at least in part in the bladder. Optionally such a stimulator is equipped with an expanding part, optionally a balloon, which dwells in the bladder, optionally an inflating part of a Foley catheter. In an exemplary embodiment of the invention, the stimulator is shaped so that access to the trigone and/or the ureter is not blocked by an enlarged prostate. Optionally the balloon is not spherical, for example a torus, for better control of location of stimulation. Optionally, the stimulator is a balloon with a concavity matching the bulging prostate area. Optionally or alternatively, the stimulator includes an adapting mechanism matching a protrusion into or distortion of the bladder caused by organ prolapse. Optionally the adapting mechanism is the ability of the device to change its form, optionally to bend to match the distortion of the bladder. Optionally, such a stimulator is designed to not mechanically interfere with urine flow, for example, including a channel for urine to the urethra and/or includes a channel for urine flow from the ureters to the bladder. Optionally the stimulator includes at least one, optionally more draining holes to fully empty the bladder. Optionally, the stimulator does not fill the entire volume of the bladder. Optionally, the stimulator includes only a wire in the urethra, thereby allowing the bladder neck to operate in its valving function. A potential advantage of a trans-pubic approach is that a direct insertion into the ureter and/or contact with a trigone area may be possible, by transfixing the bladder at a correct orientation and reducing the risk of infection.

In an exemplary embodiment of the invention, the stimulator is designed to have a contact adjacent a trigone or distal ureter area. Optionally the stimulator includes a plurality of contacts, for different areas in the bladder.

In an exemplary embodiment of the invention, the bladder is stimulated at multiple locations, for example, at non-trigone areas. It is believed that such stimulation, if applied over a sufficient surface of the bladder can activate such sensory nerves which can then trigger or modulate a vesico-vascular effect. Optionally, controlled differential stimulation of different parts of the bladder is used to provide control of the at least practically counteracting reflexes of the reno-renal reflex and the vesico-vascular reflex. Optionally, the degree of vesico-vascular excitation is controlled by one or more of controlling intensity and controlling surface area stimulated (e.g., a 20% area stimulation generates less of an effect than 60% area stimulation).

Optionally, such stimulations are applied in series, alternatively, they at least partially overlap in time. Optionally, after a reno-renal reflex is activated, a vesico-vascular reflex is applied to reduce the kidney function to a desired amount (or the trigone may be stimulated to increase the reno-renal reflex intensity). Optionally, such stimulations are applied as needed to maintain a desired physiological effect within a desired range, for example, resulting in a series of stimulations of the trigone and the rest of the bladder, not necessarily alternate stimulations.

Optionally, the stimulation used is to reduce sensitivity, for example, by hyperpolarization of nerves. Optionally, such dampening stimulation is used, for example, when stimulating the entire bladder, to first desensitize the trigone, so it does not counteract the effects of bladder stimulation (the ureter is then optionally stimulated to achieve a desired effect on the reno-renal reflex). Optionally or alternatively, the relative contributions of vesico-vascular reflex and reno-renal reflex (or other reflexes) can be controlled by reducing the contribution of one, in addition to or instead of increasing the other.

Optionally, once stimulation shows a desired effect, or instead of such stimulation, nerve endings in a portion of the bladder may be permanently ablated to reduce a reflex, such as the vesico-vascular reflex.

In some exemplary embodiments of the invention the stimulation is used to increase (or reduce) sensitivity, for example, by modification of reflex gain. Optionally this is provided by electrically stimulating other reflexes and/or nerves of the urinary system.

In an exemplary embodiment of the invention, sensitivity of various receptors, pathways and/or physiological function is tested, by stimulation and/or optionally damping stimulation, as part of a diagnosis process.

Optionally or alternatively, a protocol may include a test session to see what a patient responds to and/or what a patient may over respond to and a treatment protocol is optionally decided accordingly.

In some cases, kidney voiding problems and/or an enlarged prostate cause over stimulation of a bladder region, thereby causing over stimulation or habitation of a reflex. Optionally, such a physiological condition is treated as a way of affecting such a reflex and having a desired non-local effect as described herein. For example, a prostate may be resected or shrunk (e.g., using ablation or medication) and/or a urethra may be opened and/or a bladder be stimulated to assist in voiding and/or a bladder may be resected to reduce a surface area thereof.

In an exemplary embodiment of the invention, the stimulator includes a plurality of contacts, but only on one hemisphere thereof. Optionally, the contacts are fewer than 10. In an exemplary embodiment of the invention, the contacts, all or some, are positioned to specifically reach the trigone area. For example, if the stimulator is a balloon entering from the urethra, a distance between the urethra and the trigone is used to set the distance between the contacts (or some of them) an a part of the balloon that contacts the bladder neck.

An aspect of some embodiments of the invention relates to non-electrical stimulation of the urinary system, for example, thermal, mechanical and/or chemical stimulation of the ureter, trigone and/or kidney. In an exemplary embodiment of the invention, a device for mechanical stimulation includes an element which expands inside the ureter and thereby simulates a blockage. Optionally, the element does not block urine flow. Alternatively, it does.

An aspect of some embodiments of the invention relates to an integrated bladder dwelling stimulation system. Optionally, the system is adapted to be inserted through a urethra. Optionally or alternatively, the system is adapted to be inserted via the pubic area. Optionally, the system includes, in a single unit, sensing, control and power. Optionally, the system is designed to specifically stimulate the trigone. Optionally, the system is simple and/or designed for disposing, for example, not including an on/off control and/or including only a power control, so that a setting which is effective but not painful or causing discomfort, may be selected.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Method and Apparatus

Figure 3:
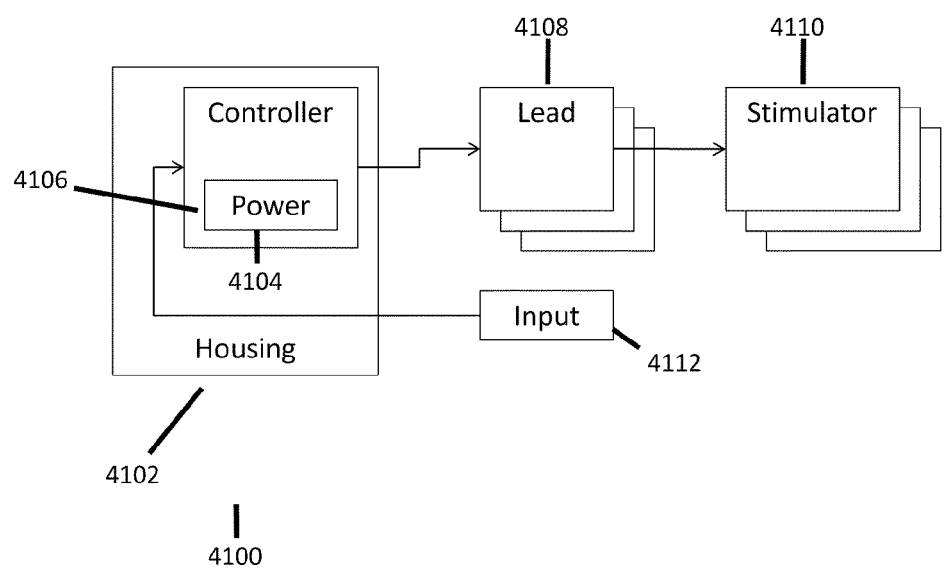
FIG. 3 is a simplified schematic block diagram of a urinary system stimulation system, in accordance with an exemplary embodiment of the invention.

Referring now to the drawings, where FIG. 1 is a flowchart of a method of controlling body physiology using stimulation of the urinary system, in accordance with an exemplary embodiment of the invention. FIG. 3 is a simplified schematic block diagram of a urinary system stimulation system 4100, in accordance with an exemplary embodiment of the invention.

In an exemplary embodiment of the invention, stimulation system 4100 comprises a stimulator 4110, optionally an electrical stimulator, but possibly a stimulator of a different type, for example, chemical, thermal or mechanical. Stimulator 4110 is optionally coupled to a controller 4104 by a lead 4108. Alternatively, a wireless coupling may be provided. In an exemplary embodiment of the invention, controller 4104 includes a power source 4106, such as a battery. Optionally, the battery has enough power for treating a patient for at least 1-3 years. In some embodiments, a small battery, suitable, for example, for 1-6 days or 1-4 weeks, is provided. Optionally, controller 4104 is enclosed in a housing 4102, for example, suitable for implantation in the body or for survival outside the body. Optionally, an input source 4112 is provided, for example, for user input or for sensor input and/or for a time signal.

At 4002 a patient is optionally diagnosed. In some cases the diagnosis is pre-existing. In other cases, stimulation of the urinary system will help in determining a diagnosis. In an exemplary embodiment of the invention, stimulation is used as part of a diagnostic method. For example, patients having hyperactivity of the renal nerves may be identified. For example, in CHF patients, there is a variability in the function of sympathetic renal nerves. It is expected that stimulation in accordance with some embodiments of the invention would have a more pronounced effect on high renal nerve activity patients. After such identification, such patients may be treated, for example, using a chronic device, using a nerve or vessel stimulator such as suggested by U.S. Pat. No. 7,162,303 and US patent publication 2006/0212078 and/or a more vigorous anti-sympathetic therapy.

Optionally or alternatively, various kidney functions may be measured. Optionally, weariness of the kidneys can be identified by determining how well the kidneys respond to stimulation. Optionally or alternatively, diagnosis comprises bypassing various parts of the renal system to see where a normal response is detected. For example, if stimulation of afferent nerves has an effect that ureter stimulation does not, this suggests a damaging of the ureteral nerve endings.

In an exemplary embodiment of the invention, a degree of renal sympathetic drive can be measured from the timescale/amplitude of the response to reno-renal stimulation. As taught by Schramm et al, activation of the reno-renal reflex reduces the attenuation of renal function during sympathetic stimulation. The reno-renal reflex can also slow the renal response to renal nerve stimulation. Optionally, a number of different intensities of stimulations are provided and the patient's response (for example blood pressure and/or urine flow) is measured. Comparison of the effects of stimulation can provide the gain of the sympathetic system and the responsiveness of the kidneys and/or the cardio vascular system.

At 4004 a treatment is optionally selected. As noted, in some cases, stimulation of the urinary system is used to help in choosing a treatment protocol, for example to see which stimulation has a therapeutic effect with acceptable side effects. In an exemplary embodiment of the invention, the treatment is selected to affect one or more of kidney function, blood chemistry and/or cardiovascular parameters, such as blood pressure and susceptibility to arrhythmia (e.g., by lowering sympathetic activity).

Figure 2:
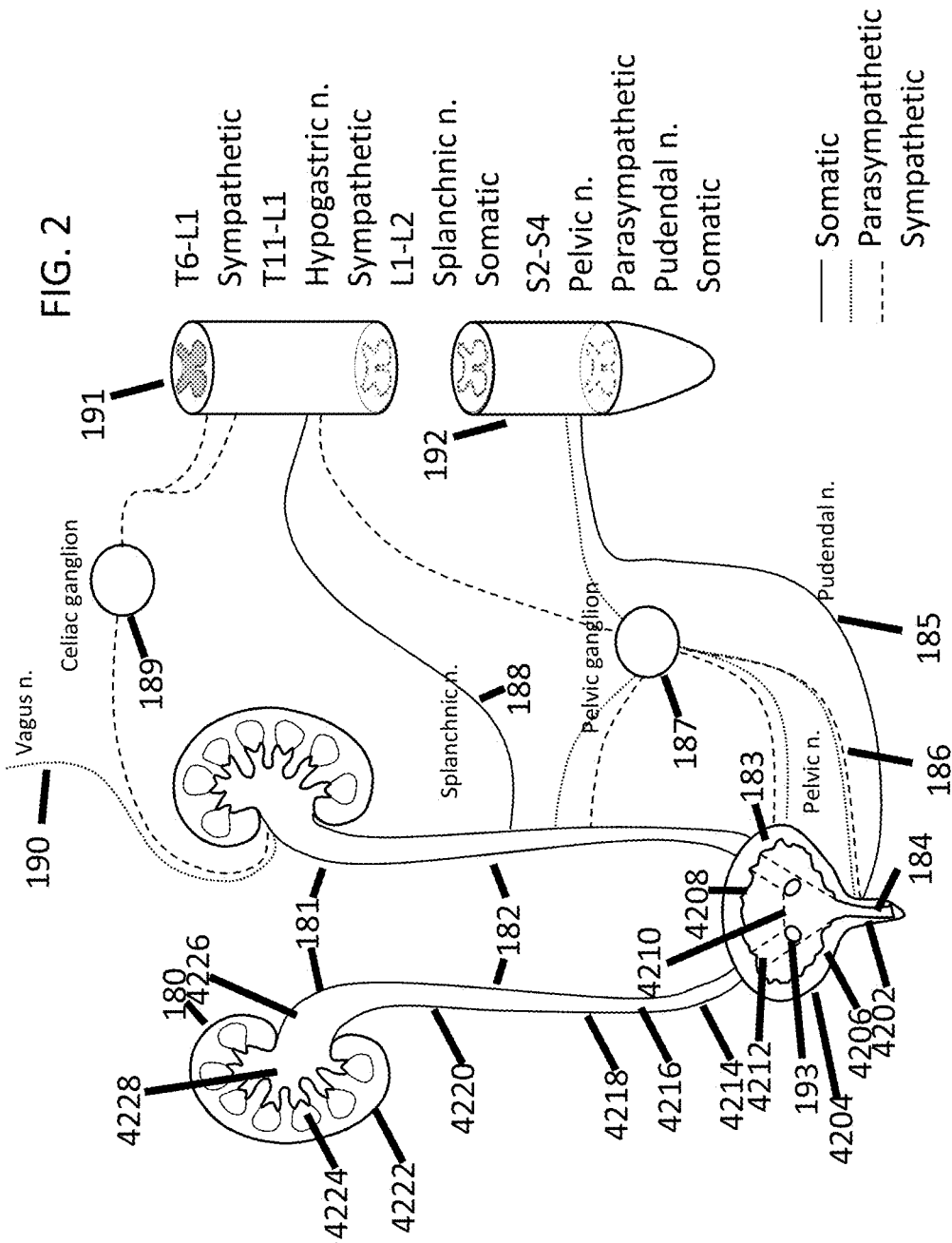
FIG. 2 is a schematic diagram of a urinary system showing exemplary target stimulation locations, in accordance with an exemplary embodiment of the invention.

At 4006, stimulator 4110 is provided, if one was not provided before. As described herein, stimulator 4110 may be, for example, external, transcutaneously implanted, trans-urethrally implanted and/or inserted in the vagina or rectum of a patient. FIG. 2 below shows exemplary target stimulation locations, in accordance with some embodiments of the invention. In an exemplary embodiment of the invention, stimulator 4110 is provided on a urinary catheter which is also used to measure urinary output and/or ensure bladder evacuation.

At 4008 the urinary system is stimulated using stimulator 4110. In an exemplary embodiment of the invention, stimulation system 4100 is programmable with a set of parameters which may be selected, for example, based on a desired treatment.

At 4010, an additional treatment is optionally provided, for example drugs (to affect the body and/or urinary system in particular) or electrical stimulation, for example, of the urinary system, nervous system and/or the heart. Optionally or alternatively, an existing treatment, such as diuretic medication may be modified to take into account the stimulation of the urinary system. Optionally or alternatively, a synergistic result is to be obtained between acts 4008 and 4010.

At 4012 feedback is optionally provided, for example, by providing a physiological indication, such as blood pressure, urine volume, GFR, blood flow, impedance, weight, blood chemistry.

At 4014, one or more stimulation parameters and/or treatment parameters (of 4010) are optionally changed taking the desired result and/or physiological indication(s) into account. This may result in repeating, for example, diagnosis, treatment selection and/or urinary system stimulation and/or other treatment.

At 4016, additional input is optionally provided, for example, user commands (e.g., reduce blood pressure, increase blood pressure, medication taken), programming and/or non-physiological sensor input (e.g., accelerometers indicating alertness or posture, laboratory/external urine analysis results), and optionally used in determining stimulation and/or treatment parameters. Optionally or alternatively, this input is used to determine which stimulator to use and/or what physiological measures to check.

At 4018 a stimulator is optionally removed (e.g., when not needed) or changed (e.g., by replacing an external stimulator having a trans-urethral stimulation with an implanted stimulator. For example, such replacement may be useful when a temporary stimulator is used to determine parameters and/or suitability of a permanent stimulator.

While various possibilities of treatment and stimulator configuration are described below, a particular exemplary stimulation system includes a trans-urethral catheter terminating in a balloon configured to electrically stimulate trigone tissue in the bladder. In an exemplary embodiment of the invention, the stimulation is used to increase kidney function including, for example, one or more of renal blood flow, filtration rate, urine production, salt excretion and/or reduction of blood pressure possibly by activating a reno-renal reflex. Optionally, such increase in kidney function is used to alleviate heart failure and/or hypertension.

It should be noted that in some embodiments of the invention, only a lead is implanted, and in some cases the implantation is temporary, being, for example, by placing in a urethra. In other embodiments implantation is longer term, includes forming new apertures in the body surface and/or organs and/or includes a more robust attachment to tissue than a structure which urges a stimulator against a tissue. For example a stimulator may be implanted for, for example, 3 days to 2 weeks, 1-6 months, 1-5 years, or shorter, intermediate or longer periods.

The above has described an exemplary system and method for stimulating a urinary system, in accordance with some embodiments of the invention. Following are examples of therapies and/or effects which may be achieved by such a system, thereafter are described several alternative subcomponents of such a system, for example, stimulator type, stimulator location and designs for different implantation methods. It is to be stressed that a practical implementation of some embodiments of the invention may include picking and choosing particular therapies, programming, structural features, options and/or implantation methods and/or adaptations from several and/or different ones of the sections below.

Exemplary Target Locations

FIG. 2 is a schematic diagram of a urinary system showing exemplary target stimulation locations, in accordance with an exemplary embodiment of the invention. It should be noted that different types of targets affect different body functions and/or have a different difficulty level in access thereto and/or stimulation thereof. There is also a difference between the targets with respect to the order of their effect on kidney and/or body functions. For example, some targets cause the secretion of hormones, some targets are active organs (like nephrons), some targets are general nerves of the body or blood vessels that lead blood to the kidneys and some, in an exemplary embodiment of the invention, are targets that modulate or trigger existing reflexes, thereby indirectly affecting various body and/or kidney functions.

In general, the urinary system includes two kidneys 180, connected by two ureters 182 at kidney pelvises 181, the ureters further being connected to a bladder 183 by uretero-vesical junctions (UVJ) 193, which together with an orifice of a urethra 184 form a trigone area 4210. All of these body parts are adapted to hold urine, and some, such as the ureter and bladder are muscular. In some cases, the stimulation increases the force of contraction of the ureter.

In the following various potential targets are listed. Some of these targets may have been used in the art but in conjunction with other targets, other methods of control, devices and/or methods described herein, are novel. In an exemplary embodiment of the invention, targets include targets that are within a control loop of the kidney, for example, nerves and/or tissue which modulate and/or trigger existing reflexes, such as the reno-renal reflex and the vesico-vascular reflex. In an exemplary embodiment of the invention, targets are within the urine flow system, which allows ease of access for temporary implantation and/or acute treatment.

For example, one or more of the following targets may be used:

(a) the inside surface 4202 of urethra 184, e.g., using an intra-urethral electrode; this may be an easy to stimulate location which is close to trigone 4210 (e.g., if parts near UVJ 193 are stimulated), stimulation can contract the urethral sphincter and/or activate the reno-renal reflex;

(b) the outside surface 4204 of bladder 183; e.g., using implantable stimulator; Depending on the location of stimulation, different reflexes can be activated; for example the stimulation can activate the vesico-vascular reflex, but if located at posterior locations, near the ureters, can also activate the reno-renal reflex;

(c) intramuscular portions 4206 of bladder 183; e.g., using a catheter based device, an implantable lead and/or a suprapubic device; such a lead or device may include a tissue penetrating electrode such as prongs or a screw (e.g., with a contact at the prong or screw), which can be used also in a trigone area;

(d) portions of the inner bladder wall 4208; e.g., using catheter or suprapubically inserted device; optionally this uses an easy to insert device; optionally the stimulation can activate the vesico-vascular reflex;

(e) the trigone area of the bladder 4210; e.g., using a catheter, a suprapubically inserted device or an implantable device; specific activation of the trigone activates the reno-renal reflex (or dampens it, if inhibitory stimulation is used);

(f) distal portions 4212 of the ureter near or at the connection to the bladder; e.g., with a ureter catheter based device; Optionally the ureter region is used for specific reno-renal reflex activation/modulation;

(g) distal portions 4214 of the ureter, somewhat distanced from the bladder, e.g., within 2-3 or 3-5 or 5-10 centimeters from the end, optionally near a junction of nerves and the ureter;

(h) mid-ureteral regions 4218, for example, using a stimulator mounted on the ureter 182;

(i) inside surfaces 4216 (or within wall portions) of the ureter at any point thereof, for example, using an intra-ureteral catheter or an extra-ureter stimulator, either optionally connected to a implanted device;

(j) proximal portions 4220 of the ureter; e.g., with a ureter catheter or a nephrostomy device;

(k) pelvic portions 4226 of the kidney, optionally inner surfaces thereof; stimulation can optionally control ureteral peristalsis in addition to activation of the reno-renal reflex.

(l) the cortex 4222 of the kidney, for example, its outside surface (e.g., the renal capsule), optionally under a fat layer thereof;

(m) internal structures 4224 of the kidney, for example, one or more of a Renal pyramid, a Renal hilum, a Minor calyx, a Major calyx, a Renal papilla and/or a Renal column; and/or an active kidney portion such as a Nephron;

(n) lumens 4228 in the kidney.

Optionally or alternatively, nerves that innervate or otherwise affect the kidney are stimulated to affect kidney or other body function. Optionally, the nerves may be one or more of afferent nerves, somatic nerves, parasympathetic nerves and sympathetic nerves. Optionally a nerve ganglion or other plexus (e.g., the spine) is stimulated, to directly or indirectly affect such nerves. A particular advantage of stimulating afferent nerves is that such stimulations allows existing kidney feedback mechanism to be manipulated as if a real event was happening. In an exemplary embodiment of the invention, the nerve stimulated is a nerve that is directly connected to a kidney. In other embodiments, the nerve is not directly connected to a kidney, for example, a nerve connected to a spine. In one example, a vagal nerve is used to affect general body nervous tone and an additional stimulation used to specifically affect a kidney.

In an exemplary embodiment of the invention, the nerves being stimulated enervate the urinary system and/or are adjacent thereto (e.g., are stimulated within 2-5 cm, optionally 1-3 cm, optionally about 1 cm, from their connection to the urinary system). Possibly this will increase the locality of the stimulation and reduce undesired effects on other body systems In an exemplary embodiment of the invention, the targets include one or more of a Splanchnic nerve 188, a Pelvic nerve 186, a Pudendal nerve 185, a Pelvic ganglion 187, a Celiac ganglion 189, a spinal cord portion 191 or 192 and/or a Vagus nerve 190. It should be noted that, in general, nerves may be less desirable to stimulate if their stimulation is not specific and/or if there is a danger of inflammation of the nerve.

Optionally or alternatively, blood vessels (not shown) are stimulated, for example, one or more of an Interlobar artery a Renal artery, a Renal vein and an Interlobar vein. Stimulating vessels can be used to increase or reduce blood flow to the kidneys.

A particular advantage of stimulating urine holding tissues is that such tissues may be more robust and/or more muscular and easier to contact without damaging. Another potential advantage of stimulating functional tissue, rather than nerves, is that such stimulation may assist in simulating a desired behavior of the kidneys using pre-existing feedback mechanism. For example, stimulating a ureter can be used to simulate an obstruction in the ureter and/or the sensory signals caused by such obstruction, thereby triggering biologically natural reflexes and feedback loops. In another example, stimulation of sufficient parts of the bladder can simulate a full bladder, and thereby reduce kidney function. In some examples, stimulation is targeted at locations in the body which include receptors, such as force receptors and chemo receptors.

Exemplary Stimulation Effects

Figure 5:
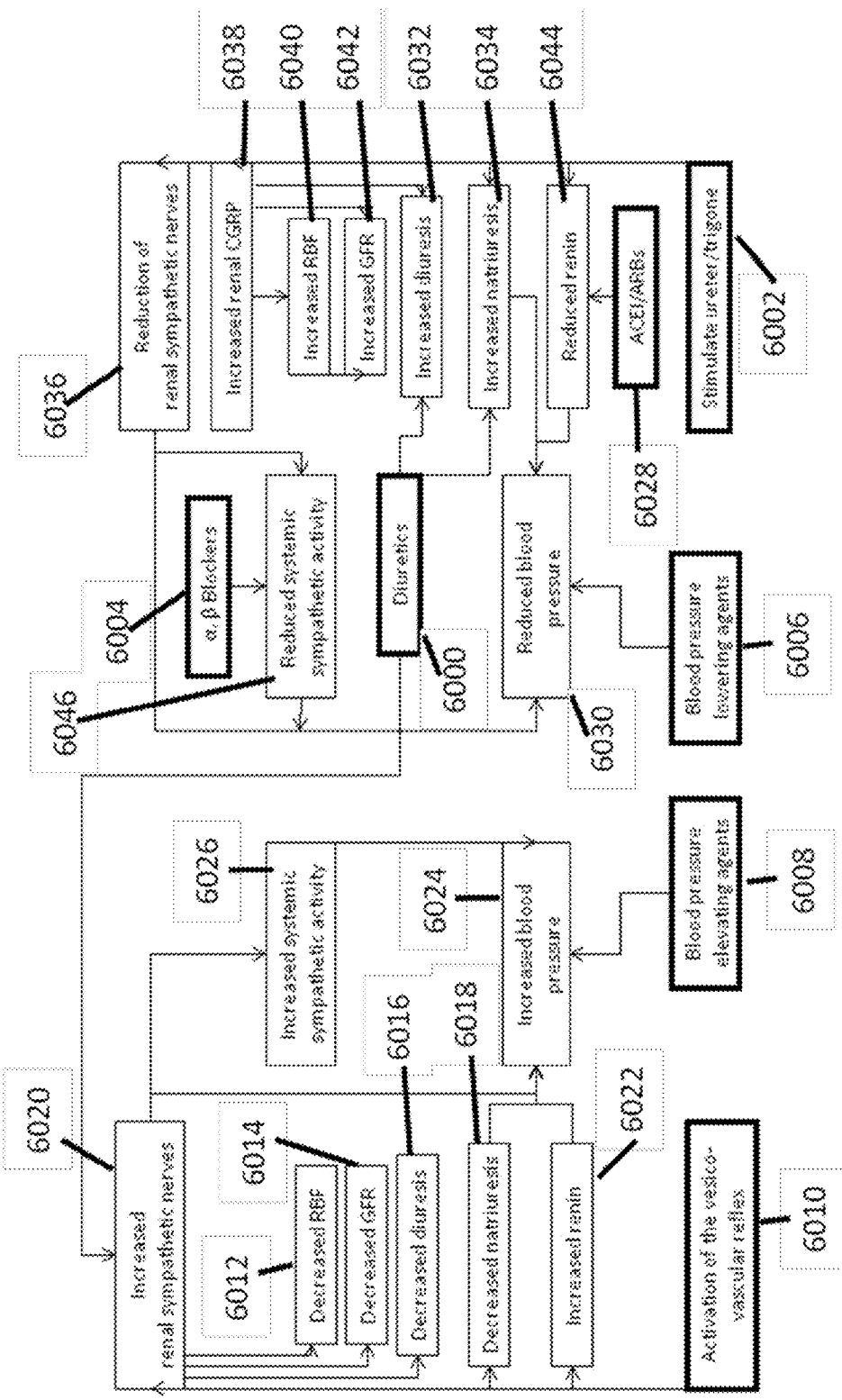
FIG. 5 is a block diagram showing exemplary effects of stimulation according to some embodiments of the present invention, on body systems.

FIG. 5 is a block diagram showing exemplary effects of stimulation according to some embodiments of the present invention, on body systems, not intending to be a complete such exposition.

Bold boxes include external stimulations, some generally known (e.g., diuretics 6000) and some novel (e.g., stimulation of the ureter 6002). Unbolded boxes indicate effects of such stimulations. An important feature shown in this figure is the multiple inputs for some of the effects. In an exemplary embodiment of the invention, to achieve a desired effect, multiple inputs may be provided, inputs which work together and/or inputs which interfere. Additionally, some inputs may be reduced (e.g., medication 6004, 6006, 6008, 6028) if they interfere with a desired effect. Optionally or alternatively, different inputs are provided at different times of day, for example, when their side effects are less bothersome and/or to provide different modes of interference with body function at different time, which may prevent habitation and/or adaptation.

As shown activation of the vesico-vascular reflex 6010 can increase renal sympathetic activity 6020, which can then lead to one or more of decreasing renal blood flow 6012, decreasing GFR 6014, decreasing diuresis 6016, decreasing natriuresis 6018 and/or increased renin secretion 6022. These last two can cause increased blood pressure 6024, optionally in cooperating with increased renal sympathetic drive 6020. Blood pressure can also be increased using blood pressure elevating medications 6008 and by systemic increased sympathetic activity 6026. Diuretics 6000 can also increase renal sympathetic drive 6020 and therefore increase blood pressure 6024.

Blood pressure lowing agents 6006 can decrease blood pressure, as can ACEI and ARBs (angiotensin blockers) 6028 which reduce renin-angiotensin-aldosterone axis activation. Alpha and beta blockers 6004 can reduce the systemic sympathetic activity 6046 and thereby reduce blood pressure 6030.

Diuretics 6000 can also increase diuresis 6032 and/or natriuresis 6034 (which can reduce blood pressure 6030).

Stimulation of the ureter and/or trigone areas 6002 can evoke the reno-renal reflex and/or, for example, reduce renal sympathetic drive 6036 and/or increase renal and/or systemic CGRP (calcitonin gene-related peptide) secretion 6038, which can then increase renal blood flow 6040, increase GFR 6042, increase diuresis 6032, increase natriuresis 6034 and/or reduce renin secretion 6044.

In general, treatment of any particular patient may be a navigation of a maze of interactions and counter-interactions between stimulations and treatment, while taking into account the responsiveness of a patient and his/her danger zones. Optionally, a stimulation system and/or a monitoring system are programmed with such interaction (e.g., 3, 4, 5 or more interactions) and used to predict and monitor the effect of treatments and/or suggest treatments and/or treatment levels.

In accordance with exemplary embodiments of the invention, one or more of the following effects on urinary system function is achieved:

(a) increasing a kidney activity and/or a function, for example, by affecting a urinary system reflex;

(b) reducing a kidney activity and/or a function, for example, by affecting a urinary system reflex;

(c) increasing or decreasing peristalsis in a ureter, for example, by overpacing a ureter or by applying a desensitizing stimulation to the ureter (e.g., a hyper-polarizing stimulation, such as DC or a high frequency stimulation); Optionally, over pacing is to above a normal rate, for example, to above 3, 4, 5 or more peristaltic waves per minute.

(d) increasing or decreasing renal blood flow, for example, by stimulating renal vessels and/or modulating a reflex; increasing renal blood flow may increase kidney function and vice versa;

(e) modulate a reflex, for example, by stimulating or dampening sensory nerves associated therewith;

(f) trigger a reflex, for example, by stimulating an input thereto;

(g) stimulate receptors to modify a baseline activity thereof (e.g., increase or decrease), thereby making a reflex weaker or stronger for a same stimulation or physiological condition;

(h) release hormones, for example, to cause local and/or body wide vasodilatation or vasoconstriction;

(i) modify nervous activity, for example, by stimulating a nerve; and/or (j) modify cardiovascular function, such as blood pressure, heart rate, vessel dilation and/or resistance and/or susceptibility to arrhythmia, for example, by releasing hormones, preventing the release of hormones, modify an intensity of a reflex and/or modifying systemic sympathetic activity.

Additional exemplary details follow.

Dampening or exciting receptors. Pressure and chemo-receptors in the urinary system can be activated by electrical stimulation. Some of these receptors are NMDA glutamate receptors, which are known to have a prolonged timescales of activation and can be pushed to long desensitization states by high frequency stimulation. In addition, activation of NMDA receptors is very frequency dependent, frequencies as low as 5 Hz stimulations can progressively increase receptor activation, for example see Polsky et al. Different patterns of electrical stimulation can selectively excite or dampen receptor activity. NMDA receptors are also the main mediators of long-term potentiation and depression, which are important mechanisms of modulation of neural activity and neural reflexes. As known in the art, to excite a nerve, electrical stimulations are usually given in short pulses of up to 10 ms in length or by sinus wave shaped currents. To dampen nerve function, long DC currents or very high (e.g., >1000 Hz) stimulation frequencies can be applied.

Activation and modulation of the reno-renal and the vesico-vascular reflexes. A team lead by DiBona and Kopp revealed in a number of seminal papers that the reno-renal reflex is normally activated by a rise in pressure or sodium concentration in the collecting system, the renal pelvis and the ureters (any of which are stimulated in accordance with an exemplary embodiment of the invention). The reflex can be naturally activated by sensing from one side of the urinary system, but the normal effect is a bilateral reduction of the sympathetic input and increase in CGRP-mediated effect to both kidneys, as found by Zhu et al. Physiologically, the reno-renal reflex increases renal blood flow, renal filtration (GFR), diuresis, natriuresis and reduces blood pressure both by promoting sodium excretion and by a direct effect on brainstem sympathetic ganglions.

The vesico-vascular reflex has a rather opposite effect on the sympathetic system and on some kidney function. It is activated by increased bladder pressure or bladder distension, as occurs during bladder outlet obstruction. Chien et al found that activation of the reflex reduces renal blood flow, GFR, sodium and water excretion and increases renin secretion by renal nerve mediated effect. Fagius and Karhuvaara reported that in human subjects the reflex also increases blood pressure in a direct proportion to the intrabladder pressures. The increase in blood pressure is independent of renal nerves activity or renal function.

Modulation of reflexes has been shown, for example, in work done by Jiang and Lindstrom in the urinary system, who demonstrated a change in responsiveness of the micturition reflex. Short (5 min) electrical stimulation of the bladder and other pelvic structures effectively increased the threshold for the reflex for at least one hour post stimulation. Possibly, the effect was mediated by change in the strengths of the synaptic connections in the reflex pathway.

In an exemplary embodiment of the invention, it is noted that the two reflexes are generally, at least in part, opposite. Optionally, the balance between the reflexes is changed, for example, by strengthening one reflex (or exciting or increasing a baseline excitement level of receptors associated therewith) and/or by weakening the other reflex (e.g., or dampening a baseline excitation level and/or sensitivity of its receptors).

Hormone release. The reno-renal reflex is mediated by two nervous systems—first, it triggers a reduction of the sympathetic activity of the kidneys. In addition, it induces release of CGRP in the kidneys. CGRP is one of the most potent vasodilators in the cardiovascular system and it is known to cause both arterial and venous vasodilatation. In addition, it can elevate renal functions; for example, in a work done by Li and Wang and it was shown to increase GFR, urine flow and natriuresis in rats. CGRP infusion to human CHF and CKD patients was shown to decrease blood pressure and increase renal blood flow and GFR (Shekhar et al and Palla et al). These studies had also shown that CGRP has a relatively long effect lasting a few hours, despite a relatively short plasma half live of about 10 min.

CGRP is probably released from simulated afferent nerves in accordance with some embodiments of the invention, as these nerves have both sensory and excretory functions.

Zhu et al had shown that activation of the reno-renal reflex by increasing ureteral pressure increased plasma CGRP levels. However, the mean CGRP concentration achieved by this stimulation was about 10 fold lower than the minimally effective infused CGRP levels. By sufficient stimulation, it is believed that these levels will be reached, for example, 7, 10, 15, 20 or more of normal levels. Optionally, such results are achieved by applying a train (e.g., 10 or 20 or intermediate or larger number) of stimulations with rest periods (e.g., 10-40 seconds or 1-15 minutes) between, so that the nerves are re-stimulated by each stimulation to excrete more CGRP.

In some embodiments of the invention, CGRP levels are measured in the urine and/or the blood. Optionally or alternatively, stimulation is repeated enough so that significant (e.g., vessel dilatation affecting) systemic levels of CGRP are provided, optionally measured by blood test and/or measuring vessel diameter (e.g., with a vessel cuff or an ultrasound transducer measuring a signal across a vessel).

Regarding the role of CGRP in ureteral innervation. Lang et al described the inhibitory effect of CGRP on the motility of the isolated renal pelvis and ureter. The effect of CGRP is especially evident in the ureter as a suppression of evoked motility: the all-or-none suppressant effect probably occurs because CGRP abolishes the firing of action potentials evoked either by electrical stimulation or chemical agents. A descending gradient exists in the guinea pig pyeloureteral tract regarding sensitivity to the inhibitory effect of CGRP: the ureter is extremely sensitive, whereas the spontaneous activity of the renal pelvis is inhibited but not suppressed by this peptide. CGRP is the main mediator involved in the local regulation of ureteral motility: its main effect can be described as a powerful suppression of latent pacemakers of the ureter smooth muscle. Optionally, motility is controlled, for example by pacing, to overcome a motility reducing effect.

It should be noted that while some of the above effects have been described in the art, they have not generally been described as being part of a system for control of bodily functions. Rather, some embodiments of the invention utilize what is known with respect to biological interactions and provide a control system based thereon.

Exemplary Relationship Between Stimulation Location and Stimulation Effect

Following are examples of relationships between stimulation location and effect on kidney function, in accordance with exemplary embodiments of the invention:

(a) stimulation of the trigone area or ureters can be used to evoke the reno-renal reflex; and (b) stimulation of the bladder can be used to simulate a full bladder and evoke a vesico-vascular reflex, or to prevent such a reflex from being evoked.

Possibly the renal pelvis is more responsive to stimulation than the ureter, and this is used for selecting some embodiments of the invention.

In some embodiments, stimulation at or near the trigone and/or of a sacral is used to affect a closing of a bladder sphincter. A combined sphincter-closing effect may be useful if there is inadvertent causing of bladder contractions and/or feelings of discomfort.

It should be noted that while some of the stimulations have a biomechanical effect (e.g., peristalsis, sphincter closing), non-mechanical physiological effects, such as on blood pressure and kidney function, are often more of interest.

Exemplary Multiple Stimulation

In an exemplary embodiment of the invention, a stimulation system is used to stimulate a plurality of targets in the body and/or urinary system. Optionally, a plurality of such targets are stimulated in a same therapeutic session. Optionally or alternatively, such targets may be stimulated substantially simultaneously, for example, within 1 minute, 5 minutes, 20 minutes, 35 minutes of each other, or intermediate or longer periods.

In an exemplary embodiment of the invention, sequential stimulation of different targets is used to modulate an effect. For example, a first stimulation target triggers a reno-renal reflex. A second stimulation is then applied after a time to, for example, evoke the vesico-vascular reflex an thereby reduce the effect of the previously evoked reno-renal reflex to a desired amount. A urinary system specific stimulation is used together with a systemic stimulation, for example, a reno-renal reflex applied at a same time as a vagal stimulation. In another example, a combination of a medication and a stimulation is used, for example, evoking the reno-renal reflex to counteract a reduction in renal functions or enhance the effect of a diuretic.

Optionally, different kidneys are differently controlled, for example, by supplementing the reno-renal reflex using another stimulation method. One of the stimulations may be a baseline stimulation for one or both kidneys and the other used for modulation of both kidneys or only one.

In accordance with some exemplary embodiments of the invention, what is provided is a controller for urinary and/or other body functions. In an exemplary embodiment of the invention, the controller is used to directly or indirectly affect the underlying patho-physiological causes of some important diseases. Optionally, such a controller can replace, enhance/decrease and/or support existing body feedback cycles, receptors and/or sensor function. In an exemplary embodiment of the invention, such a controller substitutes normal or corrected responses for sensed body conditions, in a manner which compensates for damaged receptor pathways and/or prevents a self-reinforcing syndrome, such as a cardio-renal syndrome. Optionally or alternatively, such a controller can provide long term therapy and/or short term therapy, as desired. Optionally, such a controller can be used to specifically modulate a function of one organ, optionally the kidneys, for example providing opposite effects (e.g., otherwise physiologically incompatible) on different organs.

Exemplary Treatment Combinations

Several exemplary treatment combinations follow. These are only exemplary combinations and many of the stimulations described herein can be combined with stimulations of types known in the art to provide a myriad of different treatment options, optionally with a synergistic, compensating and/or side-effect-reducing effect.

(a) Reno-renal reflex activation+systemic vasoconstrictors that may include sympathetic activation (alpha and/or beta agonists); vasopressin agonists; somatostatin agonists—this combination can elevate blood pressure and ensure perfusion to the heart and brain without compromising renal blood flow.

(b) Reno-renal reflex activation+diuretics—boost the effectiveness of diuretics by enhanced renal delivery due to increased renal blood flow.

(c) Reno-renal reflex activation+sympathetic inhibition (e.g., beta-blockers)/ACEFARBs—increase the blockage of the renal sympathetic activity and its negative effects on cardiorenal interactions.

(d) Reno-renal reflex activation+water and/or saline infusion that increases plasma volume, for example to increase blood pressure and renal function and aid in salt removal.

(e) Reno-renal reflex activation+splanchnic vasoconstrictors (e.g., vasopressin V1), to redistribute blood flow from the splanchnic circulation to the kidneys.

(f) Reno-renal reflex activation+Vesico-vascular reflex activation simultaneously or not, to control renal and cardio-vascular function as desired.

(g) Vesico-vascular reflex activation to increase blood pressure.

(h) Inhibition of the vesico-vascular reflex to reduce blood pressure. Reduction of the reflex can be performed with a pharmacological agent such as capsaicin (e.g., infused into bladder, optionally while protecting trigone area) or by electrical stimulation, for example by a high frequency electrical stimulation or DC stimulation.

Exemplary Systemic Effects

In an exemplary embodiment of the invention, the above effects on kidney function and/or direct effects of urinary system stimulation on body functions are used to provide one or more of the following systemic effects:

(a) Blood pressure reduction. This may be achieved, for example, by increasing renal urine and sodium output, for example by increasing kidney function in one or both kidneys. This also can be achieved by decreasing sympathetic activity, for example by activation of the reno-renal reflex or decreasing of the vesico-vascular reflex.

(b) Blood pressure increase, for example by activation of the vesico-vascular reflex or inhibition of the reno-renal reflex.

(c) Diversion of blood to other organs, while optionally maintaining at least a minimum renal blood flow. This can be done by a number of methods, according to a desired effect. For example, systemic or specific (for example splanchnic) vasoconstrictor agents can be given, together with activation of the reno-renal reflex. In this way blood flow will be redirected from the systemic or splanchnic circulation to the vital organs (heart, brain) and to the kidneys. Vesico-vascular reflex can decrease renal blood flow and increase peripheral vascular resistance.

(d) Change in cardiac load. Cardiac afterload is reduced by reduction of blood pressure, as provided for example by examples described herein. Activation of the reno-renal reflex reduces the total body sympathetic activity and therefore will reduce the sympathetic chronotropic and inotropic effects on the heart.

(e) Temporal redistribution of kidney function and/or load on body systems, temporal modulation of kidney function, for example, to when blood flow is needed in other body parts (e.g., when walking) or not (e.g., when sleeping). This may compensate for damaged blood flow physiological regulation mechanisms.

(f) Kidney rest. Selective control of kidney function by a combination of reno-renal and vesico-vascular reflexes in combination with systemic treatments can halt and restart the activity of the kidney as needed.

(g) Change plasma sodium concentration. Activation of the reno-renal reflex alone or in combination with infusion of sodium will lead to a change in plasma sodium concentration, depending on the intensity of reno-renal activation and sodium load.

(h) Control of total-body water amount can be achieved by increasing and decreasing water balance by the vesico-vascular and reno-renal reflexes respectively.

(i) Increase of renal function, for example by activation of the reno-renal reflex or inhibition of the vesico-vascular reflex.

(j) Various disease states which may benefit by increasing or reducing systemic sympathetic activity. Many disease states can be affected by such modifying, for example, irritable bowel syndrome. In an exemplary embodiment of the invention, modifying sympathetic activity using methods as described herein are used as treatment in diseases where such modification may be useful and/or to counteract an undesired modification caused by another therapy.

It should be noted that some of the above effects are short term effects and some are longer term effects. Optionally, when a longer term effect is desired, the stimulation leading to a short term effect is repeated. Optionally, during a calibration state, a patient is tested to determine his response to stimulations and the duration of effect to be expected. Optionally, the system automatically applies a stimulation and logs its effect. Optionally, the system tries out a plurality of stimulations with different parameters and finally selects one according to its beneficial effect. Optionally, a user is called to select between options and/or reprogram the device based on logged effect. In an exemplary embodiment of the invention, a user has a programmer that can be used to communicate with the device, downloading logs and/or uploading programs and/or tables indicating what stimulation to apply under what condition (e.g., of sensed signals or input).

Exemplary Treatment of Clinical Conditions

In an exemplary embodiment of the invention, the above kidney effects and system effects, optionally together with other bodily control methods are used for treatment of clinical conditions.

In many conditions, including some cases of CHF, the treatment is optionally formulated to correct a hemodynamic imbalance. As such, a control of blood flow in different vascular beds is often desirable. In an exemplary embodiment of the invention, fine tuning of the renal blood flow is provided: renal blood flow should be high enough to maintain adequate renal function. However, in conditions of reduced cardiac output, care should generally be taken to insure an adequate perfusion of other tissue when renal circulation is increased.

For CHF patients, exemplary treatment protocol may include measurements of one or more of patient weight, blood pressure, amount of diuresis, natriuresis, GFR and subjective and objective analysis of dyspnea. Optionally, one or more of cardiac output, renal sympathetic activity (catecholamine spillover), renal blood flow and/or wedge pressure are measured as well.

In the case of finding signs of shock and hypoperfusion, the immediate treatment can be a combination of bladder stimulation to activate the vesico-vascular reflex or administration vasoconstrictors and/or activation of the reno-renal reflex, for example to obtain a positive effect on both blood pressure and renal function, or activation of both vesico-vascular reflex and reno-renal reflex.

In this case, blood pressure and kidney function monitoring may be especially important to assess the progression of the treatment, as excessive vesico-vascular reflex activation may result in hypertension or acute renal failure. One proposed limit of vesico-vascular activation can be stimulation till the mean blood pressure reaches a target value (for example 80 mmHg) or GFR deteriorates by a fixed amount (for example, 20% from control values).

In CHF patients suffering from increased blood pressure, dyspnea, hypernatremia or reduced renal function, activation of the reno-renal reflex with or without concomitant diuretic administration can decrease blood pressure, reduce weight, effectively remove water and sodium, increase the effectiveness of diuretics, increase renal function, decrease cardio-renal interactions and attenuate dyspnea. In these patients, the treatment may continue till the patient reaches a target weight. Optionally, more complex treatment protocols may be used. For example, treatment with stimulation of the reno-renal reflex is commenced till a fixed amount of diuresis is reached (for example, 1 cc/kg/min), the stimulation is then stopped until diuresis drops below predetermined value (for example 0.5 cc/kg/min) or GFR decreases (for example, by more than 20%). Alternatively stimulation can be stopped if a negative effect occurs, for example, if the mean blood pressure drops below 80 mmHg or if severe hyponatremia is found (for example on a blood analysis). The stimulation may be given in a short session, for example during a hospitalization for acute heart failure. In this clinical setup the effects of reno-renal stimulation may be double; first, the short term effect of diuresis to reduce body water levels and reduce dyspnea and ascites/edema symptoms, and/or second, a long term (e.g., one or more weeks or months or years) protective effect on GFR (e.g., no or reduced GFR reduction, or GFR increase). Diuretic treatment alone is known to reduce GFR both acutely but more importantly chronically. Renal function, mainly GFR, is one of the most important prognostic factors in patient morbidity and mortality in CHF. Maintaining GFR during hospitalization is one of the primary goals of CHF treatment. Reno-renal reflex activation increases renal filtration and therefore can protect the kidneys during hospitalization, and reduce the rehospitalization rates due to lesser cardio-renal syndrome intensity.

Stimulation of the reno-renal reflex may be used to specifically inhibit the lethal cardio-renal syndrome present in CHF patients. No current treatment modality usefully reduces the sympathetic drive to the kidneys, which is one of the most important mediators of the cardio-renal syndrome. The cardio-renal syndrome, which can be acute or chronic, reduces renal function, increases water and sodium retention and leads to hypertension, and progressive heart and kidneys deterioration. Breaking of this pathological process may have a number of beneficiary effects in CHF patients. First, reno-renal stimulation frees the kidneys to exert their normal function and correctly control the homeostasis of the body. Second, the stimulation may lead to a synergistic effect with other current treatments of CHF, as increased renal blood flow will increase renal drug delivery and renal metabolism of drugs, so that they or their metabolites will not reach toxic plasma levels. Optionally or alternatively, load on the heart may be reduced.

Chronic modulation of kidney function, for example by activation of the reno-renal reflex, or inhibition of the vesico-vascular reflex may have a paramount importance in treating CHF patients and reducing the chronic cardio-renal syndrome. Optionally, the treatment may be in a form of multiple preventive acute sessions, for example with a catheter based device. Alternatively, the treatment may include implantation of an implantable device and continues stimulation. The added value of such stimulation is patient comfort and prevention of heart and kidney function deterioration, lesser hospitalizations and a better quality of life.

In an exemplary embodiment of the invention, for treatment of CHF and/or hypertension, it is assumed that receptors and/or nerve pathways for the reno-renal reflex are damaged. Optionally, such damage is at least partly overcome by over stimulation and/or by stimulating nerves instead of allowing the receptors to act naturally. Optionally, stimulation is at the location of damaged receptors and either prompts such receptors into action or directly stimulates nerve endings, or other parts thereof, at the location, bypassing the damaged receptors.

Some CHF patients suffer from hyponatremia, which can complicate diuretic treatment. In these patients it is possible to selectively activate the reno-renal reflex to increase GFR and diuresis but not natriuresis. The reno-renal reflex can be combined with sodium infusion and diuretics to elevate plasma sodium levels and increase the effectiveness of diuretics. In these patients, the decision upon treatments can involve body weight measurements (treatment stopped when a target body weight is reached) and/or serum/urine electrolyte measurements. For example, stimulation of the reno-renal reflex can be stopped if high urine sodium excretion is found on urine analysis or plasma sodium levels are reduced above some preset value. Optionally, renal sympathetic stimulation at a desired level is provided to counteract some effects of the reno-renal reflex activation.

When the patient is found to have high renal sympathetic activity, for example by analysis of renal vein catecholamine amount or renal nerve activity (e.g., optionally implanted nerve activity sensors), a chronic reno-renal stimulation may be appropriate; with continuation of may optionally depending on renal sympathetic activity measurements.

For hypertensive patients the workup may optionally include one or more of cardiovascular parameters such as blood pressure, and renal function analysis (GFR and possibly proteinurea). Renal sympathetic activity may be measured as well and treated if abnormal.

In hypertension patients, the reno-renal reflex may not function properly, possibly due to a dysfunction of sensory receptors. The proposed treatment can include direct reno-renal reflex activation by electrical stimulation alone or in combination with known hypertension treatment modalities (for example, diuretics, alpha and beta-blockers, ACEI and ARBs, calcium channel inhibitors, etc.). Activation of the reno-renal reflex reduces blood pressure on the short timescale by reducing total body sympathetic system activity and on prolonged basis because of a more efficient water and sodium removal. Other treatment options may include a combination of the reno-renal reflex with additional stimulation targets (for example carotid sinus stimulation) or renal nerve ablation. Length and intensity of reno-renal stimulation may depend upon blood pressure measurements, so that it can be stopped or weakened when a target blood pressure is reached. Treatments may be provided intermittently, when high blood pressure is detected or suspected by a patient, or continuously, for example with an implantable stimulator, for maintenance purposes.

For patients suffering from CKD, renal function parameters in addition to blood pressure are optionally measured. Renal sympathetic activity can be determined as well. For example, one or more of the following may be measured: renal sympathetic activity, GFR, diuresis, natriuresis, body weight, and hemoglobin.

The treatment may depend on the pathophysiology of renal dysfunction. For example, for patients suffering from malignant blood pressure and increased renal sympathetic activity, activation of the reno-renal reflex can be combined with aggressive antihypertensive treatment, such as treatment known in the art. For patients suffering from reduced GFR and reduced water and solute excretion, the reno-renal reflex may be stimulated together with diuretic treatment, to assist in water and sodium removal without the risk of renal diuretic-mediated shutdown. In this case, the stimulation can be discontinued or weakened if the level of diuresis is satisfactory (for example 1 cc/kg/min), and commenced if reduction of GFR is noticed (for example 0.1 mgdl increase in plasma creatinine).

Acute renal failure is optionally first treated by determining and ameliorating the cause of the renal function deterioration. Reno-renal reflex activation may be provided during the initial stages of renal dysfunction as determined by renal function and urine analysis. In some selected cases renal shutdown, for example by activation of the vesico-vascular reflex, may be preferable, for example during intoxication with a substance that is known to affect the kidneys, the treatment optionally coupled with dialysis to remove the offensive agent. Monitoring of the patient and the treatment efficiency may include body weight as proxy for fluid retention. In the case that body weight increases above desired, or if the patient exhibits other signs of hypervolemia/uremia (for example subjective or objective dyspnea, increase in serum creatinine and/or urea above preset value) the vesico-vascular reflex can be stopped and/or a reno-renal reflex activated. Similarly, if the toxic material is removed from the body or detoxified, vesico-vascular stimulation may be stopped. Stimulation of the reno-renal reflex may be discontinued or reduced if urine analysis reveals elevation of protein levels or appearance of casts indicating hyperfiltration nephron damage. Optionally, renal blood flow is intentionally increased or decreased, optionally by renal vessel stimulation and/or renal nerve stimulation.

A rare, but lethal, hepatorenal syndrome can be managed for example by redirecting blood flow to the kidneys. In patients suffering from this syndrome, weight, blood pressure and/or kidney function analysis are optionally taken. Optionally the pressure in the splanchnic circulation is also measured, either directly or estimated based on clinical signs. Optionally, if kidney functions show progressive deterioration, the reno-renal reflex can be activated (or vesico-vascular reflex depressed or other method used), optionally to increase renal blood flow and renal function. The treatment may be discontinued when desired levels of renal blood flow is reached. If hypotension or portal hypertension is found, the reno-renal reflex may be activated together with systemic or splanchnic vasoconstrictors or a surgical intervention to reduce the portal pressure. This treatment may optionally continue till systemic or blood pressure normalizes, or kidney function improves (for example, a reduction of 0.2 mgdl in createnine levels).

In patients suffering from edema and/or ascites, body weight and renal function can be assessed for signs of reduced diuresis. The reno-renal reflex may be then activated to remove the excessive fluids.

For shock patients, it may be appropriate to increase the blood pressure, increase peripheral resistance but preserve the renal blood flow so as not to damage the kidneys. As mentioned above, a number of possible stimulation methods may be appropriate. The reno-renal reflex can maintain renal perfusion, while vasoconstrictors or vesio-vascular reflex increase systemic blood pressure.

Women suffering from preeclampsia may benefit from activation of the reno-renal reflex. In these patients, blood pressure, kidney function and the fetal distress signs are optionally assessed to decide upon the treatment. If maternal and fetal status do not require urgent delivery, reno-renal reflex stimulation may be used, optionally to reduce blood pressure and prolong the pregnancy. Monitoring may include blood pressure and fetal sonography. The treatment may continue either intermittently when high blood pressure is determined, or intermittently, for example as a preventive treatment.

In cases of Dyspnea, high wedge pressure, diuretics are optionally administered for venous vasodilatation and a reno-renal reflex evoked to maintain GFR.

In an exemplary embodiment of the invention, of treating hypertension, a short term effect is lowering sympathetic drive. This can have an effect in seconds. On a longer term effect, of hours or days or weeks, reduction in sodium and fluid levels can reduce fluid volume in the body and blood pressure.

In an exemplary embodiment of the invention, restimulation at short intervals is used to enhance and/or maintain the effect on the sympathetic system.

The described systems/methods can work together and affect working of a cardiac pacemaker. One example follows. Activation of a reno-renal reflex is expected to reduce the whole body sympathetic activity. In an otherwise healthy individual, decrease of the sympathetic system leads to reduction of the heart rate. In many cases of patients equipped with a pacemaker, the pacemaker determines the rhythm of the heart. To mimic the correct physiologic response, the described device can optionally signal the pacemaker to reduce the pacing frequency. In another example, the pacemaker and urinary stimulator together affect cardiac output by, for example, control of afterload or preload using the urinary stimulator with appropriate cardiac stimulation by the pacemaker. Optionally, during an arrhythmia or fibrillation, flow to the kidneys is shut down, for example, to improve flow to the brain.

Control Specificity

In some cases, a single stimulation location affects several kidney and/or system function simultaneously. Optionally, two or more stimulations are applied together to result in a desired more specific effect, with one stimulation modulating the other. Optionally or alternatively, some effects (e.g., the acute effect on blood pressure vs. change in GFR) have different time constants from others (e.g., due to an inherently different time constant of the cause, such as the cause being hormones or sympathetic activity and/or due to an effective time constant mediated by the activation of various homeostatic and other feedback controls of the body) and closing a feedback loop on one effect to reduce the efficacy of providing a second, undesired effect.

Optionally, one or more of the following methods are used to provide increased specificity:

(a) The sympathetic drive to the kidney affects different aspects of kidney function according to the strength of the sympathetic activity. Lowest strength triggers renin secretion (and thus elevates blood pressure) stronger intensity reduces diuresis and natriuresis and the strongest intensity leads to reduction of renal blood flow and GFR. In an exemplary embodiment of the invention, the sympathetic control of the kidney is modulated together with another stimulation, thereby providing additional specificity. Optionally, sympathetic drive is modulated by stimulating the carotid body (e.g., with a direct effect on renal nerves).

(b) Optionally or alternatively, cooling (e.g., with a contact cooler) or heating (e.g., with a contact heater) of the skin is used, with cooling generally increasing GFR on a transient basis and/or rediverting blood flow towards organs other than the skin.

(c) Optionally or alternatively, modulation of hepatic pressure (e.g., by placing a constricting or valve in or on the portal vein or stimulating the splanchnic nerve is used, wherein increased hepatic pressure reduces renal blood flow.

(d) Optionally or alternatively, pressure is modified in renal veins (e.g., using a valve or an external constriction, such as an inflatable balloon), wherein increased renal venous pressure reduces renal blood flow.

(e) Pharmacology can be used to provide addition effects or counteract some effects of stimulation. For example, a reno-renal reflex may be evoked while providing vasoconstrictors for shock treatment, thereby avoiding kidney damage due to low blood flow. Optionally, kidney blood flow is provided at an increasing or cycling amount, for example, with a lowest amount provided when shock is first treated and then additional blood flow provided after a time (e.g., 30-45 minutes), possibly only in an amount sufficient to prevent kidney damage.

Exemplary System Design

Figure 4:
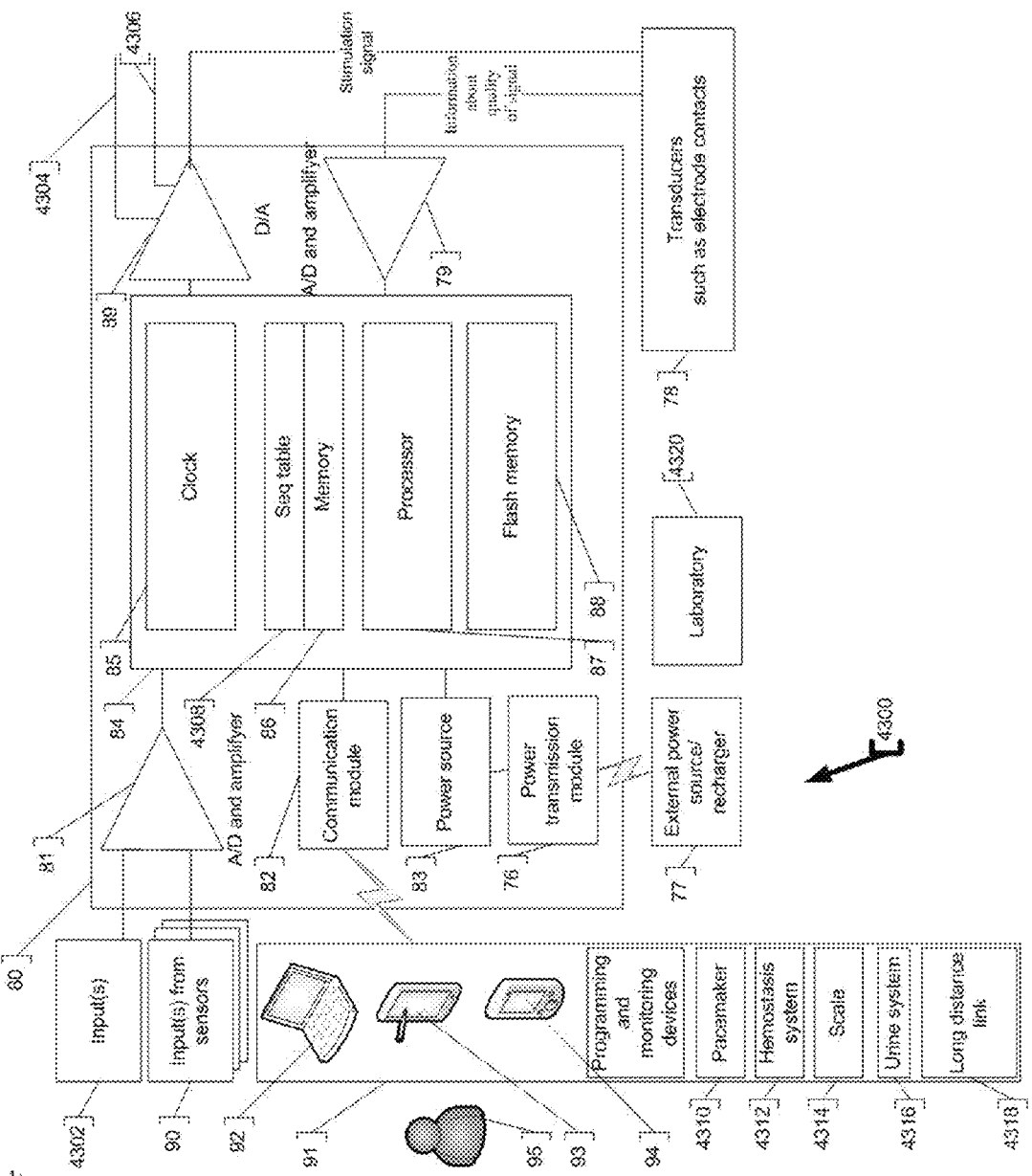
FIG. 4 is a more complete schematic block diagram of a urinary system stimulation system, in accordance with an exemplary embodiment of the invention.

FIG. 4 is a schematic block diagram of a urinary system stimulation configuration 4300, in accordance with an exemplary embodiment of the invention. It should be noted that the actual device may have a different design from the configuration described below. Rather, this configuration is used to highlight various optional features which may be provided in devices according to some exemplary embodiments of the invention.

As shown, an exemplary design includes a circuitry component 80, transducers 78 (e.g., stimulating electrical contacts), one or more optional sensors 90 and/or various optional external elements.

Referring first to circuitry component 80, which is optionally provided in a housing, component 80 optionally includes a controller 84. As shown, controller 84 can include an optional clock 85, a memory 86, optionally including a stimulation sequence table 4308, a processor 87 and more permanent storage 88, such as flash memory. Optionally, storage 88 is used to store a log, for example, a log of activations and/or measurements and/or of analyses thereof. Optionally or alternatively, processor 87 is provided as dedicated circuitry. Optionally or alternatively, memory 86 includes algorithms for analyzing sensor inputs and selecting a sequence from table 4308 and/or for calculating a sequence to be applied. Optionally or alternatively, memory 86 includes a set(s) of stimulation and/or control parameters for controlling a plurality of parameters. Optionally or alternatively, the memory includes a plurality of application protocols. Optionally or alternatively, the memory includes possible ranges of stimulation parameters. Optionally or alternatively, the memory includes times and/or events at which to apply certain stimulations. Optionally or alternatively, the memory includes a link between inputs and a disease state, and suitable physiological effect targets and/or stimulation sequences for certain disease states.

In an exemplary embodiment of the invention, controller 84 generates or triggers a stimulation signal via stimulation circuitry 89, for example, a capacitor with a switch. Optionally, two or more sets of stimulation circuitry are provided.

In an exemplary embodiment of the invention, one or more leads (4305, 4304, 4306) are provided. Each such lead may terminate with a transducer (e.g., an electrode contact or thermal stimulator contact) 78. Various transducer and lead designs are described below. Optionally, a circuit 79 is provided for evaluating the quality of the transduction and/or delivery, for example, by monitoring lead and/or contact impedance. An exemplary method of evaluating quality is described below.

In an exemplary embodiment of the invention, circuitry component 80 includes a sensor and input processing circuitry 81, which, for example, processes input from one or more sensors 90 and/or input from one or more inputs 4302. Some exemplary sensors and inputs and possible feedback mechanisms are described below.

In an exemplary embodiment of the invention, circuitry component 80 includes a power source 83, such as a battery or a mains supply. Additional exemplary embodiments of power sources include a primary battery, a rechargeable battery such as a lithium ion battery, an electrolytic capacitor, or a super- or ultra-capacitor. Optionally, power (e.g., for operation and/or for charging the power source) is provided by wireless coupling, for example, using an external power source/recharger 77 and an internal power transmission module 76 for receiving such power, for example, using inductive coupling coils, an RF link, an optical link, and/or an ultrasonic link.

In an exemplary embodiment of the invention, circuitry component 80 includes one or more communication modules 82, for communicating with external devices. Such communication can be, for example, wired, for example, for sending or receiving signals from other implanted devices or other out of body devices. In another example, circuitry component 80 includes a USB connector for connecting to a computer. Optionally or alternatively, a wireless communication mode is supported, for example, using radio-frequency (RF) (e.g., a local link such as BlueTooth, Zigbee or WiFi), optical coupling, thermal coupling, ultrasonic coupling or electromagnetic coupling. In one example, the communication module comprises an inductive coil (not shown) for receiving and transmitting RF data and/or power, an integrated circuit (IC) chip for decoding and storing stimulation parameters and optionally additional discrete electronic components required to complete the electronic circuit functions, e.g. capacitor(s), resistor(s), coil(s), and the like. Optionally, the IC is used to generate stimulation pulses (e.g., intermittent or continuous).

In an exemplary embodiment of the invention, communication module 82 and power transmission module 76 are unified. In an exemplary embodiment of the invention, input(s) 4302 and/or communication module 82 are used to enter external data, for example, laboratory results from an external laboratory or test unit 4320, for example, a unit which analyses urine and/or blood chemistry. Additional examples of externally entered data are weight, medication ingestions and/or general feeling (headache, malaise, etc.).

In an exemplary embodiment of the invention, communication module 82 is used to connect to one or more programming and/or monitoring and/or co-operating systems. In some embodiments of the invention communication is with other stimulator system(s), other implanted devices and/or devices 91 external to a patient's body using one or more different communication protocols.

In one example, a laptop 92, a cellular telephone 93 or a miniaturized computer or PDA 94 are used by a user 95 for programming circuitry component 80 and/or monitoring its operation and/or generating commands thereto.

Optionally or alternatively, a pacemaker 4310 (or other cardiac control device) commands circuitry 80, is commanded by circuitry 80 or coordinates therewith. In one example, a combined therapy is used for heart failure. In another example, blood flow to the kidneys is reduced when pacing is applied, to compensate for reduced cardiac output. In another example, circuitry 80 is disabled when a defibrillation signal is generated by device 4310. In another example, circuitry 80 senses pacing signals and uses such signals to decide on an operational mode thereof. In another example, pacing rate is reduced when stimulation of the urinary system is used to reduce sympathetic drive. In another example, pacing is used to increase cardiac output when vasodilatation is caused by urinary system stimulation.

Optionally or alternatively, a pacemaker or other controller for a heart, stomach and/or other organ shares components, such as a housing, a power supply, a controller and/or a communication module with a urinary system stimulation system. It is noted that in some embodiments of the invention stimulation of the urinary system uses a periodicity which is significantly lower than cardiac pacing, for example, $\frac{1}{2}$, $\frac{1}{4}$, $\frac{1}{10}$ or less or intermediate parts of the periodicity of cardiac pacing (typically 1-2 per second). Optionally or alternatively, the power used for the urinary system is lower than in the cardiac system. This may be, for example, for one or both of two reasons. First, in pacing, "capture" by the heart is essential. In the urinary system, there is usually no immediate threat by missing a single activation. Second, in the heart, stimulation of a significant area of muscle tissue is often required. In the urinary system, in some embodiments of the invention smaller areas and/or more sensitive tissue (e.g., nerve receptors) are stimulated. For example, the power of a single exciting stimulus train in the urinary system may be, for example, less than $\frac{1}{2}$, $\frac{1}{4}$, $\frac{1}{10}$, $\frac{1}{20}$ or intermediate portions of that used to capture a heart during pacing of the left ventricle from the apex in the right ventricle (e.g., 5-8 mA for 2 ms). This may allow a longer battery life and/or the use of smaller batteries.

In another example, multiple stimulation systems for a urinary system are provided, for example, one system for nerves and one for ureters. One or both systems may be implanted.

In another example, stimulation system 4100 is part of (or receives input from) a homeostasis system, for example, as may be provided in an ICU to control hydration levels and blood chemistry by, for example, providing medications or infusions depending on measurement of body parameters. In one example, circuitry 80 provides instructions to modify fluid provision and/or provision of medication of blood components, food or ions. Alternatively, an external system controls multiple fluid and chemistry modifying sub-systems, one of which is system 4100. Optionally or alternatively, system 4100 is instructed to stimulate a reno-renal reflex if salt levels are up in the blood and/or if urine levels are down.

In another example, a scale 4314, for example, a scale equipped with a wireless transmitter is used to indicate to circuitry 80 a patient's weight, which may be used to automatically change a fluid retention schedule thereof.

In another example, system 4100 may include or be coupled to a urine system 4316, for example, for measuring urine flow and/or content. Such measurements may be used to, for example automatically, modify system operation.

In another example, a lung-fluid monitoring system is used, for example, to provide feedback on ability of the system to improve fluid in the lung conditions and/or trigger an increase in renal output to reduce fluid retention in the lungs.

In another example, system 4100 may include or be connectable to a long distance link 4318, such as using a land line or a cellular communication protocol. For some applications, urinary system stimulation configuration 4300 includes a hemostasis system 4312.

Exemplary Implantable Device

Figure 6:
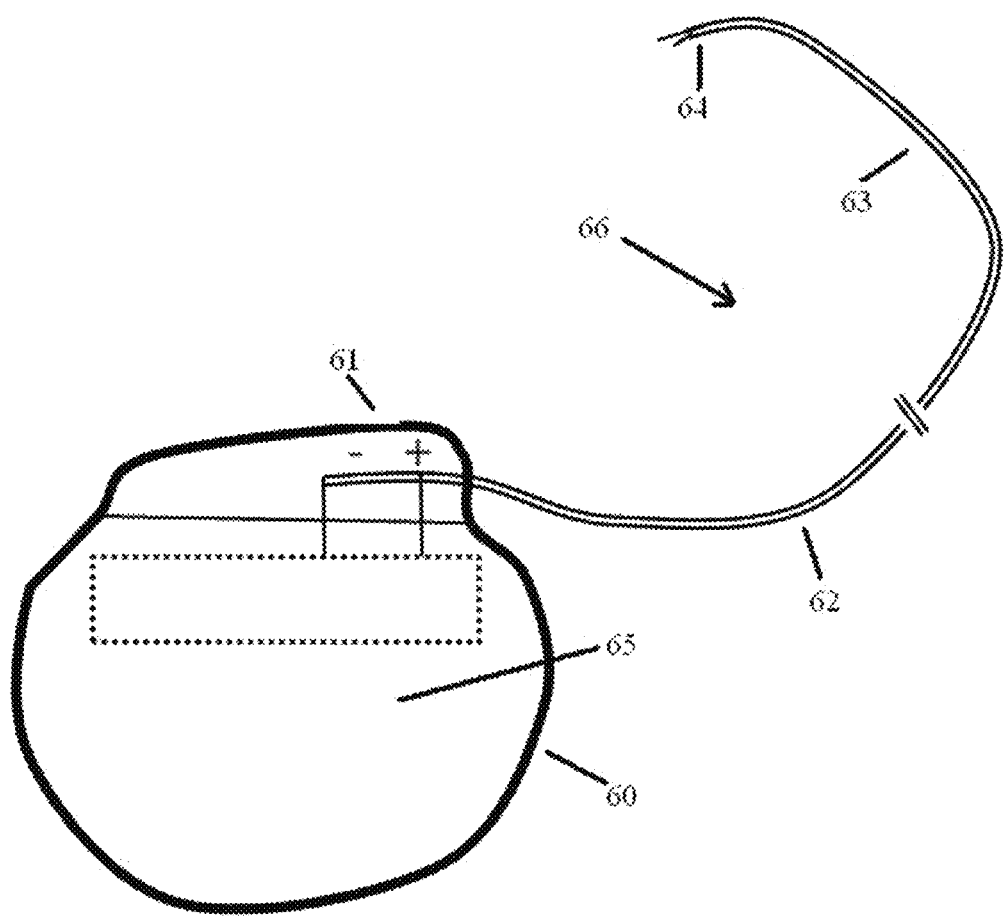
FIG. 6 illustrates an implantable stimulation system according to an exemplary embodiment of the invention.

In some embodiments, circuitry component 80 is implantable. FIG. 6 shows an exemplary implantable system 60 in which a capsule 65 is provided which encloses circuitry component 80.

An electrical stimulator 66 (e.g., a lead 62 with a distal side 63 and a proximal side 64), terminates with one or more electrical contacts 64, and is coupled to system 60 using a connector 61, for example of a type known in the art, for example, with connectors to 2, 3, 4 or more leads or other wires. Optionally, capsule 65 serves as a ground or other electrode. In an exemplary embodiment of the invention, contact(s) 64 are adapted for coupling to a ureter, for example, as described below.

Capsule 65 can be of a design known in the art of pacemakers and is optionally a pacemaker capsule including cardiac pacemaker circuitry programmed to provide stimulation as described herein.

Exemplary electrode and lead designs are provided below.

Capsule 65 is optionally made or coated with biocompatible materials, such as noble or refractory metals, materials or compounds, such as platinum, iridium, tantalum, titanium, titanium nitride, niobium, or alloys thereof, or of a polymer. Optionally, capsule 65 is hermetic to liquid and/or vapor passage. Optionally, capsule 65 is designed to permit passage of electromagnetic (or other) fields used to transmit data (including commands) and/or power.

The shape of the stimulator 60 is optionally determined by the structure of the desired anatomy, the surrounding area, and the method of insertion or deployment, and can be, for example, of a standard pacemaker for the heart, or an elongate element which does not interfere with bending of the body.

Exemplary dimensions of a housing are, for example, between 3-5 cm by 3-5 cm by 0.5-1.5 cm. An exemplary volume is less than 30 cc, less than 20 cc, less than 10 cc or intermediate volumes.

Exemplary Trans-Urethral Device

In some embodiments, circuitry component 80 is left outside the body. This may be the case, for example, if the stimulation is via a transurethral stimulator, but in other cases as well, for example as shown below.

Figure 7:
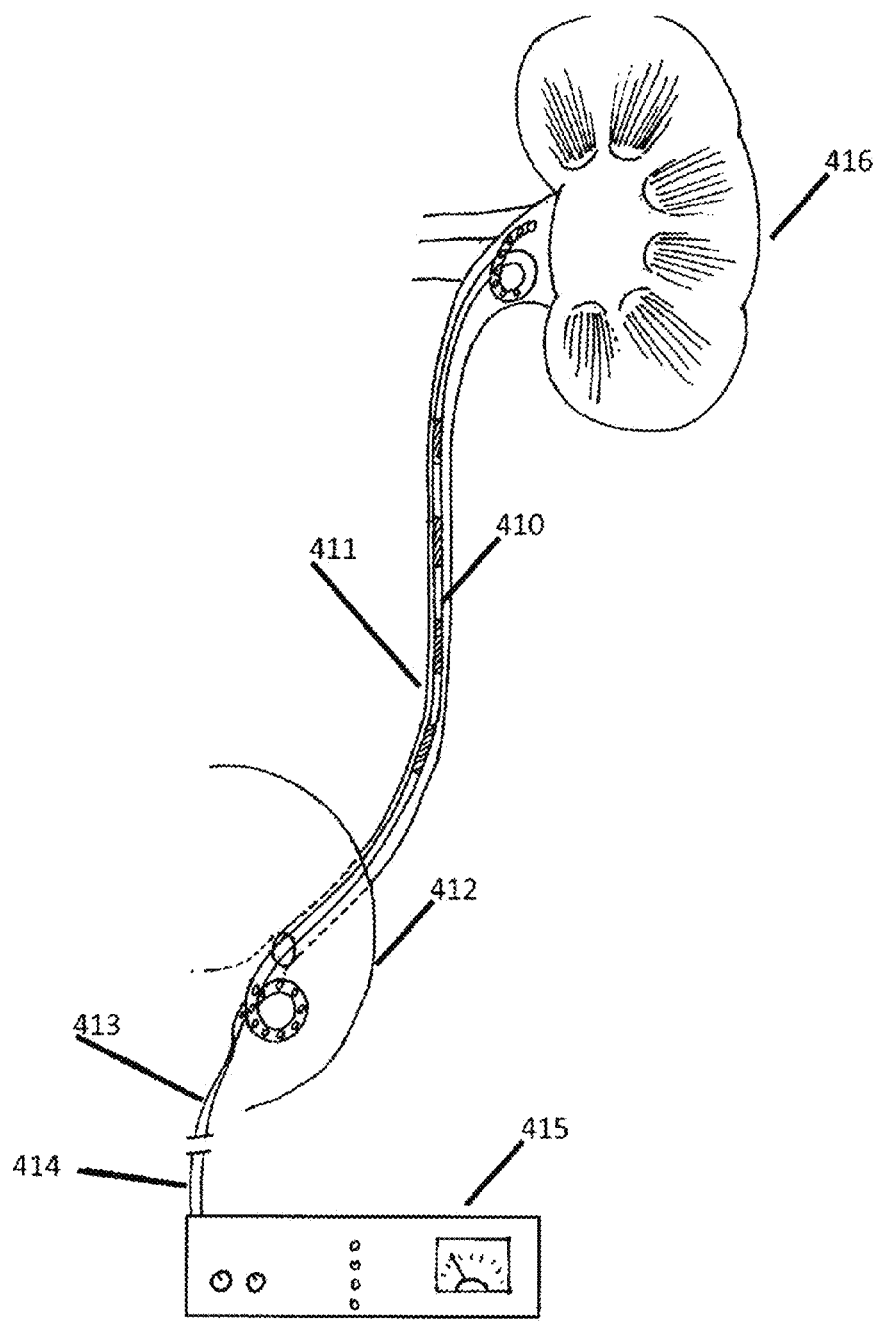
FIG. 7 illustrates an external and ureter-dwelling stimulation system according to an exemplary embodiment of the invention.

FIG. 7 shows an optional embodiment of an electrical stimulator where the control circuitry is provided within an external unit 415. Unit 415 is optionally connected to one or more optional electrodes, for example to an electrode lead 413, optionally coupled through a connector 414. As shown, lead 413 is optionally integrated with a stimulator based on an ureteral indwelling catheter 410 including one or more contacts, which typically lies in a ureter 411 between a urinary bladder 412 and a kidney 416.

Other embodiments described below show embodiments where lead 413 is part of an in-bladder device, such as a stimulator based on a Foley catheter which is configured to electrically stimulate parts of the bladder, in particular a trigone area thereof.

Dimensions of an external stimulator control unit can be, for example, between 1-5 cm by 1-5 cm by 0.5-1.5 cm. Optionally, the unit is cylindrical and has a size of about 1-2 cm diameter and 3-5 cm in length. An exemplary volume is less than 30 cc, less than 12 cc, less than 5 cc or intermediate volumes.

Exemplary Sensors

Various sensors may be used with a urinary stimulation system, including, for example, one or more of the following. It should be noted there are various packaging options for the sensors. For example, the sensors can be packaged with circuitry 80. In some cases the sensors are connected to circuitry 80 using a lead, optionally sharing a lead with a stimulator. In some cases the sensors are connected using wireless means. In some cases, the sensors provide their input via human intervention. For example, the following types and exemplary sensors, while being only examples, may be used:

(a) Device functionality. Sensed signals can include impedance measurements, optionally to determine contact efficiency between electrodes and tissue. This sensor can help with performing focal stimulation of selected region. Optionally the sensor is connected to an output to the user indicating whether focal stimulation can be commenced. Impedance sensing can be important when both an anode and a cathode are in the bladder, whereby if there is poor wall contact urine may short circuit the stimulation. In some embodiments, at least one electrode is outside the bladder and in contact with body tissue and not urine.

(b) Urinary system physical behavior. Sensed signals can indicate various aspects of urinary system behavior, such as ureteral urine flow that can be optionally determined by a flow sensor located inside or outside of the ureter, by ultrasound (US) methods or by external device, as known in the art. Ureteral motility/electrical activity can be used a proxy for ureter urine flow, ureteral motility can be measured for example by a pressure sensor located within or outside of the ureter. Ureteral electrical activity can be detected by a sensor located inside or outside of the ureter, in the bladder or in other pelvic organs; ureteral electrical activity can be isolated from other signals by a distinct signal shape, the vector of propagation and/or signal frequency. Urine flow within the ureter can be used as an indicator of stimulation efficiency or need for a stimulation. Additionally, bladder volume can be measured by ultrasound, by radio frequency radiation, mechanically or electrically, for example by impedance. Bladder pressure can be measured by intravesical or extravesical pressure sensor. Optionally the pressure sensor is located on the outside of the body part of the stimulation device. Bladder volume/pressure can indicate efficiency of stimulation and/or activation of the vesico-vascular reflex. In an exemplary embodiment of the invention, urine flow is used to indicate low kidney function, or efficiency of treatment. For example, urine flow can indicate when additional stimulation should be given. The sensor can be located within the lumen of the catheter.

(c) Kidney function. Sensed signals can include sensing of renal blood flow, for example by electric, mechanic or ultrasound flow meter located inside or outside or renal arteries or veins. Additionally, renal blood flow can be measured pharmacologically, as known in the art. Renal sympathetic activity can be measured using renal nerve electrical activity measurement or by measuring catecholamine levels, preferably in the renal vein. Urine concentration or composition can be determined by a sensor located within the urinary system (for example ion electrodes to measure sodium and potassium) or by external urine analysis. Sensing of GFR can be performed by measurements of plasma/urine levels of inulin, creatinine, urea or other markers as known in the art. Creatinine and urea can be measured inside the body by dedicated electrodes, as known in the art, or using suitable optical sensors. Additional sensed signals may be hormone secretion from the kidney, from example renin, CGRP or erythropoietin, optionally measured in the renal vein or urine. Sensed signals can be used to indicate efficiency of treatment, need for a treatment and/or as indication to the user of a change in renal function. For example, a drop in the sensed GFR above preset amount (for example 20%) may activate stimulation of the reno-renal reflex.

(d) Cardiovascular parameters. In an exemplary embodiment of the invention, the sensed signals indicate cardiovascular parameters that may mirror cardiovascular function. For example, blood pressure can be measured by a pressure sensor located in or on a artery, optionally the renal artery or measured externally as known in the art. An additional signal that may be measured is blood flow, measured by a flow sensor. ECG signals, heart rate, cardiac output and/or vascular resistance may be measured by sensors located within or on blood vessels or optionally by ultrasound sensors. Cardiovascular parameters can be used to indicate efficiency of treatment, need for a treatment and/or as indication to the user. For example, reduced blood pressure sensing may suggest stimulation of the vesico-vascular reflex or vasoactive substance secretion or elution into the body, for example, using a medicament pump to pump this and/or other medicaments under control of the stimulation system. Increased blood pressure sensing may suggest stimulation of the reno-renal reflex.

(e) Blood and systemic. In an exemplary embodiment of the invention, the sensed signals indicate the status of body systems, such as the blood, for example blood analysis optionally performed on blood samples taken from the patient; body temperature measured by internal or external thermometer, optionally the thermometer is integrated into the stimulating device; plasma and/or urine glucose levels, measured by internal or external glucose meter; systemic sympathetic activity optionally measured from plasma or urine catecholamine levels or from electrical recordings of muscle twitching; input from external fluid status monitoring systems and oxygenation level optionally from a pulse oximeter. Sensing of these signals may be used to direct treatment; for example, a change in liver functionality may indicate progression of a hepatorenal syndrome and can be used to start and/or modulate reno-renal reflex stimulation.

(f) Indirect sensing. Sensing may include patient weight; position of the patient; input from the patient about her well being and motion of the patient. These external sensed signals can be used as indicators of stimulation efficiency or a need for a stimulation. For example, increase in body weight above preset number in a CHF patient may be used a signal for reno-renal reflex stimulation. An additional example is movements of the patient which may interfere with the stimulation/sensing of electrical signals (e.g., so stimulation/sensing may wait for such movement to stop and/or may be corrected for it).

Exemplary Control Loops

Stimulation system 4100, may be provided with one or more feedback modes, depending, for example, on its implementation and/or programming. In one example, system 4100 operates in an open loop mode. In such a mode, the device is programmed to provide stimulation at set times, periods and/or other parameters. One example where this may be useful is when a patient is identified as having high fluid retention and system 4100 is used to reduce fluid load by increasing kidney activity. A standard protocol, such as application for 2-10 hours or 3-10 days may be provided. In another protocol, chronic stimulation is used, for example, for 2-4 months or 2-4 years. Optionally, even in an open loop mode, a safety feedback is provided to stop operation of system 4100 or perform a counter-operation and/or provide an alert if a safety threshold is passed or a safety problem otherwise detected. For example, when the electrical charge provided by the stimulation may harm the stimulated structure. In one example, low renal blood flow, low blood pressure or high blood pressure, caused by over stimulation is detected. Optionally, the maximum allowed renal blood flow and/or output are set and the system optionally applies a suitable stimulation or stops stimulation if a threshold is passed. Such safety features may be used with other renal/urinary stimulation systems as well.

Another exemplary mode is a semi-open loop mode, in which feedback is provided relatively infrequently, for example, once an hour, once a day, once a week or at intermediate length times. This may be used, for example, for body weight (optionally including an input for patient to indicate intake of food and/or fluid, which may be corrected for.

Another exemplary mode is closed loop mode, in which feedback is provided on a time scale similar to the effect on the body system being controlled by stimulation system 4100. For example, feedback on blood pressure may be provided every minute. An additional exemplary closed loop may include measures to prevent patient dehydration and/or hyponatremia. Optionally, a manual input to the device is first made indicating the actual vs. the desired weight of the patient, and/or plasma sodium levels. Optionally, the device has sensors to measure urine flow and/or urinary sodium concentration. By counting the amount secreted it is possible to discontinue the stimulation when the desired fluid removal is reached, or when the amount of excreted sodium may lead to hyponatremia. An additional exemplary closed loop may be an automatic stimulation of the reno-renal reflex when renal function deteriorates. Optionally, the device senses GFR or urine flow, for example once an hour. If renal function is reduced below some preset value, as sensed, the device may start stimulation of the reno-renal reflex, optionally until renal function improves. An additional exemplary closed loop may be an enhancement of a naturally occurring reno-renal reflex. It is possible that in patients suffering from hypertension the reno-renal reflex may not be functioning sufficiently to excrete fluid and sodium from the kidneys. Optionally, stimulation of the reno-renal reflex may be imitated when a natural stimulus of reno-renal reflex activation, such as increased urine flow or urine sodium levels are detected by the sensory element. The benefit from this method of stimulation may be a more physiological activation of the reno-renal reflex as needed for example when the patient consumed large amount of water or sodium. Optionally, the sensing includes bladder volume/pressure sensing and inhibition of the vesico-vascular reflex to prevent activation of the sympathetic system. In one example, closed loop operation is pre-limited to a certain time frame and/or to a certain number of measurement-stimulation cycles. It is note however, that in general, system 4100 need not take a measurement before each stimulation event. For example, measurements values can be estimated instead of measuring, or feedback may be defined to be taken periodically or on some other basis.

In an exemplary embodiment of the invention, a stimulation sequence parameter set includes one or more of stimulation sequence, desired short and/or long term effects, safety parameters of one or more physiological sensors, a feedback mode and/or a logic for determining and acquiring feedback or further instructions.

In an exemplary embodiment of the invention, the mode of operation takes into account a residual effect of stimulation. As shown below some stimulations have an effect on kidney function lasting at least up to several hours after application. Such stimulation sequences may be considered to be inherently open-loop or semi-open loop. In some cases, such effects are counteracted by additional stimulations, if limitation thereof is desired. Optionally, the stimulation applied depends on patient specific parameters, for example, cardiac output. This may be instead of or in addition to setting of safety parameters such as threshold amounts of change in blood pressure.

In an exemplary embodiment of the invention, reflexes are controlled directly. For example, a base-line activity of a reno-renal reflex and/or a vesico-vascular reflex may be measured directly, for example, by measuring nerve activity or indirectly by measuring effect. Optionally, a control loop is closed by the stimulation system raising and/or lowering a level of activity of the reflex, for example, by stimulation of receptors and/or nerves involved in the reflex. In some embodiments, this is an example of external control of an existing control loop. In some embodiments, the control is instead of diminished body control.

In some embodiments of the invention, information or commands to close the loop are provided externally, form a user. For example, a user can indicate when a feeling of malaise starts and when it finishes. Optionally, the control circuitry may be configured to modify and/or otherwise process user input. For example, even if a user indicates to stop stimulation, the circuitry may continue stimulation, for example, to provide an easing off, or if measured parameters indicate a continuation and/or changing of stimulation.

Figure 8:
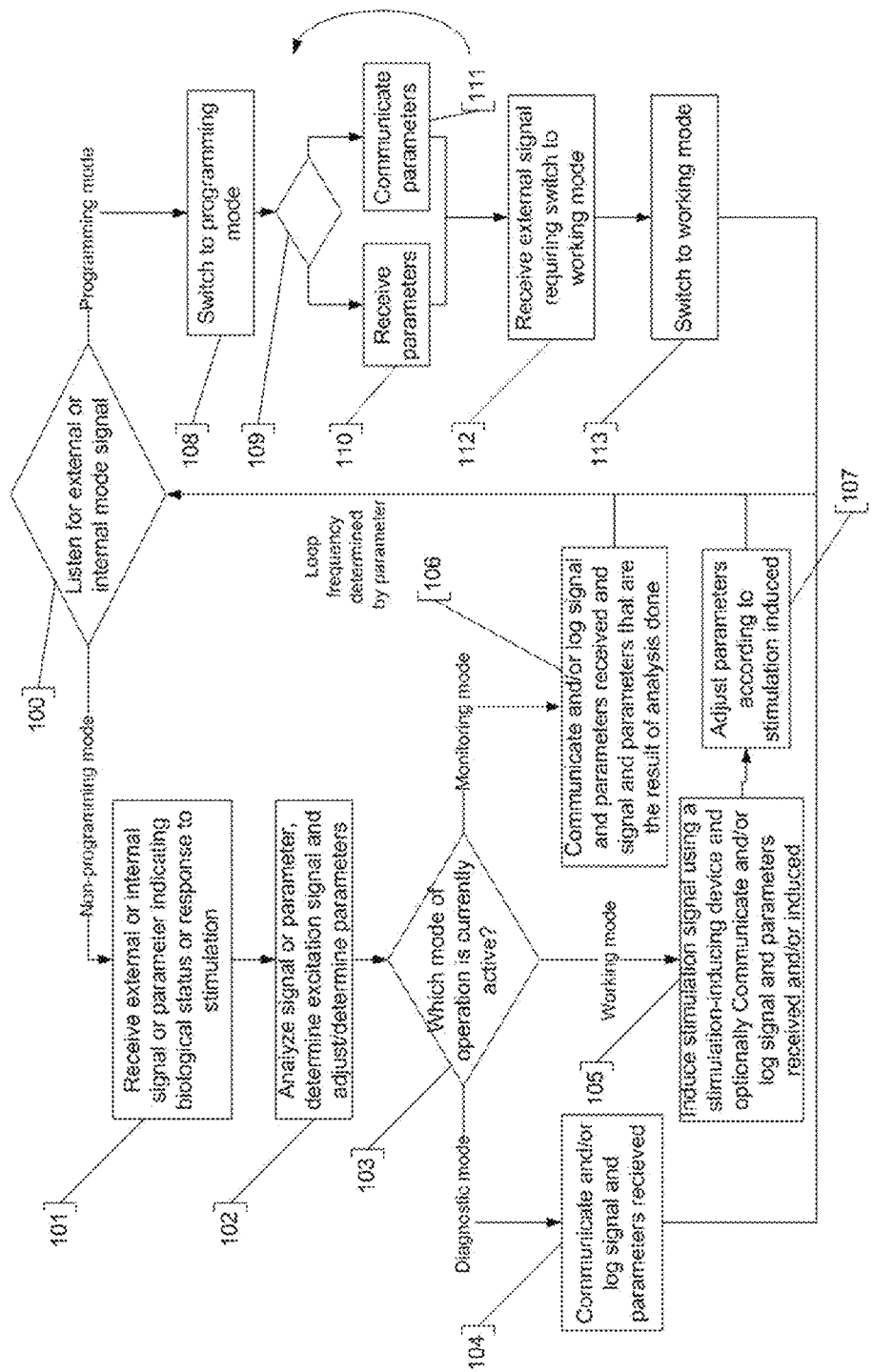
FIG. 8 illustrates a feedback process, according to an exemplary embodiment of the invention.

FIG. 8 illustrates a feedback process in accordance with an exemplary embodiment of the invention.

At 100, a mode of operation (programming or non-programming) is selected, for example, based on an internal command or an internal processing.

In an exemplary embodiment of the invention, when in non-programming mode an external and/or internal signal and/or parameter optionally indicating biological status or response to stimulation is received at 101 (e.g., feedback or command). The signal or parameter received is optionally analyzed at 102 and a desirable stimulation (e.g., excitation) signal is determined. Optional adjustment or determination of algorithm parameters (e.g., stimulation parameter set) may also be done at 102.

In an exemplary embodiment of the invention, at 103, a sub-mode of operation is determined, diagnostic, working or monitoring. When in a diagnostic mode (104) the signal(s) and/or parameter(s) received are optionally communicated and/or logged. When in a monitoring mode (106) the signal(s) and/or parameter(s) received and/or the parameters that are the result of the analysis done by system 4100 are optionally communicated and/or logged. When in working mode (105) the stimulation signal is induced. Optionally the signal(s) and/or parameter(s) received and/or induced are communicated and/or logged. Following signal induction the algorithm parameters may be adjusted according to the stimulation induced and/or its effect (107). Other exemplary feedback methods which may be used together or instead, are described herein.

When in a programming mode (108), system 4100 optionally receives parameters in stage 110 and/or communicates parameters in stage 111 optionally as part of a recurring loop (109). When programming is completed, system 4100 optionally receives an external signal (112) causing a switch to working mode (113) and optionally a return to listening (100).

Optionally, when no external or internal signals are received to indicate otherwise, system 4100 passes from 100 to 101 automatically.

Exemplary Stimulation Modalities

While electrical stimulation is preferred for some embodiments of the invention, other stimulation modalities are provided in accordance with some embodiments of the invention. It is a feature of some embodiments of the invention that stimulation affects various receptors in the urinary system, for example, afferent nerves, pressure receptors and/or tension receptors. It is a feature of some embodiments of the invention that stimulation is used to trigger an existing reflex, rather than control a process. These two features, together or separately, can make it useful to use non-electrical stimulation, which is less specific with respect to magnitude and/or more specific with respect to receptors being triggered.

In one example, afferent nerves are stimulated using light, chemicals, ultrasonic vibration and/or heat.

In another example, mechanical receptors are triggered by stretching, pressure or vibration. For example, expanding an object in a ureter can simulate blockage of the ureter by a reno-renal reflex. Such expansion, for example as shown below, need not block the ureter, but can be used to selectively reduce output from the "blocked" kidney and/or increase output from an opposite kidney.

In an example of chemical stimulation, chemical stimulation of the reno-renal reflex can be by saline, potassium, hydrogen ions (low pH) and capsaicin to the ureter or bladder. Chemical substance can be released by perfusion from a nephrostome, ureter catheter, bladder-dwelling stimulator and/or implanted container. In an exemplary embodiment of the invention, chemicals are released via one or more pores (e.g. 1-10) each having a surface area of between, for example, 0.1 square mm to 1 square mm. Optionally or alternatively, chemicals are eluted, for example, using iontophoreses or other electrical driving scheme, for example, from a gel, solid or hollow storage element, optionally using an electric field which causes stimulation intentionally or a field which does not. Optionally or alternatively, chemicals are provided using a pump. Optionally or alternatively, chemicals are released using a sustained release method and/or chemical matrix, as known in the art for drug delivery methods.

One option for a chemical stimulation of the bladder is intermittent (e.g., each "puff being, for example, 1-5 minutes and spaced apart 1-3 hours) puffs of capsaicin to the trigone by a Foley like device with delivery element close to the trigone, arranged similar to the electrical contacts. Optionally or alternatively, stimulation of the rest of the bladder, possibly with longer duration is used to reduce vesico-vascular reflex. It is expected that a capsaicin puff will lead to desensitization of the receptors, which may be good for reducing vesico-vascular reflex.

In an example of mechanical stimulation in the ureter, mechanical stimulation is optionally intermittent, as chronic dilatation of the ureter may result in refractoriness, with the ureter possibly expanding to a larger volume.

Optionally, the ureter is expanded by a balloon. Optionally or alternatively, the trigone is mechanically activated by one or both of an additional balloon (on the bladder filling balloon) and/or a stiff mechanical element that is moved by an external or an internal engine or by magnetism.

Specific examples of non-electrical stimulators are provided below.

Exemplary Stimulation Parameters

Before relating to specific stimulation parameters, it is noted that a stimulation sequence may be applied in response to an event, in response to a command and/or in response to a time. Further, the sequence applied may be modified, for example, based on a history of application, a desired long term effect and/or based on a physiological (or other) input. Such variation can also be applied to a continuously applied stimulation sequence. It should also be noted that a stimulation of the urinary system and/or the body may involve multiple stimulators, each such stimulator being controlled as described herein, optionally, but not necessarily, in a synchronized manner, with known delays and/or synchronized to events or sensed values.

In an exemplary embodiment of the invention, various application parameters as described herein are applied and/or modified automatically by the control circuitry of system 4100.

Referring now to an arbitrary stimulation sequence (e.g., electrical, but possibly other modality as well). A sequence can have a length of, for example between 0.01 seconds and 2 hours, for example, between 10 seconds and 19 minutes, for example, about 10 minutes long. Optionally, such a sequence comprises a train of pulses or a long pulse or a series of sub-trains of pulses, with delays there between. Within a sequence, there can be, for example, a plurality (e.g., between 1 and 100, for example, above 4 and/or below 30) of different pulses and/or sub-trains. In an exemplary embodiment of the invention, the actual stimulation parameters used are varied to reduce adaptation, habitation and/or perceptible and/or painful sensations. Optionally, a set of 2-20 (e.g., 3-4) or more different sequences with a same expected effect are cycled to reduce such habitation.

In an exemplary embodiment of the invention, pulses and/or sub-trains and/or sequences are charge balanced (e.g., biphasic) and/or designed so that there will not be too much charge asymmetry in a given period of time.

In an exemplary embodiment of the invention, delays between sub-trains and/or between applications of sequences are selected according to one or more consideration, for example, continued effect of a stimulation after it stops, desired for tissue to recover, desire for tissue to apply other, uncontrolled functionality and/or desire for tissue to return to a baseline so that baseline can be measured.

In an exemplary embodiment of the invention, a single pulse can have a single frequency, for example, between 0.1 and 100 kHz, for example, between 5 and 1 kHz, for example, between 20 and 100 Hz. Optionally or alternatively, a pulse may be a combination of frequencies, for example, two, three or more frequencies. In an exemplary embodiment of the invention, a pulse has an energy of between 0.00001 Joule and 0.1 J. In an exemplary embodiment of the invention, a sequence has an energy of 0.001 Joule and 10 J, for example, between 0.01 and 0.1 Joule. In some embodiments, pulses are generated by a voltage source and the voltage of a pulse is between 0.5 Volt and 100V, for example, between 1 and 10 Volts. Optionally or alternatively, a pulse may be generated by a current source and its current set to be between 0.1 mA and 100 mA, for example, between 1 and 10 mA. Allowed parameters may depend on the frequencies, contact area and/or desired effect.

In an exemplary embodiment of the invention, stimulation is provided in sessions that total at least 2 hours, 3 hours, 5 hours or intermediate or longer times a day. Within such a session, there may be inter-sequence delays. Optionally, such a session is repeated at least twice a day and/or at least 3 times in three days.

In an exemplary embodiment of the invention, delays between stimulations are selected to reduce pain and/or sensation, while still providing effects as described herein. For example, stimulation signals with a lasting effect may be used so that stimulation is less continuous.

In some cases the stimulation depends on the frequencies and the waveform of the stimulation. For sinusoidal stimulations, the efficacy of stimulation may be higher for low frequency stimulation (for example 5-250 Hz). The stimulation intensity is, for example, up to 1.5 mA for 5 Hz and 2.5 mA for 250 Hz. Optionally, an absolute threshold stimulation intensity is about 10 mA for all frequencies as this may cause pain. Other thresholds may be provided as well. In some cases, higher stimulation frequencies require higher thresholds of stimulations, for example, at 2000 Hz the stimulations need to be about twice as powerful as in 250 Hz to achieve a same effect. In some cases, stimulation frequencies are selected to be frequencies that do or do not (or some lesser degree of selectivity) stimulate one or more of nerve tissue smooth muscle tissue, sensory receptors and/or skeletal muscle.

For square pulses, much higher input can often be applied without pain. For square pulses, pulse width is optionally wider than 1 ms. Optionally, stimulation intensities can reach 10 times the values cited for 250 Hz (e.g., 25 mA).

Optionally, the pain is adjusted for patient condition (optionally automatically by a programming system or by the stimulation system, optionally manually). For example, a patient with diabetes may have twice the pain threshold. Optionally or alternatively, with age, for example, between age 50 and 80, there is an increase in threshold of a factor of 2. Intermediate ages may have a threshold based on an assumption of constant reduction in sensitivity per year.

In an exemplary embodiment of the invention, 100 Hz continuous or 30 seconds on/30 sec off stimulation is applied for durations of 30 minutes. Shorter or longer durations and/or lower or higher duty cycles, for example, 90%, 80%, 60%, 50%, 30%, 20%, 10% or intermediate duty cycles within a sub-train of pulses and/or other frequencies may be used in some embodiments of the invention.

In an exemplary embodiment of the invention, each pulse has a shape selected from square-wave, rectangular wave, triangular wave, saw-tooth and sinusoidal. Optionally, the leading angle is smaller (or larger) than the trailing angle. While the pulse may be bi-polar, optionally the pulse is unipolar. In some embodiments, the pulse is a DC pulse. Optionally, a DC baseline or other baseline is added onto the pulse.

In some cases a composite pulse is applied, for example, a first part stimulating and a second part modulating the effect of stimulation. Optionally or alternatively, a pulse has an FM modulation.

In an exemplary embodiment of the invention, the stimulation is enveloped, for example, convoluted with a low frequency signal, such as a sine wave or a sawtooth or a triangle envelope. Optionally or alternatively, the convolution provides a change in frequency over time, for example, a ratio of 1:1.1, 1:2, 1:4, 1:10 or intermediate or large ratios between different frequencies in different parts of a pulse.

While the pulses in a pulse train may be uniform, in some embodiments they vary, for example, there being an envelope which defines changes in amplitude and/or frequency and/or other pulse characteristics along the train and/or sequence. This may be useful to reduce adaptation. In some cases, the sequence is simply a single uniform pulse.

In an exemplary embodiment of the invention, the sequence is applied using bipolar electrodes. This may assist in locality. Optionally or alternatively, at least some sequences are applied using a unipolar electrode with a common ground and/or using a pair of spaced apart unipolar electrodes. Such electrodes may be spaced apart, for example, 3 mm, 1 cm, 2 cm, 3 cm or smaller or intermediate or larger distances. Optionally, the casing of an implantable stimulator system or an external electrode, acts as a return electrode. Optionally, a ground, common or return electrode is placed in contact with the suprapubic skin.

In some cases a therapy (or other application) includes applying stimulation at a plurality of locations. Optionally, all such locations are stimulated simultaneously. Alternatively, at least some locations are stimulated after other locations. This may be useful, for example, to simplify power circuitry (e.g., using a switch between electrodes instead of multiple electrode drivers). In another example, peristalsis may be encouraged using timed spaced apart stimulations along the ureter.

In some cases, multiple sequences are applied together to obtain a desired effect, some of the sequences not being applied to the urinary system or being applied to different parts thereof. Optionally, such sequences are applied together. Optionally, such sequences are synchronized using a clock and/or sensing of an event.

In an exemplary embodiment of the invention, at least two sequences are designed to be applied at spaced apart times, for example, a pre-set time and/or based on measurements. For example, one sequence may cause a function and another sequence may stop the function and/or otherwise modulate it. For example, electrical stimulation may activate one reflex, optionally the reno-renal reflex, for example by a 5-1000 Hz pulses, and additional stimulation inhibit the vesico-vascular reflex, for example by a DC input.

In an exemplary embodiment of the invention, sensing is synchronized to sequence application, for example, being at a delay relative thereto or being timed to occur within inter-train delays in the sequence. Optionally, some sensing is done during or right after a sequence is applied, for example, to measure the applied stimulation and/or its direct effect. In one example, sensing of nerve activity is provided while stimulating the nerve at a different location.

In an exemplary embodiment of the invention, sensing is separate from stimulation. In other embodiments, sensing of electrical activities and/or electrode impedance and/or tissue interface quality uses the same electrodes as used for stimulation.

Exemplary parameters for non-electrical stimulation, above the above described pulse parameters, which apply to other stimulations include, for example: flow rate and concentration of chemical stimulants. In an exemplary embodiment of the invention, NaCl (or other sodium salt) at a molarity of, for example, 0.5M, 0.8M, 0.9M, 1.1M, 2M or larger or intermediate concentration is used to stimulate a reno-renal reflex. Optionally or alternatively, Capsaicin at 1 uM, 5 uM, 10 uM, 20 uM or smaller, intermediate or larger concentrations is used in the ureter and/or bladder. The molarity used may depend on the chemical and its effect on the targeted tissue and/or may be limited by toxicity.

For mechanical stimulation, pressure, in-tissue tension, vibration rate and/or amplitude may be controlled. In an exemplary embodiment of the invention, mechanical stimulation in the ureter is by expansion of the ureter and applies pressure of for example, 1-200 mmHg, for example, 30-70 mmHg. A relationship between ureteral pressure and blood pressure is shown, for example, in the Schrum (1975) paper in the background.

For light stimulation, wavelength, power and/or energy density may be controlled.

For thermal stimulation, temperature difference, temperature sign, area and/or rate of temperature change may be controlled. For example, temperatures of 42 degrees Celsius may be used for exercitation. Temperatures of lower than 35, 32, 30 or intermediate degrees Celsius may be used for dampening excitability.

For acoustic stimulation, frequency, power and/or energy density may be controlled.

Exemplary Usage Scenarios

In some embodiments of the invention, a stimulation system is implanted when its need is determined, for example, instead of providing medication or as part of a global therapy, for example in patients suffering from hyperactivity of the renal sympathetic nerves. Optionally, a minimally invasive system is used for a while (e.g., 2-10 hours, 2-10 days or 2-4 weeks or intermediate times) to determine stimulation parameters and/or expected benefits. Optionally, a single stimulation session is used to determine system suitability and/or initial parameters.

In some cases, when in use, a system according to some embodiments of the invention reduces hospital stays, for example, by 20%, 40%, 80% in duration and/or number and/or increases quality of life, for example, by 30%, 50% or more. Desirably, a system according to some embodiments of the invention is used in a manner which reduces morbidity, for example, by 30%, 80% or intermediate or greater amounts.

In some embodiments the stimulation system, or at least a stimulator portion thereof, is implanted by default, for example, being provided with a Foley-like catheter which may also be used for urine collection. This may be, for example, in ICUs and in heart failure patients with acute events.

Temporary implantation may be useful also for in-ureter stimulators.

In an exemplary embodiment of the invention, implantation for an implanted device is by open or laparoscopic surgery used to connect stimulators to the outsides of structures (or to pierce such structures) and then implantation of a control unit (optionally in the abdominal region, as for some pacemaker. For some embodiments of the invention, it may be beneficiary to check proper device location and/or monitor an insertion process by external means, for example by X-ray, CT, MRI or ultrasound methods. Optionally, such input may be inserted manually to the stimulation device, for example to change the location of the stimulation. Optionally or alternatively, optical means mounted on (or in) a stimulator and/or which carry the stimulator are used during implantation and/or at a later checkup.

In an exemplary embodiment of the invention, a transurethral device is inserted via a urethra, optionally without a cystoscope, into the bladder. A control unit may also be inserted (e.g., dwell in the bladder) or lie outside and connected wirelessly or by wire with the inserted stimulator portion. In an alternative embodiment, a stimulator is inserted through the flesh of the pubic region into the bladder.

Optionally, once in the bladder, a stimulator may be left in the bladder. In some embodiments, the stimulator is a transureteral stimulator which is advanced into one (or two ureters. Optionally, the stimulator is advanced into the kidney, for example, to reside in a kidney pelvis thereof. Various attachment mechanisms for the stimulator inside the urinary system are described below.

In another embodiment, a stimulator is inserted into a kidney transcutaneously (e.g., using a nephrostomy procedure).

In another embodiment, implantation of the leads and a stimulator may be by a minimally invasive procedure. Optionally, the lead is introduced to and then out of the inside of a urinary lumen, for example a ureter by a cystoscope and/or ureter catheter. Optionally, the lead pierces the ureter or other urine carrying organ and is tunneled to a subcutaneous stimulator.

Optionally, the procedure is performed under imaging guidance, for example CT, MRI and/or ultrasound. The target organ is optionally first visualized by the imaging technique, and then a lead is placed near/through or inside it by a minimally invasive method, as known in the art.

In still other embodiments, the stimulator is mounted on a vaginal or rectal tampon and resides in the rectal or vaginal area. Alternatively, the stimulator is inserted past the rectal and/or vaginal wall, for example, to closer approximation with the urinary tract. Optionally, vaginal, rectal and/or transurethral insertion is used for treating a non-acute cardio-renal syndrome.

In another usage scenario, preventive treatment and/or ongoing intermittent treatment is provided. In this example, a patient visits a physician periodically receives a short stimulation session (e.g., 15 minutes or up to 3 hours) and is released home.

In an exemplary embodiment of the invention, the system includes one or more controls control which allows a patient to reduce stimulation power and/or effect and/or delay a stimulation responsive to the patient being bothered by the stimulation and/or its effect.

In an exemplary embodiment of the invention, implantation is sometimes followed or preceded by a calibration act. Optionally or alternatively, calibration is repeated as the patient's physiological state changes and/or as device shifts and/or otherwise interacts with the body. In an exemplary embodiment of the invention, such calibration includes applying a series of stimulations and/or stimulation combinations and determine a response of the body thereto. Optionally, the body is placed in a certain physiological state for some such stimulations, for example, using medication or diet. Optionally, the device is programmed with the results of such calibration and/or with a set of stimulation sequences and/or "case-stimulate" pairs, according to the stimulation results. Optionally, an initial programming includes determining specific safety problems for the patient and selecting sequences more likely to avoid such problems. Optionally, the stimulation sequences programmed include desired long term effects. Optionally, the stimulation sequences are programmed to change as time goes on and/or as physiology changes and approaches a desired outcome and/or approaches an undesired outcome. For example, more gentle stimulation may be applied as long as renal functions are above one threshold and stronger stimulation if baseline renal activity goes below such a threshold.

In an exemplary embodiment of the invention, calibration is fast (e.g., with a round lasting 1-20 seconds or 1-5 minutes), for example, using patient feedback on nervous effects as sensed by the patient, or based on sensing signals.

In an exemplary embodiment of the invention, the device is configured for diagnosis and/or includes a diagnosis-related display, for example, showing one or more stimulations used and their effects on one or more parameters. Such a device can be an integral device or a two part device (stimulator and controller).

Diagnosis of nervous function in a patient may be assessed for example by providing a stimulation and observing whether the stimulation induces or reduces bladder and/or sphincter contractions. Optionally, the information obtained by such means may be used to track a progression of a nephropathy in a diabetes patient.

In hypertension patients, stimulation may be used to diagnose the origin of the disease. For example, stimulation of a reno-renal reflex and measuring urine flow, natriuresis and/or blood pressure of a patient. In patients suffering from a hypoactivity of the reno-renal reflex such stimulation may have a significant effect on these parameters. In addition, hyper activation of the vesico-vascular reflex may also be a contributing factor to hypertension. Activation or depression of the vesico-vascular reflex by stimulation of the bladder or afferent nerves can be used for diagnosis of such hyper activation and the treatment may be to provide a chronic stimulation to inhibit the vesio-vascular reflex or amending the clinical condition contributing to said reflex activation, for example treating bladder neck obstruction in patients suffering from an enlarged prostate.

Exemplary Lead Properties

Many of the exemplary leads described below fall under two main categories—leads outside urinary tract and leads inside urinary tract. In general, electrical leads outside urinary tract can be of any design known for stimulator leads in the art, concerning, for example, flexibility, diameter and biocompatibility. A specific issue for leads attached to the urinary tract is that the bladder and ureters move, for example, due to muscular action and due to changes in patient posture and/or digestion, as well as other motion causing events. Optionally, the lead is soft enough and/or has a large enough diameter to avoid damaging nearby tissues. In an exemplary embodiment of the invention, a lead length is between 1 and 50 cm, for example, between 7 and 25 cm. Optionally, the lead is axially elastic, for example, having an elongation of 20% without damage.

For non-electrical stimulation, the lead optionally delivers electrical power to a suitable transducer. In some embodiments, the lead includes a lumen or two lumens for delivering and/or circulating a fluid and/or chemical to a suitable transducer.

For leads inside the urinary tract, chemical resistance to urine is optionally provided, for example, using suitable coatings, such as silicone. Optionally, such an indwelling lead is hollow, to allow urine flow therethrough. Optionally or alternatively, the diameter of the lead is small enough to allow urine flow past. Optionally or alternatively, the lead shape (e.g., including a groove) is elected to support urine flow therepast. Optionally, urine flow is supported in kidney, ureter, bladder and/or urethra, as appropriate.

In an exemplary embodiment of the invention, the lead is thin enough and/or soft enough to not interfere with valves in the ureter, valves in the bladder and/or urine gating mechanisms of the bladder.

In some embodiments, no lead is provided, rather, power is transmitted to the transducers of the stimulator.

In an exemplary embodiment of the invention, the lead body is a coil of metal covered by a biocompatible layer, with the coil providing resistance to breakage and/or flexibility.

In an exemplary embodiment of the invention, a lead is formed of a stainless steel coil and coated with a polymer.

In an exemplary embodiment of the invention, a lead electrifies between 1 and 10 contacts. Optionally, each contact is separately electrifiable, or at least 3 or 5 contacts are separately electrifiable. Specific exemplary lead designs are provided below.

In an exemplary embodiment of the invention, the lead and/or other elongate elements described herein, have a length:width (or diameter) ratio of better than 2:1, 4:1 10:1, 20:1 or intermediate ratios.

Exemplary Electrode Contact Construction

In an exemplary embodiment of the invention, a lead terminates in and/or has one or more electrode (or non-electrical transducers) contacts along its length. In some embodiments, the contacts are arranged in a line. Alternatively, the contacts may be arranged in a two dimensional array. Optionally or alternatively, the contacts are arranged in the shape of an outside of a cylinder (e.g., for intra-ureteral stimulators) or a cone (e.g., for kidney pelvis stimulators).

Optionally, the contact design provides anchoring, for example, a stent like anchor in a ureter or a pig-tail screw-in tip for muscular tissue. Alternatively, the lead or other means provides anchoring. For example, a double pig tail ureteral design may anchor a lead with contacts in a ureter. Exemplary contact shapes include, springs (e.g., for lodging in a ureter), discs (e.g., for contacting a trigone area), spheres, (e.g., for contacting intra-kidney structure). Optionally, multiple contacts are provided adjacent to each other, for example, as concentric rings or spirals or springs, for example, to provide bipolar stimulation, e.g., with each conductor coupled to a different wire in a lead.

In an exemplary embodiment of the invention, the contact design and/or anchoring mechanisms are selected so as not to interfere with natural movements of urinary system components, in particular flexing of ureters and peristalsis. As shown below, this may be achieved, using a flexible contact.

In an exemplary embodiment of the invention, contact area between an electrical contact and tissue is between 0.1 square mm and 20 square cm, or smaller, intermediate or larger areas, for example, between 1 square mm and 3 square cm. Optionally or alternatively, contact area between the contact and body fluids is increased by using a porous coating to increase surface area and/or reduce impedance. Optionally, the surface area of the target covered is between 1% and 90% of its area, for example, between 3% and 10% thereof.

In an exemplary embodiment of the invention, the contact is made of or coated with one or more of a conducting material as is known and accepted in the art or other conducting materials, for example including but not limited to stainless steel, nitinol, platinum, iridium, tantalum, titanium, titanium nitride, niobium, or alloys of any of these, conducting silicone or other soft conductors and/or a capacitive coating.

In an exemplary embodiment of the invention, a multi-point electrode or mesh electrode is provided for contacting a part of the outside of the bladder, optionally at a trigone area. Optionally, the mesh is defined with one or more slots for receiving the ureters. Optionally or alternatively, such a mesh, optionally rolled into a cylinder, is used for stimulating the outside of a ureter. Optionally, such a mesh has dimensions of 1-3 cm by 0.5-3 cm.

Exemplary electrode designs and/or their combination with various lead designs and/or suitability for various targets are described below.

As used herein, the term "coat" does not necessarily relate to the process of coating, but to a physical design in which there is a conducting portion or surface adjacent or overlaying a non-conducting surface. For example, an insulation covered wire which includes a bare portion, maybe considered to include a conducting area coated thereat, in some embodiments of the invention. In some embodiments, a contact would be attached or otherwise mounted at the bare portion. It should be noted that in some embodiments of the invention, conducting portions may be conducting to only DC (e.g., of a certain polarity) or only AC (e.g., of certain frequency ranges).

Stimulation Localization

A particular feature of some stimulation targets is that they are located in the abdominal cavity or the groin area where there are many stimulatable tissue regions and there is a potential for stimulating unwanted tissue. Some embodiments of the invention deal with this issue by stimulating within lumens or within walls of urinary system elements. In some embodiments of the invention, bi-polar electrodes are used so that the field at a short distance from an electrode contact is low. Optionally or alternatively, the electrode contact area is shielded, for example, using a ground electrode and/or using an isolating layer, so that electrical fields do not extend in unwanted directions for example, it may be desirable to focus stimulation so that at least 50%, 70%, 80%, 90% or more is focused at a target, for example, in a spatial angle of less than 90 degrees.

In some cases, an external common electrode, possibly the casing of the stimulation circuitry housing, is used.

Exemplary Bladder Stimulation Systems

As noted above, in exemplary embodiments of the invention, the stimulator resides in the bladder and is used to stimulate the trigone area or distal ends of the ureters and/or, optionally, other parts of the bladder. In an exemplary embodiment of the invention, such stimulation can be used to activate or depress a reno-renal reflex or a vesico-vascular reflex. In a particular embodiment, a trigone area is stimulated to increase excitation thereof. Optionally or alternatively, the trigone area is stimulated to reduce sensitivity thereof. Optionally or alternatively, the rest of the bladder is stimulated. In some cases, a stimulator is designed specifically to stimulate only parts of the bladder that are not the trigone.

In an exemplary embodiment of the invention, stimulator includes a balloon or other expandable structure. Optionally, the structure is designed so as to automatically position a stimulator contact in contact with a trigone area or other desired location. A typical trigone is triangle like with a base of 2-3 cm and a height of about 1.5 cm. Optionally, the stimulator includes multiple contacts and an optional mechanism for selecting which contact to activate. Optionally or alternatively, the contacts are designed to be local in effect, for example, by ensuring contact with the bladder wall and/or by using bi-polar electrification.

Optionally, the structure is rotationally symmetric. Alternatively, the structure is asymmetric.

In an exemplary embodiment of the invention, the structure is designed to overcome deformations of the bladder, caused, for example, by an enlarged prostate or organ prolapse. Optionally, the structure is manipulatable and/or comes in several sizes.

Figure 9A:
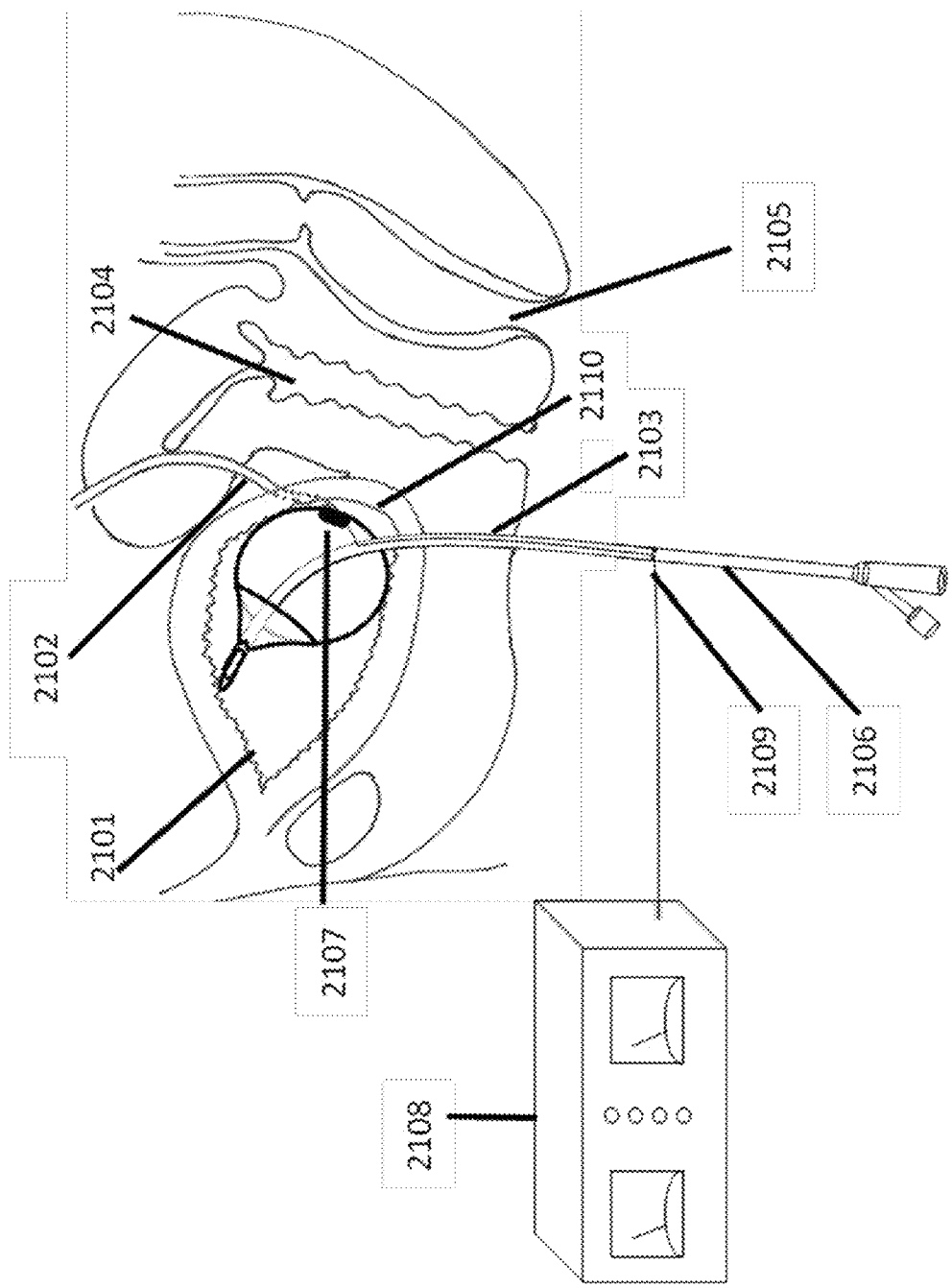
FIG. 9A is a cross sectional view of female pelvic structures and an optional transurethral insertion and the location of an intra-bladder stimulator connected to external stimulator controller, in accordance with an exemplary embodiment of the invention.
Figure 9B:
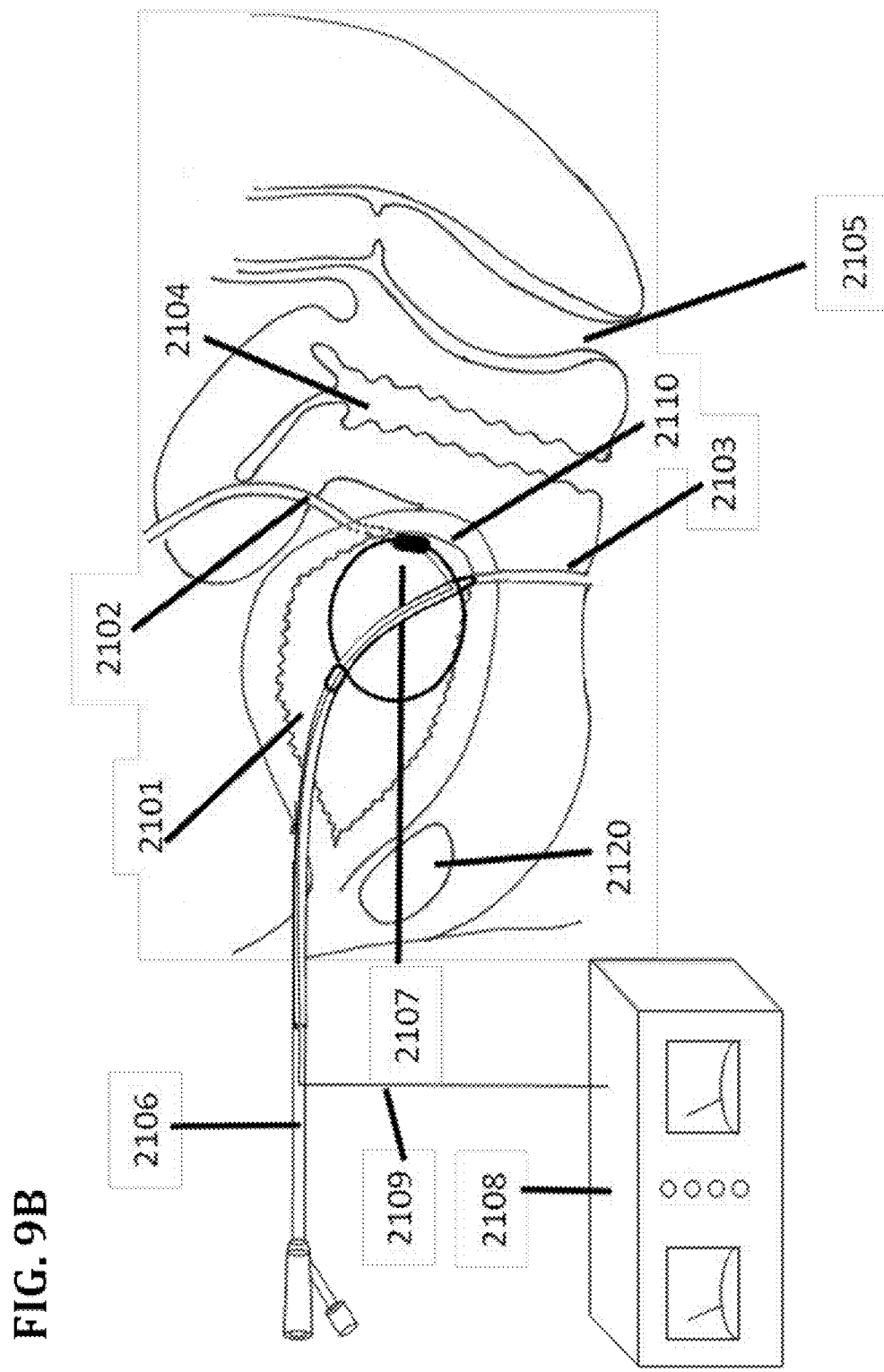
FIG. 9B is a cross sectional view of female pelvic structures and an optional suprapubic insertion and the location of an intra-bladder stimulator connected to external stimulator controller, in accordance with an exemplary embodiment of the invention.
Figure 9C:
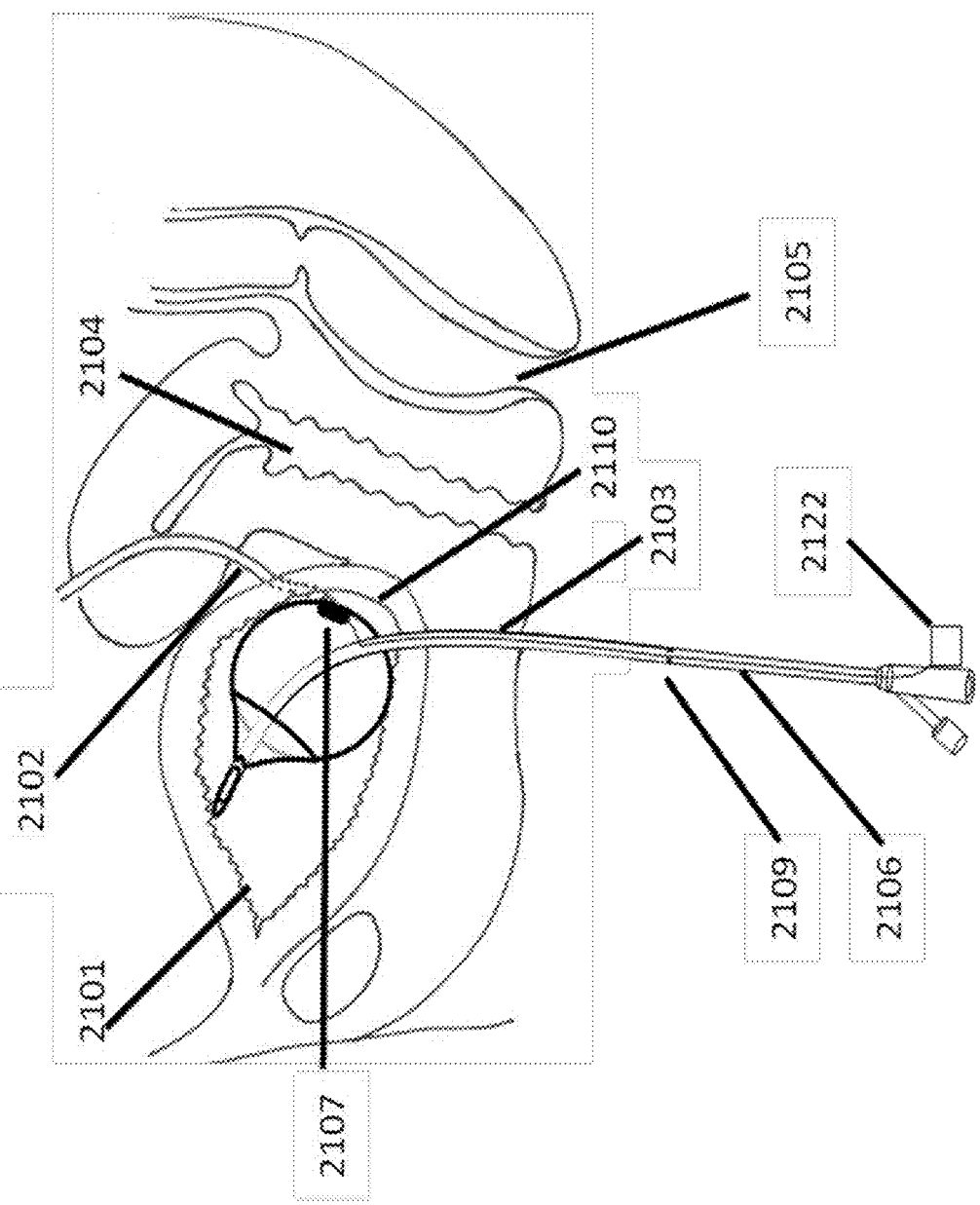
FIG. 9C is a cross sectional view of female pelvic structures and the location of an intra-bladder stimulator equipped with internal stimulator controller, in accordance with an exemplary embodiment of the invention.

FIGS. 9A-9C are cross sectional views of female pelvic structures (but may also be used for males) and the location of an intra-bladder stimulator 2106 in accordance with exemplary embodiments of the invention. As shown in the figures, a typical female pelvis includes a bladder 2101, a ureter 2102, a urethra 2103, a vagina 2104, a rectum 2105 and a trigone area 2110 of the bladder.

Optionally, stimulator 2106 includes at least one electrode 2107, optionally designed to be in contact with a selected portion of bladder 2101, for example, trigone 2110. As shown, in an exemplary embodiment of the invention, stimulator 2106 includes a bladder-dwelling balloon. Optionally, such a balloon is coated or is formed of and/or with a hydrophobic layer, which may improve electrical contact with the bladder walls.

In an exemplary embodiment of the invention, according to FIG. 9A stimulator 2106 is inserted to bladder 2101 through urethra 2103. A wire 2109, for example, extends from electrode 2107 to external stimulator controller 2108.

FIG. 9B shows an alternative method of insertion of a stimulator 2106, through the skin. Optionally stimulator 2106 (optionally carried within a stiff channel and/or mounted on a sharp stylet), is inserted, optionally above the pubic bone 2120.

FIG. 9C shows an integrated device in which a small control circuitry 2122 is integrated with a stimulator 2106. Optionally, circuitry 2122 is light weight and/or small. Optionally or alternatively, circuitry 2122 includes a control knob (not shown), for example, for controlling an intensity of stimulation. Optionally, only a single control is provided for circuitry 2122.

In an exemplary embodiment of the invention, circuitry 2122 includes an electrode positioning and/or impedance sensing circuitry as described herein. Optionally or alternatively, circuitry 2122 includes a feedback device such as a light or sound generator (not shown). Optionally, feedback is provided if the system is unable to stimulate for a certain period of time.

In an exemplary embodiment of the invention, the device of FIG. 2106 is used by a user (e.g., a nurse) opening a sealed package and removing an isolating element (e.g., a battery disconnect) so that circuitry 2122 is activated. Optionally, circuitry 2122 includes an integral battery which lasts for several days or weeks. Optionally, the nurse adjusts the control until a patient feels pain and/or until a desired outcome (e.g., urine flow) is provided. Optionally, the nurse readjusts the setting every few minutes, hours and/or days, according to results of stimulation and/or patient sensation.

Optionally, circuitry 2122 includes a timer to limit the duration of stimulation (e.g., to days or weeks). Optionally or alternatively, circuitry 2122 includes a sensor (e.g., urine flow) which is used to ensure a safely level with respect to the kidneys, for example, preventing over stimulation thereof or starving thereof. For example, a urine outflow below a certain level may indicate low renal blood flow.

In an exemplary embodiment of the invention, circuitry 2122 includes a connector (e.g., a USB connector) for programming a threshold and/or stimulation sequence and/or therapy plan into a memory thereof.

Optionally, the device of FIG. 9C is used to treat shock and ensure a minimal flow of blood and/or kidney function, e.g., by stimulation of a reno-renal reflex, as needed.

In an exemplary embodiment of the invention, the balloon is not overinflated to stretch the bladder. Rather the bladder is emptied so it collapses. Optionally, several balloon sizes are provided, for example, for patients with distended bladders. In some embodiments, the balloon (or other expandable body, such as extendible arms) is inflated to intentionally activate a vesico-vascular reflex.

In some embodiments of the invention, the stimulation delivered depends on sensed signals, for example, signals indicating peristalsis or signals indicating trigone activity.

Figure 10:
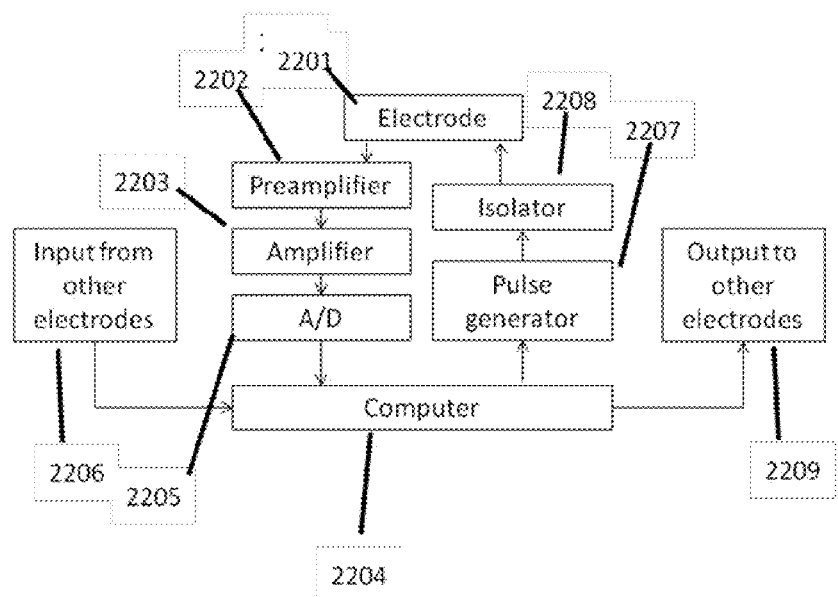
FIG. 10 is schematic block diagram of a feedback methodology, in accordance with an exemplary embodiment of the invention.

FIG. 10 is a block diagram of an exemplary stimulation system with feedback, in accordance with an exemplary embodiment of the invention. An electrical input from an electrode 2201 is optionally amplified by a preamplifier 2202 and/or an amplifier 2203. Optionally, the amplified input is fed to a computer 2204 (or other circuitry), optionally using an analog to digital converter 2205. Computer 2204 may optionally receive input from other electrodes 2206, optionally amplified and digitalized. According to one embodiment of a feedback method, computer 2204 performs calculations at least partially based on the input from electrodes. According to one embodiment of a feedback method, the computer 2204 controls the electrode to deliver the stimulation, the timing, the amplitude and/or other parameters of the stimulation. Such stimulation is optionally provided by a pulse generator 2207 and/or an isolator 2208. According to one embodiment of the invention, computer 2204 may control output of multiple electrodes 2209.

Figure 11:
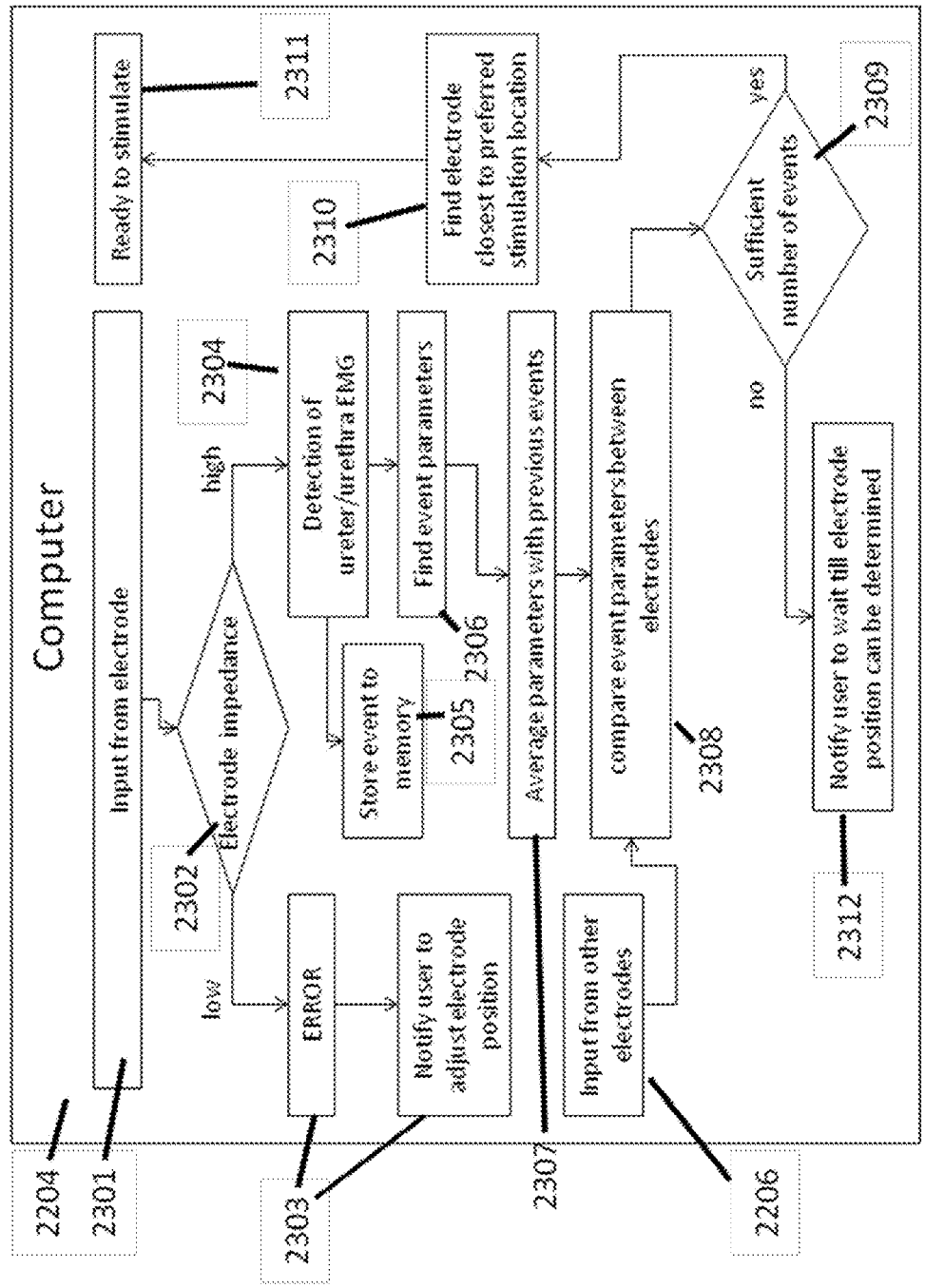
FIG. 11 is a schematic block flow diagram of a method of selecting stimulation parameters, in accordance with an exemplary embodiment of the invention.

FIG. 11 is a flowchart of a method of selecting stimulation parameters, in accordance with an exemplary embodiment of the invention. At 2301, an input from an electrode is received (e.g., at computer 2204). At 2303 electrode impedance is optionally checked. If the impedance is low (e.g., lower than a preset value), it is often an error condition (2303) possibly indicating short circuit of electrical contacts by urine and the user may be notified to readjust electrode position. In a mobile system, a sound may be emitted.

If the impedance is high, a determination may be made to see if the electrode is at a correct location. For example, at 2304, urethra, bladder and/or ureter EMG may be searched for. A measured signal may be stored (2305). Optionally or alternatively, measured signals may be analyzed to determine their parameters (2306), optionally by averaging with previous measurements (2307). Data from other electrodes may be provided (2206) and compared to the current data (2308). If enough data is collected (2309) an electrode which shows signal characteristics closest to those of the desired target position is optionally determined (2310) and optionally stimulated (2311). Alternatively, a user may be notified to wait until an electrode is selected (2312). Optionally, the results of a stimulation are monitored to determine if the stimulated tissue reacted as expected. If not, this may indicate incorrect stimulation or incorrect tissue. Optionally, such comparing is by comparing to a complication, such as a table of expected results and/or ranges of signal parameters.

Such methods may also be used for stimulating in other parts of the urinary system and for stimulating using non-balloon stimulators.

In an exemplary embodiment of the invention, a circuit for detecting correct placement of electrodes is mounted on the stimulator and for example for a patient which can configure and/or apply stimulation by himself or by a caregiver, for example, at home or in an old-age home; the patient can be notified (e.g., LED color) if he can stimulate and/or if a stimulation is expected to operate correctly.

Figure 12:
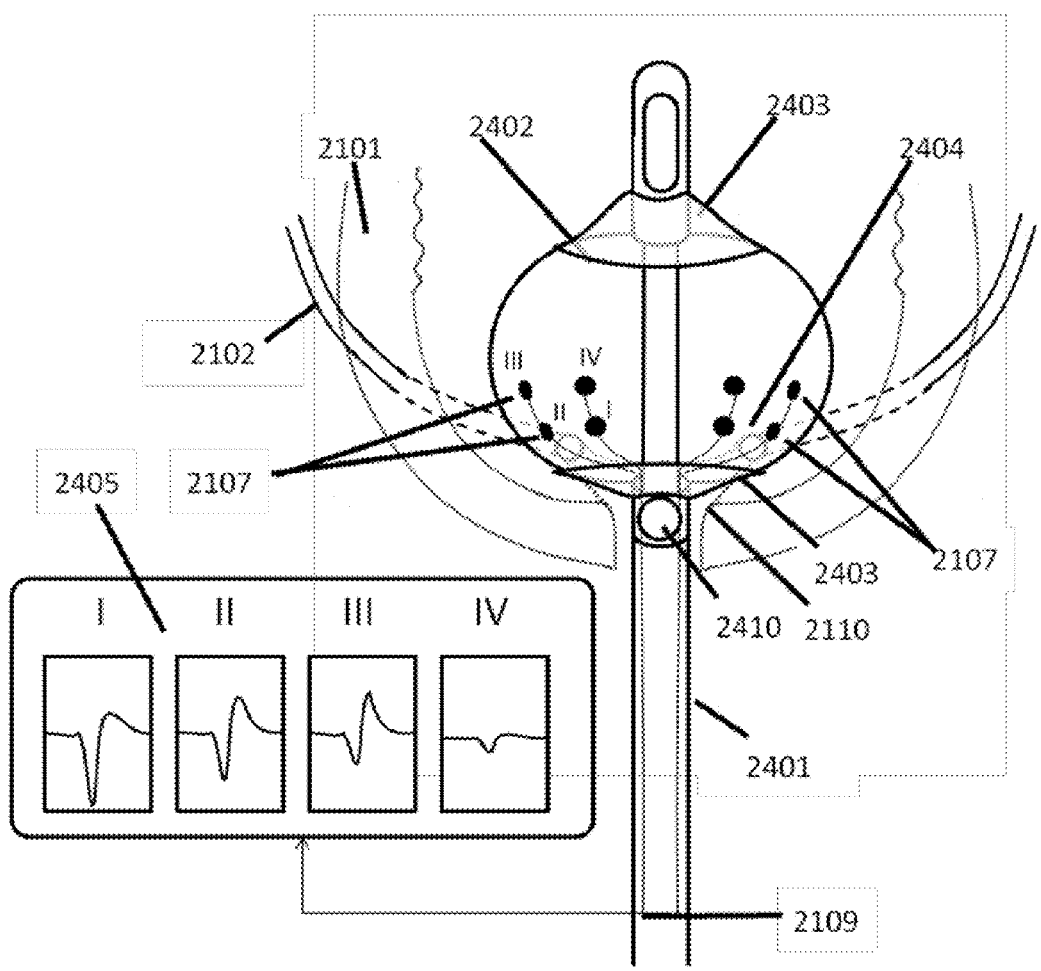
FIG. 12 illustrates an intra-bladder stimulator with recorded physiological signals, in accordance with an exemplary embodiment of the invention.

FIG. 12 illustrates an intra-bladder stimulator 2106 with recorded physiological signals, in accordance with an exemplary embodiment of the invention. According to one embodiment stimulator 2106 is based on a modified Foley catheter (e.g., has similar dimensions and softness and/or may be made by retrofitting a Foley catheter with several electrodes).

In an exemplary embodiment of the invention, a distal part 2401 of stimulator 2106 lies in bladder 2101 and comprises an inflating balloon section 2402. Optionally, stimulator 2106 has at least one electrode 2107 attached in proximity to inflating balloon 2402. Optionally, simulator 2106 includes has at least one covering sheath 2403 located near insertion site of the balloon 2402 to catheter body optionally to ease catheter insertion and prevent damage to the urethra by the electrodes. A covering sheath may be used in other urethral (or other) insertions.

In this and other embodiments it may be desirable to empty substantially all urine form the bladder. Optionally, an aperture (e.g., 2410 as shown in FIG. 12) is provided adjacent the urethral exit (e.g., underneath the balloon, if any), to void urine and/or other fluids. Optionally or alternatively, the balloon forms on or more urine flow channels on its surface.

In an exemplary embodiment of the invention, electrodes 2107 are connected by conducting wires 2109 to a stimulation controller 2108, optionally located outside of the body. Optionally, controller 2108 has sensing capabilities, so that electric activity from electrodes 2107 can be read out and analyzed. A display 2405 optionally associated with controller 2108 can is illustrated as showing signals measured form four electrodes 2107 (I-IV).

In an exemplary embodiment of the invention, using for example, the methods of FIG. 11, electrical activity of one or both ureters 2102, the urethra 2103 or bladder 2101 is analyzed by stimulation device 2108 and/or compared (e.g., possibly by a human). In an exemplary embodiment of the invention, location of electrodes 2107 relative to structures of one or more of the bladder 2101, the ureter 2102, ureteral orifice 2404, urethra 2103 are found by analysis of this electric activity. Trigone 2110 may have its own unique electrical activity signature which can be detected and/or stored by a system and used for estimating placement. Optionally, stimulator 2106 is repositioned (e.g., rotated or otherwise manipulated) based on analysis of electric activity. According to some embodiments of the present invention, stimulation is performed by at least one of the electrodes 2107 based on its location relative to one/both ureters 2102, urethra 2103, vagina 2104 and/or rectum 2105. For example, stimulation may be selected to have an intensity low as to not stimulate unwanted structure and/or to be large enough to reach nearby structures whose stimulation is desired.

Figure 13A:
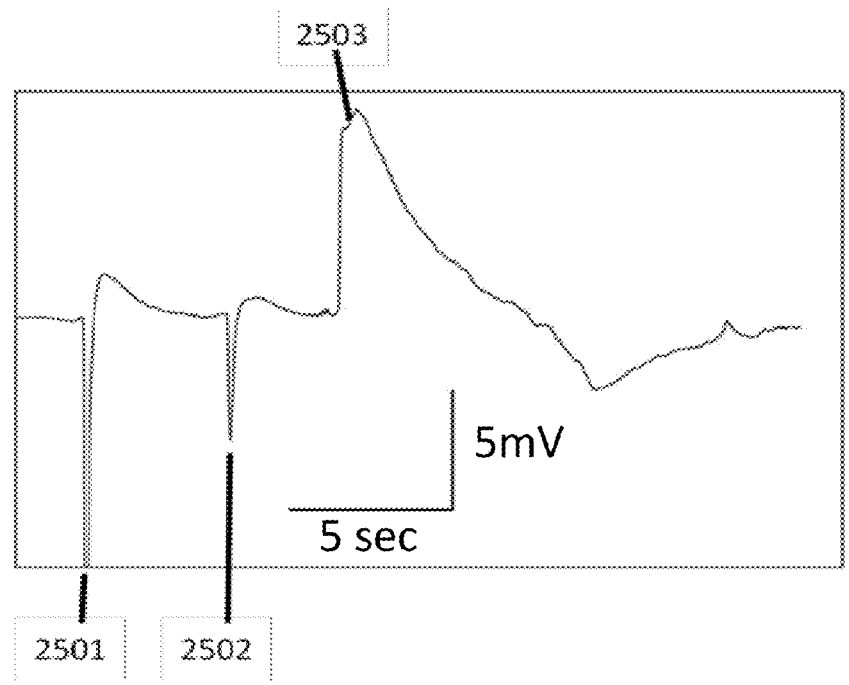
FIG. 13A-B illustrate physiological signals recorded from the bladder, using the system of FIG. 12, in accordance with an exemplary embodiment of the invention.
Figure 13B:
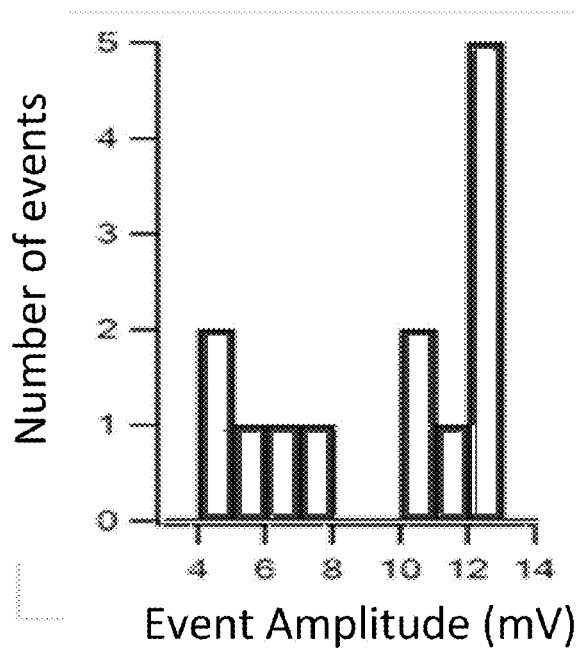

FIGS. 13A-B illustrate physiological signals recorded from the bladder, using the system of FIG. 12, in accordance with an exemplary embodiment of the invention. FIG. 13A provides an example of a 20-second-long recording of an intra-bladder electric activity by an electrode located near the left ureteral orifice. In the graph are marked peristaltic activity of the left ureter 2501, peristaltic activity of the right ureter 2502 and contraction of urethra 2503.

FIG. 13B provides an analysis of the amplitude of an electrical signal of ureteral peristaltic activity from a 140 second recording. Amplitude distribution clearly shows two peaks, indicative of different distances from the two ureters. Optionally, if the device is equipped with more than one electrode, stimulation can be provided by the electrode with the highest recorded signals, optionally ureter signals. Alternatively, the device can be rotated and sensing continued, optionally till higher signal intensities are recorded. Optionally, stimulation can be provided to regions of lowest recorded activity, for example lowest urethra signals, so as for example not to interfere with urethral sphincter function.

In a patient with an enlarged prostate (or organ prolapse), the bladder is distorted inwards near the urethra. This can make it more difficult to reach the trigone area with a regular balloon. In an exemplary embodiment of the invention, balloons with a topology that better matches that of a distorted bladder are provided. Optionally or alternatively, other methods of avoiding or working around the distortion are provided.

Figure 14A:
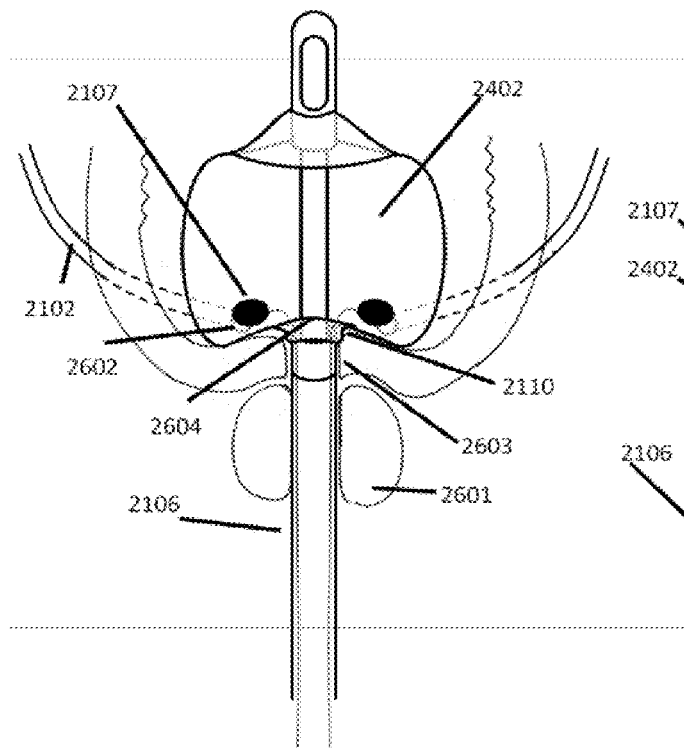
FIGS. 14A-C illustrate an intra-bladder stimulator designed for overcoming an enlarged prostate, in deployed and undeployed device configurations, in accordance with an exemplary embodiment of the invention.
Figure 14B:
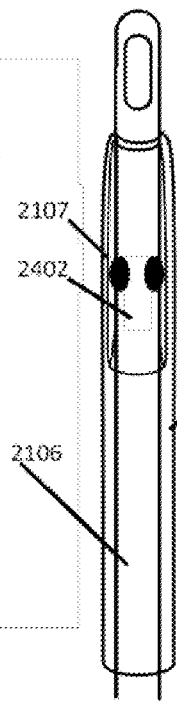
Figure 14C:
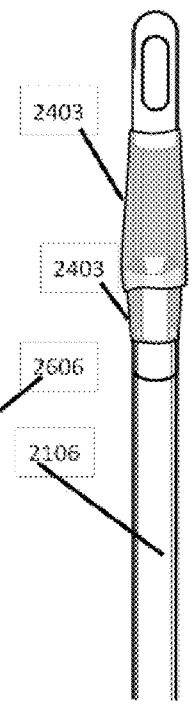

FIG. 14A-C illustrate an intra-bladder stimulation device designed for overcoming an enlarged prostate, in deployed and undeployed device configurations, in accordance with an exemplary embodiment of the invention.

FIG. 14A shows a stimulator 2106, optionally suited for the male population in accordance with an exemplary embodiment of the invention. In some cases of prostate 2601 hypertrophy, the lower segment of the bladder assumes a concave shape and the distal part of the ureter 2102 and ureteral orifices 2602 may be located below the level of urethral sphincter 2603. In an exemplary embodiment of the invention, stimulator 2106 has a non-spherical balloon 2402 that during inflated state comes in close proximity with bladder wall and/or ureteral orifice 2602 and/or intra-bladder part of the ureter 2102 and/or the trigone 2110, as desired, and, in general, may better match the topology of the distorted bladder, for example including a concavity where the prostate would fit.

According to one embodiment the balloon 2402 is shaped like a sphere with concave depression 2604. According to one embodiment of the present invention, at least one electrode 2107 is attached in proximity to the inflating balloon 2402, optionally located near ureteral orifice 2602, intra-bladder part of the ureter 2102 and/or the trigone area 2110. In an exemplary embodiment of the invention, the diameter of the concavity (e.g., in a plane perpendicular to the balloon diameter) is between 1 and 4 cm, for example, 2.5 cm. In an exemplary embodiment of the invention, an electrode (center) can be located, for example, just outside (e.g., 1-2 cm outside) the concavity, on its rim and/or inside the concavity.

FIG. 14B shows stimulator 2106 in a deflated condition, in accordance with an exemplary embodiment of the invention. Optionally, deflated balloon 2402 and electrodes 2107 are covered by a sheath 2606. Optionally, covering sheath 2606 can be removed from stimulator 2106. In an exemplary embodiment of the invention, sheath 2606 is used to protect the urethra and bladder from injury during the insertion of stimulator 2106. Such a sheath may also be used in other embodiments of the invention, especially if there are electrodes (or other non-smooth shapes), especially extending electrodes on the outside of the inserted stimulator.

FIG. 14C shows an alternative sheath design for a sheath 2403, in accordance with an exemplary embodiment of the invention, in which sheath 2403 is attached on both sides of the stimulator 2106 and slides away when balloon 2402 is expanded. In this way the stimulator 2106 is protected both during insertion and during removal of the device.

Figure 15A:
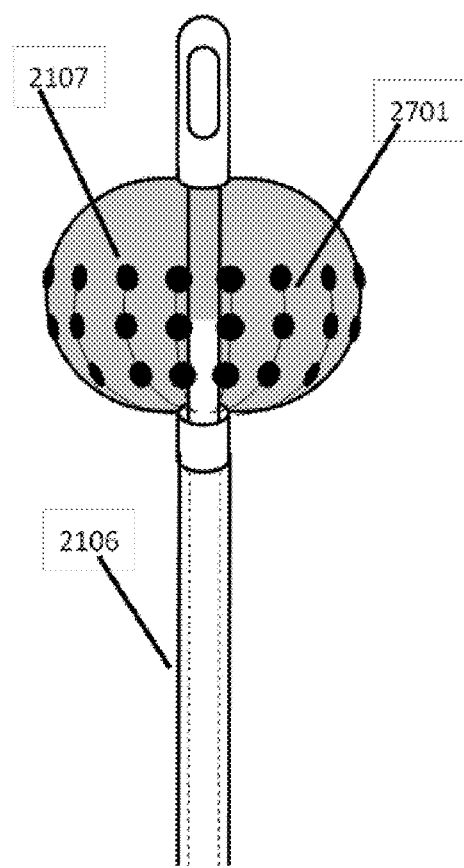
FIGS. 15A-B illustrate multi-electrode intra-bladder stimulator, in accordance with exemplary embodiments of the invention.
Figure 15B:
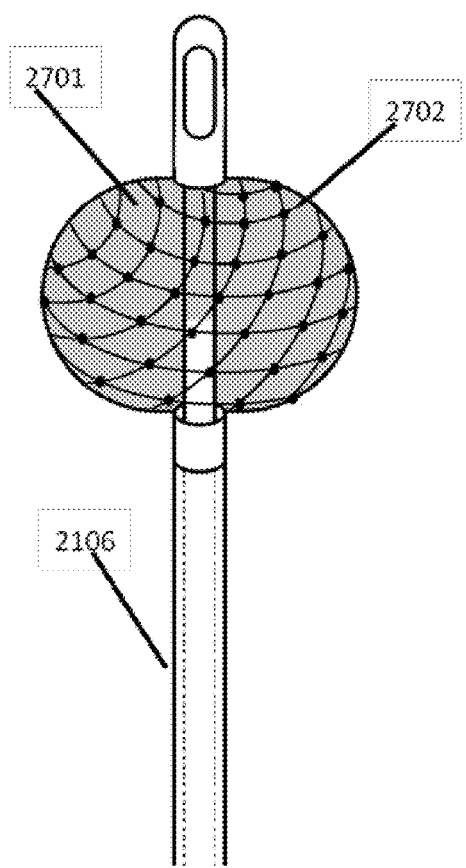

FIGS. 15A-B illustrate multi-electrode intra-bladder stimulation devices, in accordance with exemplary embodiments of the invention. In some cases it may be desirable to stimulate large areas of the bladder or to select one of several electrodes to stimulate. The arrays shown here can be mounted on other stimulator designs shown here. Optionally, as shown in FIG. 15A the electrodes (e.g., an array 2701) are concentrated or provided only at a lower hemisphere of the balloon. Optionally, the electrodes are arranged in asymmetry relative to the trigone, rather than the urethra. Optionally, the electrodes (2107) are mounted on leads or ribbons which extend along the axis of the balloon and do not interfere with its expansion. Optionally, such leads are flexible. Alternatively, there is no symmetry. FIG. 15B shows an embodiment where electrode array 2701 is provided as part of flexible grid 2702 in which multiple independent electrodes are optionally integrated.

FIGS. 16A-F illustrate an intra-bladder stimulator 2106 with extending electrodes 2022 and 2801, in accordance with an exemplary embodiment of the invention. In general, the electrodes are mounted on arms, which arms are spread open and/or pushed against bladder wall tissue, by expansion of the balloon. While the arms are shown slightly curved inwards, in some embodiments, they curve outwards, to provide better contact, for example.

FIG. 16B shows stimulator 2106 in deflated state, in which electrode contacts 2801 are substantially flush with the body of stimulator 2106 and suitable for insertion (optionally a sheath is used).

FIG. 16C is a top cross-sectional view through the balloon, showing an array, of, for example, 4 electrodes 2801. Fewer (e.g., 1, 2, 3, 4) or more (e.g., 5, 6, 10, 12, 16 or more or intermediate numbers) electrodes may be provided, for this and/or for other multi-contact and/or array stimulators. Also, balloon 2402 (and, optionally the other designs shown herein) need not be rotationally symmetrical. Optionally, such asymmetry enables better contact of the electrodes to the tissue and prevents/reduces device rotation within the bladder. Also shown (FIG. 16D) is the same cross-section in undeployed configuration.

FIGS. 16E and 16F show cross-sections of the shaft of stimulator 2106, according to an exemplary embodiment of the invention, showing a plurality of electrode leads 2026, a balloon inflation lumen 2025 and a urine flow lumen 2024. Optionally, an additional lumen (not shown) is used for irrigating the balder, for example, with nerve modifying fluids.

FIGS. 17A-C illustrate an asymmetric intra-bladder stimulator 2106 with extending electrodes, in accordance with an exemplary embodiment of the invention. In this design, balloon 2402 does not extend equally in all directions. For example, as shown in a side view FIG. 17A and a top view, FIG. 17C, extension is one directional and serves to extend a limited number of electrodes at, for example, UVJ areas of the trigone or ureteral orifice 2602. FIG. 17B shows stimulator 2106 when balloon 2402 is uninflated. Optionally, such asymmetry enables better contact of the electrodes to the tissue (e.g., trigone) and/or prevent device rotation within the bladder. It should be noted that such a design and/or asymmetry may also be used for balloons that have the electrodes mounted thereon and/or for other intra-bladder devices as describe herein.

It should also be noted that if the bladder is emptied, as it is in some intra-bladder devices of the invention, the bladder collapses on the balloon and asymmetry in the balloon design can assist in preventing of rotation thereof.

Mechanisms other than balloons may be used to engage the bladder wall with electrodes. For example, mechanical structures that deflect and/or expand, may be used. FIGS. 18A-C illustrate a split-tip intra-bladder stimulator 2106, in accordance with an exemplary embodiment of the invention.

In this stimulator, a tip 3001 of stimulator 2106 is configured to split into, for example, two or three parts 3002, with an electrode 3003 associated with each part. Optionally, parts 3002 curve away from stimulator 2106 and optionally back towards the urethral entrance. Optionally, they are preventing from curving by a sheath used during insertion. Alternatively, other bending mechanisms may be used, such as known in the art. Optionally, stimulator 2106 is hollow so that urine can flow between parts 3002.

FIG. 18C is a top view of stimulator 2106 located within bladder 2101. Optionally, the size and shape and/or other mechanical properties of parts 3002 are selected so that electrodes 3003 (or at least one or two thereof) contact desired stimulation locations in the bladder, for example, near the ureter 2103, ureteral orifice 2602 and/or the trigone 2110. Optionally, the size and the shape and/or other mechanical properties are different between different parts 3002, so that current orientation of the stimulator 2106 within the bladder 2101 is maintained. For example, one or more of the parts 3002 can be longer than the others, so that it can specifically point to the anterior part of the bladder 2101 and optionally assist in location and/or fixating the stimulator in the bladder.

Optionally, in some embodiments (this or other) of the invention, correct orientation is by including a mark on an extra-body portion and the user orients this mark with an external anatomical landmark to ensure correct orientation.

Figures 19A, 19B, 19C:
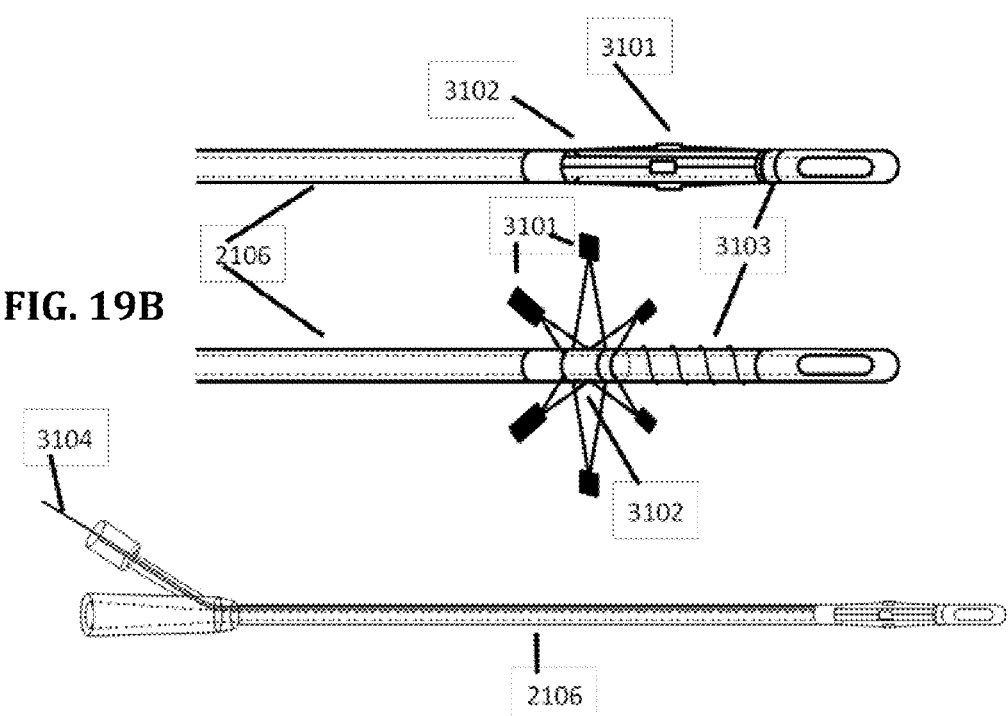
FIGS. 19A-C illustrate an intra-bladder stimulator with radially extending electrodes, in accordance with an exemplary embodiment of the invention.

FIG. 19A-C illustrates an intra-bladder stimulator 2106 with radially extending electrode contacts 3101, in accordance with an exemplary embodiment of the invention. Optionally, when deployed, the electrodes curve or bend back towards the urethral opening, so as to better contact the trigone area in cases of enlarged prostate and/or organ prolapse.

In an exemplary embodiment of the invention, a wire 3104 or other type of control, such as a cable, which optionally extends to outside of the body, is used to retract a deployment mechanism 3102, optionally against the force of a spring 3103. Absent the pulling of wire 3104, spring 3103 optionally collapses mechanism 3102 and the electrodes lie flat. Optionally or alternatively, wire 3104 also provides electrical power to the contacts 3101. Optionally or alternatively, the spring is used to deploy the electrodes and the cable is used to retract the electrodes. In an exemplary embodiment of the invention, mechanism 3102 comprises a plurality of wires, configured to bend at electrodes 3101, which, when shortened by having one end pulled towards the other, extend out of the surface of stimulator 2106. Optionally, mechanism 3102 comprises a tubular layer with multiple axial slots or slits formed therein.

FIGS. 20A-C illustrates an alternative pull-wire activated stimulator 2106, in which pulling on a wire 3203 (or other control) causes extension of one or more electrodes. In the embodiment shown, one or more electrodes 3201 are mounted on a flexible (and optionally elastic) wire 3202. In resting position, the wire may lie flat against stimulator 2106. Pulling on wire 3202 approximates two ends of the wire, so that its new resting position is with electrodes 3201 extended.

FIG. 20C shows stimulator 2106 in a bladder, showing electrodes 3201 against desired stimulation targets.

Figure 21:
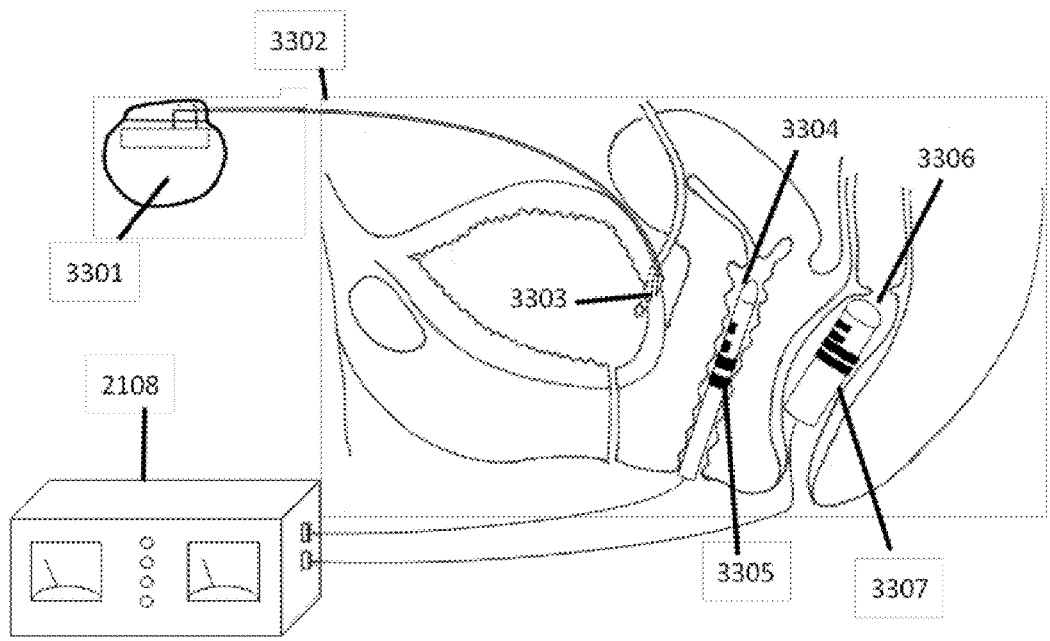
FIG. 21 illustrates stimulators for stimulating a urinary system via a pubic, vaginal and/or rectal approach, in accordance with an exemplary embodiment of the invention.

When stimulating the trigone and/or ureters, stimulation from outside the bladder is optionally practiced. FIG. 21 illustrates stimulators for stimulating a urinary system from a vagina or rectum, in accordance with an exemplary embodiment of the invention. A vaginal tampon/probe 3304 (optionally self-powered) can have one or more electrode contacts 3305 (or other transducers) positioned thereon for stimulating a trigone, for example. Optionally, such electrodes are used for detecting electrical activity of targets, as described above, and for selecting an electrode and/or stimulation properties thereof, accordingly.

A rectal probe/tampon 3306 with a similar electrode set-up 3307 is also shown and may be more suitable for male patients.

Also shown is a trans-pubic stimulator 3301, with a lead 3302 extending into the body (e.g., at the pubic area) into contact with a target area, and optionally including an anchoring portion 3303, for example, an intra-muscle screw, a clip or a suture. Optionally or alternatively, the stimulator passes through the bladder body to lodge in and/or contact the trigone area. Optionally, the control circuitry is implantable.

It should be noted that in a supra-pubic approach, the location of a concavity (if any) and electrodes will generally be at a distal side of the device, to match an expected point of contact with a trigone or other stimulation target. Similarly, while symmetry relative to the trigone may be the same, symmetry relative to an elongate lead body may change according to the insertion method.

Figure 22:
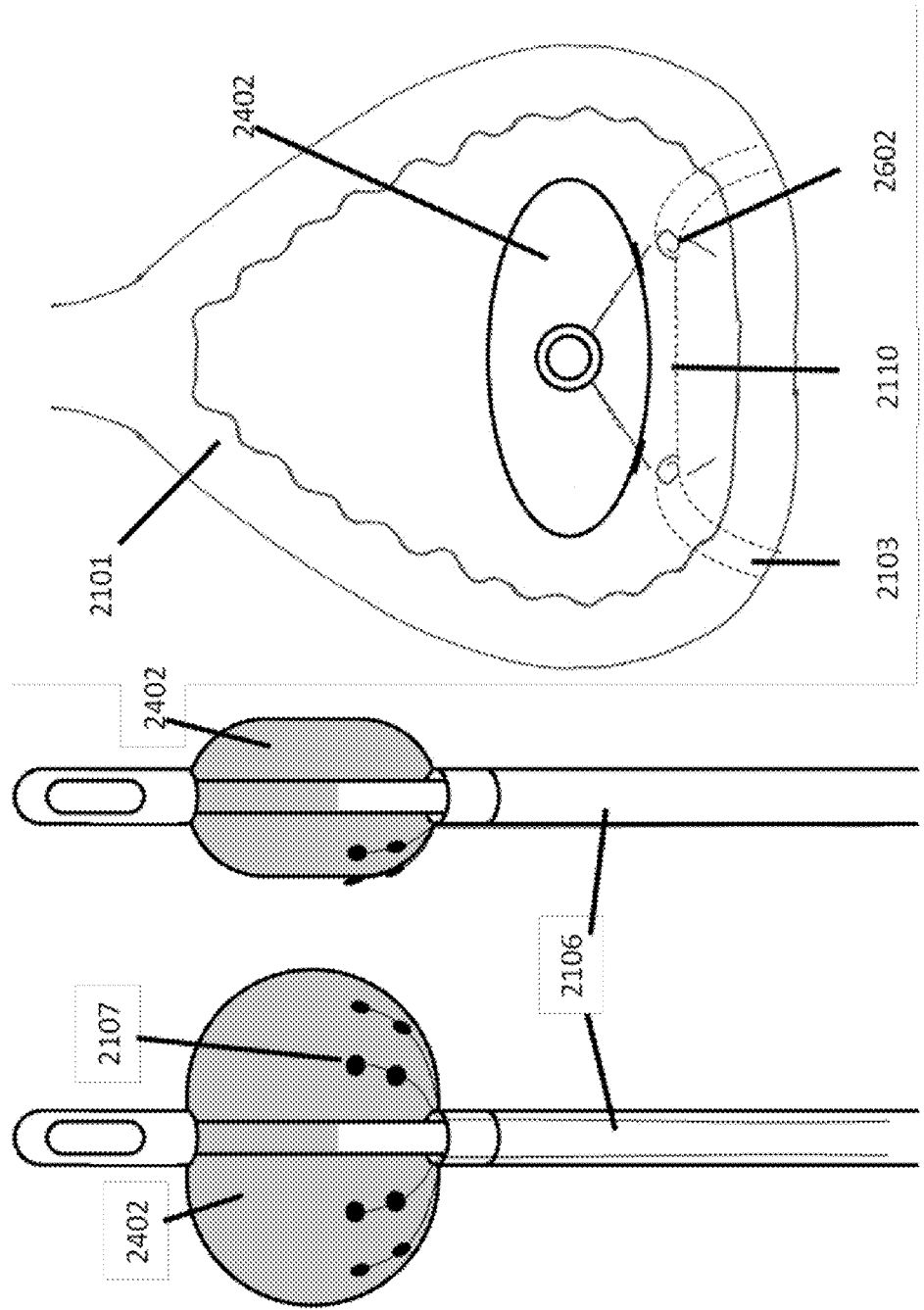
FIGS. 22A-C shows an expanding in-bladder stimulator design, in accordance with an exemplary embodiment of the invention.

FIGS. 22A-C shows an expanding in-bladder catheter design, in accordance with an exemplary embodiment of the invention. The design of stimulator 2106 in this figure illustrates two features which need not be provided together. A first optional feature is that balloon 2402 is asymmetric, as shown in FIG. 22C, it can have, for example, an elliptical cross-section, or even a triangular cross-section, to match the shape of the bladder. This can reduce rotation and/or aid in positioning thereof. This may be in addition to or instead of an asymmetry (if any) caused by providing a concavity at one side of the balloon. Another optional feature shown is having electrodes 2107 only on part thereof, for example, on only one quadrant thereof, for example, on less than 50%, 40%, 30%, 20%, 10% or smaller or intermediate percentages of surface area (as defined by the area of a convex polygon connecting the electrodes). This may assist in limiting stimulation to a trigone area.

Figure 23:
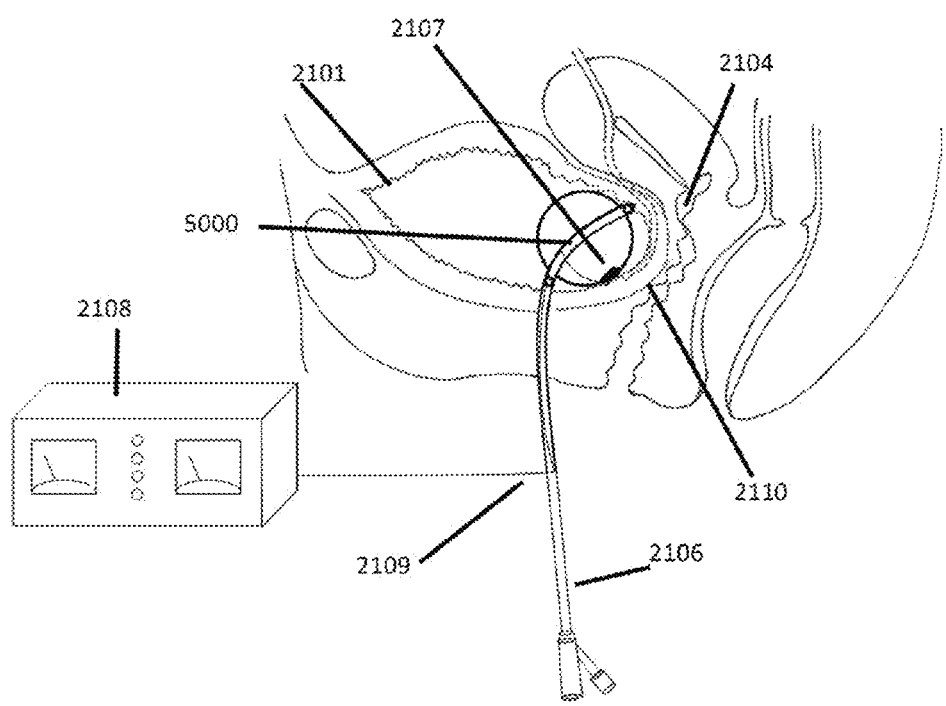
FIG. 23 shows an expanding in-bladder stimulator design with a bending shaft, in a prolapsed female, in accordance with an exemplary embodiment of the invention.

FIG. 23 shows an expanding in-bladder stimulator 2106 with a bending shaft 5000, in a prolapsed female bladder 2101, in accordance with an exemplary embodiment of the invention. In the example shown, a female with a prolapse, the bladder is distorted. Optionally, a shaft 5000 of stimulator 2106 is bendable, for example, using bending mechanisms known in the art (e.g., pull wires attached to spaced apart points at its distal end) or using a stylet. Optionally or alternatively, such a design has one or more electrodes reaching further up the balloon (e.g., above a midline thereof), to compensate for the greater rotation of the balloon to ensue contact with a trigone area, for example.

Figure 24:
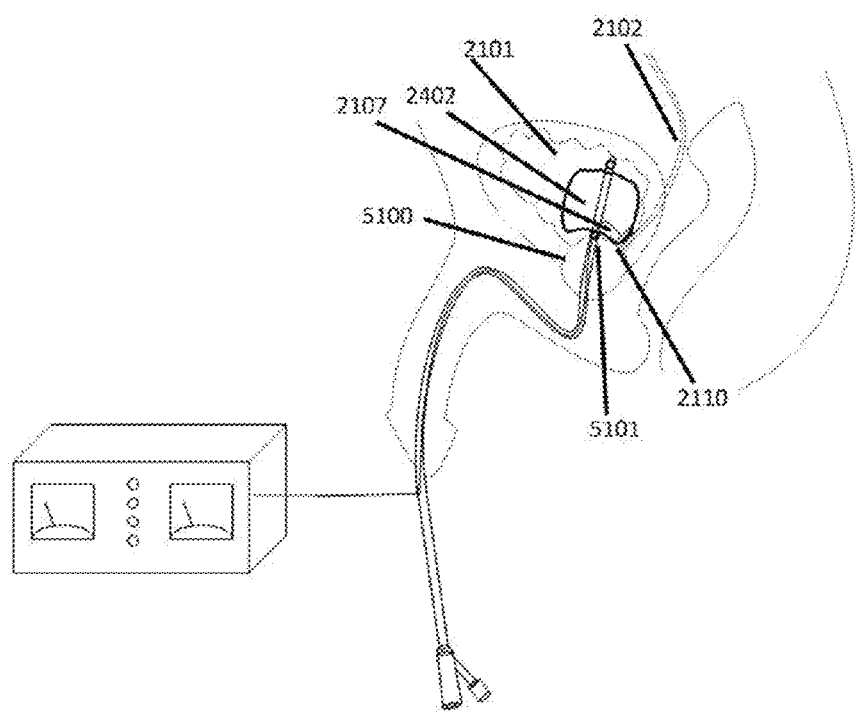
FIGS. 24 an expanding in-bladder stimulator design with a concavity implanted in a male with an enlarged prostate, in accordance with exemplary embodiments of the invention.

FIG. 24 shows an expanding in-bladder catheter design (e.g., for example as shown in FIG. 14) with a concavity implanted in a male with an enlarged prostate, in accordance with exemplary embodiments of the invention. A balloon 2402 with a concavity that is large enough (e.g., a depth of between 0.5 and 2 cm, for example 1 cm and a diameter between 1 and 3 cm) to conform to a distance between a urethra 5101 and a trigone 2110, distorted by a prostate 5100.

FIG. 55A presents a side view and FIG. 55B presents a front view of an inflated urinary catheter 7100 that optionally has one or more expandable parts 7101 and 7102, and a shaft 7110 (e.g., the catheter may be a double balloon bladder catheter), in accordance with some applications of the present invention. Optionally, at least some of the expandable parts are connected to a pressure source via tubes 7103 and 7104 so that the expandable parts can be inflated and deflated.

Optionally, urine drainage is facilitated via one or more urine-drainage holes 7105 and/or 7106, which are located proximally or distally with respect to the expandable parts. Typically, the urine-drainage holes are connected to a drainage channel 7107 in the catheter shaft. Optionally, an additional drainage tube and/or port 7108 is in fluid communication with drainage channel 7107. For some applications, drainage tube 7108 is curved so as to facilitate urine drainage from the bladder even in the presence of a deformation of the bladder, such as a deformation caused by a bulging prostate and/or a prolapsed bladder. Optionally, at least one electrical contact 7109 is connected to at least one of the expandable parts 7101 or 7102. The electrical contacts are typically used to stimulate at least a portion of the subject's bladder, as described herein.

FIGS. 56A-B show an array 7201 of electrical contacts 7109 disposed on expandable part 7102, in accordance with some applications of the present invention. Optionally, array 7201 includes a plurality of electrical contacts 7109, the plurality of electrical contacts being individually controlled. FIG. 56A shows expandable parts 7101, 7102 in deflated states, and FIG. 56B shows the expandable parts in inflated states.

Figure 57:
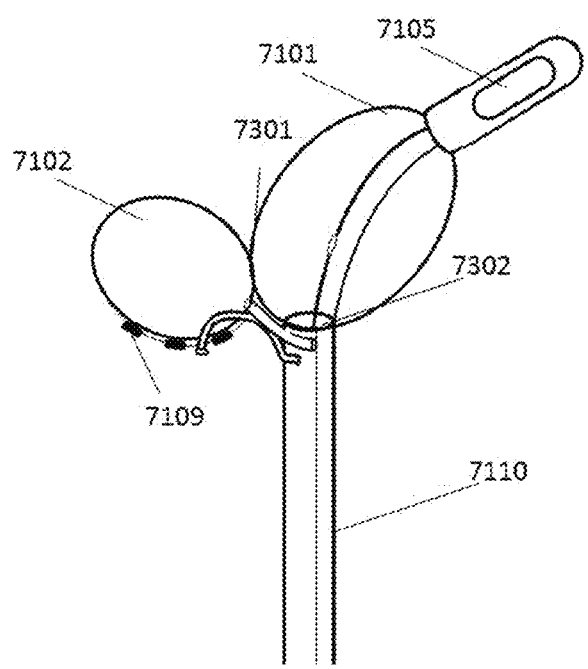
FIG. 57 illustrates a side view of the double balloon bladder catheter of FIG. 55, the double balloon having been inflated to a larger inflation volume than shown in FIG. 55, thereby causing greater bending of the catheter than that shown in FIG. 55, in accordance with some applications of the present invention.

As shown in FIG. 57, for some applications of the present invention, one or more of expandable parts 7101, 7102 is connected to catheter shaft 7110 at a connecting location 7302. For some applications, one of the expandable parts is connected to the other expandable part at a connecting location 7301. Optionally, the position of expandable parts 7101, 7102 with respect to each other is controlled by the constitution, width, elastic properties or location of the expandable parts. Upon being inflated, expandable parts 7101, 7102 may rotate and/or change their position relative to the catheter shaft 7110. Optionally, the angle between the expandable parts 7101, 7102 may depend on the pressure or volume to which the expandable parts are inflated.

Figure 58:
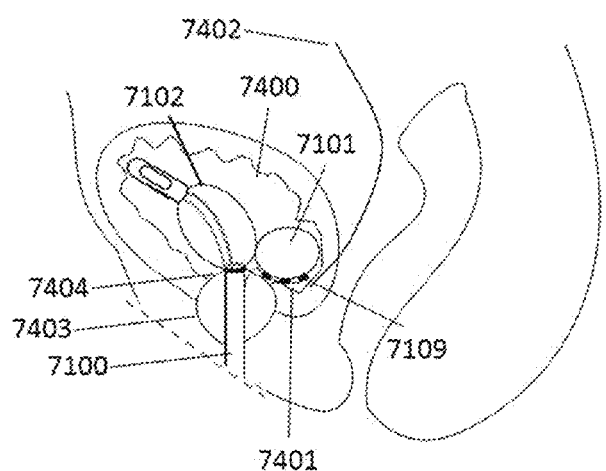
FIG. 58 illustrates a double balloon bladder catheter placed in the bladder of a male subject that has an enlarged prostate, in accordance with some applications of the present invention.

FIG. 58 shows catheter 7100 placed in a urinary bladder 7400 of a male subject, in accordance with some applications of the present invention. For some applications, expandable part 7101 is inflated such that electrical contacts 7109 are in direct contact with a specific part of the bladder, e.g., trigone 7401, or distal part of the ureters 7402. For some applications, expandable parts 7101, 7102 are configured such that contacts 7109 (which are disposed on at least one of the expandable parts) are placed in contact with the trigone 7401, or distal part of the ureters 7402, in male subjects that have an enlarged prostate 7403. As shown, the expandable parts are configured such that contact between the contacts and the trigone or distal part of the ureters is not impeded by an enlarged middle lobe 7404 of the enlarged prostate. For some applications, contact between tissue of the subject and electrical contacts 7109 is measured (e.g., by resistance or pressure measurements), and expansion of the expandable parts is performed responsively to the measurements.

Figure 59:
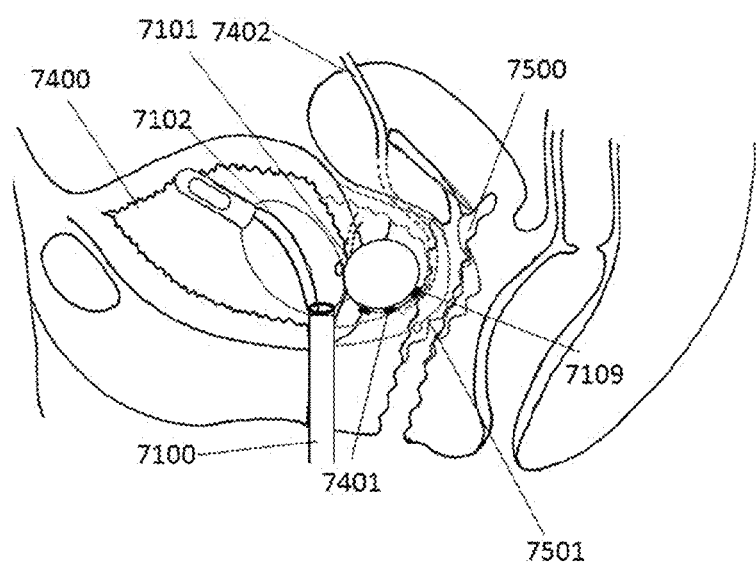
FIG. 59 illustrates a double balloon bladder catheter placed in the bladder of a female subject that has a cystocele, in accordance with some applications of the present invention.

FIG. 59 shows catheter 7100 placed in a urinary bladder 7400 of a female subject, in accordance with some applications of the present invention. For some applications, expandable parts 7101, 7102 are configured such that contacts 7109 (which are disposed on at least one of the expandable parts) are placed in contact with the trigone 7401 or distal part of the ureters 7402 in female subjects having aberrant anatomy, such as a cystocele 7501 that prolapses to the vagina 7500. For some applications, contact between tissue of the subject and electrical contacts 7109 is measured (e.g., by resistance or pressure measurements), and expansion of the expandable parts is performed responsively to the measurements.

Reference is now made to FIGS. 60A-62C, which are schematic illustrations of respective cross-sectional views of catheter 7100. FIGS. 60A-B show longitudinal cross-sections of the catheter. FIG. 60A shows a longitudinal cross-section along a central longitudinal line 7701 of the catheter. The location of central longitudinal line 7701 is indicated in FIGS.

61A-C. FIG. 60B shows a longitudinal cross-section along a line 7702 that is at a lateral location with respect to line 7701. The location of line 7702 is indicated in FIGS. 61A-C.

Figure 61A:
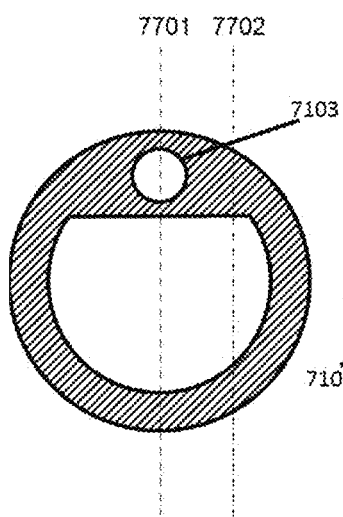
FIGS. 61A-C illustrate respective cross-sectional views of the inflatable portion of double balloon bladder catheter shown in FIG. 60, in accordance with some applications of the present invention.
Figure 61B:
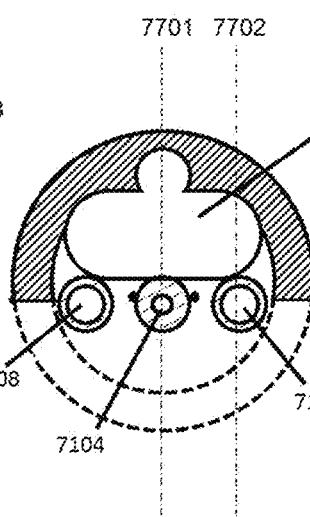
Figure 61C:
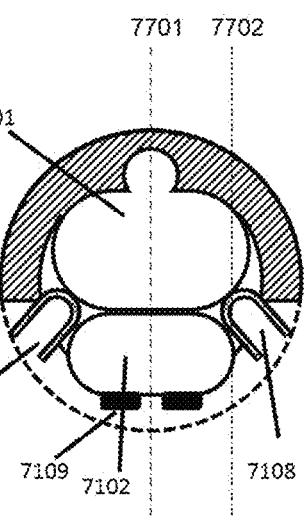
Figures 62A, 62B, 62C:
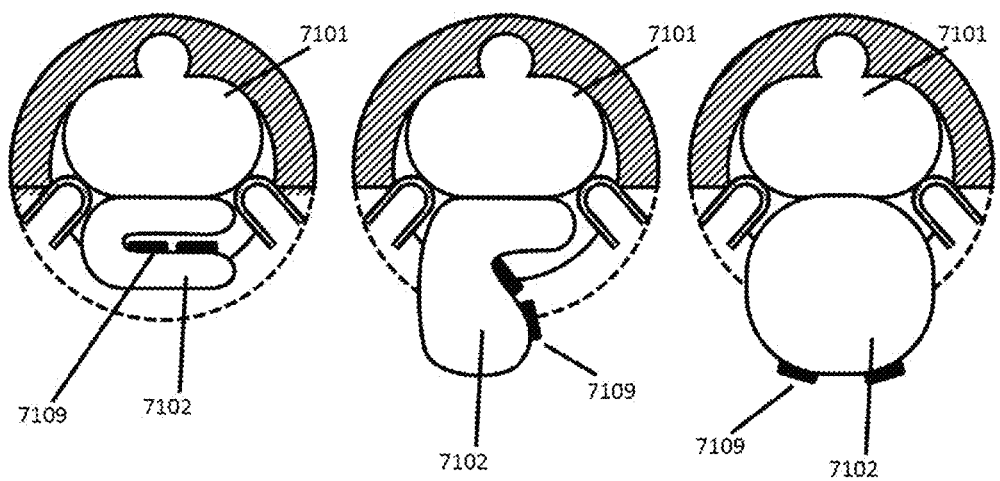
FIGS. 62A-C illustrate cross-sectional views of the inflatable portion of a double balloon bladder catheter having electrical contacts that are covered during insertion of the catheter into the bladder, at respective stages of the inflation of the double balloon, in accordance with some applications of the present invention.

FIG. 61A shows a transverse cross-section along a proximal transverse line 7603, FIG. 61B shows a transverse cross-section along a central transverse line 7602, and FIG. 61C shows a transverse cross-section along a distal transverse line 7601. The locations of lines 7601, 7602, and 7603 are indicated in FIGS. 60A-B. FIGS. 62A-C show transverse cross-section views of catheter 7100 along distal transverse line 7601.

As shown in FIG. 60A, for some applications, when not inflated, both expandable parts 7101 and 7102 do not protrude from the profile of the catheter 7100, and are optionally located within the lumen 7107 (which may also function as the urine-drainage channel, as described hereinabove). Optionally, tube 7104 is made of an elastic material, so it can expand when one of the expandable parts 7101 or 7102 are inflated.

FIGS. 62A-C show transverse cross-sectional views of catheter 7100, respectively, when expandable parts 7101 and 7102 are in deflated stated, in partially inflated states, and deflated states thereof, in accordance with some applications of the present invention. As shown, for some applications, when the expandable parts are in deflated states (FIG. 62A), electrical contacts 7109 are covered (e.g., engulfed) by expandable part 7102. Optionally, this can reduce irritation to tissue (e.g., urethral tissue) of the subject during device deployment, relative to if the contacts were exposed during device deployment, the contacts thereby contacting tissue of the subject.

Figure 63:
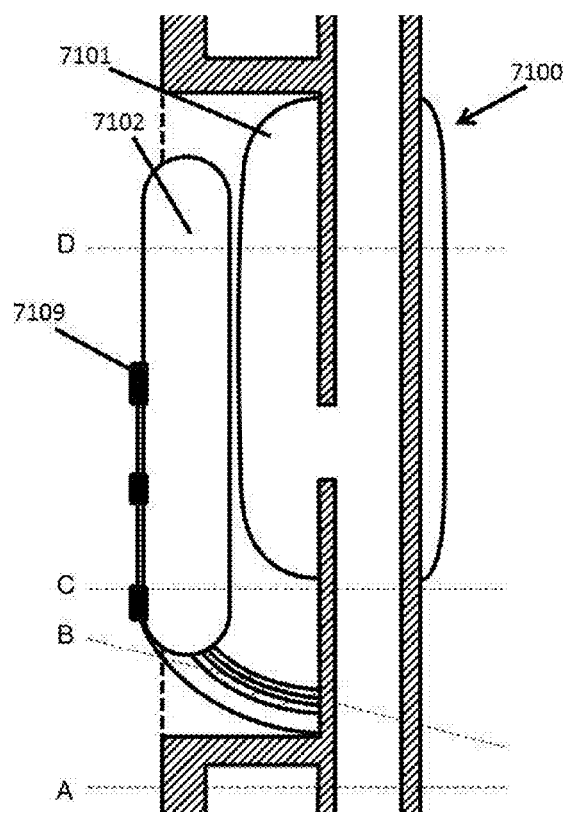
FIG. 63 illustrates a side view of the inflatable portion of a double balloon bladder catheter, in accordance with some applications of the present invention.

FIG. 63 shows a longitudinal cross-section of catheter 7100 in the deflated state, in accordance with some applications of the present invention. For some applications, at least one of expandable parts 7101, 7102 covers at least a portion of shaft 7110 of catheter 7100. FIGS. 64A-D show respective transverse cross-sectional views of catheter 7100, as shown in FIG. 63. The locations of the transverse cross-sectional views of the catheter that are shown in FIGS. 64A-D are indicated in FIG. 63 by lines A, B, C, and D, respectively.

Figure 65A:
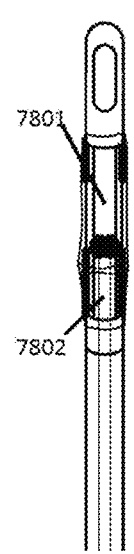
FIGS. 65A-C illustrate a bladder catheter that includes a balloon and electrical contacts at a distal portion thereof, the flexibility of the balloon varying between respective locations of the balloon, in accordance with some applications of the present invention.
Figure 65B:
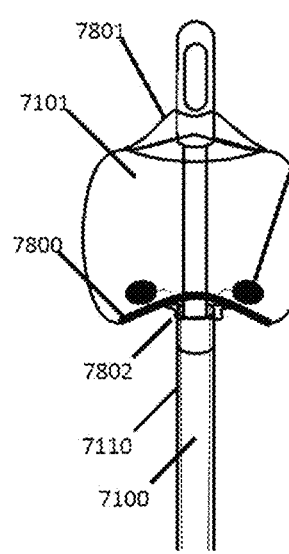
Figure 65C:
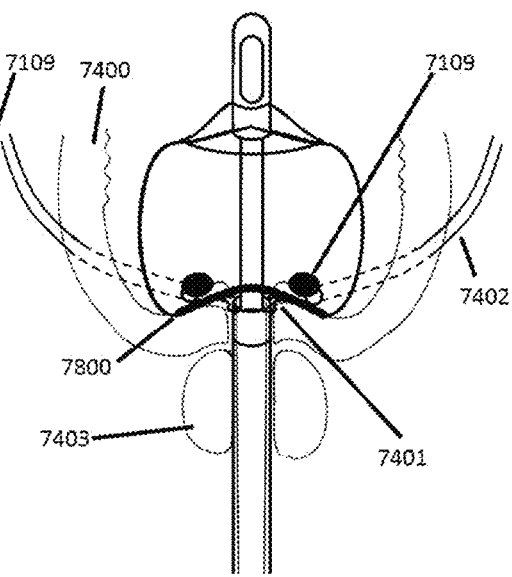

FIGS. 65A-C show catheter 7100, expandable part 7101 of the catheter having at least one (and optionally, more than one) region 7800 having variable elasticity or width, in accordance with some applications of the present invention. FIG. 65A shows an application of the present invention according to which, during deployment of catheter 7100, expandable part 7101 and/or regions 7800 are covered by protective sheaths 7801 and 7802. Optionally, upon expansion of the expandable parts 7101 and/or 7102, sheaths 7801 and 7802 are pushed back and expose electrical contacts 7109.

For some applications, region 7800 is a region of expandable part 7101 that is characterized by being of greater thickness compared to other portions of 7101. In accordance with respective applications of the invention, the change in thickness of the expandable part at region 7800 with respect to surrounding portions of the expandable part is gradual or discrete. For some applications, region 7800 is located near the connection between expandable part 7101 and shaft 7110 of catheter 7100, as shown in FIG. 65B.

FIG. 65C shows catheter 7100 disposed in a bladder 7400 of a male subject who has an enlarged prostate 7403, in accordance with some applications of the present invention. For some applications, region 7800 is more rigid (e.g., less expandable) than other parts of the expandable part 7101. Region 7800 is configured such that upon expanding expandable part 7101, region 7800 forms a concave dent in expandable part 7101. For some applications, the concave dent enables the electrical contacts 7109 to come into direct contact with ureter 7402 and/or trigone 7401.

Figure 66A:
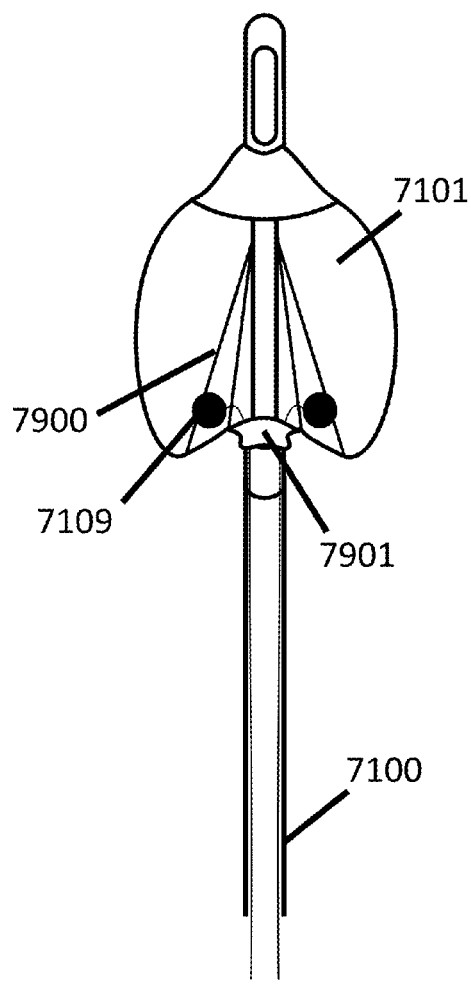
FIGS. 66A-B illustrate a bladder catheter that includes a balloon and electrical contacts at a distal portion thereof, the inflation of the balloon being controlled by internal strings, in accordance with some applications of the present invention.
Figure 66B:
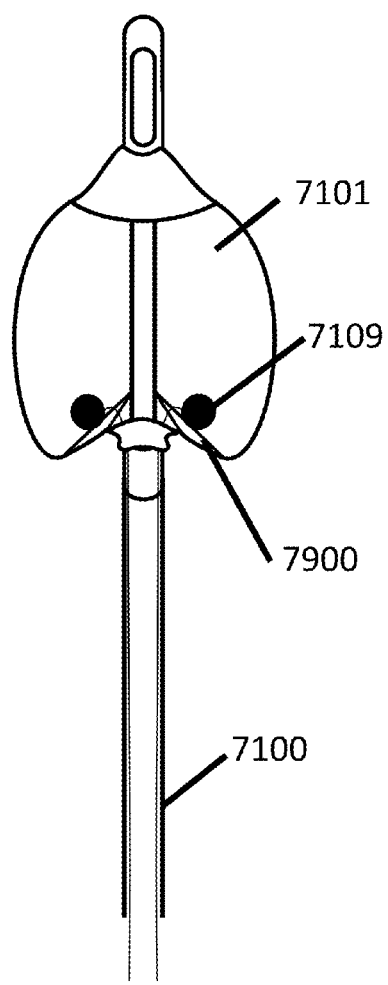

FIGS. 66A-B show catheter 7100, strings 7900 being located within one or more of expandable parts 7101, 7102, in accordance with some applications of the present invention. It is noted that for some applications, strings 7900 are located outside of the expandable parts 7101, 7102 (application not shown).

For some applications, strings 7900 are made of a material having elastic properties that are different from elastic properties of the material from which expandable part 7101, 7102 is made. Optionally, strings 7900 are rigid. Optionally, strings 7900 and expandable parts 7101, 7102 comprise the same material. For some applications, strings 7900 are connected to the expandable parts 7101, 7102 at a region in the vicinity of a pole of the expandable part, e.g., in the vicinity of bottom pole 7901 of expandable part 7101, as shown in FIG. 66A. Optionally, connection of strings 7900 to the region constricts the expansion of the region of the part 7101, 7102 to which strings 7900 are connected. For some applications, the strings are connected to the expandable part such that upon expanding expandable part 7101, the region to which the strings are connected forms a concave dent in the expandable part 7101. For some applications, the concave dent enables the electrical contacts 7109 to come into direct contact with the subject's ureters or trigone.

Figure 67A:
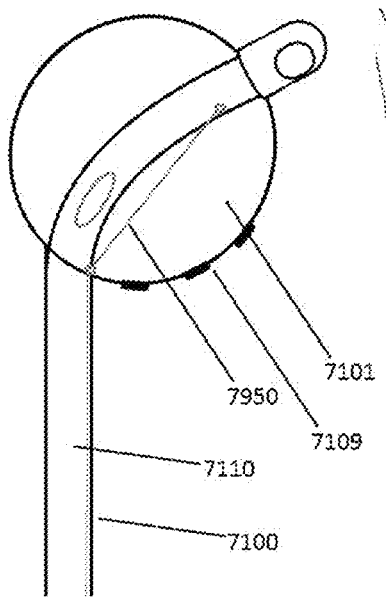
FIGS. 67A-B illustrate a bladder catheter with electrical contacts, the bending of the catheter being controlled by strings, in accordance with some applications of the present invention.
Figure 67B:
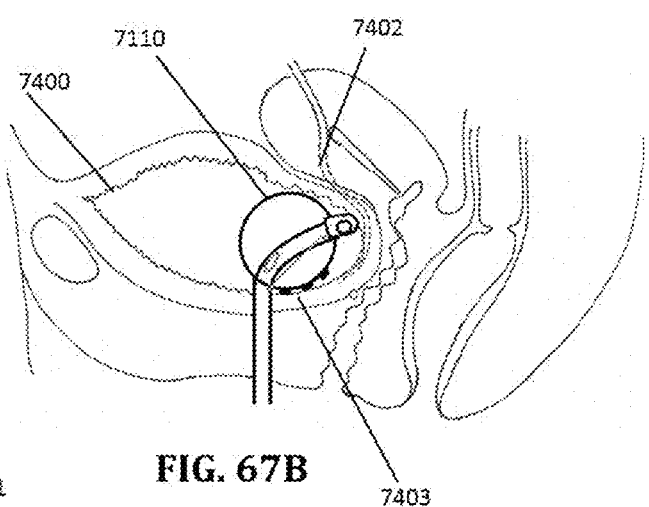

FIG. 67A shows a string 7950 connected to shaft 7110 of catheter 7100, in accordance with some applications of the present invention. For some applications, the string is connected to shaft 7110 inside expandable part 7101. Optionally, string 7950 can be pulled or released from a part of catheter 7100 located outside the subject's body. Optionally, upon pulling of the string 7950 the shaft 7110 of the catheter 7100 bends. Optionally, the bending of the shaft 7110 can be used to bring the electrical contacts 7109 into close contact with trigone 7403 and/or ureter 7402, as illustrated in FIG. 67B. Thus, for some applications, a user manipulates string 7950 from outside the subject's body, such as to bring the electrical contacts into close contact with a portion of the subject's bladder.

In an exemplary embodiment of the invention, the electrodes used are bipolar electrodes. Optionally, electrodes which may remain free-floating in the bladder (not in contact with wall) are made bipolar. This is useful, because the field which will then reach a bladder wall at unintended locations may be small.

In an exemplary embodiment of the invention, stimulation of a bladder is provided also, or only by providing a suitable chemical in the bladder. For example, a nerve stimulant or a nerve depressant may be injected into the bladder. Optionally, the trigone area is protected during such injection. A device such as described in U.S. Pat. No. 5,749,845 may be used for such injection and protection (with a possible modification by adding of a shield). Optionally, the trigone area is stimulated with electrodes during or after such chemical treatment of the bladder. Optionally or alternatively, a protective layer, for example, a patch of isolating material, or multi-layer element including a conductor may be used when stimulating the rest of the bladder (e.g., using a central electrode and an external electrode), or when ablating the bladder, for example, using RF.

In an exemplary embodiment of the invention, after stimulating the bladder to determine effect of such stimulation, part of the bladder may be ablated, so as to damage sensory nerve endings thereof. In an exemplary embodiment of the invention, such ablation and/or simultaneous stimulation of the bladder and the trigone areas may be used to achieve a desired balance and/or replace a natural balance between a reno-renal reflex triggered by trigone stimulation and a vesico-vascular reflex triggered by bladder stretching. In an exemplary embodiment of the invention, such stimulation (or ablation) of the bladder includes stimulation of, for example, 100, 80%, 50%, 40%, 30%, 20% or smaller or intermediate percentages of bladder surface area. Optionally, the bladder is intentionally stimulated to trigger and/or modulate the vesico-vascular reflex.

In one embodiment, parts of the bladder are stimulated to reduce contraction thereof and/or treated with a chemical which reduces contraction thereof, to counteract any unintentional effect of stimulation of the trigone or ureters.

In an exemplary embodiment of the invention, the stimulator includes a user input for stopping stimulation during (intended) urination or defecation. Optionally or alternatively, the stimulator (or a controller thereof) detects such activity, based, for example, on change in posture and/or changes in EMG, and stops stimulation and/or effect assistive stimulation (e.g., to enhance bladder contraction).

In an exemplary embodiment of the invention, a balance between a reno-renal reflex and a vesico-vascular reflex may be affected by reducing bladder filling (e.g., by lifestyle changes) and/or by removing or shrinking the prostate and/or opening the urethra. Optionally, shrinkage is provided using a medicament, such as an anti-androgen.

In an exemplary embodiment of the invention, a blood pressure treatment and/or medicament includes an existing blood pressure controlling medicament, such as a beta blocker, ACEI and ARBs, calcium channel blockers, diuretics and other medications as known in the art and a prostate shrinking, urethral opening and/or bladder draining medicament, such as an anti-androgen. Such medicament may be provided at a pharmaceutically acceptable dosage and in a pharmaceutically acceptable carrier, for example, for oral intake or for intravascular injection or transdermal provision.

Other drug-device combinations are possible. In one example, a drug is sold with a marker readable by the stimulation system (e.g., via a bar-code reader or an RFID tag) so that the stimulation is adjusted according to the drugs taken by the patient. This may be useful, for example in a hospital setting (or in a home setting with irregular drug taking times and/or in a care center) where a drug packet can be swiped by a stimulation system and/or a programming system before it is administered. Optionally or alternatively, a memory chip, for example, with a USB connection that can plug into the stimulation system and/or a programming system, is used. Optionally or alternatively, the drug is sold with written instructions and/or a code to input into the stimulation system and/or a programming system, for example, via a user interface, such as a mouse and keyboard (e.g., and display).

In an exemplary embodiment of the invention, the stimulation is used to compensate for side effects of drugs, for example, increase kidney sympathetic activity to compensate for beta blockers or decrease sympathetic activity so as to reduce pro-arrhythmic effects of some medication. In another example, higher amounts of diuretics may be used, if a reno-renal stimulation can be used to ensure minimal renal blood flow. For example, high dosages of Furosemide, such as 100-500 mg can be provided. In an exemplary embodiment of the invention, an otherwise life-threatening amount of medication may be provided to a patient in need thereof, using the stimulation system as a life-saving adjuvant. Optionally or alternatively, lower amounts of drugs are provided and the reminder of the desired effect is provided by stimulation.

Exemplary Lead Design

Various lead designs can be used. In particular, various lead designs known in the art can be used. Optionally, the lead is selected according to the target and/or distance between the target and stimulator and/or expected movement of the target and/or stimulator and/or according to potential to damage nearby tissues and/or according to it being permanently implanted or inserted.

It should be noted that while some stimulation methods described herein use a bipolar lead with two conductors, other embodiments use multiple conductors (e.g., if multiple different stimulations are delivered using a single lead. Optionally or alternatively, non-electrical lead designs may be provided as well. For example, for a thermal stimulator, two conductors may be used to deliver electrical energy to a thermal transducer. For chemical stimulation, a single lumen may be used to deliver a stimulating chemical. A second lumen may be used for washing and/or for suction.

Figures 25A, 25B:
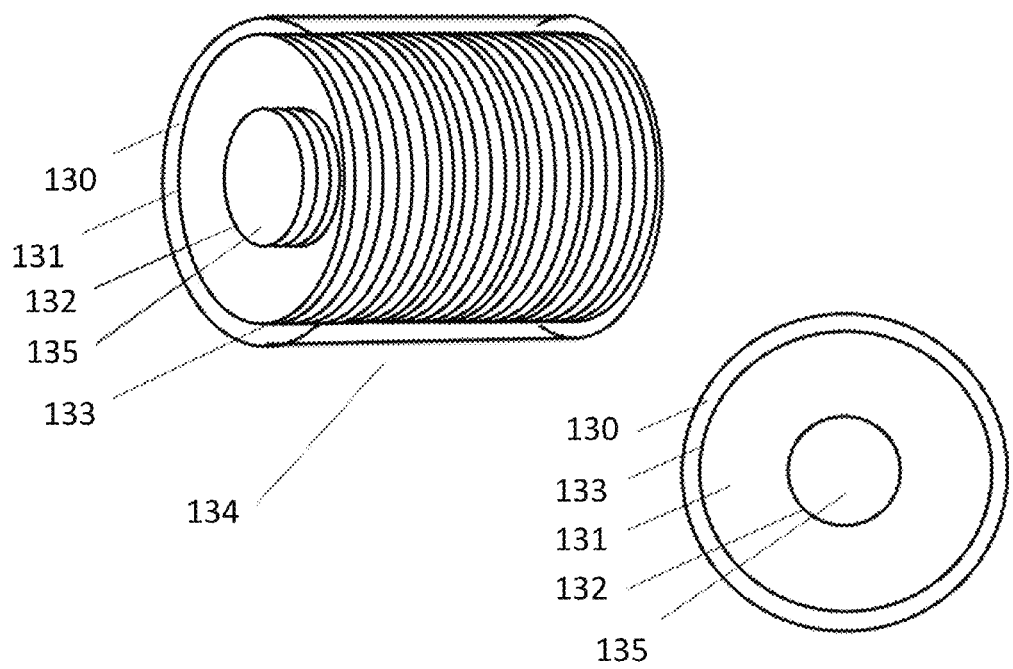
FIGS. 25A-B are cross-sectional views of a lead in accordance with an exemplary embodiment of the invention.

FIG. 25A is a perspective cross-sectional view and FIG. 25B a cross-sectional view of a section of a lead 134. Such a lead may be used, for example, for substantially any of the embodiments described herein.

In an exemplary embodiment of the invention, electrode lead 134 is in the form of a tube (e.g., with a circular, or other cross-section, including optionally a concave cross-sectional portion) with two or more concentric layers. In an exemplary embodiment of the invention, lead 134 comprises an external layer 130 optionally made of a flexible isolating bio-compatible material, for example silicone. Optionally lead 134 comprises a coil 133, which can, for example, provide structural properties to the lead and/or serve as a conduction path. Optionally, coil 133 is a spring. Other designs, such as one or more elongate ribbons, a spiral or a hypotube, may be used as well.

In an exemplary embodiment of the invention, lead 134 comprises a layer 131 made of a flexible isolating material, for example silicone. In alternative embodiments, at least part of layer 131 is hollow, or is entirely absent.

A second conductor 132, optionally in the form of a coil spring, braid or wire is optionally provided within layer 131. In an exemplary embodiment of the invention, conductor 132 is an anode and coil 133 is an anode. Optionally, component 132 is not a conductor and only provides structural properties and/or a lumen. Conductor 132 is optionally filled with an isolating layer. In some embodiments of the invention, the lead is made soft and hollow. This may allow the lead to not interfere with movement of body parts and/or urine flow.

In an exemplary embodiment of the invention, a lead as described herein has a length of between 1 and 50 cm, for example, 10-20 cm and diameter of between 0.1 and 5 mm, for example, 3 mm. Optionally, the lead is elastic, for example, having a bending radius of less than 7 cm, 5 cm or 2 cm and/or having an elongation of over 10%.

Intra Luminal Stimulators

A potential advantage of the urinary system is that, being hollow in parts, stimulators can be implanted within the system (e.g., within ureter, urethra, bladder, kidney and/or blood vessels). Such implanting may reduce interference with external tissues and/or may assist in stimulator placement and/or fixation. In an exemplary embodiment of the invention, intra-luminal electrodes are more resistant to migration because, for example, they contact only one tissue type and/or are held in place by the structure of the lumen. In an exemplary embodiment of the invention, while part of the stimulator and/or the stimulating contacts thereof are intraluminal, the rest of the stimulator may lie outside the lumen. This may further assist in anchoring.

Figure 26:
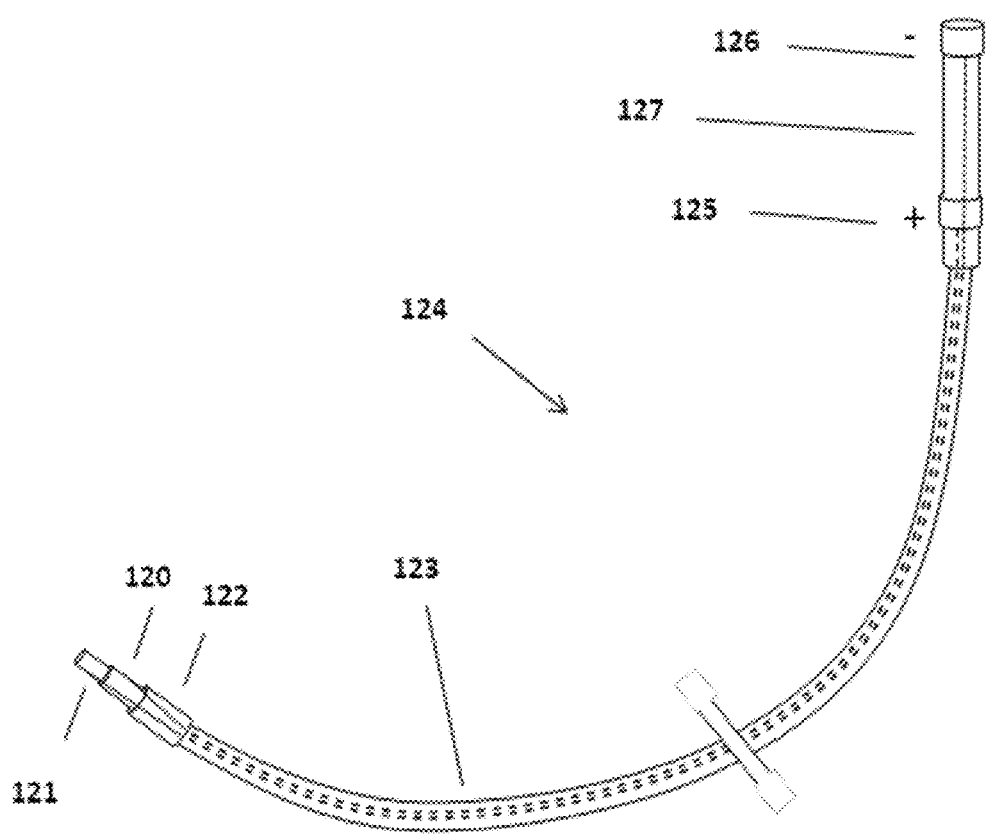
FIG. 26 illustrates an intraluminal stimulator, in accordance with an exemplary embodiment of the invention.

FIG. 26 shows an intraluminal stimulator 124 (which may also be used for extra-luminal stimulation, for example, for stimulating a bladder), in accordance with an exemplary embodiment of the invention. In the example shown, stimulator 124 includes a lead body 123, with a connector 127 at one end and electrode contacts at a distal end 122. Optionally, connector 127 includes a cathode connector 126 and an anode connector 125, but it is noted that AC stimulation may be applied as well and/or a lead may be used to deliver different stimulation levels to 2 or more electrode.

In an exemplary embodiment of the invention, at distal end 122, an electrical connector 121 extends and a ring electrode contact 120 is provided. Optionally, the two electrical contacts are separated by a layer of isolating material. Optionally or alternatively, other electrode contact designs, for example, as described below, are used. Optionally or alternatively, distal end 122 includes a screw for threaded engaging of muscle tissue.

Figures 27A, 27B, 27C:
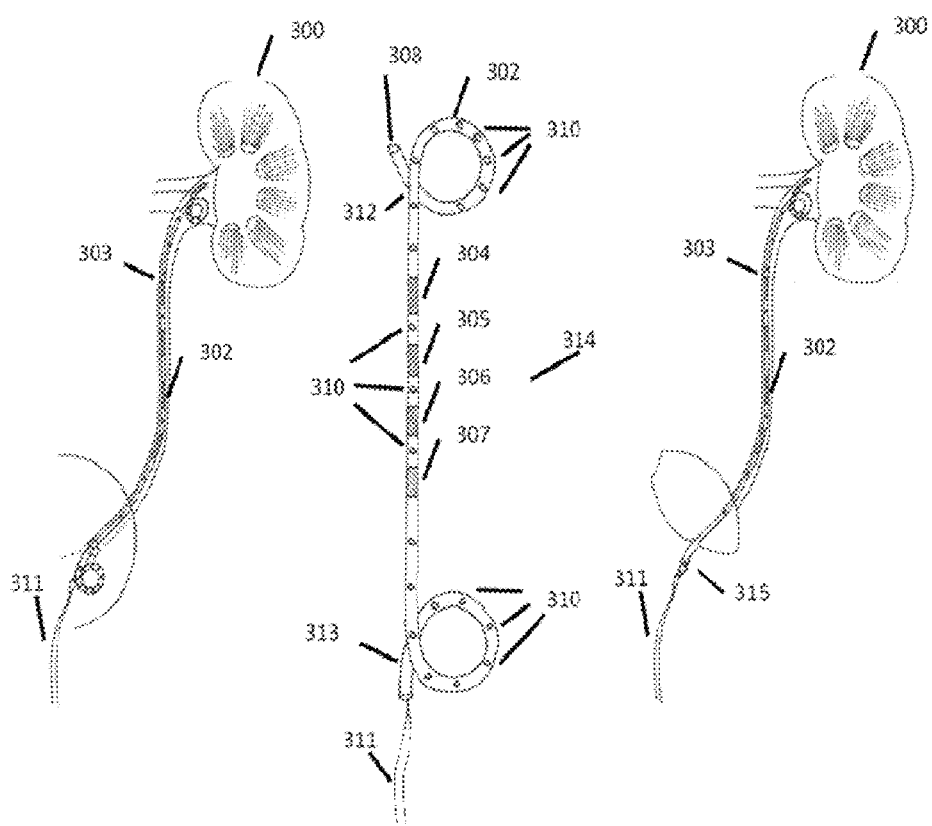
FIG. 27A illustrates an intra-ureteral stimulator, in accordance with an exemplary embodiment of the invention.
FIG. 27B illustrates the stimulator of FIG. 27A, inserted in a ureter, in accordance with an exemplary embodiment of the invention.
FIG. 27C illustrates the stimulator of FIG. 27A, inserted in a ureter, in accordance with an alternative exemplary embodiment of the invention.

FIG. 27A shows a stimulator 314 having a body 302, optionally including a pigtail or other anchoring mechanism at either end, in accordance with an exemplary embodiment of the invention. Stimulator 314 optionally comprises at least one or more conducting surfaces, for example, 1, 2, 3, 4 or more as shown 304, 305, 306, 307. These conducting surfaces can be shorted together or not, depending on the embodiment, and may be connected, for example, to an anode or to a cathode. Optionally at least one of the conducting surfaces 304, 305, 306, 307 is connected to an isolated conducting medium 311 (e.g., a wire or wire pair) that optionally exits the body through the urethra and is optionally connected to a stimulator 415 such as described in FIG. 7. Alternatively, a stimulator controller is designed to reside in the body and/or in the bladder. In other embodiments, power is transmitted using wireless means.

According to one embodiment stimulator 314 has at least one hollow lumen 308 and optionally one, two, or more pores 310 along its length and/or on distal and/or proximal ends thereof. In some embodiments of the invention, the pores may be used to allow fluid, optionally urine, optionally chemical substance, optionally a drug, to flow through stimulator 314, optionally to a target.

In an exemplary embodiment of the invention, the distal and/or the proximal ends 312 and 313 of stimulator 314 are curved, for example, pre-formed to naturally have a pigtail configuration, which may be used for anchoring in the kidney pelvis and/or bladder.

FIG. 27B shows stimulator body 302 lying within a ureter 303 and anchored in a kidney 300 and bladder, in accordance with an exemplary embodiment of the invention.

FIG. 27C shows an alternative implantation method in which body 302 extends out of the human body, for example, out through a urethra 315 or out through the pubic area.

FIGS. 28A-C3 illustrate designs for a stimulator including contacts and/or anchoring in the kidney pelvis in accordance with exemplary embodiments of the invention.

FIG. 28A shows a stimulator 320 lying in a ureter 324 and optionally including a plurality of contacts 322 in a kidney pelvis 321, in accordance with an exemplary embodiment of the invention. In an exemplary embodiment of the invention, stimulator 320 includes a body in the form of a thin and/or flexible wire 323, attached to a basket structure including optional contacts 322. Optionally or alternatively, the basket structure is mounted on a ureteral tube and/or replaces one of the pigtails of FIGS. 27A-C.

Optionally, contacts 322 include one or more cathodes and/or one or more anodes. Optionally, the field (e.g., voltage potential difference) is applied perpendicular to the ureter axis. In this and/or other embodiments, field application direction can be, for example, along the ureter (or other body part) axis, at an angle thereto and/or perpendicular thereto. Optionally, the field is applied between the inside and the outside of the ureter (e.g., using an external grounding electrode).

Optionally, stimulator 320 or the basket portion thereof is elastic (or super-elastic) and is formed, for example, of an expanding wire mesh. Alternatively, the basket may be balloon expandable or expanded by mechanical distortion or by shape-memory distortion.

FIGS. 28B1-28B3 illustrate a method of implanting stimulator 320, in accordance with an exemplary embodiment of the invention. A sheath 325 having a basket in a closed state 326 is advanced along a ureter 324 to a kidney pelvis 321 (FIG. 28B1). Sheath 325 is slightly retracted so that contacts 322 spread out (FIG. 28B2). Finally, sheath 325 is completely retracted leaving contacts 322 in contact with kidney pelvis 321 and/or anchoring therein by interference, at least against retraction (FIG. 28B3).

FIG. 28C1-28C3 illustrate alternative embodiments of a basket, for example, a basket formed of axial and trans-axial lines 327 (FIG. 28C1), a helical coil 328 widening towards the kidney pelvis (FIG. 28C2), and a plurality of (radially and optionally axially) extending arms 329 (FIG. 28C3).

FIG. 29A illustrates an intra-luminal stimulator 340 with medial electrical contacts 341, according to an exemplary embodiment of the invention. FIGS. 29B-29D2 illustrates medial contact designs suitable, for example, for contacts 341, in accordance with an exemplary embodiment of the invention.

Optionally, but not necessarily, stimulator 340 is an inter-ureteral stimulator including (e.g., as in some previous embodiments) a body with a lumen 345, a plurality of pores 344 and/or pigtails at ends 342 and 343 thereof. One or more wires 346 and/or the stimulator body may extend out of the urethra.

In an exemplary embodiment of the invention, stimulator 340 includes radially extending contacts 341, with an optional deployment mechanism 347. Optionally, additional contacts, such as any of the designs shown herein are provided. Optionally, contacts 341 extend radially to a diameter which is about 110%, 150%, 200%, 300% or smaller or intermediate or larger percentages of a diameter of the body of stimulator 340. This may cause slight distension of the ureter.

While a deployment mechanism 347 is shown, in some embodiments, there is no such mechanism and contacts 341 self extend when released by a constraining outer tube which may then be removed from the body. Optionally, mechanism 347 is a tube which can slide to cover and/or uncover contacts 341 and radially compress them.

In an exemplary embodiment of the invention, contacts 341 are or are mounted on elastic elongate elements. Such contacts may all have a same polarity or a voltage may be developed between them. Optionally or alternatively, two or more contacts may be provided axially displaced. In an exemplary embodiment of the invention, contacts 341 comprise 1, 2, 3, 4, 5, or more circumferentially displaced contacts.

FIG. 29B1-29B2 show how radially extendable contacts may be deployed in a ureter, in accordance with an exemplary embodiment of the invention. As shown a plurality of contacts 350 are radially constrained by a sleeve 348 (FIG. 29B1). When the sleeve is retracted (FIG. 29B2), for example, removed from the body, electrode contacts 350 radially extend and ensure contact with the ureter (e.g., inner walls 353 thereof) and/or provide anchoring. Optionally, the electrodes are unsmoothed and/or include small barbs to engage the ureter wall. Optionally, during insertion, contrast medium is injected, for example through the stimulator lumen, to ensure that the contacts do not interfere with a ureteral valve.

FIG. 29C1-29C2 show an embodiment of electrode contacts 350, where each contact is mounted at the tip of an extending arm.

FIG. 29D1-29D2 show an embodiment of electrode contacts 350, where each contact is mounted at the medial portion of a bent arm. This design may be less likely to cause perforation of the ureter, than the design of FIG. 29C1-29C2, but may be less well anchored.

FIGS. 30A-30D2 show exemplary intra-luminal stimulators 360 having a thin body, in accordance with an exemplary embodiment of the invention. One potential advantage of having a thin body is reduced interaction and/or interference with body structures such as the ureter and/or valves, allowing the UVJ to close, avoiding interference with kidney stones and/or ease of insertion using an enclosing catheter (e.g., smaller diameter). For example, the diameter of stimulator 360 may be, for example, less than 1 mm, less than 0.4 mm, less than 0.2 mm or intermediate diameters.

Referring to FIG. 30A, stimulator 360 optionally has a pigtail or other space filling structure at one end 361 and/or another end 362 thereof. One or more wires 363 optionally extend out of the body. An expansible medial stimulation area includes a plurality of contacts 364 which can be, for example, of any of the designs described herein. FIGS. 30A-30B2 illustrate contacts at the ends of extending arms. FIGS. 30B1 shows how such arms are temporarily prevented from extension (FIG. 30B2) and maintained in a closed configuration 366 by an overtube 367. FIG. 30C1 shows how arms amounted on arcs 368 are temporarily prevented from extension (FIG. 30C2) by a slidable overtube 367.

Optionally, deployment, in this or other embodiments, is by adhering the contacts to the body of stimulator 360 optionally using a material that dissolves in the body, softens at body heat, is made to release the arms by the provision of a chemical or otherwise releases the contacts once in the body.

FIG. 30D1 shows an electrical contact design having a spiral electrode 370 twisted around stimulator 360 and/or mounted as an undulating ribbon thereon. FIG. 30D2 shows an alternative embodiment having contacts 371 in the form of elongate contact regions.

Optionally, such regions are, for example, about 1 mm, about 2 mm, about 3 mm, about 8 mm or smaller or intermediate or greater in length.

FIG. 31A-E show intra-luminal stimulators 460 having balloon-expandable electrical contacts, in accordance with exemplary embodiments of the invention.

Stimulator 460 may be similar to any of the designs shown above, the differences being an inflatable element 470, such as a balloon with one or more contacts 461 mounted thereon or therewith. Optionally, an optional port 469 for an inflation lumen 465 is provided for inflation of balloon 470. As in some of the designs above, stimulator 460 can have a body with a lumen 465 and optional pigtails 463 and 462 at ends thereof. Optionally, one or more wires 474 extend from the body. Optionally or alternatively, inflation lumen 466 does not fill lumen 465 of stimulator 460. Optionally, lumen 465 includes one or more pores 464 which may be used for passage of fluid such as urine.

FIGS. 31B1-31B2 show stimulator 460 in a ureter 467, with (FIG. 31B2) and without (FIG. 31B1) inflation of balloon 470. As can be seen inflation may cause distension of the ureter. In some embodiments, such inflation is used without electrical (or chemical or other) stimulation or in addition to it. Optionally, lumen 466 serves as a conduit for acoustic or mechanical vibration from outside the ureter (e.g., outside the body) to the ureter. A mechanical transducer may be placed, for example, in contact with port 469 outside the body.

FIG. 31C1-31C2 show cross-sectional views of FIG. 31B1 and FIG. 31B2. Optionally, balloon 470 is not inflated enough to collapse lumen 465. Optionally, lumen 465 is stiffened thereat, for example, by thickening or by a layer of stiffer material. Optionally or alternatively, balloon 470 defines channels for urine flow along it or through it.

FIG. 31D1-31D2 shows two exemplary alternative electrode contact designs. In configuration 471 (FIG. 31D1), bands of electrodes (or meshes 472) lie transverse to the axis of stimulator 460, and are optionally separately electrified and/or act as a bipolar electrode. In design 473 (FIG. 31D2), a single mesh 472 is provided.

FIG. 31E is a cross-sectional view of a design for a stimulator 460, showing a lumen 475 for fluid (e.g., urine) and one or more lumens for a conductor 476 and optional inflation lumen 466.

In some embodiments, the contacts 461 are configured to compress radially and inflation is used to maintain them radially distended.

In some embodiments, balloon 470 is deflated once contacts 461 are extended and engage ureter walls and/or are plastically deformed by distention. Optionally, contacts 461 and wires 474 are left in the body and the rest of the delivery system (e.g., balloon 470, inflation lumen 466) are removed. This may be similar to the implantation of a stent, where contacts 461 may be formed in a cylindrical, stent-like, configuration.

In some embodiments of the invention, anchoring of any of the above designs is temporary and, for example, a stiffening element dissolves or otherwise decomposes after a time and then the stimulator is unanchored and falls out.

While the above (and below) embodiments focus on electrical stimulation, they may also be used for non-electrical stimulation in conjunction with or instead of electrical stimulation, by replacing an electrical contact with a suitable transducer. For example, a transducer can be a piezoelectric element, a light emitting element, an inflatable element, a chemical eluting element, an iontophoretic element and/or other transducers, for example, as known in the art. Optionally, the above described wires are replaced by tubes or wires or fibers, as required.

Optionally or alternatively, to the contacts being stimulators, the contacts may be used for sensing and/or may be replaced by a suitable transducer. The various structures described herein may be useful for ensuring uniform contact between the sensor transducer and the body structure being sensed.

It should be noted that while many of the described-herein electrode contact configurations appear rotationally symmetric, this need not be the case in all embodiments. For example, contacts may be provided in only some sectors of the contact configuration. Optionally or alternatively, stimulation is different at different sectors. Optionally, the level of stimulation for each sector (e.g., efficacy and/or pain considerations) and/or which sector to stimulate, are selected during a configuration stage and/or based on desired therapy. Optionally, the stimulator is designed to avoid rotation in situ.

Extra-Luminal Stimulators

In an exemplary embodiment of the invention, a stimulator is mounted outside of a lumen, or on a tubular structure, such as a nerve or ureter or a different structure, such as a kidney or bladder. As shown below, some designs of mounting methods allow the stimulator to move with the structure on which it is mounted and/or otherwise not interfere with its function.

Figure 32B:
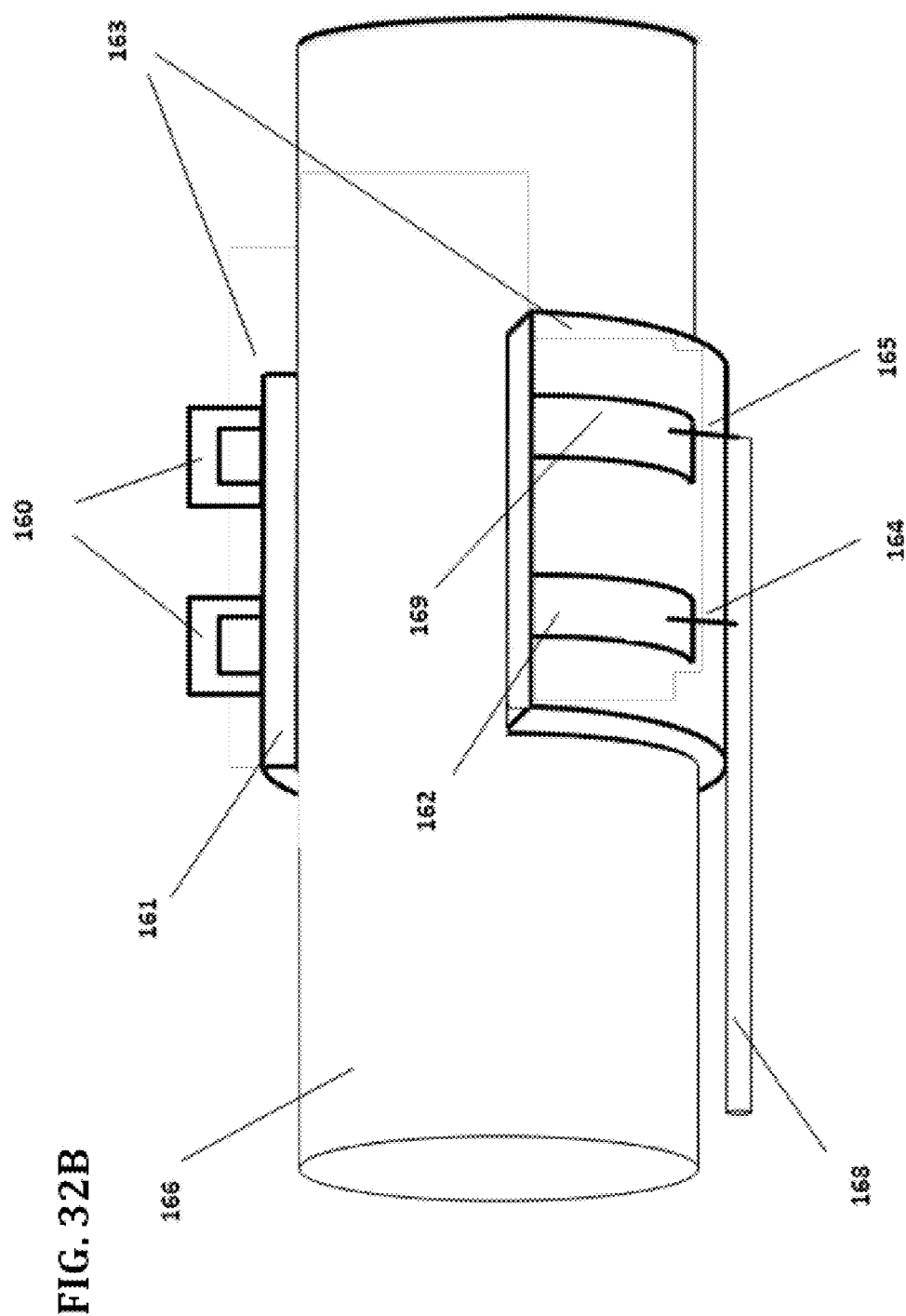
Figure 32C:
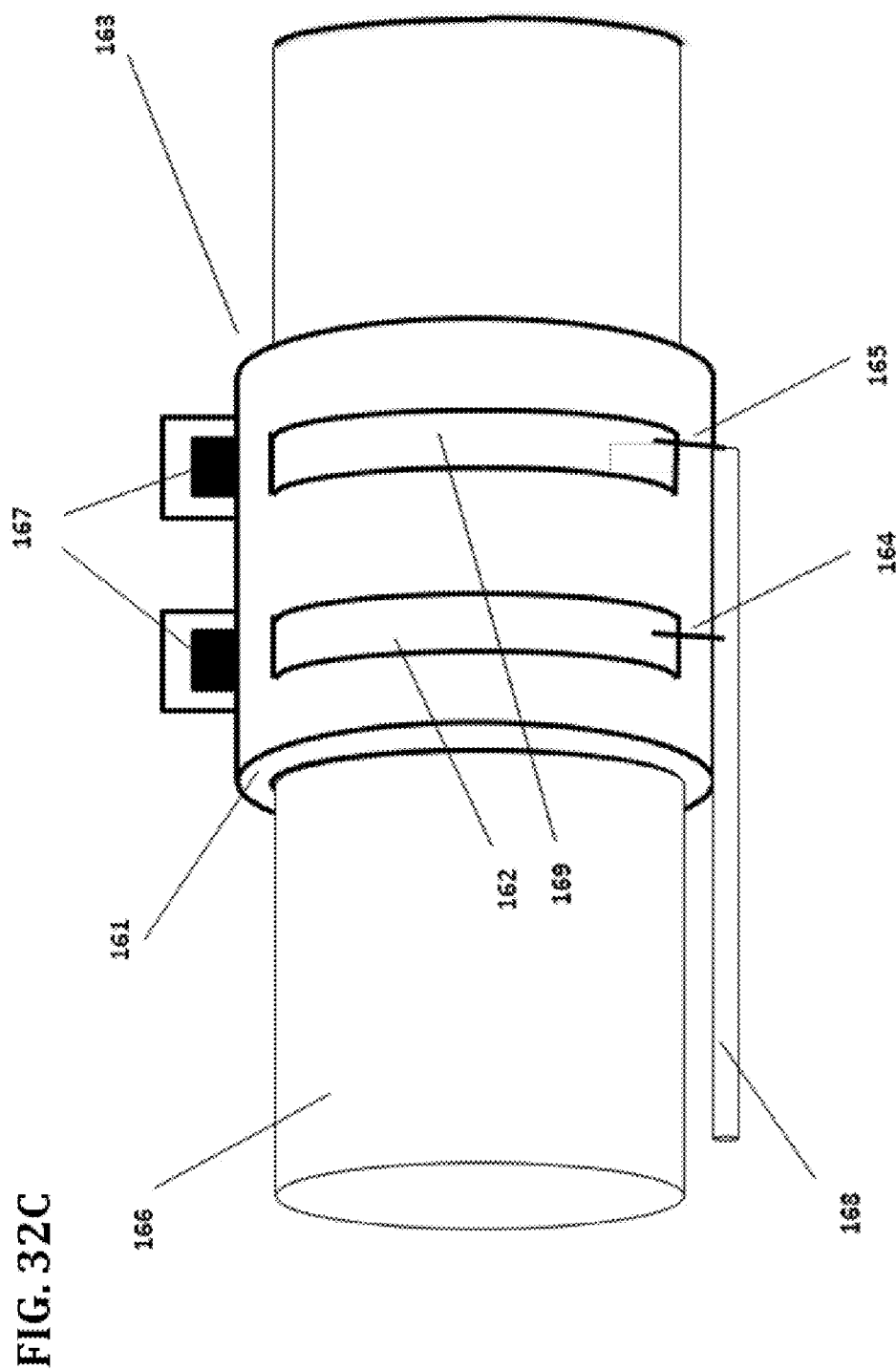

FIGS. 32A-C show an extra-luminal stimulator 163, for example, an electrode, mounted on a lumen, for example a ureter 166, in accordance with an exemplary embodiment of the invention.

Referring first to FIG. 32A, which shows stimulator 163 with a section missing (e.g., the section which completes to a cylindrical shape), stimulator 163 can include one or more contacts 162, 169. In an exemplary embodiment of the invention, at least one contact is circumferentially arranged. Optionally or alternatively, at least one contact is axially arranged. Other arrangements, such as spiral or point contacts may be used as well.

In the embodiment shown, a cylindrical body 161, optionally electrically insulating, has one or more contacts 162, 169 formed thereon and electrically coupled, e.g., via couplers 164, 165 to a lead 168. Optionally, body 161 is axially split and is lockable, for example, using a latch mechanism formed of a buckle 160 and a connector 167 (FIG. 32C). Other fastening mechanism can be used as well, for example a pin on one side that fits into a recess on the other or other interference-fit. Optionally or alternatively, body 161 is plastically deformable. Alternatively, body 161 is elastically pre-configured to retain a cylindrical shape. In some embodiments, a fastening mechanism, if any, is used to prevent inadvertent removal from the structure on which the stimulator is mounted, rather than regularly resist removal forces.

In an exemplary embodiment of the invention, body 161 is formed of silicone. Optionally or alternatively, one or more conducting components of stimulator 163 are formed of a conductive silicone.

FIG. 32B shows body 161 mounted on a ureter or other tubular structure 166.

FIG. 32C shows stimulator 163 mounted on a ureter or other tubular structure 166, with no parts hidden. Optionally, such contacts are extension of contacts 162 and/or 169 and/or are separate or additional contacts.

Optionally, buckle 160 (or other connector design) or connector 167 is used to attach to other body structures or to the tubular structure, for example, by suturing.

Optionally or alternatively, buckle 160 and/or connector 167 is replaced by or enhanced by one or more hooks or barbs positioned to engage the tubular structure or other nearby tissues.

Figure 33A:
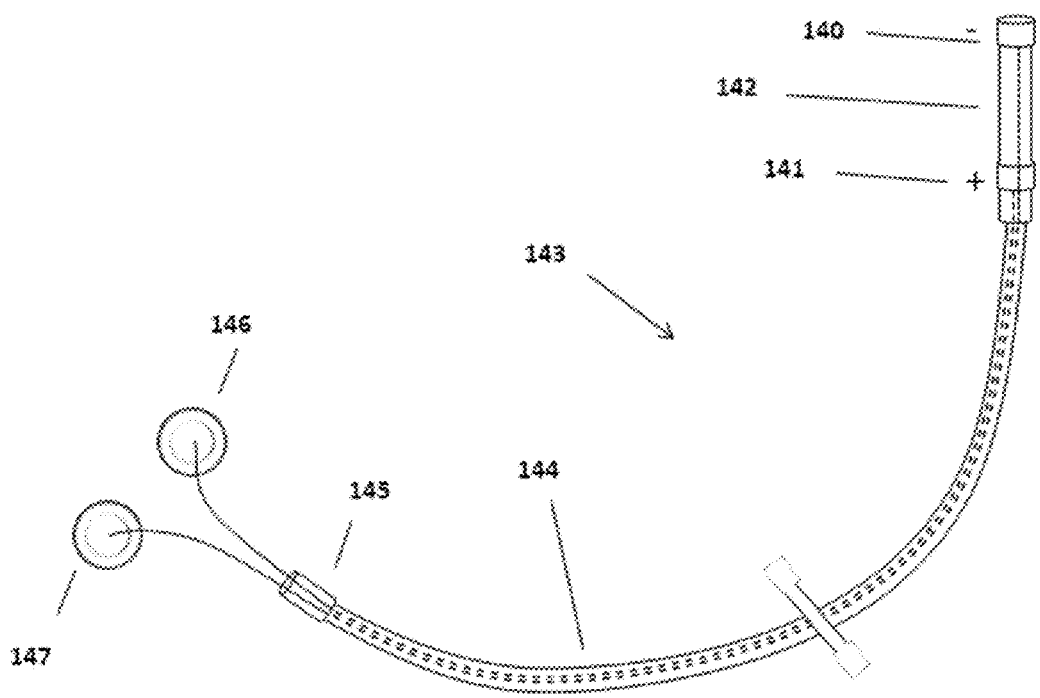
FIG. 33A illustrates an extraluminal stimulator with patch contacts, in accordance with an exemplary embodiment of the invention.

FIG. 33A shows a stimulator 143 including a lead body 144 and one or more patch contacts 146, 147, which may be, for example, electrical contacts or other stimulation transducers. In an exemplary embodiment of the invention, lead body 144 is terminated at one end by a connector 142, having (for DC stimulations) an anodal contact 141 and a cathodal contact 140. Optionally, connector 142 is designed for connection to an implantable controller.

In an exemplary embodiment of the invention, lead body 145 terminates at an opposite end with a coupler 145 which extends electrical wiring out of lead body 144, for example into separate wires for each electrode contact 146, 147. In some embodiments of the invention, distal end 145 acts as an electrical contact of one polarity while contacts 146, 147 have a different polarity. Optionally or alternatively, each contact 146, 147 (or more) can be controlled to have a different electrical potential.

In an exemplary embodiment of the invention, a contact 146 has the shape of a circle or an ellipse. Optionally, not shown, electrode contact 146 includes an attachment mechanism, for example, a clip or suture holder, for example, a clip or a hole for attaching a suture and fixating to tissue. Optionally or alternatively, the contact is coated with an adhesive layer.

FIG. 33B illustrates an exemplary alternative extraluminal stimulator design 153, which can be the same as that of FIG. 33A, except that a cuff 155 (and/or 156) is provided instead of a patch electrical contact 146, 147.

As shown in a blow-up FIG. 33C, a cuff 155 can include, for example, a split annular or ellipsoid shape 157, optionally of conducting material or including inside and/or outside a conductive material. Optionally, split shape 157 is urged shut by an elastic element (e.g., a spring loaded hinge 158) or by the elasticity of shape 157. Optionally, a cable 159 electrically connects cuff 155 to a lead body 154. Alternatively, cuff 157 is a curled elastic extension of cable 159.

Figures 34A, 34B:
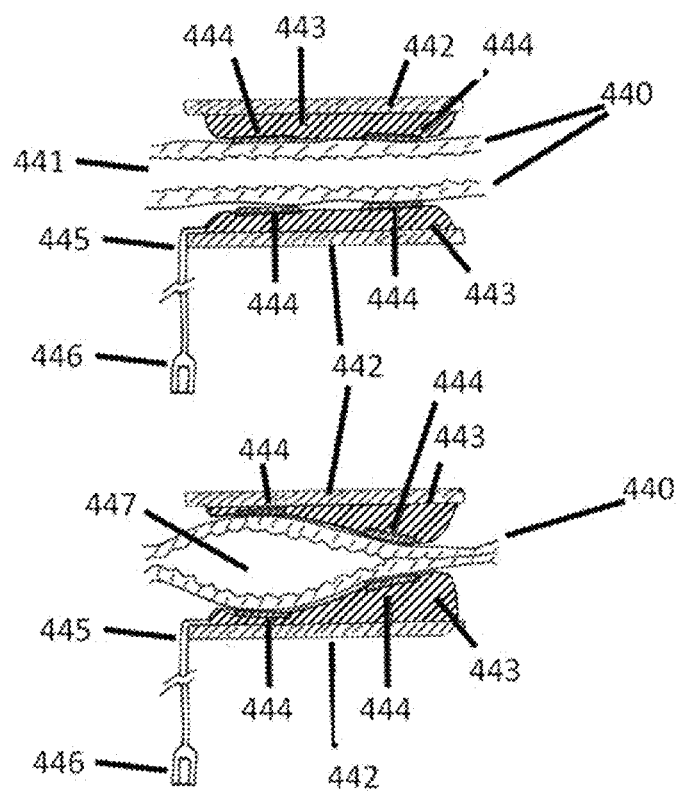
FIGS. 34A-B illustrate an extraluminal stimulator with diameter matching, in accordance with an exemplary embodiment of the invention.

FIG. 34A-B illustrates an extraluminal electrode adapted to conform to a shape and/or dynamics of an underlying structure such as a ureter, in accordance with an exemplary embodiment of the invention. In an exemplary embodiment of the invention, the electrode has a body 442 and one or more contacts 444, separated by a compressible layer 443. In use, when the underlying structure expands (FIG. 34B), compressible layer 443 is compressed, and when the underlying structure contracts, layer 443 expands. Optionally or alternatively, layer 443 ensures contact between contacts 444 and the underlying body structure.

In an exemplary embodiment of the invention, layer 443 comprises a hollow element filled with a fluid, for example saline (in which case compression may entail expansion in a different part thereof) or air or other compressible gas. In an alternative embodiment, layer 443 is formed of a sponge or a soft silicone, optionally within a flexible or elastic capsule. In an exemplary embodiment of the invention, layer 443 is selected to resist dynamic movement of the underlying structure to an extent of less than 50% (or less than 40%, 30%, 20% or intermediate percentages) of a radial force applied by the structure. In some embodiments, layer 443 is provided only underlying contacts 444 and/or otherwise incompletely encircles and/or covers the inside of body 442.

In an exemplary embodiment of the invention, body 442 is elastic, allowing it to conform to changes in diameter of underlying structures. Optionally, the body 442 can be inflated or deflated, or filler with soft medium, in order to allow tight contact with underlying structure without applying pressure on that structure, for example ureter 441. In an exemplary embodiment of the invention, body 442 is selected to have a minimum diameter at which it does not apply pressure on the underlying structure.

In an exemplary embodiment of the invention, body 442 is soft, for example, made of silicone. Optionally or alternatively, body 442 is isolating. Optionally, layer 443 serves to seal the edges of body 442 so that electrical fields (e.g., is dielectric and/or isolating) and/or chemicals provided by contacts 444 does not exit between the structure body 442 to the nearby tissues.

In an exemplary embodiment of the invention, layer 443 is inflatable and its inflation amount and/or stiffness are controlled using a fluid channel 445 connected to a valve and/or port 446, through which inflation fluid may be added and/or removed.

In the example shown, the amount of material and/or softness of layer 443 and the diameter of body 442 is selected so as to allow contact of the conductive surface 444 with ureteral wall 440 during ureteral bolus 447. Optionally, contacts 444 are flexible and soft or may be, for example, small rigid elements.

In an exemplary embodiment of the invention, an extraluminal electrode contact has a body length of, for example, 2-4 cm and/or an electrical contact area of, for example, 0.5-5 cm$^2$. Optionally or alternatively, such an electrode has an inner diameter of, for example, 4-6 mm.

In an exemplary embodiment of the invention, kinking of the ureter (or other elongate structure) by the cuff is prevented by preventing twisting of the cuff around an axis transverse to the ureter axis. Optionally, such twisting is prevented by mounting on the cuff and elongate element, not attached to any tissue, which is substantially parallel to the ureter axis. Optionally or alternatively, to an elongate element, a mesh is attached. Such a mesh and/or elongate element may mechanically lodge in tissue and/or adhere thereto, and thereby prevent substantial twisting of the cuff. Such a design may also be useful to prevent migration.

Hybrid Stimulator

In some embodiments of the invention, a stimulator includes both intraluminal stimulation and/or sensing components and extraluminal stimulation and/or sensing components.

Figure 35:
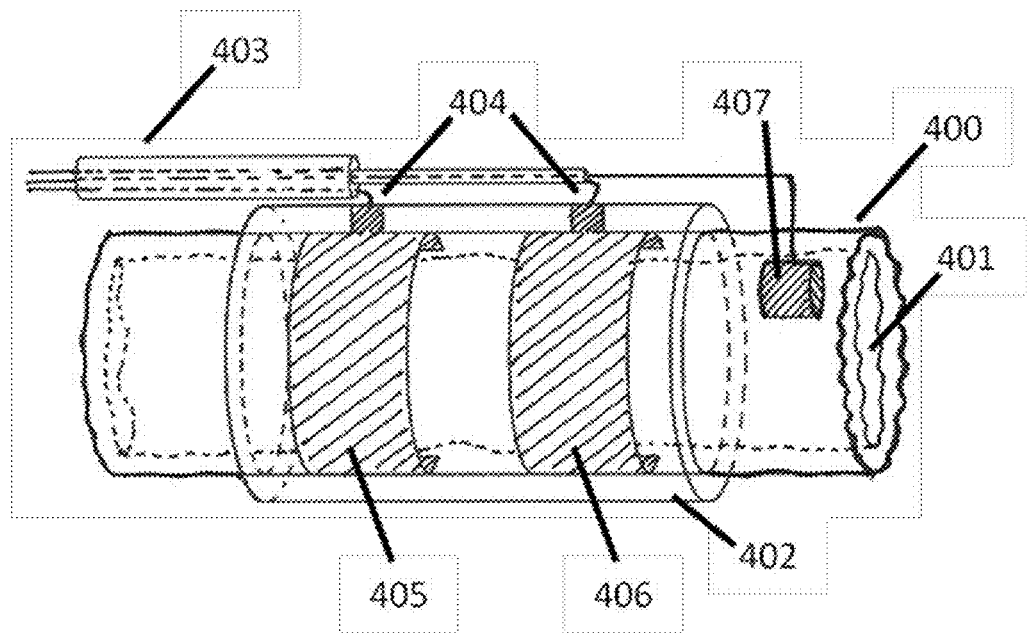
FIG. 35 illustrates a stimulator with both extra-luminal and intraluminal components, according to an exemplary embodiment of the invention.

FIG. 35 shows a hybrid stimulator including both intraluminal 401 and extra-luminal 400 components, in accordance with an exemplary embodiment of the invention. In the example shown, the components are electrical contacts. In other embodiments, one or more of the components is a non-electrical stimulating transducer and/or a sensor.

In an exemplary embodiment of the invention, the hybrid stimulator includes one or more external contacts 405 and 406 mounted on a lumen (e.g., a ureter), for example, using any of the methods describe herein, and an internal contact 407, mounted inside the lumen. Optionally, contact 407 is located proximal, distal, between or directly across the extra-luminal contacts 405, 406. Optionally, more than one contact 407 is provided.

In an alternative embodiment, component 407 is non electrical and is, for example, a piezoelectric pressure sensor or a source of ionic material for delivery into the ureter.

Contacts 405 and 406 are optionally isolated from the rest of the body by an isolating layer 402, optionally including a grounded conducting layer (not shown) within. Conductors 405 and 406 are coupled to one or more conducting lines 403 (optionally isolated from the body), by, for example, connectors or welding points 404.

Exemplary Wireless Stimulation

In some embodiments of the invention a stimulator is implanted in the body and power is provided from outside. Optionally, also control is provided from outside. Optionally, such control is provided by using power from outside to directly activate the stimulator and various stimulation sequences are provided by varying the power provision. Such a stimulator can be any of the stimulator types described herein, for any of the targets. Optionally or alternatively, power is stored locally for a short while before being used, for example, in an inductor or a capacitor. Optionally or alternatively, power is used to release a stimulant, such as a chemical and/or heat a thermal stimulator.

FIGS. 36A-E illustrate a ureter-based wireless stimulator 480, in accordance with an exemplary embodiment of the invention. In the example shown, two spaced apart electrode contacts 481 are interconnected by a coil 482, optionally isolated. The circuit can be closed, for example, by the human body or urine. Optionally, the coil receives power from outside the body for example, by RF induction or low frequency coupling. Other power antenna designs may be used, for example, patch antenna. Optionally, additional power circuitry is provided, such as a capacitor for storing power and/or pulse shaping elements.

Additional illustrated optional elements of stimulator 480 are a hollow lumen, one, two or more pores 489 that link the lumen to the outside of stimulator 480 (e.g., along its length and/or at one or both ends thereof) and optional pigtail coils for anchoring at one or both ends of stimulator 480. Such a lumen may be used, for example, to allow fluid, for example urine, or a chemical substance, optionally a drug to flow through electrode 480, optionally to a target.

In an exemplary embodiment of the invention, during implantation, stimulator 480 is inserted into the (or two are inserted, into both) ureteral lumen until a desired location thereof is reached. In one example, at the desired position, the distal curved parts of the electrode are optionally located in the renal pelvis and in the bladder.

Figure 36:
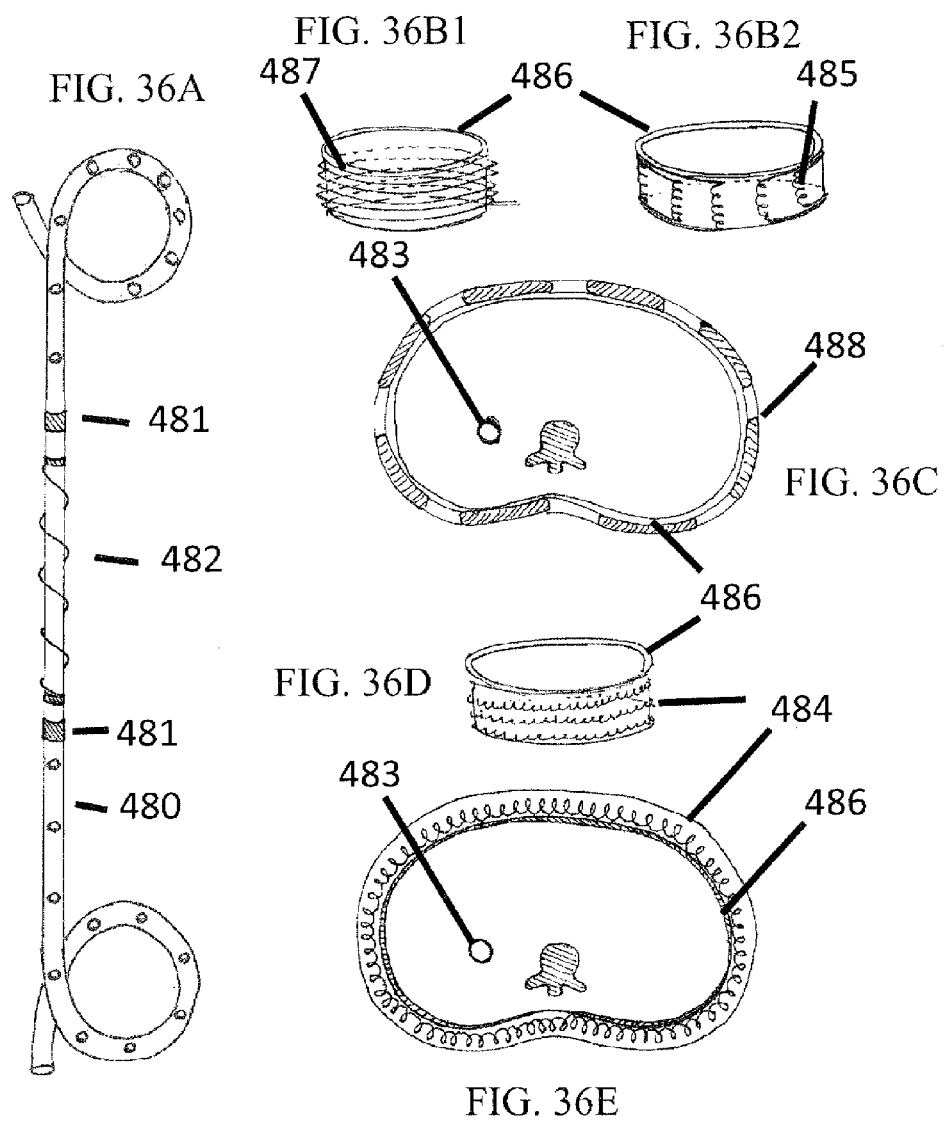
FIGS. 36A-36E illustrate an implanted wireless stimulator and extracorporeal power sources therefore, according to exemplary embodiments of the invention.

In an exemplary embodiment of the invention, power is transmitted to stimulator 480 by electrifying one or more coils outside the body. FIG. 36B1-36B2 show two examples of extracorporeal power transmitters 486 including coils 485 and/or coils 487. Optionally, as shown, such a device is made into a vest or belt 488 worn on the body (see FIG. 36C), with spaced apart stimulators, that transmit power to an indwelling stimulator, having a cross-section shown as 483.

FIGS. 36D and 36E shows an embodiment where a coil(s) 484 surround a body (FIG. 36E), with an optional isolating material 486 provided between coil 484 and the body.

In an exemplary embodiment of the invention, the orientation of the power transmitting coils is selected according to the design and implantation orientation of the stimulator. Optionally or alternatively, the stimulator and/or power transmitter include multiple orthogonal transmitting elements to ensure power delivery and reception at a range of or at all orientations.

Exemplary Nephrostomy Based Stimulation

While one route to internal urinary system lumens is via the urethra, in some embodiments of the invention, the kidney, internal kidney structures and/or urinary system lumens are accessed via a nephrostomic approach, or by a reverse nephrostomic approach.

A potential advantage of a nephrostomy approach is that there is no interference with the lower urinary tract and that the groin area, which is anatomically complex, may be avoided.

Figure 37:
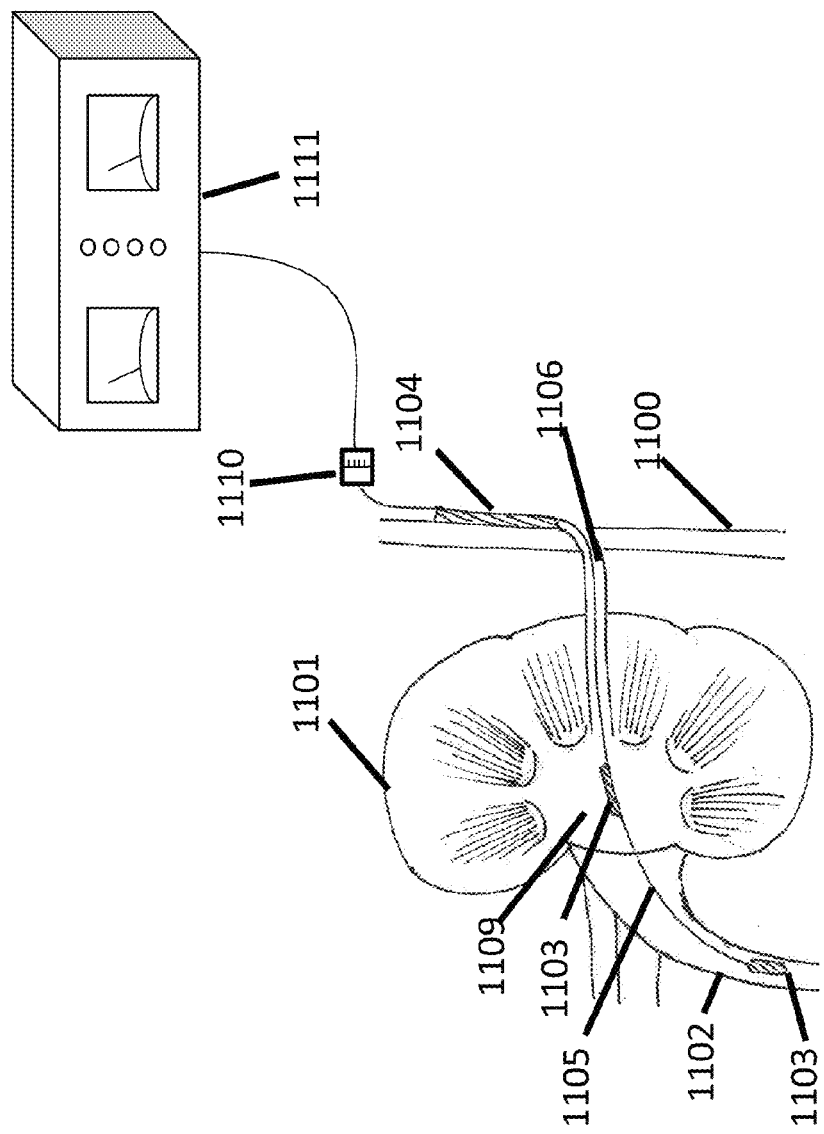
FIG. 37 shows an exemplary implantation of a stimulation system using a nephrostomic approach, in accordance with an exemplary embodiment of the invention.

FIG. 37 shows an exemplary nephrostomic stimulation device, according to an exemplary embodiment of the invention, optionally including an external control box 1111, optionally a pulse generator. In some embodiments, control box 1111 is miniaturized and/or implanted under the skin. Optionally, in this and/or other embodiments, a control box may include circuitry and/or chemicals for stimulation and/or other stimulation sources.

Figure 39:
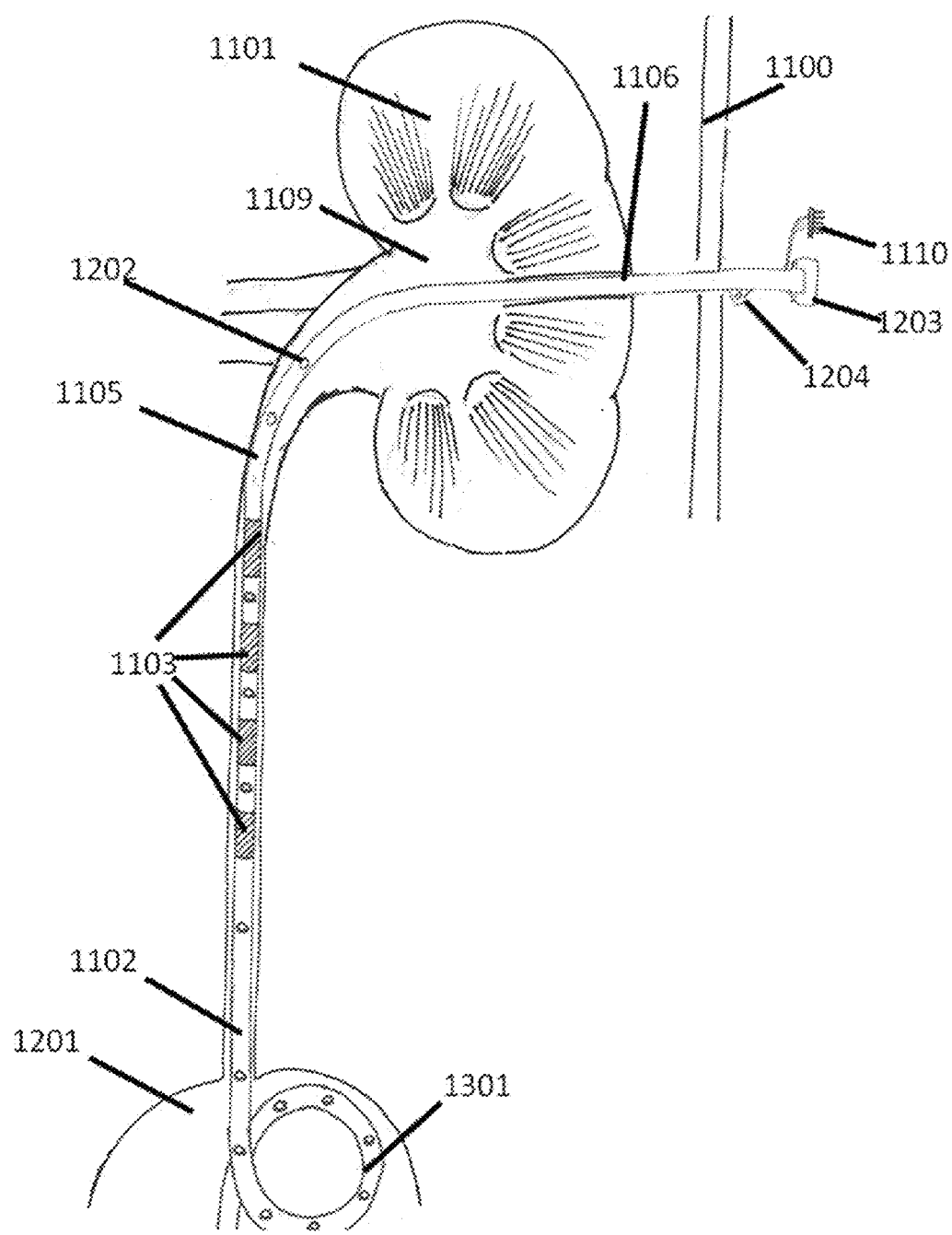
FIG. 39 illustrates a stimulation device that is located within the renal pelvis, the ureter and the bladder, in accordance with an exemplary embodiment of the invention.

In an exemplary embodiment of the invention, a stimulator 1105 is inserted through the skin, following a nephrostomy route 1106, optionally through a parenchyma of a kidney 1101 optionally to the renal pelvis 1109, optionally until the ureter 1102, optionally down to a bladder 1201 (see FIG. 39). Stimulator 1105 may be attached to (or run along) a skin at a section 1104 thereof and include an optional plug 1110 for attachment to control box 1111.

In an exemplary embodiment of the invention, stimulator 1105 includes at least one conductive surface 1103 (e.g., for an electrical stimulator; other stimulators would use other transducers). Optionally section 1104 includes a conducting portion in contact with skin 1100. Conductive surface (or portion) 1103 can be in various locations, for example, one or more of in contact with the pelvic wall and in contact with the ureter 1102. Different conductive portions are optionally configured to be separately activated.

Figure 38:
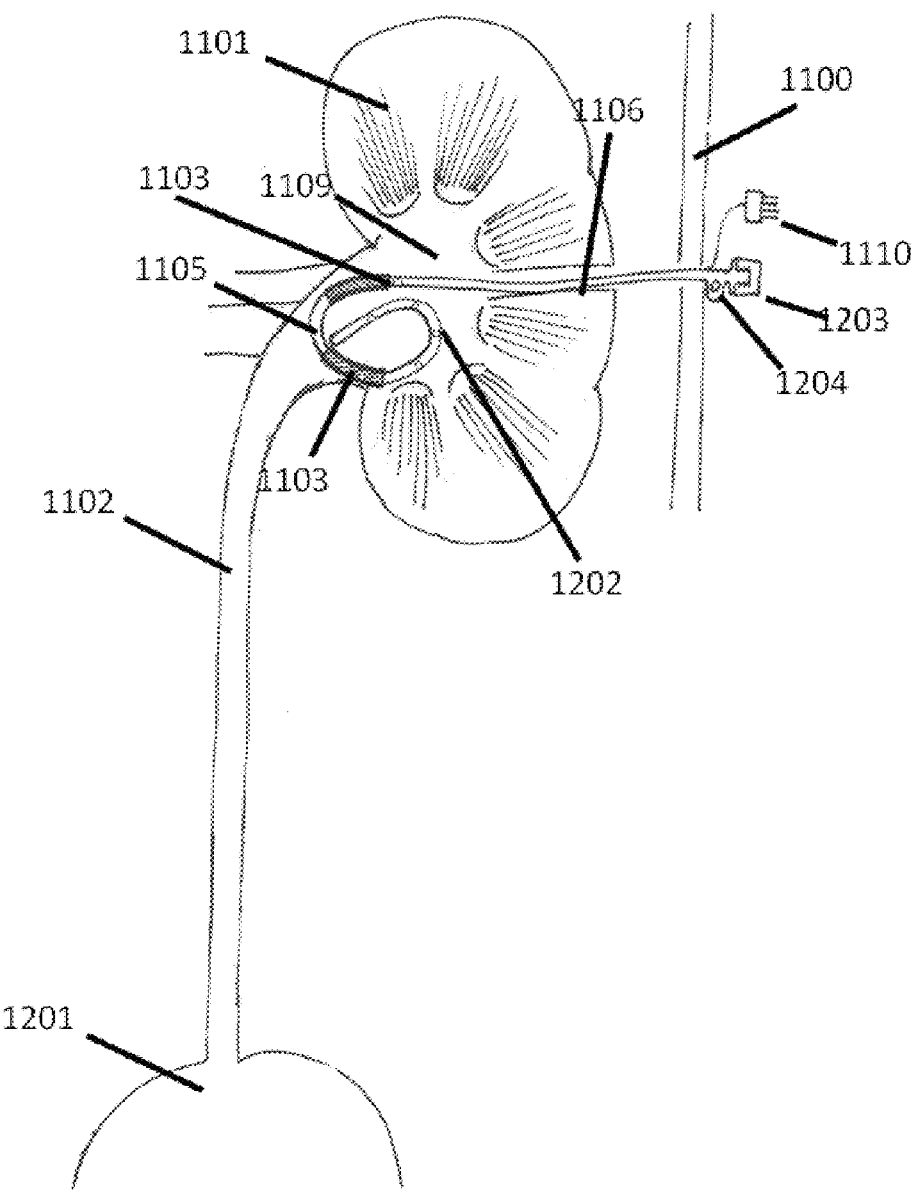
FIG. 38 illustrates a stimulation device that is located within the renal pelvis, in accordance with an exemplary embodiment of the invention.

FIG. 38 shows an embodiment where a stimulator 1105 is configured to volumetrically expand in kidney pelvis 1109, optionally providing one or more of anchoring, ensuring contact with lumen walls and multiple points of stimulation. In the embodiment shown, conducting surface(s) 1103, of which there may be, for example, 1, 2, 3 or more, are connected by a conducting element (e.g., a wire braid or ribbon) to connector 1110, optionally located outside the body. Optionally, the stimulation device 1105 has at least one hollow lumen, optionally with one or more holes 1202 that provide access to the lumen. Optionally the hollow lumen 1401 is connected to a valve 1203, optionally located outside the body. Such valve may be used, for example, to withdraw samples or to inject a chemical to stimulate the ureter. Optionally the stimulation device 1105 can be fixated on the skin by a connector 1204.

FIG. 39 shows an exemplary stimulator 1105 inserted in a kidney pelvis, ureter and bladder, in accordance with an exemplary embodiment of the invention. In the embodiment shown, a plurality of conducting portions 1103 are positioned to lie along the ureter, and a pig-tail portion 1301 coils in the bladder, optionally providing for trigone stimulation (e.g., with a conductor, not shown) or for bladder stimulation (e.g., with one or more conductors not shown) and/or for anchoring.

FIGS. 40A1-40A3 show a detailed view of stimulator 1105, in two variants thereof and in an optional relaxed state, in accordance with exemplary embodiments of the invention. FIGS. 40B1-40B3 show cross-sections of stimulator 1105, illustrating layouts of conductors in accordance with some embodiments of the invention.

FIG. 40A1 and FIG. 40A2 show two exemplary stimulators, one (FIG. 40A1) with a lumen along its entire length and conductors on its outside and another (FIG. 40A2) with one or more conductive elongate elements extending past its end (and/or an end of a lumen thereof).

FIG. 40B1-40B3 show three exemplary cross-sections of a stimulator 1105. A first cross-section (FIG. 40B1) shows two lumens, 1401 which accesses optional holes 1202 and 1404, optionally filled with a conductive material and/or used to elute chemical stimulants. Optionally, lumen 1401 is used to carry a stylet which can be used to stiffen stimulator 1105 and/or navigate it and/or assist in penetrating tissues, during insertion. After insertion such a stylet may be removed.

A second cross-section (FIG. 40B2) shows a plurality of conductive wires 1402 lying within a wall 1403 of the stimulator, and not in contact with lumen 1401 or the urinary system (e.g., except at conductors 1103).

A third cross-section (FIG. 40B3) shows a plurality of conductive wires, optionally coated, which lie along the outside of wall 1403.

FIGS. 41A-B shows two exemplary layouts of stimulators 1501 lying in a urinary system, in accordance with exemplary embodiments of the invention. In the example shown, a stimulator 1501 is optionally thin, for example, less than 1 mm in diameter and/or is soft enough to not interfere with valves in the ureter. In an exemplary embodiment of the invention, stimulator 1501, when released achieves the shapes shown in the figure—curling up in kidney pelvis (FIG. 41B) or bladder (FIG. 41A). Optionally, stimulator 1501 is inserted with a more rigid over tube which prevents premature reforming thereof.

FIGS. 41C1-41C3 shows three exemplary designs for stimulator 1501 or 1105.

In FIG. 41C1 the entire outside of the stimulator is conductive, at least for an axial length of 200 mm and/or for a complete circumference or an arc angle of 90 degrees.

In FIG. 41C2, an axial portion of the stimulator is covered by an isolating material 1502. In FIG. 41C3, an isolating axial element is periodically covered with a conductive material (or such a contact is attached onto the axial element and/or a conductor in the element is exposed.

FIG. 42A shows an alternative design for a stimulator 1105, in which a pelvic anchoring element 1601 is provided. In an exemplary embodiment of the invention, the anchoring element is selectively relaxable, to allow for removal of stimulator 1105 from the body.

FIGS. 42B1-42B2 show a self expanding element 1602 including one or more arms 1602a and an elastic element 1602b which spreads the arm(s) away from stimulator 1105. When a pull wire 1604 is pulled, arms 1602a are retracted towards the body of stimulator 1105. In an alternative design, the arms are normally closed and pulling on the string spreads them out. Other expanding anchor designs, for example those known in the art of bladder anchoring, may be used.

FIGS. 42C1-42C2 show a balloon-based anchoring, in which an inflatable element 1605 is optionally inflated (FIG. 42C1) or deflated (FIG. 42C2) to a state 1606, to control anchoring. Optionally, inflatable element 1605 is connected by a lumen 1609 to outside the body, were, for example, a valve and/or port 1608 are used to introduce or remove inflation fluid and/or measure inflation pressure and/or where an optional finger pump and/or fluid reservoir 1607 may be provided.

While a regular nephrostomic approach has been described, in some embodiments of the invention, a reverse nephrostomic approach is provided, in which a catheter or guiding element is pushed up the ureter and then out of the kidney to outside the body. Then the catheter may be retracted carrying a stimulator along with it from outside the body. Such reverse insertion may be useful, for example, in patients where aiming (e.g., using ultrasound) is not sufficient for correct placement of the stimulator in the ureter, or for patients where advancing of a catheter in the ureter is difficult or may cause damage, while reverse advancement may be easier.

Exemplary External Stimulation

In some embodiments of the invention, stimulation of the urinary system is provided non-invasively, using energy provided from outside the body.

Figure 43:
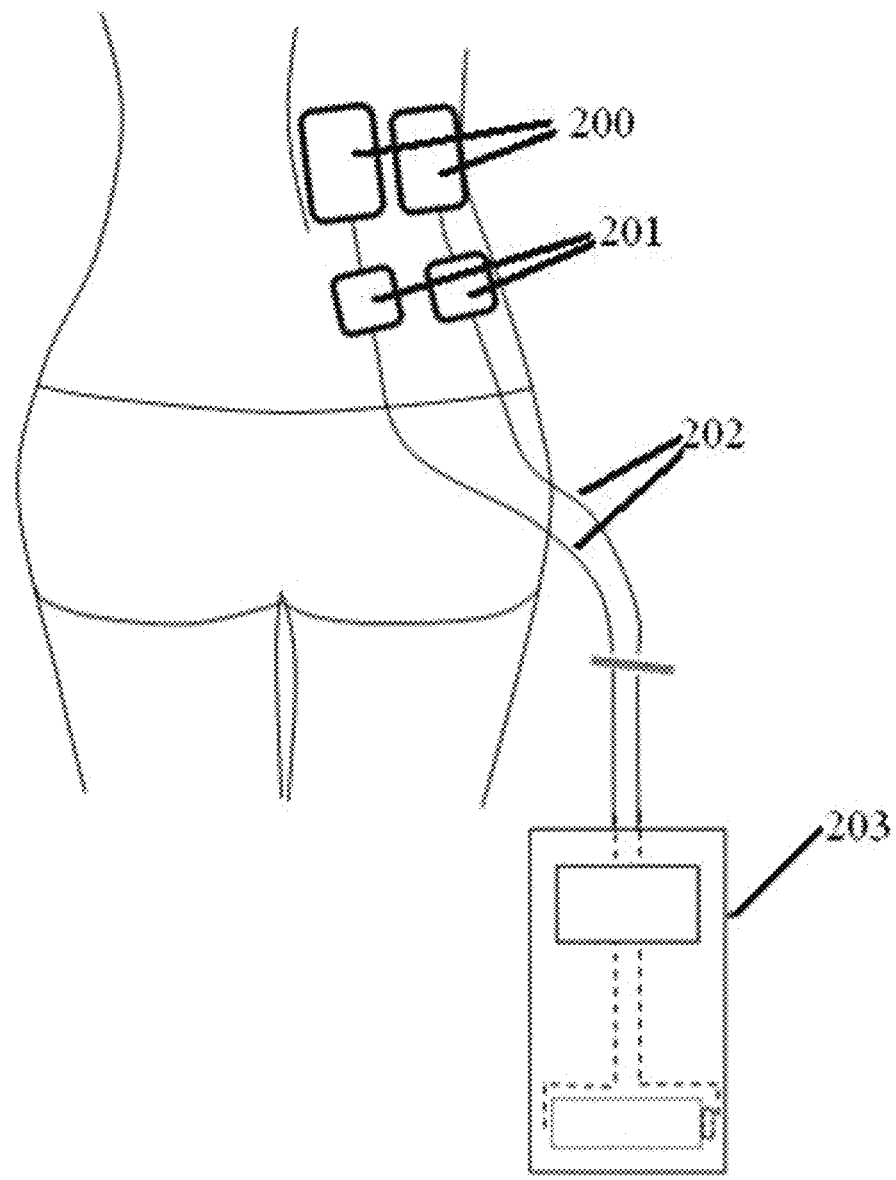
FIG. 43 illustrates a transcutaneous stimulator system and stimulation-transducing device, in accordance with an exemplary embodiment of the invention.

FIG. 43 illustrates an exemplary transcutaneous stimulation system, in accordance with an exemplary embodiment of the invention. In one example, the stimulation system uses electrical stimulation. As shown, one or more pairs of electrodes 200 and, optionally, 201 are used to create an electrical potential inside the body. Optionally, a single electrode includes both anodal and cathode contacts. Other electrode arrangements may be provided as well, for example, electrodes 200 being anodes and electrodes 200 being cathodes or vice versa.

A control circuit 203 optionally includes a user input and/or other control methods and mechanisms (e.g., including sensor input) as described above. Optionally, circuit 203 is connected to electrodes 200 and/or 201 by leads 202. Optionally or alternatively, the connection is wireless.

In an exemplary embodiment of the invention, the electrodes are configured to stimulate one or more targets in the urinary system as described above (e.g., kidney, ureters, trigone) and/or nervous tissue related to the urinary system.

In an exemplary embodiment of the invention, stimulation other than electrical stimulation is used. In one example, magnetic stimulation of eddy currents may be provided (e.g., and electrodes 200 and/or 201 be replaced by a suitable transducer). In another example, acoustic (e.g., ultrasonic) stimulation is provided and electrodes 200 and/or 201 replaced by acoustic transducers. Optionally, such transducers are used for imaging and/or other detecting of target structures. For example, the bladder may be located based on its unique reflection profile. This may assist in manual or automatic aiming of acoustic beams at the trigone and/or ensuring stimulation is aimed at correct place.

In some embodiments of the invention, during a setup phase, the patient's internal body structures are imaged, for example, using ultrasonic imaging, in order to help adjust the stimulation. Optionally or alternatively, stimulation is adjusted until a desired effect on the patient is achieved.

Exemplary Kidney Surface Stimulation

In some embodiments of the invention, the surface of a kidney and/or its interior are stimulated form the kidney surface, optionally in addition to stimulation of other parts of the urinary system, in accordance with an exemplary embodiment of the invention.

Figures 44A, 44B:
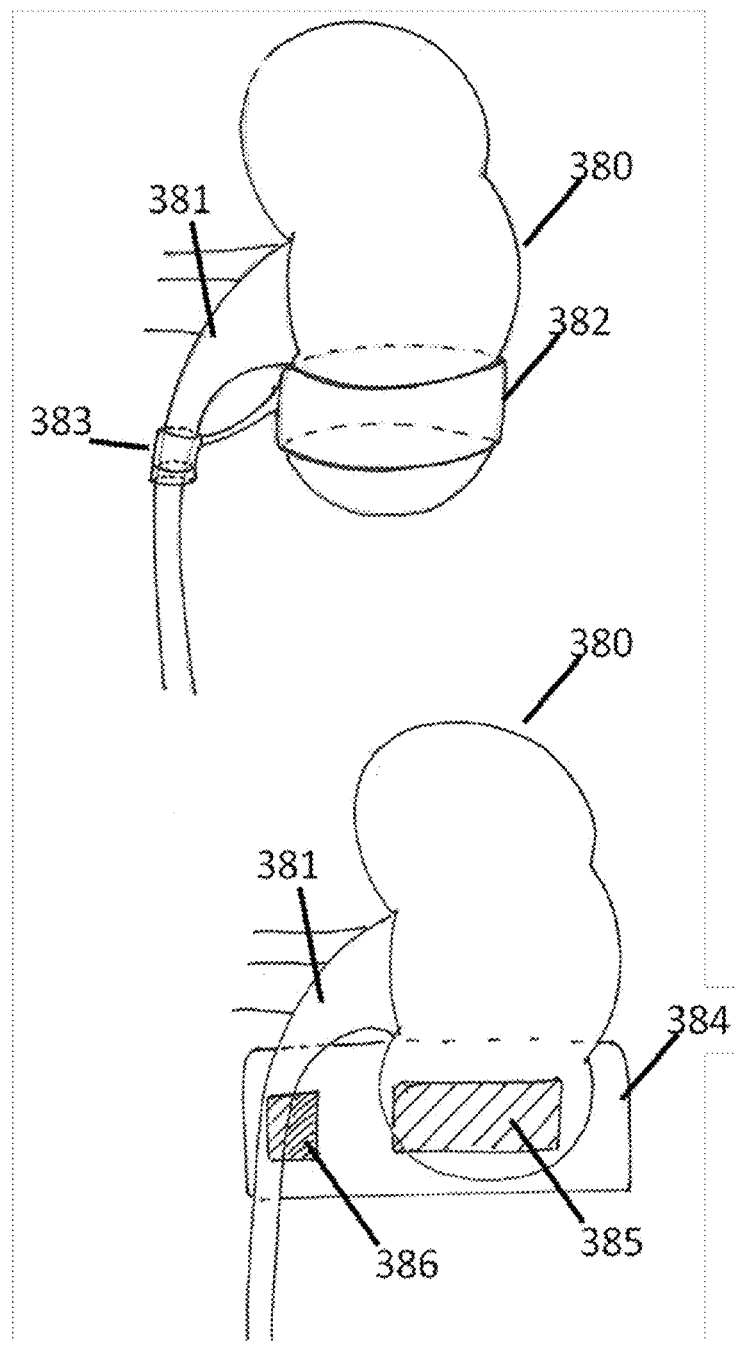
FIG. 44A illustrates a stimulator having one or more conducting surfaces coupled to one or both of a kidney and a ureter, in accordance with an exemplary embodiment of the invention.
FIG. 44B illustrates an alternative stimulator having one or more conducting surfaces coupled to one or both of a kidney and a ureter, in accordance with an exemplary embodiment of the invention.

FIG. 44A shows a stimulator 382 (e.g., an electrical stimulator with a conducting inner surface) mounted on a kidney 380 and, optionally, also including a section 383 mounted on a ureter 381. In some embodiments, only one of 382 and 383 is stimulating and the other serves for anchoring. In other embodiments, each has a different electrical potential (e.g., with 382 being an anode or a cathode). As shown, section 383 is optionally slidably mounted on ureter 381. Optionally or alternatively, stimulators are attached using adhesive, clips and/or sutures. Optionally, stimulator 382 includes a plurality of contacts so as to cause electrical potential changes inside the kidney, rather than only at its surface. Optionally, the inner surface of stimulator 382 comprises an array of electrical (or other) stimulators.

Stimulator 382 (and section 383) can be connected to substantially any stimulator control mechanism described herein. Optionally, stimulator 382 and/or section 383 include a sensor, for example, a ureter impedance sensor, ureter peristalsis sensor and/or ureteral flow sensor.

FIG. 44B shows an alternative design for a kidney stimulator, including a patch or a sleeve 384, including (the figure showing the inner layer), a kidney stimulator patch section 385 and a ureter patch section 386. Optionally, the patch sections are chemical elution sections, for example, controlled by electrical field from a stimulator control, to deliver chemicals by, for example, iontophoresis.

In an exemplary embodiment of the invention, patch 384 is non conducting sheet and is optionally composed of a soft material, optionally inserted posterior to the kidney 380.

Combination Stimulators

The above has described many types of stimulators. It should be noted that a stimulation system may include multiple of the above stimulator types in a same system. Further, in some cases, a single stimulator has multiple portions, for example, sequentially arranged, possibly spaced apart more than in the above hybrid stimulator, possibly directed at different targets and/or different body portions. For example, a bladder stimulator can include an extension which acts as a ureter stimulator, following intra-luminal designs as shown herein, for example. In another example, two ureters may be stimulated using two separate ureter stimulators. Optionally, the two stimulators share a single control/power cable exiting, for example, through the urethra. Optionally or alternatively, the two stimulators share a structural component that lies in the bladder, optionally for bladder and/or trigone stimulation. Different parts may also have different stimulation modalities (e.g., chemical, thermal, electrical).

Exemplary Specific Applications

The above has described many variants of devices and features which may be used together. The following lists some particular collections of features and usages into exemplary devices, in accordance with some embodiments of the invention.

A bladder indwelling catheter. Optionally the placement is performed as shown in FIG. 9C. Optionally the device will be used on acute decompensated heart failure patients admitted to the hospital. These patients can benefit from short term enhancement of renal function and interruption of acute cario-renal syndrome. Many of these patients undergo insertion of a regular bladder catheter for urine measurement, so a new procedure is not needed. The stimulation will optionally commence in the emergency department, and last as long as patient's status, as determined from a number of parameters, including weight, dyspnea, cardiovascular and kidney functions, require it. The stimulation will optionally be provided in short half an hour sessions given every 4-8 hours or as determined by a feedback from sensors or outside. One optional input may be blood pressure, for safety reasons (e.g., not to reduce or increase blood pressure inappropriately). Optionally, urine flow sensing can be provided from the device itself to calibrate the amount of stimulation needed, as urine flow is an easy to measure marker of kidney function. Additional optional group of patients treated by such device may include patients suffering from a hepato-renal syndrome. In this case, the stimulation may continue longer, and may optionally serve as a bridge to keep the patient alive for a liver transplant.

Insertion of an implantable device similar to FIG. 6 or FIG. 21. Patients that cannot undergo an operation for a lead/IPG placement, may benefit for ureteral catheter insertion (FIG. 30), or nephrostomy catheter insertion (FIG. 37). The stimulation may optionally be commenced for half an hour 3-6 times a day, optionally when the patient is resting, or alternatively when the patient is active. Feedback to stimulation can be from an external device, optionally measuring weight or blood pressure of a patient. Optionally, stimulation is increased when patient's weight or blood pressure increases. Patients that can benefit from this device include CHF hypertension and CKD patients. In CHF patients, interruption of a chronic cardio-renal syndrome by reduction of the renal sympathetic drive may halt disease progression and may lead to a decrease in a number of hospitalizations. Patients suffering from hypertension, or chronic kidney disease may also benefit from a chronic device implantation, as the reno-renal reflex may be dysfunctional in these patients, leading to improper sodium handling and increase blood pressure in these patients.

Optionally, a stimulation sequence for these patients may include sensing of urine flow or urine sodium concentration, performed every few seconds, minutes or hours and providing a stimulation of a reno-renal reflex when urine flow or sodium concentration increase so as to optionally substitute for a malfunctioning natural reno-renal reflex.

General

It is expected that during the life of a patent maturing from this application many relevant tissue stimulators will be developed and the scope of the term stimulator is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exempla le, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Example I

Experimental Setup

The experiments were performed on healthy SD rats that were anesthetized with Inactin. A stimulating electrode, made of two platinum plates (each with area of about 5 $mm^2$) located 2-3 mm apart, was placed under one of the ureters. Typically the electrode was placed about 1 cm from the pelvis. The lower side of the electrode was isolated from the rat's body by a silicone coating. Both ureters were then catheterized and the urine collected. Great care was given to preserve the temperature of the animal and the hydration status; the left femoral vein was catheterized and solution of saline with inulin and para-aminohippuric acid (PAH) was perfused at a constant rate of 3 cc/h.

Following the procedure the animal was left undisturbed for one hour for an equilibration of the solutes. The experiment began with baseline urine collection, followed by a stimulation session and then by a recovery period. Each collection lasted 30 minutes. In some experiments we abstained from inserting ureteral catheters, so that not to irritate the ureter. Blood samples were taken once an hour.

The ureters were stimulated with trains of biphasic 1 ms long, 2-10V pulses. The inter stimulus interval was 10 ms (train frequency of 100 Hz). In about half of the experiments stimulation trains were delivered for 30 sec, once every minute. As the results of these experiments were not different from continuous stimulation experiments they were pooled together in the statistical analysis.

Results

Following a stable baseline collection period, we stimulated the ureter by a bipolar electrode located about 1 cm from the pelvis.

Figure 45:
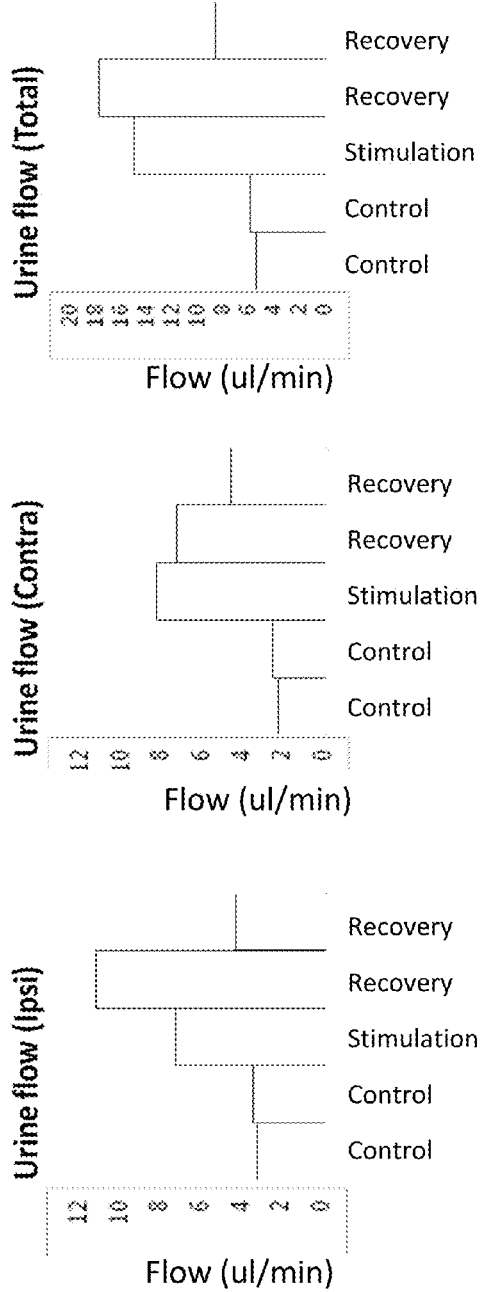
FIG. 45 illustrates urine flow collections from a single animal from the stimulated kidney (left) and the contralateral kidney (middle) together with total urine flow (right), show stable basal urine flow (two left columns in each plot), that sharply increases during stimulation (grey) and remains elevated for at least half an hour thereafter.

FIG. 45 illustrates urine flow collections from a single animal from the stimulated kidney (left) and the contralateral kidney (middle) together with total urine flow (right), show stable basal urine flow (two left columns in each plot), that sharply increases during stimulation (grey) and remains elevated for at least half an hour thereafter in both kidneys.

Figure 46:
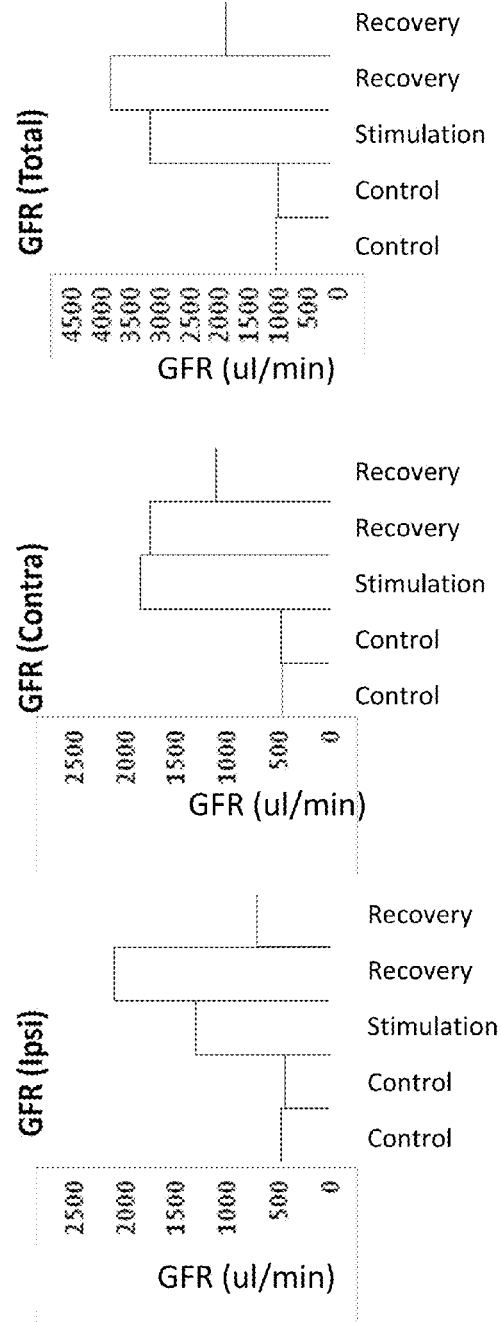
FIG. 46 illustrates GFR analysis from the same animal as above, showing increased bilateral GFR during and following ureteral stimulation.

FIG. 46 illustrates GFR analysis from the same animal as above, showing increased bilateral GFR during and following ureteral stimulation.

Figure 47:
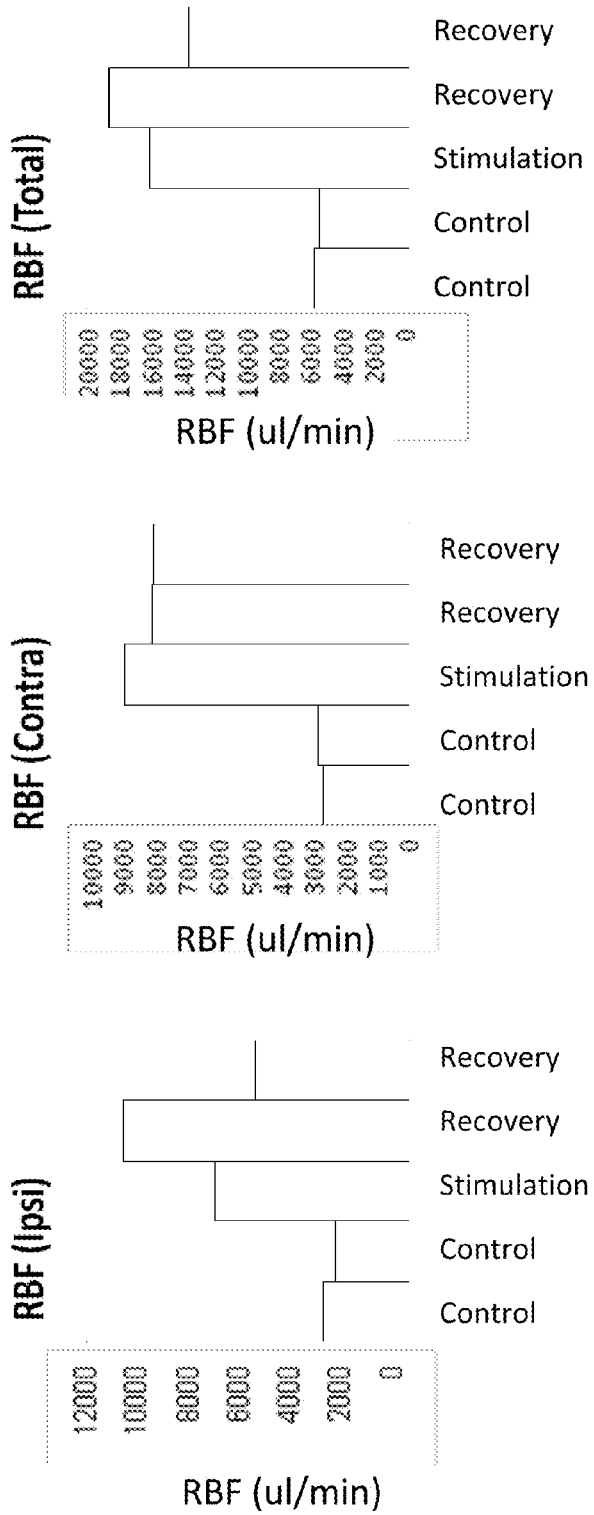
FIG. 47 illustrates RBF analysis from the same animal as above, showing increased bilateral RBF during and following ureteral stimulation.

FIG. 47 illustrates RBF analysis from the same animal as above, showing increased bilateral RBF during and following ureteral stimulation.

It should be noted that the results show, in general, that even after a stimulation of a minute or two, a lasting effect of several minutes can be detected.

The results also show a correlation between RBF, GFR and urine flow from the same animal. In general, all parameters showed a high degree of correlation; indicating that the effects shown may be due to a single intrinsic renal mechanism, such as the reno-renal reflex.

Stimulation of the ureters increased the total (bilateral) urine flow by 25±22%, GFR by 26±30% and RBF by 13±21% (n=8 animals). The increase in urine flow was statistically significant (P=0.04; n=8).

Figure 48:
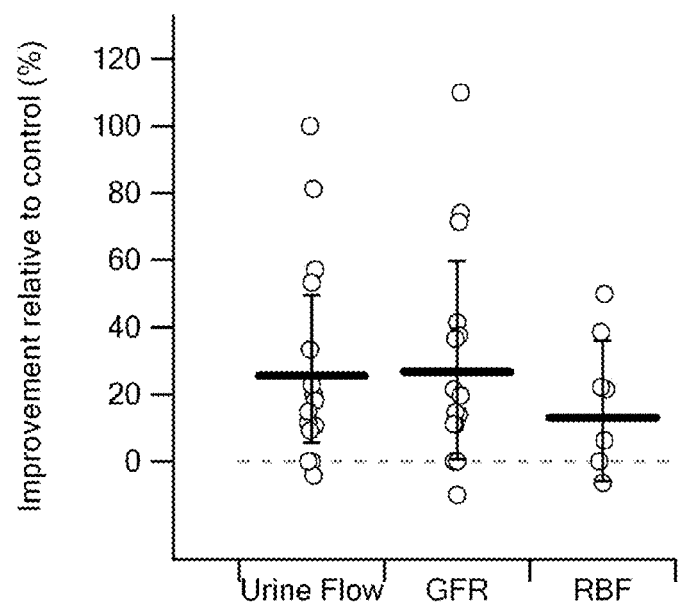
FIG. 48 illustrates the ratio of change in bilateral urine flow, GFR and RBF during ureteral nerve stimulation in relation to control measurements (n=8)

FIG. 48 illustrates the ratio of change in bilateral urine flow, GFR and RBF during ureter stimulation in relation to control measurements (n=8).

There was some experimental failure in rats, probably due to the relative size of the rat and of the stimulators, so additional experiments were performed on sheep.

Modulation of Urine Flow on a Short Time Scale

For the experiments presented above, half-an-hour urine collections were used. The long collection period was necessary for reliable measurements. In order to know the time scale of the effect of electrical stimulation of the ureter, we used a different approach to explore the immediate effect of nerve stimulation. In this set of experiments we measured urine flow along a ureter-catheter on a timescale of minutes during control/stimulation settings.

FIGS. 49A-B illustrate two examples of single kidney urine flow, as measured in a ureter catheter. In the example of FIG. 49A, stimulation of the ureter for one minute sharply increased urine flow, the effect lasting after discontinuation of the stimulation. In the example of FIG. 49B, ureteral stimulation transiently increased urine flow, without the long term effect.

In these experiments we were able to see the effect of stimulation on urine flow, bolus sizes and bolus frequency.

We noticed that electrical stimulation often produced a rapid increase in the rate of urine flow, and in many cases the effect outlasted the stimulation period. Bolus size tended to increase during stimulation, in some instances the flow became continuous. These findings indicate that stimulation may not be given continuously to achieve the desired effect. On one hand, this means that longer battery life can be maintained, on the other hand intermittent stimulations may be better tolerated by the patient.

The increase in urine flow had variable amplitude, possibly because of nerve fatigue and activation of other feedback mechanisms that control urine flow. In some embodiments of the invention, such effects are used to control the main effect.

The Effect on Blood Pressure

In 4 animals stimulation of the ureter was coupled with mean arterial blood pressure measurements.

In all animals tested, the mean blood pressure sharply decreased at the beginning of the stimulation by 7.4±3.6 mmHg, but after about 10 seconds stabilized at 2.7±1.5 mmHg below the original mean arterial pressure (not statistically significant; P=0.23) and was stable during the full course of the stimulation.

FIG. 50 illustrates an example measurement of mean arterial pressure (MAP) during electrical stimulation of the ureter. After an initial drop the MAP stabilizes to near the control values.

The initial drop in arterial pressure can be a result, for example, of an activation of parasympathetic or deactivation of the sympathetic system. Optionally, it may reflect CGRP secretion, known to be activated by reno-reno reflex stimulation. Coupled with increased urine flow, GFR and RBF, this result is highly suggestive of inhibition of the sympathetic drive. The stabilization of blood pressure following the initial drop is probably caused by activation of compensatory mechanisms, most notably the aortic baroreceptors that return the blood pressure to normal.

Interestingly, we show an increase in RBF during reduced or stable systemic blood tension. This may mean that stimulation of the ureter selectively dilates the renal vascular bed. Renal selectivity of the described device may make it an attractive option for treating the various pathologies in which renal function is impaired and systemic side effects are unwanted.

Example II

Acute Results in a Sheep

Effectiveness of electrical stimulation of the ureter was tested on one sheep that underwent nephrectomy 2 month prior to the current procedure. Anesthesia was induced with a mask and halothane (3-4%) in oxygen, the trachea was intubated, and anesthesia was maintained by ventilating the lungs with halothane (0.5-1%) in a mixture of nitrous oxide and oxygen (3:2). Abdominal cavity was opened by midsagittal incision and the ureter was gently exposed near the kidney. Bipolar stimulating electrode, made from platinum sheets (contact area of about 1 cm2) was placed on the ureter about 10 cm from the kidney the ureter was catheterized and urine collection was performed for 15 minutes. Stimulation of the ureter increased urine flow by 315%, GFR by 550% and RBF 565%.

Figure 51:
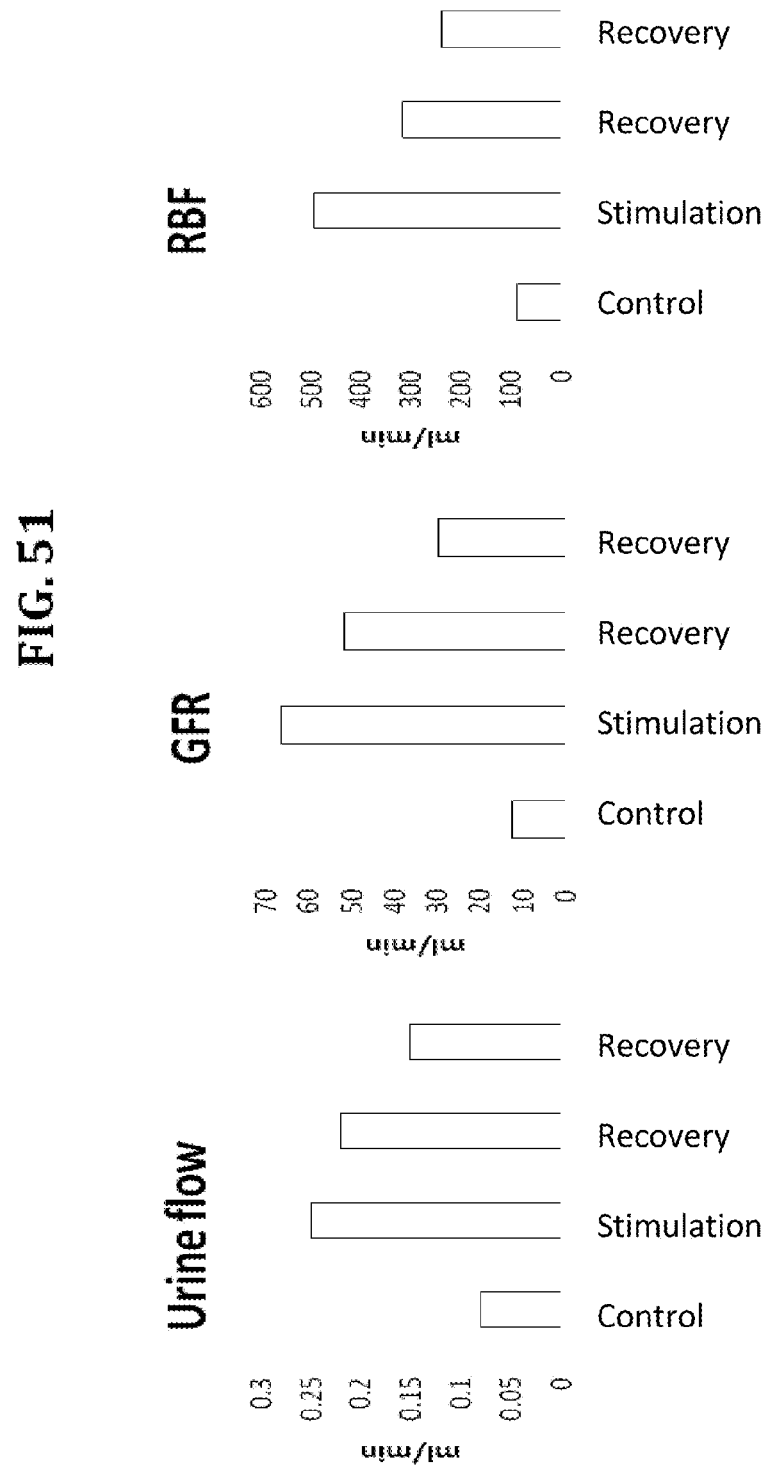
FIG. 51 illustrates Urine flow, GFR, and RBF before, during and following ureteral stimulation in a sheep, showing that stimulation of the ureter significantly improved all these parameters, in accordance with some embodiments of the invention.

FIG. 51 illustrates Urine flow, GFR, and RBF before, during and following ureteral stimulation in a sheep. As can be seen stimulation of the ureter drastically improved all these parameters.

The impressive increase in urine flow, GFR and RBF must be considered with respect to the low baseline activity of the kidneys. In this experiment, the baseline GFR was just 12 ml/min, probably due to the stress of the operation. In this respect this experiment possibly stimulated a condition of developing acute renal failure. The sharp increase in RBF points to the responsiveness of the renal system to stimulation of the afferent system during condition of increased sympathetic activation. This result is encouraging, as increased renal sympathetic activity is the hallmark of diverse medical conditions such as CHF, hypertension, CKD and ARF.

Example III

Chronic Results in a Sheep

Figure 52:
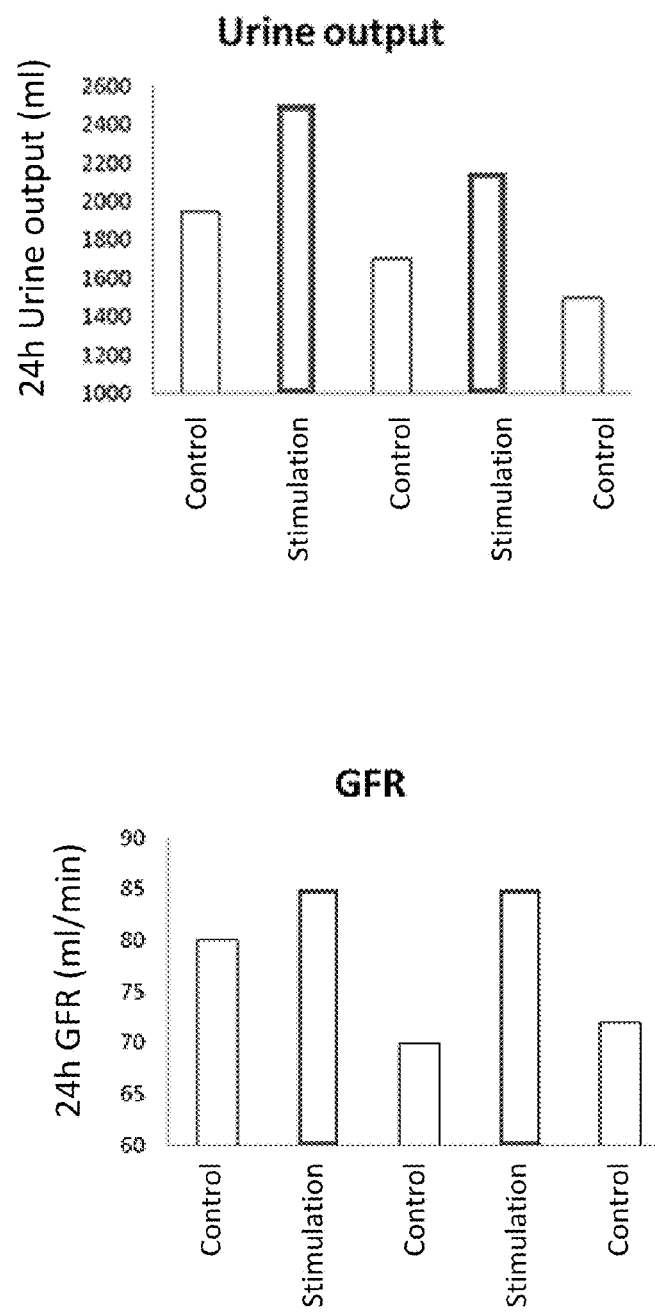
FIG. 52 illustrates Urine flow and GFR for a control and during a 24 h ureter stimulation in a sheep, showing that stimulation of the ureter increased urine flow and GFR during a prolonged stimulation session, in accordance with some embodiments of the invention.

Using a flank approach, external electrodes were implanted on both ureters, about 5 cm from the renal pelvis. The electrodes were similar to the electrodes used in the acute experiment. They were connected to wires that were tunneled subcutaneously to exit at the lumbar region. One week post operation, plasma creatinine level was 1.5 mg/dL, with corresponding GFR of about 70-80 ml/cc. One month following the operation the sheep was placed in a metabolic cage for 24 h urine collection and GFR was estimated by creatinine clearance measurements. Ureteral stimulation was performed by an external pulse generator; the stimulation lasted for 24 h. FIG. 52 shows that Urine flow and GFR increased during prolonged (24 hour) stimulation of a ureter by an implanted cuff electrode located 5 cm from the kidney pelvis. As can be seen, prolonged elevation of kidney function is possible with long term stimulation. As shown on FIG. 52, the prolonged stimulation improved urine flow by approximately 25% and GFR by up to 20% relative to control.

In general, during experimentation on sheep, same sheep were used for multiple experiments, sometimes on consecutive days and sometimes non-consecutive. No reduction in effect was noted.

Example IV

Control of Renal Function with Intravesical Stimulation Device in Sheep

The intravesical stimulator used in these experiments consisted of a specially designed bladder stimulators with 2 disk shaped platinum electrodes (electrode diameter 2-5 mm) glued to inflatable balloons of 20Fr Foley catheters. The platinum contacts were connected with coated wires to an external standard laboratory stimulation device (A-M systems, model 2100). The balloon portion of the catheter was covered by a latex sheath to ease insertion through the urethra. During balloon inflation the sheath is pushed away by the enlargement of the balloon. This arrangement assured a safe, non traumatic insertion of the catheter.

During the experiments the catheter was positioned so that the electrodes came into direct contact with the trigone, good electrical contact was assessed by measuring conductance. When in contact with tissue the conductance ranged 10-1000 Kohm. Resistance of several ohms or less than 100-800 ohm may indicate shorting by urine. If the electrodes were in contact with urine the conductance dropped to a few ohms; if the conductance indicated contact with urine the experiments were stopped and the catheter repositioned till a better location was found.

Three healthy female sheep were used in this study; the stimulators were inserted by a direct visualization of the urethra with a laryngoscope, no sedation was used. Stimulator insertion lasted less than five minutes; immediately thereafter the stimulator was connected to a urine collection bag that was kept below the level of the bladder of the animal to ensure full emptying of the bladder at all times. During the experiment, that typically lasted a few hours, the animals were not allowed to drink or eat. This was done in order to reduce the variability of renal function associated with oral fluid or meal intake.

Urine collection periods were between 30 minutes and one hour. Stimulation was commenced when stable urine production was obtained. Average urine flow was calculated by dividing the volume collected urine by collection time. GFR was analyzed from the following equation: GFR=Ucr×Uvol/Pcr, where Ucr is the urine concentration of creatinine, Uvol is collected urine volume and Pcr is the plasma concentration of creatinine. Sodium excretion rate was calculated from multiplication of urine sodium concentration by the average urine flow.

FIGS. 53A1-53B3 show that Urine flow, GFR, and sodium excretion increase (if any) following stimulation with the stimulator in healthy sheep in the trigone (FIGS. 53A1-53A3) and in the ventral wall of the bladder (FIG. 53B1-53B3). (* vs control collections; *p<0.05; ***p<0.001; # vs trigone stimulation; #p<0.05; ##p<0.01).

All stimulations started after a steady baseline in urine flow was reached. Stimulation of the trigone increased urine flow by 33±30% (p=0.01; n=16), GFR by 25±25% (p=0.001; n=15) and sodium excretion by 52±32% (p<0.0001; n=14). The effect of trigone stimulation was long lasting, with observable elevations of urine flow to 34±44% (p=0.01) and sodium excretion to 42±73% (p=0.03) in the first collection period (30 minutes) following the stimulation.

FIG. 53B shows results, in which a similar device as used for trigone stimulation was inserted into the bladder, but the leads rotated 180 degrees to face the ventral part of the bladder, away from the trigone. Stimulation of the ventral part of the bladder did not increase any of the parameters of kidney function. During the stimulation urine flow was 95±21% of control; GFR was also stable, it increased slightly to 9±15% above control (p=0.37) and sodium excretion was 97±43% of control. Compared to stimulation of the ventral wall, stimulation of the trigone lead to a statistically significant increase in all parameters of renal function (p<0.05 for stimulation collection period and half an hour post stimulation for urine flow, GFR and sodium excretion).

Non-direction selective electrical stimulation of the bladder was examined in two experiments. The intravesical stimulator used in these experiments consisted of a specially designed bladder stimulator with 6 disk shaped platinum electrodes glued to an inflatable balloon of a 20Fr Foley catheter and distributed evenly on the full circumference of the balloon, 2 cm from the lower part of the balloon (e.g., for stimulating both the trigone areas and other areas). Experimental protocol was similar as described above.

Figure 54:
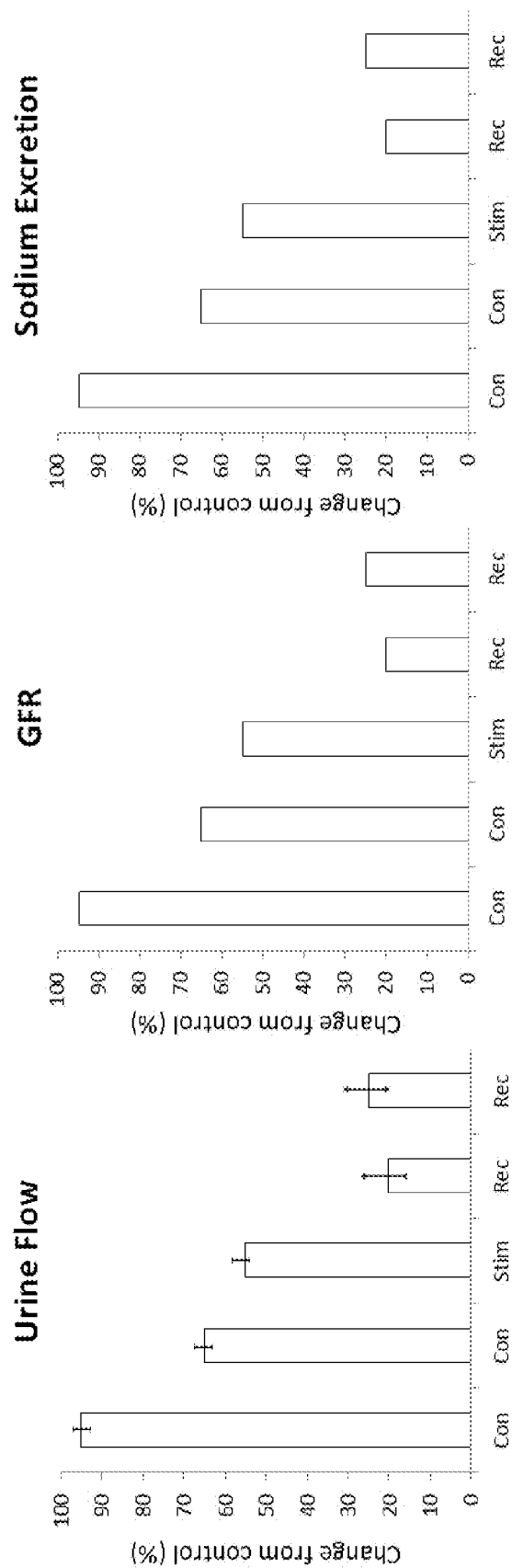
FIG. 54 is a set of charts showing the effect of 360 degrees intra-bladder stimulation on urine flow, GFR and sodium excretion.

FIG. 54 shows that Urine flow, GFR and sodium excretion were all reduced during stimulation. The urine flow was reduced to 66±7.4% of control values (p<0.05), the reduction was significant for at least one hour following the stimulation. Similarly to urine flow, both GFR and sodium excretion were reduced for a prolonged time period following bladder stimulation. These findings indicate activation of the vesico-vascular reflex by the stimulation, showing that different reflexes can be activated by different stimulation locations.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of controlling a physiological state of a subject, comprising:
    (a) determining that it is desired to affect functioning of a system of the subject, the functioning being selected from the group consisting of: renal functioning, and cardiovascular functioning; and
    (b) in response thereto, affecting the selected functioning in the desired manner, by electrically stimulating a urine carrying portion of a urinary system of the subject selected from the group consisting of: a ureter, a trigone, a uretero-vesical junction, a urethra, a renal pelvis, an internal structure of the kidney, a lumen in the kidney, and a bladder, the electrical stimulation of the selected portion causing a therapeutic change in a value of at least one parameter, relative to a value of the parameter in an absence of the electrical stimulation being applied to the selected portion, the parameter being selected from the group consisting of: glomerular filtration rate, renal blood flow, diuresis, and natriuresis.

2. The method according to claim 1, wherein said stimulating comprises modulating a gain of a sympathetic drive to the kidney.

3. The method according to claim 1, wherein said stimulating comprises modulating activity of an afferent nerve innervating the urinary system.

4. The method according to claim 1, wherein said stimulating comprises affecting the selected functioning by performing an action selected from the group consisting of: activating and modulating, with respect to at least one nervous reflex.

5. The method according to claim 1, further comprising administering systemic medication to the subject, the stimulating being configured to interact with the administration of the medication to the subject.

6. The method according to claim 1, wherein said stimulating comprises causing an increase by at least a factor of 1.1 in one or more of the parameters.

7. The method according to claim 1, wherein said stimulating comprises stimulating one or more portions of the subject's body selected from the group consisting of: a ureter, a trigone, a uretero-vesical junction, and a bladder.

8. The method according to claim 1, wherein said stimulating comprises stimulating via a stimulator that remains in the subject's body for three days to two weeks.

9. The method according to claim 1, wherein said stimulating comprises stimulating via a stimulator that is implanted in the subject's body for at least two weeks.

10. The method according to claim 1, wherein said stimulating comprises treating at least partially one or more conditions selected from the group consisting of: acute heart failure, congestive heart failure, hypertension, acute renal failure, contrast nephropathy, chronic renal failure, shock, septic shock, nephrotic syndrome, cardio-renal syndrome and myocardial infarct.

11. The method according to claim 1, wherein said stimulating comprises stimulating for at least 2 hours a day.

12. The method according to claim 1, wherein said stimulating comprises stimulating in such a manner that the selected functioning is affected for at least 30 minutes after stimulation is stopped.

13. The method according to claim 1, further comprising receiving an input during the stimulation, and modifying a parameter of the stimulation in response thereto.

14. The apparatus according to claim 13, further comprising determining a physiological parameter of the subject during the stimulation, wherein receiving the input comprises receiving an input that is indicative of the physiological parameter of the subject.

15. The method according to claim 14, wherein determining the physiological parameter comprises determining urine flow of the subject during the stimulation, and wherein modifying the parameter of the stimulation comprises modifying the parameter of the stimulation in response to the determined urine flow.

* * * * *